US011225650B2

United States Patent
Pierce et al.

(10) Patent No.: US 11,225,650 B2
(45) Date of Patent: *Jan. 18, 2022

(54) METHODS OF USING FIX POLYPEPTIDES

(71) Applicant: Bioverativ Therapeutics Inc., Waltham, MA (US)

(72) Inventors: Glenn Pierce, Cambridge, MA (US); Samantha Truex, Sudbury, MA (US); Robert T. Peters, Needham, MA (US); Haiyan Jiang, Belmont, MA (US); Mark Brader, Lexington, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 444 days.

This patent is subject to a terminal disclaimer.

(21) Appl. No.: 15/619,196

(22) Filed: Jun. 9, 2017

(65) Prior Publication Data

US 2018/0002684 A1 Jan. 4, 2018

Related U.S. Application Data

(63) Continuation of application No. 14/430,848, filed as application No. PCT/US2013/061747 on Sep. 25, 2013.

(60) Provisional application No. 61/863,859, filed on Aug. 8, 2013, provisional application No. 61/839,439, filed on Jun. 26, 2013, provisional application No. 61/829,755, filed on May 31, 2013, provisional application No. 61/811,412, filed on Apr. 12, 2013, provisional application No. 61/800,163, filed on Mar. 15, 2013, provisional application No. 61/759,796, filed on Feb. 1, 2013, provisional application No. 61/705,607, filed on Sep. 25, 2012.

(51) Int. Cl.
*A61K 38/36* (2006.01)
*C12N 9/64* (2006.01)
*C07K 14/745* (2006.01)
*C07K 16/36* (2006.01)
*A61K 38/00* (2006.01)

(52) U.S. Cl.
CPC ............ *C12N 9/644* (2013.01); *C07K 14/745* (2013.01); *C07K 16/36* (2013.01); *A61K 38/00* (2013.01); *C07K 2317/76* (2013.01); *C07K 2319/30* (2013.01); *C12Y 304/21022* (2013.01)

(58) Field of Classification Search
None
See application file for complete search history.

(56) References Cited

U.S. PATENT DOCUMENTS

| | | | |
|---|---|---|---|
| 4,786,726 A | 11/1988 | Smith | |
| 5,981,285 A | 11/1999 | Carroll et al. | |
| 6,372,716 B1 | 4/2002 | Bush et al. | |
| 6,686,179 B2 | 2/2004 | Fleer et al. | |
| 7,112,580 B2 | 9/2006 | Raymond et al. | |
| 7,217,798 B2* | 5/2007 | Hinton | C07K 14/5437 435/326 |
| 7,348,004 B2 | 3/2008 | Peters et al. | |
| 7,404,956 B2 | 7/2008 | Peters et al. | |
| 7,566,565 B2* | 7/2009 | Peters | C12Y 304/21022 435/325 |
| 7,592,010 B2 | 9/2009 | Rosen et al. | |
| 7,790,415 B2 | 9/2010 | Gillies et al. | |
| 8,367,805 B2 | 2/2013 | Chamberlain et al. | |
| 9,233,145 B2* | 1/2016 | Pierce | A61K 38/4846 |
| 9,623,091 B2* | 4/2017 | Pierce | A61K 38/4846 |
| 9,629,903 B2* | 4/2017 | Pierce | A61K 38/4846 |
| 9,670,475 B2* | 6/2017 | Pierce | A61K 38/4846 |
| 9,675,676 B2* | 6/2017 | Pierce | A61K 38/4846 |
| 9,867,873 B2* | 1/2018 | Pierce | A61K 38/4846 |
| 10,548,954 B2* | 2/2020 | Pierce | C12N 9/96 |
| 2001/0031721 A1 | 10/2001 | Webb et al. | |
| 2003/0203845 A1 | 10/2003 | Knudsen et al. | |
| 2005/0032174 A1 | 2/2005 | Peters et al. | |
| 2007/0060597 A1 | 3/2007 | Qi et al. | |
| 2007/0135343 A1* | 6/2007 | Webb | A61P 7/02 424/680 |
| 2008/0260755 A1* | 10/2008 | Metzner | C07K 14/745 424/178.1 |
| 2009/0092582 A1 | 4/2009 | Bogin et al. | |
| 2009/0163699 A1 | 6/2009 | Chamberlain et al. | |
| 2009/0252720 A1 | 10/2009 | Ostergaard et al. | |
| 2009/0264627 A1 | 10/2009 | Gillies et al. | |
| 2010/0150940 A1 | 6/2010 | Adam et al. | |
| 2010/0189682 A1 | 7/2010 | Schellenberger et al. | |
| 2010/0222554 A1 | 9/2010 | Weimer et al. | |

(Continued)

FOREIGN PATENT DOCUMENTS

EP 2353588 A1 8/2011
EP 2900328 A1 8/2015
(Continued)

OTHER PUBLICATIONS

Peters et al,, Blood. Mar. 11, 2010 ;115(10):2057-64. doi: 10.1182/blood-2009-08-239665. Epub Jan. 7, 2010.*
Hansen, L. et al"The pharmacokinetics of a long-acting Factor IX (40K PEG-RFIX) in minipigs suggests at least a once-weekly dosing regime," 0C-M0-085, Oral Presentation abstract, Journal Compilation International Society on Thrombosis and Haemostasis 7 (Suppl. 2), 1-1204, p. 134 (published online Jun. 15, 2009).*
Ticho, B., "Long-acting Clotting Factor Fc Fusion Proteins for Potential Use in Hemophilia," Biogen Idec, Mar. 25, 2009, 9 pages.*

(Continued)

*Primary Examiner* — Michael Szperka
(74) *Attorney, Agent, or Firm* — Lathrop GPM LLP; James H. Velema, Esq.

(57) ABSTRACT

The present invention provides methods of administering long-acting Factor IX; methods of administering long-acting, chimeric and hybrid polypeptides comprising Factor IX; and methods of producing such chimeric and hybrid polypeptides using cells.

20 Claims, 23 Drawing Sheets

Specification includes a Sequence Listing.

(56) References Cited

U.S. PATENT DOCUMENTS

| | | |
|---|---|---|
| 2010/0239554 A1 | 9/2010 | Schellenberger et al. |
| 2011/0236412 A1 | 9/2011 | Drew |
| 2012/0208759 A1 | 8/2012 | Fima et al. |
| 2013/0171175 A1 | 7/2013 | Pierce et al. |
| 2013/0202595 A1 | 8/2013 | Pierce et al. |
| 2016/0000888 A1 | 1/2016 | Brader |
| 2016/0166657 A1 | 6/2016 | Pierce et al. |
| 2016/0243206 A1 | 8/2016 | Pierce et al. |
| 2016/0257943 A1 | 9/2016 | Pierce et al. |
| 2016/0346365 A1 | 12/2016 | Pierce et al. |

FOREIGN PATENT DOCUMENTS

| | | | |
|---|---|---|---|
| EP | 3542861 A1 | 9/2019 | |
| JP | 2009525724 A | 7/2009 | |
| JP | 2009539391 A | 11/2009 | |
| JP | 2010063462 A | 3/2010 | |
| WO | WO-9835689 A1 | 8/1998 | |
| WO | WO-0240544 A2 | 5/2002 | |
| WO | WO-03020764 A2 | 3/2003 | |
| WO | WO-2004101740 A2 | 11/2004 | |
| WO | WO-2005001025 A2 | 1/2005 | |
| WO | WO-2006074199 A1 | 7/2006 | |
| WO | WO-2007090584 A1 | 8/2007 | |
| WO | WO-2007103515 A2 | 9/2007 | |
| WO | WO-2007115724 A2 * | 10/2007 | ............... C12N 9/14 |
| WO | WO-2007144173 A1 | 12/2007 | |
| WO | WO-2007149406 A2 | 12/2007 | |
| WO | WO-2008022151 A1 | 2/2008 | |
| WO | WO-2008118507 A2 | 10/2008 | |
| WO | WO-2009023270 A2 | 2/2009 | |
| WO | WO-2009051717 A2 | 4/2009 | |
| WO | WO-2009130198 A2 | 10/2009 | |
| WO | WO-2009130602 A2 | 10/2009 | |
| WO | WO-2009137254 A2 | 11/2009 | |
| WO | WO-2009140015 A2 | 11/2009 | |
| WO | WO-2010020690 A1 | 2/2010 | |
| WO | WO-2010091122 A1 | 8/2010 | |
| WO | WO-201200624 A2 | 1/2012 | |
| WO | WO-2012006624 A2 * | 1/2012 | ......... A61K 38/4846 |
| WO | WO-2014052490 A1 | 4/2014 | |
| WO | WO-2014144549 A1 | 9/2014 | |

OTHER PUBLICATIONS

Matsumoto et al., J Thromb Haemost. Feb. 2006;4(2):377-84.*

Ahnstrom, J., et al., "A 6-year Follow-Up of Dosing, Coagulation Factor Levels and Bleedings in Relation to Joint Status in the Prophylactic Treatment of Haemophilia," Haemophilia 10(6):689-697, Blackwell Publishing Ltd., England (2004).

Andersson, L.O., et al., "Purification and Characterization of Human Factor IX," Thrombosis Research 7(3):451-459, Pergamon Press, Inc., United States (1975).

Armour, K.L., et al., "Recombinant Human IgG Molecules Lacking Fcγ Receptor I Binding and Monocyte Triggering Activities," European Journal of Immunology 29(8):2613-2624, Wiley-VCH, Germany (1999).

Beal, S.L., "Ways to Fit a PK Model with Some Data Below the Quantification Limit," Journal of Pharmacokinetics and Pharmacodynamics 28(5):481-504, Plenum Publishing Corporation, United States (2001).

Bergstrand, M. and Karlsson, M.O., "Handling Data Below the Limit of Quantification in Mixed Effect Models," The AAPS Journal 11(2):371-380, American Association of Pharmaceutical Scientists, United States (2009).

Bjorkman, S., and Ahlen, V., et al., "Population Pharmacokinetics of Plasma-Derived Factor IX in Adult Patients with Haemophilia B: Implications for Dosing in Prophylaxis," European Journal of Clinical Pharmacology 68(6):969-977, Springer-Verlag, Germany (2012).

Bjorkman, S. and Berntorp, E., "Pharmacokinetics of Coagulation Factors: Clinical Relevance for Patients with Haemophilia," Clinical Pharmacokinetics 40(11):815-832, Adis International Ltd., New Zealand (2001).

Bjorkman, S., et al., "Pharmacokinetics of Factor IX in Patients With Haemophilia B. Methodological Aspects and Physiological Interpretation," European Journal of Clinical Pharmacology 46(4):325-332, Springer-Verlag, Germany (1994).

Bjorkman, S., et al., "Pharmacokinetics of Recombinant Factor IX in Relation to Age of the Patient: Implications for Dosing in Prophylaxis," Haemophilia 7(2):133-139, Blackwell Science Ltd., England (2001).

Bjorkman, S., "Population Pharmacokinetics of Recombinant Factor IX: Implications for Dose Tailoring," Haemophilia 19(5):753-757, John Wiley & Sons Ltd., England (2013).

Bjorkman, S., "Prophylactic Dosing of Factor VIII and factor IX from a Clinical Pharmacokinetic Perspective," Haemophilia 9(1):101-110, Blackwell Publishing Ltd., England (2003).

Brendel, K., et al., "Are Population Pharmacokinetic and/or Pharmacodynamic Models Adequately Evaluated? A Survey of the Literature from 2002 to 2004," Clinical Pharmacokinetics 46(3):221-234, Adis Data Information BV, New Zealand (2007).

Brinkhous, K.M., et al., "Recombinant Human Factor IX: Replacement Therapy, Prophylaxis, and Pharmacokinetics in Canine Hemophilia B," Blood 88(7):2603-2610, The American Society of Hematology, United States (1996).

Brutlag, D.L., et al., "Improved Sensitivity of Biological Sequence Database Searches," Computer Applications in the Biosciences 6(3):237-245, Oxford University Press, England (1990).

Burmeister, W.P., et al., "Crystal Structure of the Complex of Rat Neonatal Fc Receptor with Fc," Nature 372(6504):379-383, Nature Publishing Group, England (1994).

Byon, W., et al., "Establishing Best Practices and Guidance in Population Modeling: an Experience with an Internal Population Pharmacokinetic Analysis Guidance," CPT: Pharmacometrics & Systems Pharmacology 2:e51:1-8, ASCPT, United States (2013).

Carlsson, M., et al., "Multidose Pharmacokinetics of Factor IX: Implications for Dosing in Prophylaxis," Haemophilia 4(2):83-88, Blackwell Publishing Ltd., England (1998).

Chang, C.W., et al., "Non-Ionic Amphiphilic Biodegradable PEG-PLGA-PEG Copolymer Enhances Gene Delivery Efficiency in Rat Skeletal Muscle," Journal of Controlled Release 118(2):245-253, Elsevier B.V., Netherlands (2007).

Chang, L.C., et al., "Sustained Release of Transgenic Human Factor IX: Preparation, Characterization, and in Vivo Efficacy," Molecular Pharmaceutics 8(5):1767-1774, American Chemical Society, United States (2011).

Chitlur, M., et al, "Inhibitors in Factor IX Deficiency a Report of the ISTH-SSC International FIX Inhibitor Registry (1997-2006)," Haemophilia 15(5):1027-1031, Blackwell Publishing Ltd., England (2009).

Collins, P., et al., "Break-Through Bleeding in Relation to Predicted Factor VIII Levels in Patients Receiving Prophylactic Treatment for Severe Hemophilia A," Thrombosis and Haemostasis 7(3):413-420, Blackwell Publishers, England, (2009).

Communication Pursuant to Article 94(3) EPC, dated Mar. 4, 2016, for EP Application No. EP11804476.7, European Patent Office, Germany, 6 pages.

Notice of Allowance dated Aug. 14, 2017 in U.S. Appl. No. 14/982,934, inventors Pierce, G., et al., filed Dec. 29, 2015, 13 pages.

Döbeli, H., et al., "Role of the Carboxy-Terminal Sequence on the Biological Activity of Human Immune Interferon (IFN-γ)," Journal of Biotechnology 7:199-216, Elsevier Science Publishers B.V., Netherlands (1988).

Dimichele, D., "Inhibitor Development in Haemophilia B: an Orphan Disease in Need of Attention," British Journal of Haematology 138(3):305-315, Blackwell Publishing Ltd., England (2007).

Dimichele, D., "Inhibitors: Resolving Diagnostic and Therapeutic Dilemmas," Haemophilia 8(3):280-287, Blackwell Science Ltd., England (2002).

Dumont, J.A., et al., "Monomeric Fc Fusion Molecules," in Therapeutic Monoclonal Antibodies from Bench to Clinic, Chapter 33, pp. 779-795, John Wiley & Sons., Inc., United States (2009).

(56) References Cited

OTHER PUBLICATIONS

Dumont, J.A., et al., "Monomeric Fc Fusions: Impact on Pharmacokinetic and Biological Activity of Protein Therapeutics," BioDrugs 20(3):151-160, Springer International, New Zealand (2006).
Ette, E.I. and Ludden, T.M., "Population Pharmacokinetic Modeling: the Importance of Informative Graphics," Pharmaceutical Research 12(12):1845-1855, Plenum Publishing Corporation, United States (1995).
Extended European Search Report for Application No. EP 13842864.4, Munich, Germany, dated Apr. 11, 2016, 8 pages.
Final Office Action dated Jun. 1, 2015, in U.S. Appl. No. 13/793,796, Pierce, G., et al., filed Mar. 11, 2013.
Food and Drug Administration, "Guidance for Industry on Population Pharmacokinetics; Availability," Federal Register 64(27):6663-6664, Food and Drug Administration, HHS, United States (1999).
Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).
Gayle, R.B., III., et al., "Identification of Regions in Interleukin-1α Important for Activity," The Journal of Biological Chemistry 268(29):22105-22111, The American Society for Biochemistry and Molecular Biology, Inc., United States (1993).
Giangrande, P., "Haemophilia B: Christmas Disease," Expert Opinion on Pharmacotherapy 6(9):1517-1524, Ashley Publications Ltd., England (2005).
Gillis, S., et al., "γ-Carboxyglutamic Acids 36 and 40 do not Contribute to Human Factor IX Function," Protein Science 6(1):185-196, Wiley-Blackwell, United States (1997).
Gui, T., et al., "Circulating and Binding Characteristics of Wild-type Factor IX and Certain Gla Domain Mutants in Vivo," Blood 100(1):153-158, American Society of Hematology, United States (2002).
Hansson, K. and Stenflo, J., "Post-Translational Modifications in Proteins Involved in Blood Coagulation," Journal Thrombosis and Haemostasis 3(12):2633-2648, Blackwell Pub., England (2005).
Huang, C., "Receptor-Fc Fusion Therapeutics, Traps, and MIMETIBODY Technology," Current Opinion in Biotechnology 20(6):692-699, Current Biology, England (2009).
International Search Report and Written Opinion for Application No. PCT/US2011/043569, ISA/US, Alexandria, Virginia, United States, dated Feb. 14, 2012, 11 pages.
International Search Report and Written Opinion for Application No. PCT/US2013/061747, ISA/US, Alexandria, Virginia, United States, dated Dec. 16, 2013, 9 pages.
Jonsson, E.N. and Karlsson, M.O., "Xpose—an S-plus Based Population Pharmacokinetic/pharmacodynamic Model Building Aid for NONMEM," Computer Methods and Programs in Biomedicine 58(1):51-64, Elsevier Science Ireland Ltd., Ireland (1999).
Karlsson, M.O. and Sheiner, L.B., "The Importance of Modeling Interoccasion Variability in Population Pharmacokinetic Analyses," Journal of Pharmacokinetics and Biopharmaceutics 21(6):735-750, Plenum Publishing Corporation, United States (1993).
Kiang, T.K.L., et al., "Fundamentals of Population Pharmacokinetic Modelling, Modelling and Software," Clinical Pharmacokinetics 51(8):515-525, Springer International Publishing AG, New Zealand (2012).
Kisker, C.T., et al., "Prophylaxis in Factor IX Deficiency Product and Patient Variation," Haemophilia 9(3):279-284, Blackwell Publishing Ltd., England (2003).
Kuo, T.T. and Aveson, V.G., "Neonatal Fc Receptor and IgG-based Therapeutics," MAbs 3(5):422-430, Taylor & Francis, United States (2011).
Lambert, C. and Prange, R., "Posttranslational N-glycosylation of the hepatitis B Virus Large Envelope Protein," Virology Journal 4:45, BioMed Central Ltd., England, 9 pages (2007).
Lindbom, L., et al., "Perl-speaks-NONMEM (PsN)—a Perl Module for NONMEM Related Programming," Computer Methods and Programs in Biomedicine 75(2):85-94,Elsevier Ireland Ltd., Ireland (2004).

Mahmood, I., "Theoretical Versus Empirical Allometry: Facts Behind Theories and Application to Pharmacokinetics," Journal of Pharmaceutical Sciences 99(7):2927-2933,Wiley-Liss, Inc. and the American Pharmacists Association, United States (2010).
Mannucci, P.M. and Tuddenham, E.G., "The Hemophilias—from Royal Genes to Gene Therapy," The New England Journal of Medicine 344(23):1773-1779, Massachusetts Medical Society, United States (2001).
Martinowitz, U., et al., "Pharmacokinetic Properties of IB1001, an Investigational Recombinant Factor IX, in Patients With Haemophilia B: Repeat Pharmacokinetic Evaluation and Sialylation Analysis," Haemophilia 18(6):881-887, Blackwell Publishing Ltd., England (2012).
"MASAC Recommendations Concerning Products Licensed for the Treatment of Hemophilia and Other Bleeding Disorders," Hemophilia.org, accessed at http://www.hemophilia.org/Researchers-Healthcare-Providers/Medical-and-Scientific-Advisory-Council-MASAC/All-MASAC-Recommendations/Recommendations-Concerning-Products-Licensed-for-the-Treatment-of-Hemophilia-and-Other-Bleeding-Disorders, accessed on Sep. 8, 2014, 37 pages.
McCarthy, K., et al., "Pharmacokinetics of Recombinant Factor IX After Intravenous and Subcutaneous Administration in Dogs and Cynomolgus Monkeys," Thrombosis and Haemostasis 87(5):824-830, Schattauer GmbH, Stuttgart, Germany (2002).
Mei, B., et al., "Expression of Human Coagulation Factor VIII in a Human Hybrid Cell Line, HKB11," Molecular Biotechnology 34(2):165-178, Humana Press Inc., United States (2006).
Negrier, C., et al., "Enhanced Pharmacokinetic Properties of a GlycoPEGylated Recombinant Factor IX: A First Human Dose Trial in Patients with Hemophilia B," Blood 118(10):2695-2701, The American Society of Hematology, United States (2011).
Neumann, E., et al., "Gene Transfer into Mouse Lyoma Cells by Electroporation in High Electric Fields," The EMBO Journal 1(7):841-845, IRL Press Limited, England (1982).
Nilsson, I.M., et al., "Twenty-Five Years' Experience of Prophylactic Treatment in Severe haemophilia A and B," Journal of Internal Medicine 232(1):25-32, Blackwell Scientific Publications, England (1992).
Non-Final Office Action dated Feb. 19, 2015, in U.S. Appl. No. 13/793,796, Pierce, G., et al., filed Mar. 11, 2013.
Non-Final Office Action dated Sep. 28, 2015, in U.S. Appl. No. 13/809,276, Pierce, G., et al., 371(c) date Apr. 24, 2013.
Non-Final Office Action dated Sep. 15, 2016, in U.S. Appl. No. 13/809,276, Pierce, G., et al., 371(c) date Apr. 24, 2013
Non-Final Office Action dated Jun. 2, 2016, in U.S. Appl. No. 15/043,457, inventors Pierce, G., et al., filed Feb. 12, 2016.
Non-final Office Action dated May 19, 2016, in U.S. Appl. No. 15/043,455, inventors Pierce, G., et al., filed Feb. 12, 2016.
Non-Final Office Action dated Sep. 7, 2016, in U.S. Appl. No. 15/043,445, Pierce, G., et al., filed Feb. 12, 2016.
Notification of Material Filed Under Section 27 mailed Jan. 12, 2016 in Australian Patent Application No. 2011274414, filed Jul. 11, 2011, 13 pages.
Oganesyan, V., et al., "Structural Characterization of a Human Fc Fragment Engineered for Extended Serum Half-Life," Molecular Immunology 46(8-9):1750-1755, Pergamon Press, England (2009).
Page, D., "The Blood Factor: Breakthrough in Factor IX Products, Canadian Study Results Point to Importance of Early Prophylaxis," Hemophilia Today 45(3):29, Canadian Hemophilia Society, Canada (Nov. 2010).
Peters, R., Abstract entitled "Enhanced Pharmacokinetics of Factor IX as a Monomeric Fc Fusion," 2007 J. Throm. & Haemostasis S2(5):O-M-001-O-M-096 at O-M-016, 1 page.
Peters, R., Slides entitled "Enhanced Pharmacokinetics of Factor IX as a Monomeric Fc Fusion Protein," presented to the International Society on Thrombosis and Haemostasis Jul. 9, 2007, 14 pages.
Peters, R., Slides entitled *"Improved Pharmacokinetics of Factor IX as a Monomeric Fc Fusion Protein,"* presented at National Hemophilia Foundation Workshop Mar. 30, 2006, 11 pages.
Ragni, M.V., et al., "Use of Recombinant Factor IX in Subjects with Haemophilia B Undergoing Surgery," Haemophilia 8(2):91-97, Blackwell Science, England (2002).

(56) References Cited

OTHER PUBLICATIONS

Reagan-Shaw, S., et al., "Dose Translation from Animal to Human Studies Revisited," Federation of American Societies for Experimental Biology Journal 22(3):659-661, The Federation, United States (2008).
Ron, D., et al., "Expression of Biologically Active Recombinant Keratinocyte Growth Factor: Structure/Function Analysis of Amino-Terminal Truncation Mutants," The Journal of Biological Chemistry 268(4):2984-2988, American Society for Biochemistry and Molecular Biology, United States (1993).
Roopenian, D.C. and Akilesh, S., "FcRn: the Neonatal Fc Receptor Comes of Age," Nature Reviews Immunology 7(9):715-725, Nature Publishing Group, England (2007).
Roth, D.A., et al., "Human Recombinant Factor IX: Safety and Efficacy Studies in Hemophilia B Patients Previously Treated with Plasma-Derived Factor IX Concentrates," Blood 98(13):3600-3606, The American Society of Hematology, United States (2001).
Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (1995).
Savic, R.M. and Karlsson, M.O., "Importance of Shrinkage in Empirical Bayes Estimates for Diagnostics: Problems and Solutions," The AAPS Journal 11(3):558-569, American Association of Pharmaceutical Scientists, United States (2009).
Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (2009).
Schulte, S., "Half-life Extension Through Albumin Fusion Technologies," Thrombosis Research 124(Suppl. 2):S6-S8, Pergamon Press, United States (2009).
Screenshot of "Special Issue: Abstracts of XXIXth International Congress of the World Federation of Hemophilia, Buenos Aires, Argentina, Jul. 10-14, 2010," Haemophilia 16(Suppl. 4):1-170.
Shapiro, A.D., et al., "Abstracts of the XXIXth International Congress of the World Federation of Hemophilia," Haemophilia 16(Suppl. 4):1-158, Abstract 07FP07 at 30, Buenos Aires, Argentina, Jul. 10-14, 2010.
Shapiro, a.D., et al., "The Safety and Efficacy of Recombinant Human Blood Coagulation Factor IX in Previously Untreated Patients with Severe or Moderately Severe Hemophilia B," Blood 105(2):518-525, American Society of Hematology, United States (2005).
Shapiro, A.D., et al., "Use of Pharmacokinetics in the Coagulation Factor Treatment of Patients with Haemophilia," Haemophilia 11(6):571-582, Blackwell Publishing Ltd., England (2005).
Shapiro, A.D., "Recombinant factor IX-Fc fusion protein (rFIXFc) demonstrates safety and prolonged activity in a phase 1/2a study in hemophilia B patients," Blood 119(3):666-672, The American Society of Hematology, United States (2012).
Sherwin, C.M.T., et al., "Fundamentals of Population Pharmacokinetic Modelling, Validation Methods," Clinical Pharmacokinetics 51(9):573-590, Springer International Publishing AG, New Zealand (2012).
Shields, R.L., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 276(9):6591-6604, American Society for Biochemistry and Molecular Biology, United States (2001).
Srivastava, A., et al., "Guidelines for the Management of Hemophilia," Haemophilia 19(1):e1-e47, Blackwell Publishing Ltd., England (2013).
Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).
Summary of Product Characteristics for BENEFIXTM, Electronic Medicines Compendium, medicines.org.uk, accessed at http://www.medicines.org.uk/emc/medicine/20376/SPC/BENEFIXTtm/#PHARMACODYNAMIC_PROPS, accessed on Sep. 16, 2014, 11 pages.
Supplementary European Search Report for Application No. EP11804476, Munich, Germany, dated Mar. 5, 2014, 6 pages.
Vaccaro, C., et al., "Engineering the Fc region of Immunoglobulin G to Modulate in vivo Antibody Levels," Nature Biotechnology 23(10):1283-1288, Nature America Publishing, United States (2005).
Wade, J.R., et al., "A Guide for Reporting the Results of Population Pharmacokinetic Analyses: a Swedish Perspective," The AAPS Journal 7(2):45:E456-E460, American Association of Pharmaceutical Scientists, United States (2005).
Wang, D.D., et al., "Fixed Dosing Versus Body Size-Based Dosing of Monoclonal Antibodies in Adult Clinical Trials," The Journal of Clinical Pharmacology 49(9):1012-1024, American College of Clinical Pharmacology, United States (2009).
Ward, E.S. and Ghetie, V., "The Effector Functions of Immunoglobulins: Implications for Therapy," Therapeutic Immunology 2(2):77-94, Blackwell Science Ltd., England (1995).
White, G.C. II., et al., "Recombinant Factor IX," Thrombosis and Haemostasis 78(1):261-265, F.K. Schattauer Verlagsgesellschaft mbH, Germany (1997).
White, G.C. II., et al., "Variability of in Vivo Recovery of Factor IX after Infusion of Monoclonal Antibody Purified Factor IX Concentrates in Patients with Hemophilia B. The Mononine Study Group," Thrombosis and Haemostasis 73(5):779-784, Stuttgart, Schattauer, Germany (1995).
Wigler, M., et al., "Biochemical Transfer of Single-Copy Eucaryotic Genes Using Total Cellular DNA as Donor," Cell 14(3):725-731, Cell Press, United States (1978).
Xu, X.S., et al., "Shrinkage in Nonlinear Mixed-effects Population Models: Quantification, Influencing Factors, and Impact," The AAPS Journal 14(4):927-936, American Association of Pharmaceutical Scientists, United States (2012).
Hansen, L., et al., "The pharmacokinetics of a long-acting Factor IX (40K PEG-RFIX) in minipigs suggests at least a once-weekly dosing regime," Journal of Thrombosis and Haemostasis 7(Suppl. 2): 134, International Society on Thrombosis and Haemostasis, England, Abstract OC-MO-085 (2009).
Shapiro, A.D., et al., "Safety and prolonged biological activity following a single administration of a recombinant molecular fusion of native human coagulation factor IX and the Fc region of immunoglobulin G (IgG) (rFIXFc) to subjects with hemophilia B," Haemophilia 16(Suppl. 4): 30, Blackwell Publishing Ltd., United Kingdom, Abstract 07FP07 (Jul. 2010).
U.S. Food and Drug Administration, "Highlights of Prescribing Information, ALPROLIX," revised Mar. 2014.
Communication pursuant to Rule 114(2) EPC, dated Oct. 30, 2015, Third Party Observations (Article 115 EPC) for Application No. EP11804476.7, European Patent Office, Germany.
Ezban, M., et al., "Pharmacokinetic (PK) and pharmacodynamics (PD) properties of a new recombinant long acting factor IX (40KPEG-RFIX) product after intravenous (IV) administration to hemophilia B dogs," PP-TH-579, Poster Presentation, Journal of Thrombosis and Haemostasis 7(Suppl. 2): 1-1204:134, International Society on Thrombosis and Haemostasis, United States (Jun. 2009).
Ezban, M., et al., "Pharmacokinetic (PK) and pharmacodynamics (PD) properties of a new recombinant long acting factor IX (40KPEG-RFIX) product after intravenous (IV) administration to hemophilia B (HB) dogs," PP-TH-579, Poster Presentation, presented at XXII Congress of the International Society of Thrombosis and Haemostasis, Boston, MA, USA, Jul. 11-16, 2009. (Best Available Copy).
Non-Final Office Action dated Jun. 1, 2015 in U.S. Appl. No. 13/793,796, filed Mar. 11, 2013.
Final Office Action dateed Nov. 29, 2016, in U.S. Appl. No. 15/043,455, inventors Pierce, G., et al., filed Feb. 12, 2016.
Final Office Action dated Nov. 30, 2016, in U.S. Appl. No. 15/043,457, inventors Pierce, G., et al., filed Feb. 12, 2016.
National Hemophilia Foundation, "Hemophilia B," hemophilia.org, accessed at https://www.hemophilia.org/Bleeding-Disorders/Types-of-Bleeding-Disorders/Hemophilia-B, accessed on Mar. 4, 2014, 2 pages.

(56) References Cited

OTHER PUBLICATIONS

Non-Final Office Action dated Aug. 11, 2016, in U.S. Appl. No. 14/430,848, inventors Pierce, G., et al., filed Sep. 25, 2013.
White, G.C. II., et al., "Scientific and Standardization Committee Communication, Definitions in Hemophilia, Recommendation of the Scientific Subcommittee on Factor VIII and Factor IX of the Scientific and Standardization Committee of the International Society on Thrombosis and Haemostasis" Thromb Haemost 85:560, Schattauer GmbH, Germany (2001).
Final Office Action dated Dec. 12, 2016, in U.S. Appl. No. 14/430,848, inventors Pierce, G., et al., filed Sep. 25, 2013.
Metzner, H.J., et al., "Genetic fusion to albumin improves the pharmacokinetic properties of factor IX," Thrombosis and Haemostasis 102(4):634-644, Stuttgard, Schattauer, Germany (2009).
Office Action for Appl. No. 102134557 issued by Intellectual Property Office dated Jan. 10, 2017, 4 pages.
English-Translation of Office Action for Appl. No. 102134557 issued by Intellectual Property Office dated Jan. 10, 2017, 5 pages.
Extended European Search Report for European Application No. 19151700.2, dated Jun. 19, 2019.
Peters et al., (2010) "Prolonged activity of factor IX as a monomeric Fc fusion protein," Blood, 115(10):2057-2064.
Ticho, B., "Long-acting Clotting Factor Fc Fusion Proteins for Potential Use in Hemophilia," Biogen Idec, Dated Mar. 25, 2009, 9 pages.
Biogen IDEC, "Biogen Idec and Swedish Orphan Biovitrum Present Data on Long-Lasting Hemophilia B Therapy at the World Federation of Hemophelia Congress", Swedish Orphan Biovitrum (SOBI), Jul. 12, 2010, 3 pages.
Third Party Pre-Issuance Submission Under 37 C.F.R. 1.290, and Concise Description of Relevance for U.S. Appl. No. 14/430,848, filed Nov. 3, 2015, 8 pages.
Third Party Pre-Issuance Submission Under 37 C.F.R. 1.290, and Concise Description of Relevance for U.S. Appl. No. 14/430,848, filed Nov. 3, 2015, 10 pages.
Third Party Pre-Issuance Submission Under 37 C.F.R. 1.290, and Concise Description of Relevance for U.S. Appl. No. 14/430,848, filed Nov. 3, 2015, 7 pages.
Third Party Pre-Issuance Submission Under 37 C.F.R. 1.290, and Concise Description of Relevance for U.S. Appl. No. 14/430,848, filed Nov. 3, 2015, 6 pages.
C.A. No. 17-914-RGA—Defendants' Motion for Summary Judgment of Invalidity of All Asserted Patent Claims, dated Nov. 1, 2019.
C.A. No. 17-914-RGA—Plaintiffs' Answering Brief in Opposition to Defendants' Motions for Summary Judgment and to Exclude Expert Opinions and Exhibits, filed on Nov. 21, 2019 (Redacted Public Version).
C.A. No. 17-914-RGA—Reply Brief in Support of Defendants' Motion for Summary Judgment and Motions to Exclude Expert Opinions and Exhibits, dated Dec. 6, 2019 (Redacted Public Version).
C.A. No. 17-914-RGA—Memorandum Opinion Denying Defendants' Motion for Summary Judgement, dated Mar. 5, 2020.
C.A. No. 20-332-RGA—Bioverativ's Complaint, dated Mar. 4, 2020.
C.A. No. 20-332-RGA—Answer, Defenses, and Counterclaims of CSL Behring LLC, CSL Behring GmbH, CSL Behring Lengnau AG, dated May 4, 2020.
C.A. No. 20-332-RGA—Plaintiffs' Opening Brief in Support of Its Rule 12 Motion to Dismiss and Strike Defendants' Inequitable Conduct Allegations and Exhibits, dated Jun. 9, 2020.
C.A. No. 20-332-RGA—CSL Behring's Answering Brief in Opposition to Plaintiffs' Motions to Dismiss and Strike Defendants' Inequitable Conduct Allegations, dated Jun. 23, 2020.
C.A. No. 20-332-RGA—Plaintiffs' Reply Brief in Support of Its Rule 12 Motion to Dismiss and Strike Defendants' Inequitable Conduct Allegations, dated Jun. 30, 2020.
Third Party Observations under Article 115 EPC against European Patent Application No. 19151700.2, filed Oct. 4, 2021.

* cited by examiner

Goodness-of-fit plots of the population PK model

Visual Predictive Check (VPC) plots of the population PK model.

Proposed Output for Individual PK Assessment

For clinicians who are interested in determining the PK for their patients, the program will recommend 2 – 3 optimized PK sampling time points Clinician will input –
- body weight
- diagnostic (baseline) factor level
- dosing history if PK samples were taken from multiple doses
- actual dose
- actual time of PK sampling
- factor activity level Program will output –
- PK curve
- PK parameters
  - incremental recovery (Cmax/Dose)
  - mean residence time
  - terminal t1/2
  - clearance
  - Vss
  - AUC/Dose

FIG. 15

Proposed Output for Dosing Regimen Selections without Individualized PK Assessment (2)

> Alternatively, for clinicians who skip individualized PK estimation, post product label (see below) without providing the option to estimate other potential doses, intervals, or troughs

| Dose, IU/kg | EOI median [5th, 95th] | Day 1 median [5th, 95th] | Day 3 median [5th, 95th] | Day 5 median [5th, 95th] | Day 7 median [5th, 95th] | Day 10 median [5th, 95th] | Day 14 median [5th, 95th] |
|---|---|---|---|---|---|---|---|
| 50 | 52.6 [32.1, 89.3] | 16.9 [11.2, 26.1] | 7.17 [3.85, 12.3] | 4.16 [1.93, 7.83] | 2.67 [1.02, 5.49] | NA | NA |
| 100 | 102 [60.0, 166] | 30.0 [19.6, 46.7] | 12.0 [6.62, 19.9] | 6.78 [3.24, 12.2] | 4.28 [1.82, 8.06] | 2.29 [0.688, 5.33] | 1.07 [0.0758, 3.23] |

EOI, end of infusion; NA, not applicable.

FIG. 18

SEQUENCE LISTING

<160> NUMBER OF SEQ ID NOS: 4

<210> SEQ ID NO 1
<211> LENGTH: 7583
<212> TYPE: DNA
<213> ORGANISM: Artificial Sequence
<220> FEATURE:
<223> OTHER INFORMATION: FIX-Fc Chain

<400> SEQUENCE: 1

| | | | | |
|---|---|---|---|---|
| gcgcgcgttg | acattgatta | ttgactagtt | attaatagta | atcaattacg | gggtcattag | 60 |
| ttcatagccc | atatatggag | ttccgcgtta | cataacttac | ggtaaatggc | ccgcctggct | 120 |
| gaccgcccaa | cgaccccgc | ccattgacgt | caataatgac | gtatgttccc | atagtaacgc | 180 |
| caatagggac | tttccattga | cgtcaatggg | tggagtattt | acggtaaact | gcccacttgg | 240 |
| cagtacatca | agtgtatcat | atgccaagta | cgccccctat | tgacgtcaat | gacggtaaat | 300 |
| ggcccgcctg | gcattatgcc | cagtacatga | ccttatggga | ctttcctact | tggcagtaca | 360 |
| tctacgtatt | agtcatcgct | attaccatgg | tgatgcggtt | ttggcagtac | atcaatgggc | 420 |
| gtggatagcg | gtttgactca | cggggatttc | caagtctcca | ccccattgac | gtcaatggga | 480 |
| gtttgttttg | gcaccaaaat | caacgggact | ttccaaaatg | tcgtaacaac | tccgccccat | 540 |
| tgacgcaaat | gggcggtagg | cgtgtacggt | gggaggtcta | tataagcaga | gctctctggc | 600 |
| taactagaga | acccactgct | tactggctta | tcgaaattaa | tacgactcac | tatagggaga | 660 |
| cccaagcttc | gcgacgtacg | gccgccacca | tgcagcgcgt | gaacatgatc | atggcagaat | 720 |

```
caccaggcct catcaccatc tgccttttag gatatctact cagtgctgaa tgtacaggtt    780
tgtttccttt tttaaaatac attgagtatg cttgccttt agatatagaa atatctgatg    840
ctgtcttctt cactaaattt tgattacatg atttgacagc aatattgaag agtctaacag    900
ccagcacgca ggttggtaag tactgtggga acatcacaga ttttggctcc atgccctaaa    960
gagaaattgg ctttcagatt atttggatta aaaacaaaga ctttcttaag agatgtaaaa   1020
ttttcatgat gttttctttt ttgctaaaac taaagaatta ttcttttaca tttcagtttt   1080
tcttgatcat gaaaacgcca acaaaattct gaatcggcca agaggtata attcaggtaa    1140 attggaagag tttgttcaag ggaatctaga gagagaatgt atggaagaaa agtgtagttt   1200
tgaagaagca cgagaagttt ttgaaaacac tgaaagaaca actgaatttt ggaagcagta   1260
tgttgatgga gatcagtgtg agtccaatcc atgtttaaat ggcggcagtt gcaaggatga   1320
cattaattcc tatgaatgtt ggtgtccctt tggatttgaa ggaaagaact gtgaattaga   1380
tgtaacatgt aacattaaga atggcagatg cgagcagttt tgtaaaaata gtgctgataa   1440
caaggtggtt tgctcctgta ctgagggata tcgacttgca gaaaaccaga agtcctgtga   1500
accagcagtg ccatttccat gtggaagagt ttctgtttca caaacttcta agctcacccg   1560
tgctgagact gttttcctg atgtggacta tgtaaattct actgaagctg aaaccatttt   1620
ggataacatc actcaaagca cccaatcatt taatgacttc actcggggttg ttggtggaga   1680 agatgccaaa ccaggtcaat tcccttggca ggttgttttg aatggtaaag ttgatgcatt   1740
ctgtggaggc tctatcgtta atgaaaaatg gattgtaact gctgcccact gtgttgaaac   1800
tggtgttaaa attacagttg tcgcaggtga acataatatt gaggagacag aacatacaga   1860
gcaaaagcga aatgtgattc gaattattcc tcaccacaac tacaatgcag ctattaataa   1920
gtacaaccat gacattgccc ttctggaact ggacgaaccc ttagtgctaa acagctacgt   1980
tacacctatt tgcattgctg acaaggaata cacgaacatc ttcctcaaat ttggatctgg   2040
ctatgtaagt ggctggggaa gagtcttcca caaagggaga tcagctttag ttcttcagta   2100
ccttagagtt ccacttgttg accgagccac atgtcttcga tctacaaagt tcaccatcta   2160
taacaacatg ttctgtgctg gcttccatga aggaggtaga gattcatgtc aaggagatag   2220
tgggggaccc catgttactg aagtggaagg gaccagtttc ttaactggaa ttattagctg   2280
gggtgaagag tgtgcaatga aaggcaaata tggaatatat accaaggtgt cccggtatgt   2340
caactggatt aaggaaaaaa caaagctcac tgacaaaact cacacatgcc accgtgccc    2400 agctccggaa ctcctgggcg gaccgtcagt cttcctcttc cccccaaaac ccaaggacac   2460
cctcatgatc tcccggaccc ctgaggtcac atgcgtggtg gtggacgtga gccacgaaga   2520
ccctgaggtc aagttcaact ggtacgtgga cggcgtggag gtgcataatg ccaagacaaa   2580
gccgcgggag gagcagtaca acagcacgta ccgtgtggtc agcgtcctca ccgtcctgca   2640
ccaggactgg ctgaatggca aggagtacaa gtgcaaggtc tccaacaaag ccctcccagc   2700
ccccatcgag aaaaccatct ccaaagccaa agggcagccc cgagaaccac aggtgtacac   2760 cctgcccca tcccgggatg agctgaccaa gaaccaggtc agcctgacct gcctggtcaa   2820
aggcttctat cccagcgaca tcgccgtgga gtgggagagc aatgggcagc cggagaacaa   2880
ctacaagacc acgcctcccg tgttggactc cgacggctcc ttcttcctct acagcaagct   2940
caccgtggac aagagcaggt ggcagcaggg gaacgtcttc tcatgctccg tgatgcatga   3000
ggctctgcac aaccactaca cgcagaagag cctctccctg tctccgggta aatgagaatt   3060
cagacatgat aagatacatt gatgagtttg gacaaaccac aactagaatg cagtgaaaaa   3120
```

-continued

```
aatgctttat ttgtgaaatt tgtgatgcta ttgctttatt tgtaaccatt ataagctgca  3180
ataaacaagt tggggtgggc gaagaactcc agcatgagat ccccgcgctg gaggatcatc  3240
cagccggcgt cccggaaaac gattccgaag cccaaccttt catagaaggc ggcggtggaa  3300
tcgaaatctc gtagcacgtg tcagtcctgc tcctcggcca cgaagtgcac gcagttgccg  3360
gccgggtcgc gcagggcgaa ctcccgcccc cacggctgct cgccgatctc ggtcatggcc  3420
ggcccggagg cgtcccggaa gttcgtggac acgacctccg accactcggc gtacagctcg  3480
tccaggccgc gcacccacac ccaggccagg gtgttgtccg gcaccacctg gtcctggacc  3540
gcgctgatga acagggtcac gtcgtcccgg accacaccgg cgaagtcgtc ctccacgaag  3600
tcccgggaga acccgagccg gtcggtccag aactcgaccg ctccggcgac gtcgcgcgcg  3660
gtgagcaccg gaacggcact ggtcaacttg gccatggttt agttcctcac cttgtcgtat  3720
tatactatgc cgatatacta tgccgatgat taattgtcaa cacgtgctga tcagatccga  3780
aaatggatat acaagctccc gggagctttt tgcaaaagcc taggcctcca aaaaagcctc  3840
ctcactactt ctggaatagc tcagaggcag aggcggcctc ggcctctgca taaataaaaa  3900
aaattagtca gccatggggc ggagaatggg cggaactggg cggagttagg ggcgggatgg  3960
gcggagttag gggcgggact atggttgctg actaattgag atgcatgctt tgcatacttc  4020
tgcctgctgg ggagcctggg gactttccac acctggttgc tgactaattg agatgcatgc  4080
tttgcatact tctgcctgct ggggagcctg ggactttcc acaccctcgt cgagctagct  4140
tcgtgaggct ccggtgcccg tcagtgggca gagcgcacat cgcccacagt ccccgagaag  4200
ttgggggggag gggtcggcaa ttgaaccggt gcctagagaa ggtggcgcgg ggtaaactgg  4260
gaaagtgatg tcgtgtactg gctccgcctt tttcccgagg gtgggggaga accgtatata  4320
agtgcagtag tcgccgtgaa cgttcttttt cgcaacgggt ttgccgccag aacacaggta  4380
agtgccgtgt gtggttcccg cgggcctggc ctctttacgg gttatggccc ttgcgtgcct  4440
tgaattactt ccacctggct ccagtacgtg attcttgatc ccgagctgga gccaggggcg  4500
ggccttgcgc tttaggagcc ccttcgcctc gtgcttgagt tgaggcctgg cctgggcgct  4560
ggggccgccg cgtgcgaatc tggtggcacc ttcgcgcctg tctcgctgct ttcgataagt  4620
ctctagccat ttaaaatttt tgatgacctg ctgcgacgct ttttttctgg caagatagtc  4680
ttgtaaatgc gggccaggat ctgcacactg gtatttcggt ttttggggcc gcgggcggcg  4740
acggggcccg tgcgtcccag cgcacatgtt cggcgaggcg gggcctgcga gcgcggccac  4800
cgagaatcgg acggggtag tctcaagctg gccggcctgc tctggtgcct ggcctcgcgc  4860
cgccgtgtat cgccccgccc tgggcggcaa ggctggcccg gtcggcacca gttgcgtgag  4920
cggaaagatg gccgcttccc ggccctgctc caggggctc aaaatggagg acgcggcgct  4980
cgggagagcg ggcgggtgag tcacccacac aaaggaaagg ggcctttccg tcctcagccg  5040
tcgcttcatg tgactccacg gagtaccggg cgccgtccag gcacctcgat tagttctgga  5100
gcttttggag tacgtcgtct ttaggttggg gggaggggtt ttatgcgatg gagtttcccc  5160
acactgagtg ggtggagact gaagttaggc cagcttggca cttgatgtaa ttctccttgg  5220
aatttgccct ttttgagttt ggatcttggt tcattctcaa gcctcagaca gtggttcaaa  5280
gttttttttct tccatttcag gtgtcgtgaa cacgtggtcg cggccgcgcc gccaccatgg  5340
agacagacac actcctgcta tgggtactgc tgctctgggt tccaggttcc actggtgaca  5400
aaactcacac atgcccaccg tgcccagcac ctgaactcct gggaggaccg tcagtcttcc  5460
```

```
tcttcccccc aaaacccaag gacacccTca tgaTcTccCg gaccccTgag gTcacaTgcg   5520
tggtggtgga cgtgagccac gaagaccctg aggtcaagtt caactggtac gtggacggcg   5580
tggaggtgca taatgccaag acaaagccgc gggaggagca gtacaacagc acgtaccgtg   5640
tggtcagcgt cctcaccgtc ctgcaccagg actggctgaa tggcaaggag tacaagtgca   5700
aggtctccaa caaagccctc ccagccccca tcgagaaaac catctccaaa gccaagggc    5760 agccccgaga accacaggtg tacaccctgc cccatcccg cgatgagctg accaagaacc    5820
aggtcagcct gacctgcctg gtcaaaggct tctatcccag cgacatcgcc gtggagtggg   5880
agagcaatgg gcagccggag aacaactaca agaccacgcc tcccgtgttg gactccgacg   5940
gctccttctt cctctacagc aagctcaccg tggacaagag caggtggcag caggggaacg   6000
tcttctcatg ctccgtgatg catgaggctc tgcacaacca ctacacgcag aagagcctct   6060
ccctgtctcc gggtaaatga ctcgagagat ctggccggct gggcccgttt cgaaggtaag   6120
cctatccctc acccctctcct cggtctcgat tctacgcgta ccggtcatca tcaccatcac   6180
cattgagttt aaacccgctg atcagcctcg actgtgcctt ctagttgcca gccatctgtt   6240
gtttgcccct ccccgtgcc ttccttgacc ctggaaggtg ccactcccac tgtcctttcc   6300
taataaaatg aggaaattgc atcgcattgt ctgagtaggt gtcattctat tctgggggt    6360 ggggtggggc aggacagcaa ggggggaggat tgggaagaca atagcaggca tgctggggat   6420
gcggtgggct ctatggcttc tgaggcggaa agaaccagtg gcggtaatac ggttatccac   6480
agaatcaggg gataacgcag gaaagaacat gtgagcaaaa ggccagcaaa aggccaggaa   6540
ccgtaaaaag gccgcgttgc tggcgttttt ccataggctc cgcccccctg acgagcatca   6600
caaaaatcga cgctcaagtc agaggtggcg aaacccgaca ggactataaa gataccaggc   6660
gtttccccct agaagctccc tcgtgcgctc tcctgttccg accctgccgc ttaccggata   6720
cctgtccgcc tttctccctt cgggaagcgt ggcgctttct catagctcac gctgtaggta   6780
tctcagttcg gtgtaggtcg ttcgctccaa gctgggctgt gtgcacgaac cccccgttca   6840
gcccgaccgc tgcgccttat ccggtaacta tcgtcttgag tccaacccgg taagacacga   6900
cttatcgcca ctggcagcag ccactggtaa caggattagc agagcgaggt atgtaggcgg   6960
tgctacagag ttcttgaagt ggtggcctaa ctacggctac actagaagaa cagtatttgg   7020
tatctgcgct ctgctgaagc cagttacctt cggaaaaaga gttggtagct cttgatccgg   7080
caaacaaacc accgctggta gcggtggttt ttttgtttgc aagcagcaga ttacgcgcag   7140
aaaaaaagga tctcaagaag atcctttgat cttttctacg gggtctgacg ctcagtggaa   7200
cgaaaactca cgttaaggga ttttggtcat gacattaacc tataaaaata ggcgtatcac   7260
gaggcccttt cgtctcgcgc gtttcggtga tgacggtgaa aacctctgac acatgcagct   7320
cccggagacg gtcacagctt gtctgtaagc ggatgccggg agcagacaag cccgtcaggg   7380
cgcgtcagcg ggtgttggcg ggtgtcgggg ctggcttaac tatgcggcat cagagcagat   7440
tgtactgaga gtgcaccata tatgcggtgt gaaataccgc acagatgcgt aaggagaaaa   7500
taccgcatca ggcgccattc gccattcagg ctgcgcaact gttgggaagg gcgatcggtg   7560
cgggcctctt cgctattacg cca                                            7583
```

<210> SEQ ID NO 2
<211> LENGTH: 642
<212> TYPE: PRT
<213> ORGANISM: Artificial Sequence
<220> FEATURE:
<223> OTHER INFORMATION: FIX-Fc Chain

<400> SEQUENCE: 2

| | | | | | | | | | | | | | | |
|---|---|---|---|---|---|---|---|---|---|---|---|---|---|---|
Tyr Asn Ser Gly Lys Leu Glu Glu Phe Val Gln Gly Asn Leu Glu Arg
1               5                  10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Asp

```
                    405                 410                 415
Lys Thr His Thr Cys Pro Pro Cys Pro Ala Pro Glu Leu Leu Gly Gly
                420                 425                 430

Pro Ser Val Phe Leu Phe Pro Pro Lys Pro Lys Asp Thr Leu Met Ile
            435                 440                 445

Ser Arg Thr Pro Glu Val Thr Cys Val Val Val Asp Val Ser His Glu
    450                 455                 460

Asp Pro Glu Val Lys Phe Asn Trp Tyr Val Asp Gly Val Glu Val His
465                 470                 475                 480

Asn Ala Lys Thr Lys Pro Arg Glu Glu Gln Tyr Asn Ser Thr Tyr Arg
                485                 490                 495

Val Val Ser Val Leu Thr Val Leu His Gln Asp Trp Leu Asn Gly Lys
            500                 505                 510

Glu Tyr Lys Cys Lys Val Ser Asn Lys Ala Leu Pro Ala Pro Ile Glu
        515                 520                 525

Lys Thr Ile Ser Lys Ala Lys Gly Gln Pro Arg Glu Pro Gln Val Tyr
    530                 535                 540

Thr Leu Pro Pro Ser Arg Asp Glu Leu Thr Lys Asn Gln Val Ser Leu
545                 550                 555                 560

Thr Cys Leu Val Lys Gly Phe Tyr Pro Ser Asp Ile Ala Val Glu Trp
                565                 570                 575

Glu Ser Asn Gly Gln Pro Glu Asn Asn Tyr Lys Thr Thr Pro Pro Val
            580                 585                 590

Leu Asp Ser Asp Gly Ser Phe Phe Leu Tyr Ser Lys Leu Thr Val Asp
        595                 600                 605

Lys Ser Arg Trp Gln Gln Gly Asn Val Phe Ser Cys Ser Val Met His
    610                 615                 620

Glu Ala Leu His Asn His Tyr Thr Gln Lys Ser Leu Ser Leu Ser Pro
625                 630                 635                 640

Gly Lys

<210> SEQ ID NO 3
<211> LENGTH: 741
<212> TYPE: DNA
<213> ORGANISM: Artificial Sequence
<220> FEATURE:
<223> OTHER INFORMATION: Fc Portion

<400> SEQUENCE: 3
atggagacag acacactcct gctatgggta ctgctgctct gggttccagg ttccactggt      60
gacaaaactc acacatgccc accgtgccca gcacctgaac tcctgggagg accgtcagtc     120
ttcctcttcc ccccaaaacc caaggacacc ctcatgatct cccggacccc tgaggtcaca     180
tgcgtggtgg tggacgtgag ccacgaagac cctgaggtca agttcaactg gtacgtggac     240
ggcgtggagg tgcataatgc caagacaaag ccgcgggagg agcagtacaa cagcacgtac     300
cgtgtggtca gcgtcctcac cgtcctgcac caggactggc tgaatggcaa ggagtacaag     360
tgcaaggtct ccaacaaagc cctcccagcc cccatcgaga aaccatctc caaagccaaa      420 gggcagcccc gagaaccaca ggtgtacacc ctgcccccat cccgcgatga gctgaccaag     480
aaccaggtca gcctgacctg cctggtcaaa ggcttctatc ccagcgacat cgccgtggag     540
tgggagagca atgggcagcc ggagaacaac tacaagacca cgcctcccgt gttggactcc     600
gacggctcct tcttcctcta cagcaagctc accgtggaca gagcaggtg gcagcagggg      660 aacgtcttct catgctccgt gatgcatgag gctctgcaca accactacac gcagaagagc     720
```

```
ctctccctgt ctccgggtaa a                                        741
```

<210> SEQ ID NO 4
<211> LENGTH: 227
<212> TYPE: PRT
<213> ORGANISM: Artificial Sequence
<220> FEATURE:
<223> OTHER INFORMATION: Fc Portion

<400> SEQUENCE: 4

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

METHODS OF USING FIX POLYPEPTIDES

CROSS-REFERENCE TO RELATED APPLICATIONS

This application is a continuation application of U.S. application Ser. No. 14/430,848, filed on Mar. 24, 2015 under 35 U.S.C. § 371 and which is based on International Appl. No. PCT/US2013/061747, filed Sep. 25, 2013, which claims the benefit of U.S. Provisional Appl. No. 61/863,859, filed Aug. 8, 2013; U.S. Provisional Appl. No. 61/839,439, filed Jun. 26, 2013; U.S. Provisional Appl. No. 61/829,755, filed May 31, 2013; U.S. Provisional Appl. No. 61/811,412, filed Apr. 12, 2013; U.S. Provisional Appl. No. 61/800,163, filed Mar. 15, 2013; U.S. Provisional Appl. No. 61/759,796, filed Feb. 1, 2013; and U.S. Provisional Appl. No. 61/705,607, filed Sep. 25, 2012, the contents of all of which are hereby incorporated by reference in their entireties.

REFERENCE TO A SEQUENCE LISTING SUBMITTED ELECTRONICALLY

The content of the electronically submitted sequence listing (Name: 4159.3990008_SequenceListing.txt; 19,327 bytes; and Date of Creation: Jun. 8, 2017) was originally submitted in the parent application (U.S. application Ser. No. 14/430,848) and is incorporated herein by reference in its entirety.

BACKGROUND OF THE INVENTION

Field of the Invention

The present invention relates generally to the field of therapeutics for hemostatic disorders.

Background Art

Hemophilia B (also known as Christmas disease) is one of the most common inherited bleeding disorders in the world. It results in decreased in vivo and in vitro blood clotting activity and requires extensive medical monitoring throughout the life of the affected individual. In the absence of intervention, the afflicted individual will suffer from spontaneous bleeding in the joints, which produces severe pain and debilitating immobility; bleeding into muscles results in the accumulation of blood in those tissues; spontaneous bleeding in the throat and neck may cause asphyxiation if not immediately treated; renal bleeding; and severe bleeding following surgery, minor accidental injuries, or dental extractions also are prevalent.

Normal in vivo blood coagulation at minimum requires the serine proteases Factors II (prothrombin), VII, IX, X and XI (soluble plasma proteins); cofactors including the transmembrane protein tissue factor and the plasma proteins Factors V and VIII; fibrinogen, the transglutaminase Factor XIII, phospholipid (including activated platelets), and calcium. Additional proteins including kallikrein, high molecular weight kininogen, and Factor XII are required for some in vitro clotting tests, and may play a role in vivo under pathologic conditions.

In hemophilia, blood clotting is disturbed by a lack of certain plasma blood clotting factors. Hemophilia B is caused by a deficiency in Factor IX that may result from either the decreased synthesis of the Factor IX protein or a defective molecule with reduced activity. Without effective prophylaxis, recurrent haemarthroses lead to the development of progressive and disabling arthropathy and poor quality of life (Giangrande P., Expert Opin Pharmacother. 2005; 6:1517-24). The treatment of hemophilia occurs by replacement of the missing clotting factor by exogenous factor concentrates highly enriched in Factor IX. However, generating such a concentrate from blood is fraught with technical difficulties, as is described below.

Purification of Factor IX from plasma (plasma derived Factor IX; pdFIX) almost exclusively yields active Factor IX. However, such purification of factor IX from plasma is very difficult because Factor IX is only present in low concentration in plasma (5 ug/mL). Andersson, Thrombosis Research 7: 451 459 (1975). Further, purification from blood requires the removal or inactivation of infectious agents such as HIV and HCV. In addition, pdFIX has a short half-life and therefore requires frequent dosing, which contributes to reduced adherence to prophylactic treatment. Recombinant factor IX (rFIX) is also available, but suffers from the same short half-life and need for frequent dosing (e.g., 2-3 times per week for prophylaxis) as pdFIX. rFIX also has a lower incremental recovery (K value) compared to pdFIX, which necessitates the use of higher doses of rFIX than those for pdFIX.

Reduced mortality, prevention of joint damage and improved quality of life have been important achievements due to the development of plasma-derived and recombinant Factor IX. Prolonged protection from bleeding would represent another key advancement in the treatment of hemophilia B subjects. However, to date, no products that allow for prolonged protection have been developed. The relatively short-half-lives of currently available FIX products require frequent intravenous injections (2-3 times weekly), which reduces adherence to prophylaxis. See White G. C., et al., *Thrombosis and Haemostasis* 78: 261-5: 1997. In children, the use of central venous access devices (CVAD) is often required, which further exposes them to risks of infection and thrombosis. See Hacker M. R., et al., *Hemophilia*, 10: 134-46 (2004). A serious potential risk associated rFIX treatment is the development of inhibitors (neutralizing antibodies), which typically occur within the first 50 exposure days (EDs). Inhibitors pose a challenge to establishing hemostasis and can be associated with anaphylaxis. See Chitlur M., et al., *Hemophilia*, 15: 1027-31 (2009). Therefore, there remains a need for improved methods of treating hemophilia due to Factor IX deficiency that are more tolerable and more effective than current therapies.

BRIEF SUMMARY OF THE INVENTION

The present invention provides a method of administering a long-acting Factor IX (FIX) polypeptide to a human subject in need thereof, comprising administering to the subject a dose of about 10 IU/kg to about 200 IU/kg of the long-acting FIX polypeptide at a dosing interval of about once a week or longer. In one embodiment, the dose of the long-acting FIX polypeptide is about 10 IU/kg to about 50 IU/kg, about 10 IU/kg to about 100 IU/kg, about 25 IU/kg to about 50 IU/kg, about 25 IU/kg to about 75 IU/kg, about 25 IU/kg to about 100 IU/kg, about 25 IU/kg to about 125 IU/kg, about 25 IU/kg to about 150 IU/kg, about 50 IU/kg to about 100 IU/kg, about 50 IU/kg to about 150 IU/kg, about 100 IU/kg to about 150 IU/kg, about 150 IU/kg to about 200 IU/kg, or any combinations thereof. In another embodiment, the dose of the long-acting FIX polypeptide is for prophylaxis of one or more bleeding episodes. In one example, the dose for prophylaxis of one or more bleeding disorders is about 50 IU/kg. In another example, an annualized bleeding rate of the bleeding episodes after administration of a long-acting FIX polypeptide is less than 2, less than 3, less than 4, less than 5, less than 6, less than 7, less than 8, less than 9, or less than 10.

In another embodiment, the dose of the long-acting FIX polypeptide is for individualized interval prophylaxis of one or more bleeding episodes. In one example, the dose of the long-acting FIX polypeptide is about 100 IU/kg. In another example, an annualized bleeding rate of the bleeding episodes after administration of a long-acting FIX polypeptide is less than 1, less than 2, less than 3, less than 4, less than 5, less than 6, less than 7, less than 8, or less than 9. In other embodiments, the dose of the long-acting FIX polypeptide is for on-demand treatment of one or more bleeding episode. In one example, an annualized bleeding rate of the bleeding episode after administration of a long-acting FIX polypeptide is less than 10, less than 11, less than 12, less than 13, less than 14, less than 15, less than 16, less than 17, less than 18, less than 19, less than 20, less than 21, less than 22, less than 23, less than 24, less than 25, or less than 26. In still other embodiments, the dose of the long-acting FIX polypeptide is for perioperative management of a bleeding disorder.

In certain embodiments, the dose is administered at a dosing frequency of about once a week to about once a month. In one aspect, the dosing frequency is about once a week, about once in two weeks, about twice a month, about once in three weeks, about once in four weeks, or about once a month. In another aspect, the dosing frequency is about once a week. In other aspects, the dosing frequency is about once in two weeks or about twice a month.

In some embodiments, the dosing interval is about every five days, about every six days, about every seven days, about every eight days, about every nine days, about every ten days, about every 11 days, about every 12 days, about every 13 days, about every 14 days, about every 15 days, about every 16 days, about every 17 days, about every 18 days, about every 19 days, about every 20 days, or about every 21 days. In further embodiments, the dosing interval is every 7 days to 14 days.

The long-acting FIX polypeptide can have a $T_{1/2beta}$ (activity) of at least about 40 hours, at least about 50 hours, at least about 60 hours, at least about 70 hours, at least about 80 hours, at least about 90 hours, at least about 100 hours, at least about 110 hours, at least about 120 hours, at least about 130 hours, at least about 140 hours, at least about 150 hours, at least about 160 hours, at least about 170 hours, at least about 180 hours, or at least about 190 hours. In a particular example, the $T_{1/2beta}$ (activity) is about 40 hours to about 193 hours. In another example, the mean of the $T_{1/2beta}$ (activity) is about 82 hours.

The long-acting FIX polypeptide can also have a $T_{1/2beta}$ (antigen) of at least about 60 hours, at least about 80 hours, at least about 100 hours, at least about 120 hours, at least about 140 hours, at least about 160 hours, at least about 180 hours, at least about 200 hours, at least about 220 hours, at least about 240 hours, at least about 260 hours, at least about 280 hours, at least about 300 hours, at least about 320 hours, at least about 340 hours, at least about 360 hours, or at least about 370 hours. In a particular embodiment, the $T_{1/2beta}$ (antigen) is about 63 hours to about 372 hours.

In some embodiments, the plasma trough level of the long-acting FIX polypeptide is maintained at about 1% above the baseline in the subject after the administration. In other embodiments, the plasma trough level of the long-acting FIX polypeptide is maintained between about 1% and about 5%, between about 1% and about 6%, between about 1% and about 7%, between about 1% and about 8%, between about 1% and about 9%, between about 1% and about 10%, between about 1% and about 11%, between about 1% and about 12%, between about 1% and about 13%, between about 1% and about 14%, between about 1% and about 15% above the baseline in the subject.

In one embodiment of the method of the invention, the dose is about 50 IU/kg, and the dosing interval is about 7 days. In another embodiment, the dose is about 100 IU/kg and the dosing interval is at least about 14 days. In other embodiments, the dose is about 150 IU/kg and the dosing interval is at least about 21 days.

The long-acting FIX polypeptide can be a chimeric polypeptide comprising a FIX polypeptide and an FcRn binding partner. In one embodiment, the FcRn binding partner comprises an Fc region. In another embodiment, long-acting FIX polypeptide further comprises a second FcRn binding partner. In other embodiments, the second FcRn binding partner comprises a second Fc region. In a particular embodiment, the long-acting FIX polypeptide is FIX monomer dimer hybrid.

In some embodiments, the subject is in need of control or prevention of bleeding or bleeding episodes. In other embodiments, the subject is in need of control or prevention of bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain.

In one embodiment, the subject is in need of perioperative management. In another embodiment, the subject is in need of management of bleeding associated with surgery or dental extraction. In other embodiments, the subject will undergo, is undergoing, or has undergone major surgery. In one aspect, the major surgery is orthopedic surgery, extensive oral surgery, urologic surgery, or hernia surgery. In another aspect, the orthopedic surgery is replacement of knee, hip, or other major joint.

In some embodiments, the subject is in need of treatment of a bleeding disorder, e.g., hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. In other embodiments, the subject is in need of surgical prophylaxis, peri-operative management, or treatment for surgery, e.g., the surgery is minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In some embodiments, the dose is administered intravenously or subcutaneously.

The invention also includes a method of estimating a rFIXFc dosing information individualized for a patient, the method comprising: (a) receiving, by a computer-based system containing the rFIXFc population pharmacokinetic (popPK) model of Example 6 and a Bayesian estimation program, at least one of patient information and desired treatment outcome information, (b) calculating, by the computer-based system, individualized rFIXFc dosing information using the popPK model, the Bayesian estimation program, and the received information, and (c) outputting, by the computer-based system, the individualized dosing information.

In some embodiments, the method also comprises selecting a dosing regimen based on the output individualized dosing information of (c) and administering rFIXFc to the patient according to the selected dosing regimen.

In some embodiments, the desired treatment outcome information is desired rise in plasma FIX activity level following dosing and the output information is dose for acute treatment.

In some embodiments, the desired treatment outcome information is desired dosing interval and the output information is dose for prophylaxis.

In some embodiments, the desired treatment outcome information is desired dose and the output information is interval for prophylaxis.

The invention also includes a method of estimating a rFIXFc dosing regimen based on median popPK, the method comprising: (a) receiving, by a computer-based system containing the rFIXFc popPK model of Example 6 and a Bayesian estimation program, at least one of patient information and desired treatment outcome information, (b) calculating, by the computer-based system, median rFIXFc PK information using the popPK model, the Bayesian estimation program, and the received information, and (c) outputting, by the computer-based system, the median PK information.

In some embodiments, the method also comprises selecting a dosing regimen based on the output median PK information of (c), and administering rFIXFc to a patient according to the selected dosing regimen.

The invention also includes a method of estimating individual patient rFIXFc PK, the method comprising: (a) receiving, by a computer-based system containing the rFIXFc population pharmacokinetic (popPK) model of Example 6 and a Bayesian estimation program, individual rFIXFc PK information, (b) estimating, by the computer-based system, individualized patient rFIXFc PK information using the popPK model, the Bayesian estimation program, and the received information, and (c) outputting, by the computer-based system, the individualized patient PK information.

In some embodiments, the method also comprises selecting a dosing regimen based on the output individualized patient PK information of (c), and administering rFIXFc to the patient according to the selected regimen.

In some embodiments (a) further comprises receiving, by the computer-based system, patient information.

In some embodiments the patient information is age or body weight.

Additional embodiments include a computer readable storage medium having instructions stored thereon that, when executed by a processor, cause the processor to perform any of the above methods.

Additional embodiments include a system comprising a processor and a memory, the memory having instructions stored thereon that, when executed by the processor, cause the processor to perform any of the above methods.

BRIEF DESCRIPTION OF
DRAWINGS/FIGURES

FIG. 1 shows study design and CONSORT chart. Efficacy data that were collected outside of the efficacy period were not included in the efficacy analyses. *PK subgroup dosed with rFIX followed by PK assessment and washout (greater than or equal to 5 days) prior to rFIXFc dosing for PK evaluation. rFIX sampling was done as follows: pre-injection, 10 (±2) min, 1 hour (±15 min), 3 hr (±15 min), 6 hr (±15 min), 24 (±2) hr, 48 (±2) hr, 72 (±3) hr, and 96 (±3) hr (4 d) from the start of the injection. rFIXFc sampling was done as follows: pre-injection, 10 (±2) min, 1 hour (±15 min), 3 hr (±15 min), 6 hr (±15 min), 24 (±2) hr, 48 (±2) hr, 96 (±3) hr (4 d), 144 (±3) hr (6 d), 168 (±3) hr (7 d), 192 (±3) hr (8 d), and 240 (±3) hr (10 d) from the start of the injection. Infusion was within 10 minutes. Blood samples were collected over 96 hours for each subject. A repeat PK assessment of rFIXFc was also performed at Week 26. ED=exposure day; PK=pharmacokinetics.

Figure 3A:
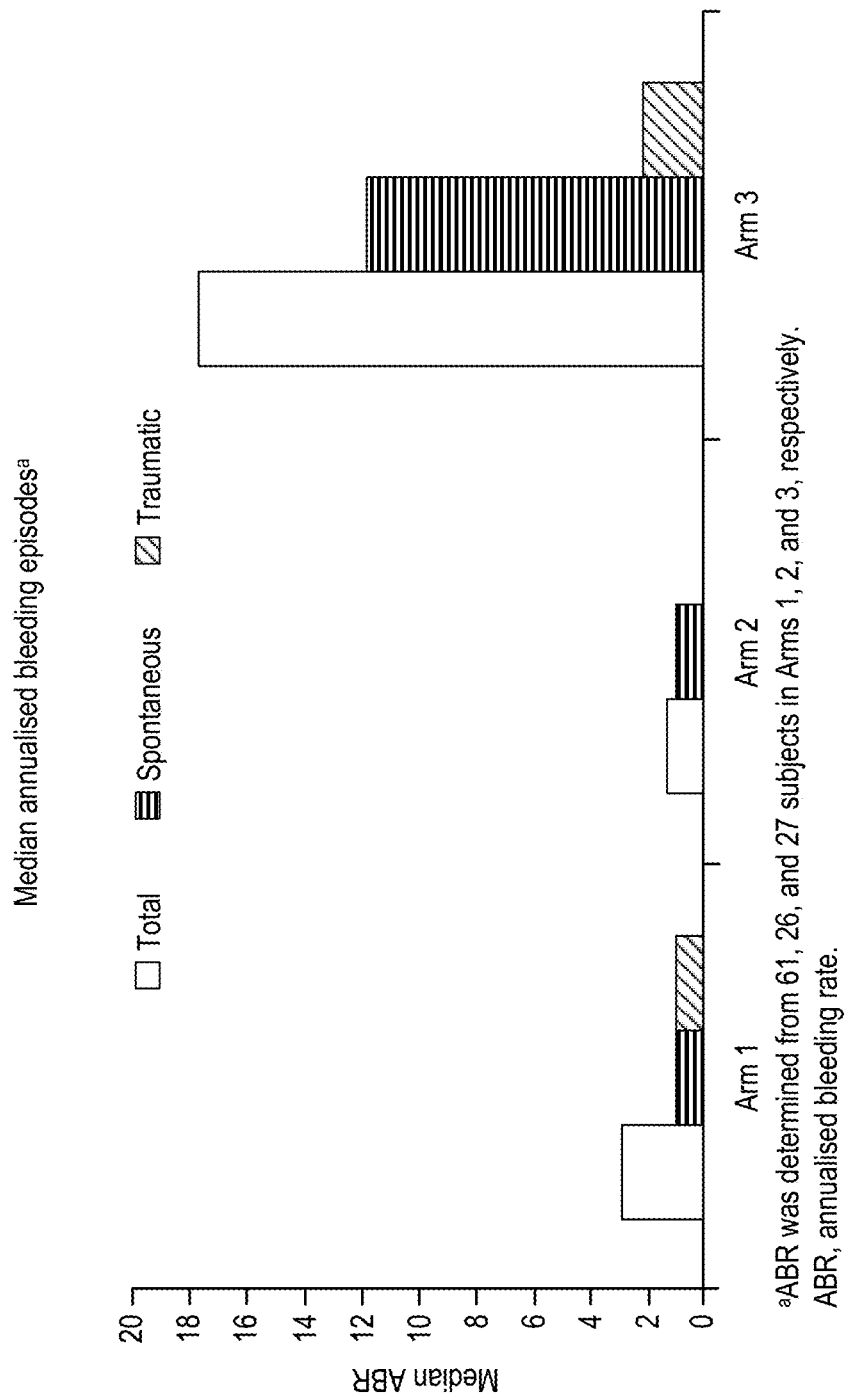
FIG. 3A shows a chart of median annualised bleeding rate (ABR) for subjects in Arms 1, 2 and 3, respectively. For each arm bars for total, spontaneous and traumatic bleeding are shown respectively.
Figure 3B:
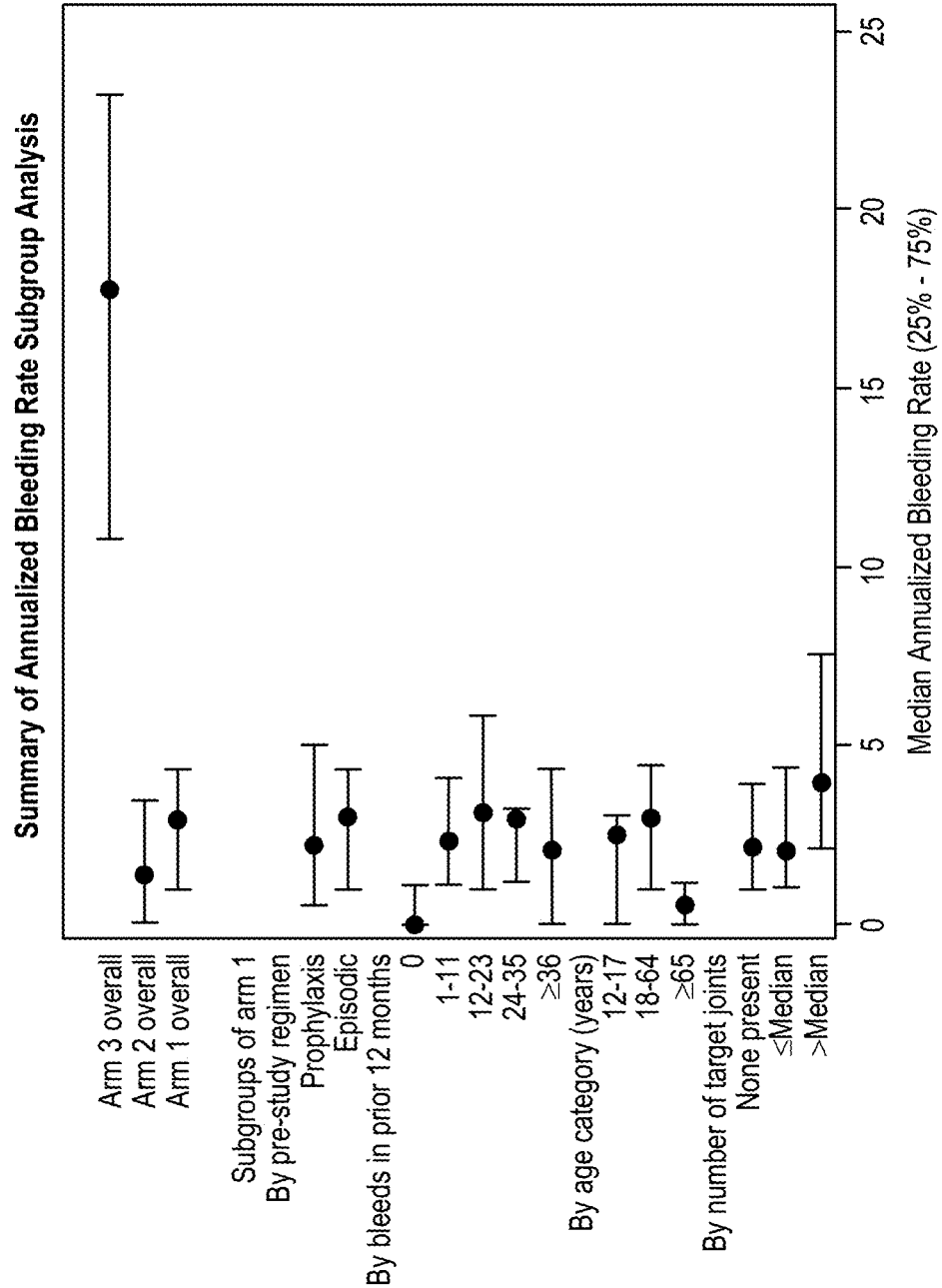

FIG. 3B shows a summary of annualized bleeding rates by subgroups. All analyses were consistent with the primary efficacy analysis, showing a reduction in bleeding rates in all subgroups. Arm 1 was the only arm with a sufficient number of patients to display subgroup analyses graphically.

Figure 4:
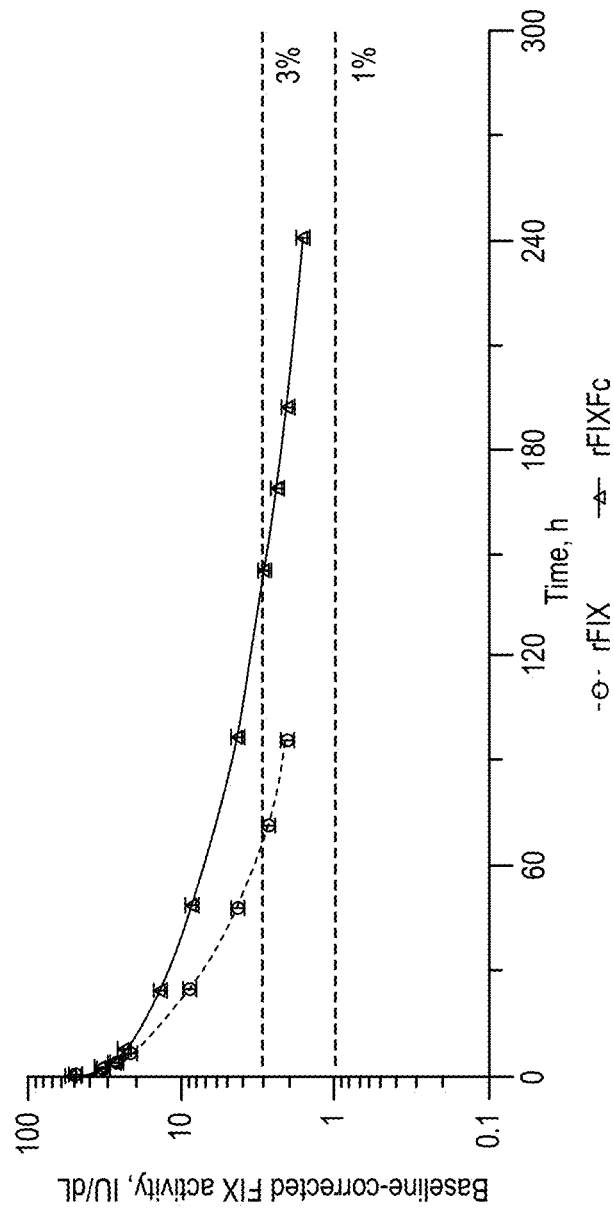

FIG. 4 shows a graph of Baseline-corrected mean FIX activity (IU/dL) in rFIX and rFIXFc treated individuals over time using the one-stage clotting assay (logarithmic scale) in the sequential pharmacokinetic group (Arm 1).

Figure 5:
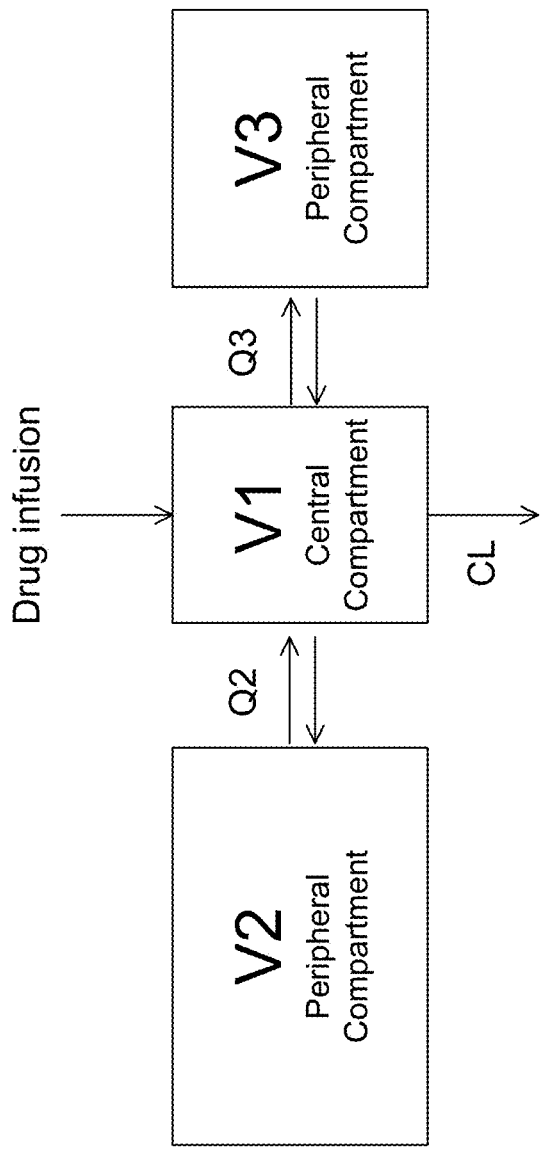

FIG. 5 shows a diagram of the three-compartment model for predicting population PK for rFIXFc. CL, clearance; V, volume of distribution; Q, inter-compartmental clearance.

Figure 6:
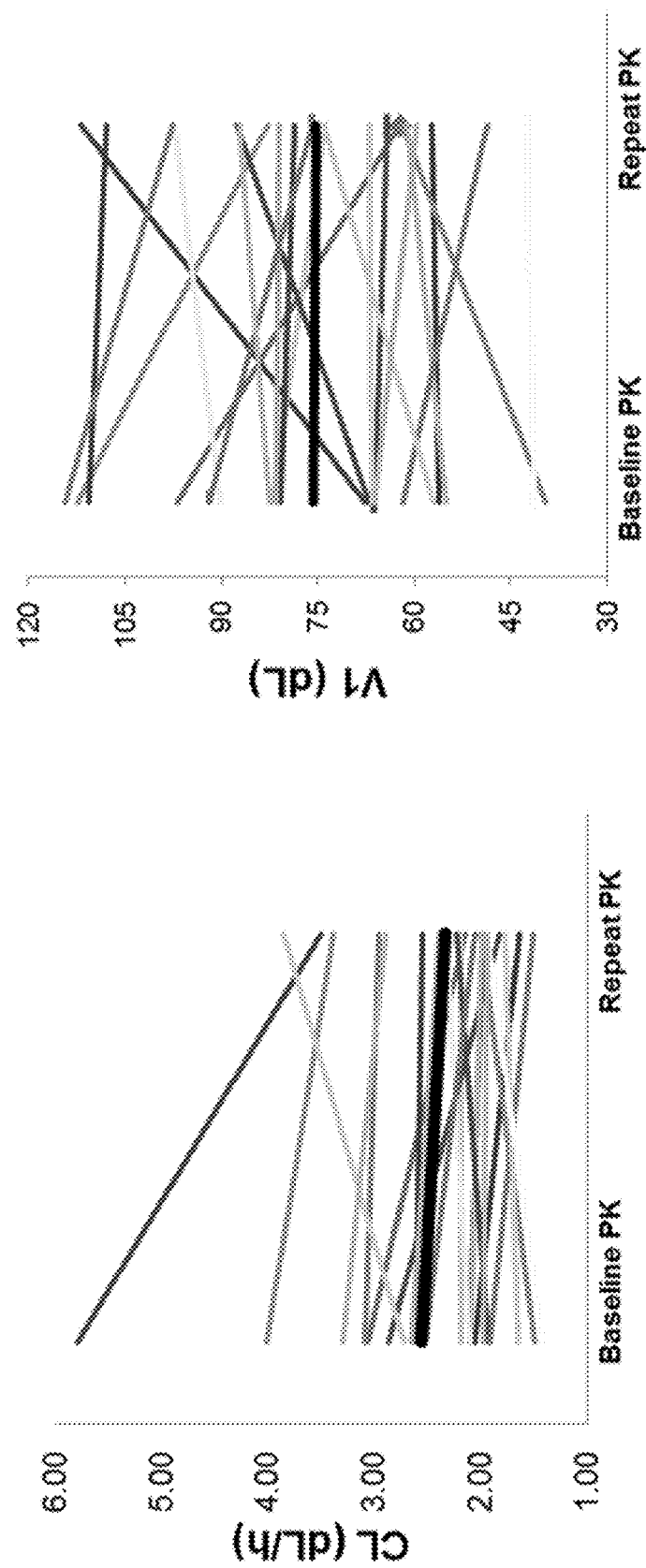

FIG. 6 shows clearance (CL) and V1 estimates of baseline (week 1) and repeat PK (week 26) profiles (black line indicates mean, which did not change much between two occasions).

Figure 7:
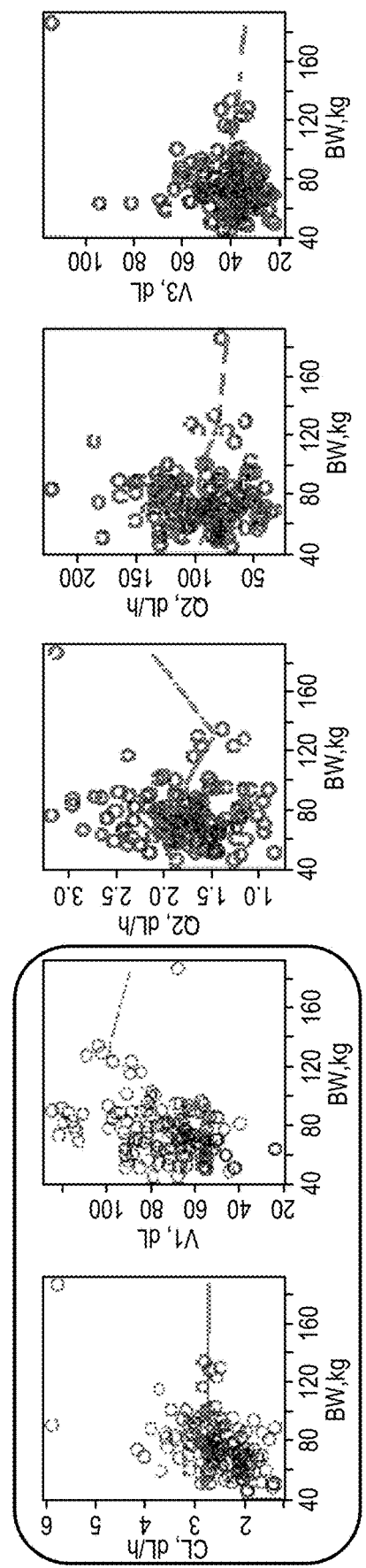

FIG. 7 shows individual PK parameters versus body weight (BW).

Figure 8A:
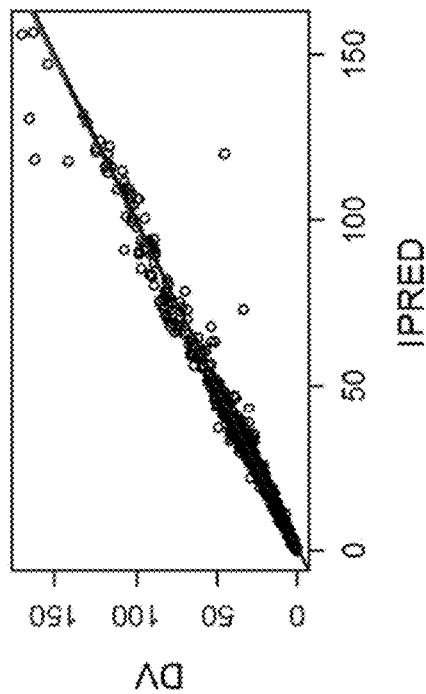
Figure 8B:
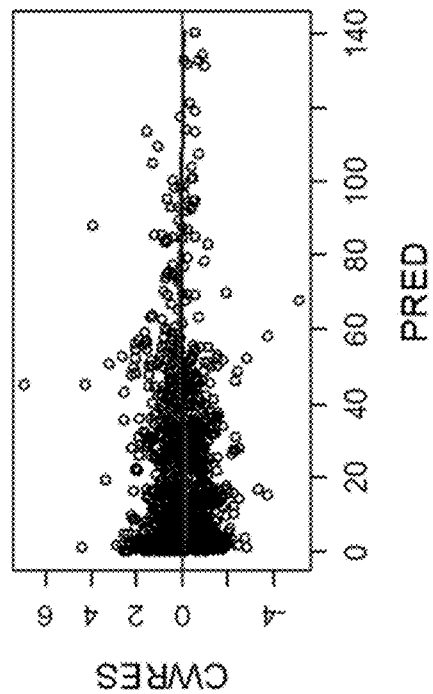
Figure 8C:
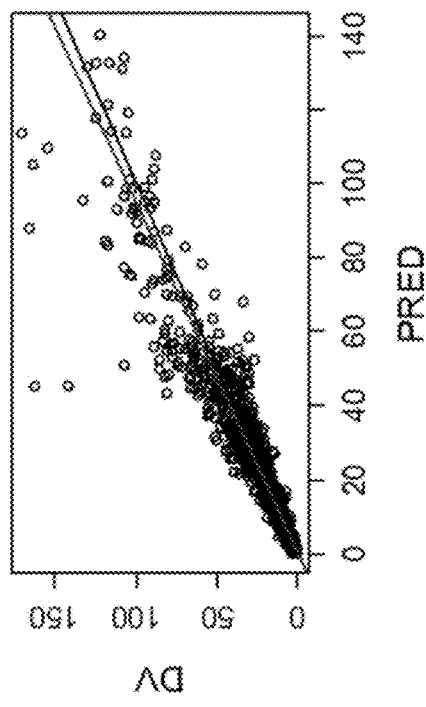
Figure 8D:
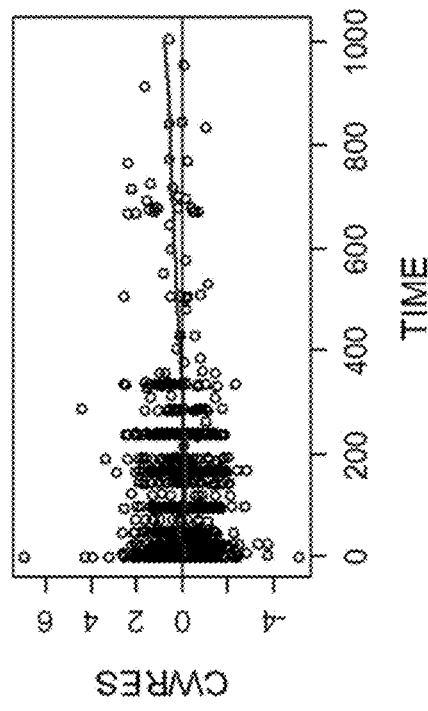

FIGS. 8A-8D show goodness-of-fit plots of FIX activity predicted by the population or individual PK model compared to observed FIX activity. FIG. 8A shows DV (observed FIX activity adjusted for baseline activity and residual decay) as a function of PRED (the prediction by population PK parameter estimates). FIG. 8B shows DV as a function of IPRED (the prediction by individual PK parameter estimates). FIG. 8C shows CWRES (conditional weighted residual) as a function of Time (hours). FIG. 8D shows CWRES as a function of PRED.

FIGS. 9A-9D show Visual Predictive Check (VPC) plots of the population PK model for 50 IU/kg (FIGS. 9A and 9C) or 100 IU/kg (FIGS. 9B and 9D) doses. Dashed and solid lines represent 10th, 50th, and 90th percentile of the simulated (dashed) and observed (solid) data, respectively.

Figure 10:
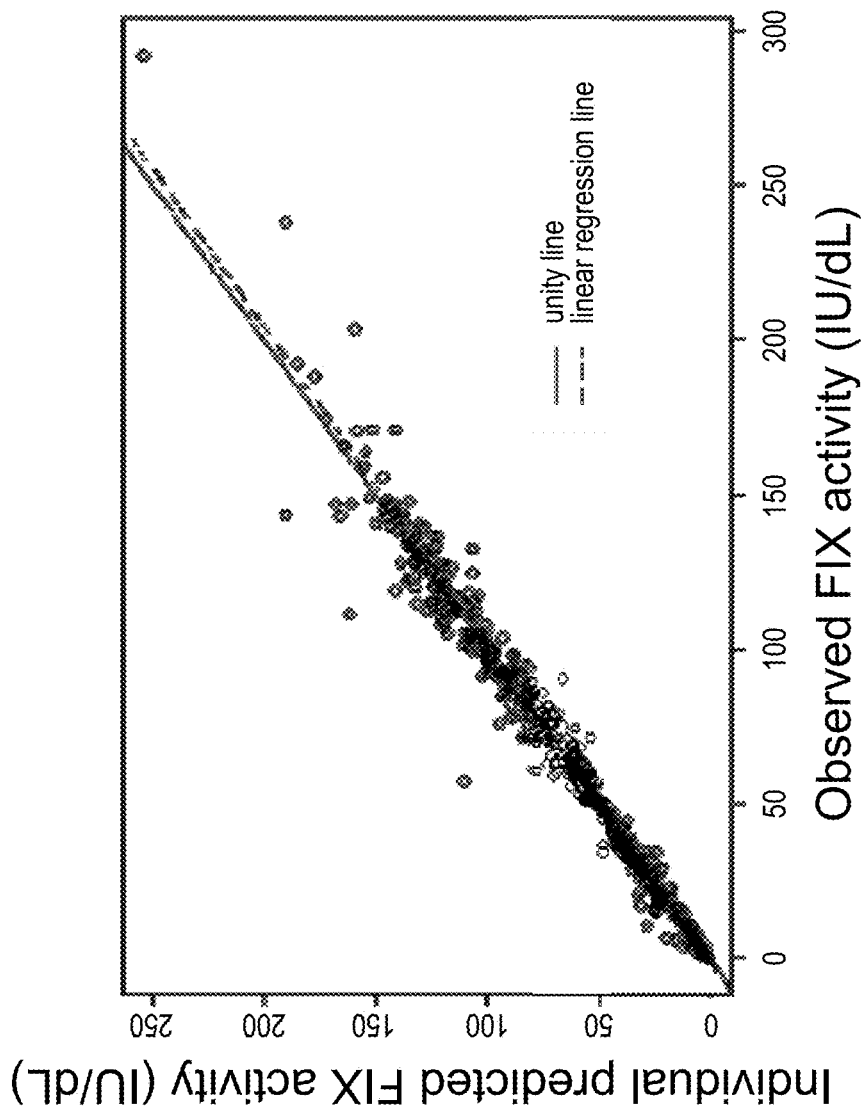

FIG. 10 shows validation of the population PK model with the trough/peak records. R2=0.9857, P<0.001.

Figure 11:
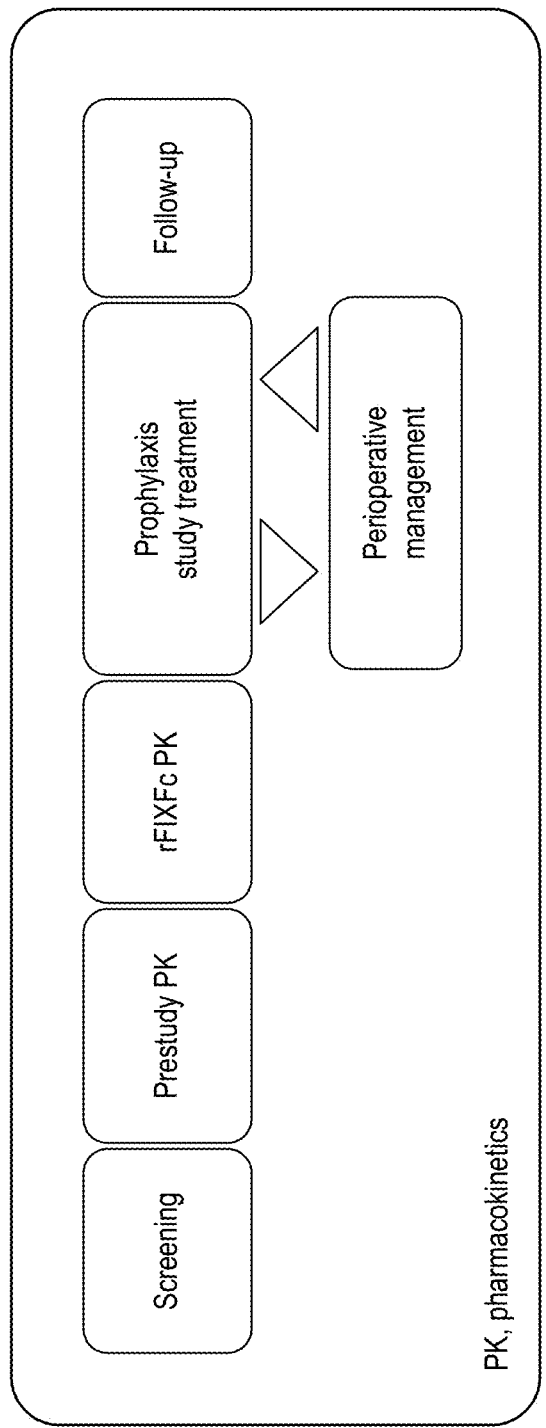

FIG. 11 shows a diagram of the rFIXFc paediatric study design.

Figure 12:
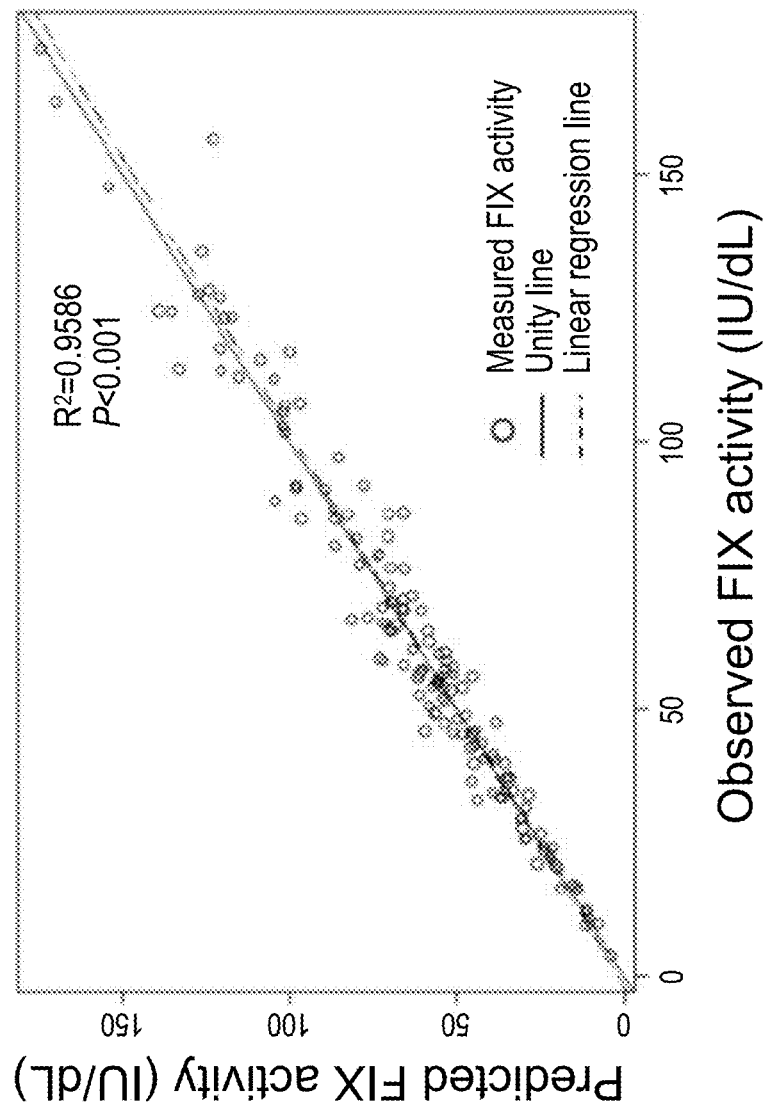

FIG. 12 shows a representative plot of observed and predicted perioperative FIX activity.

Figures 13A, 13B, 13C:
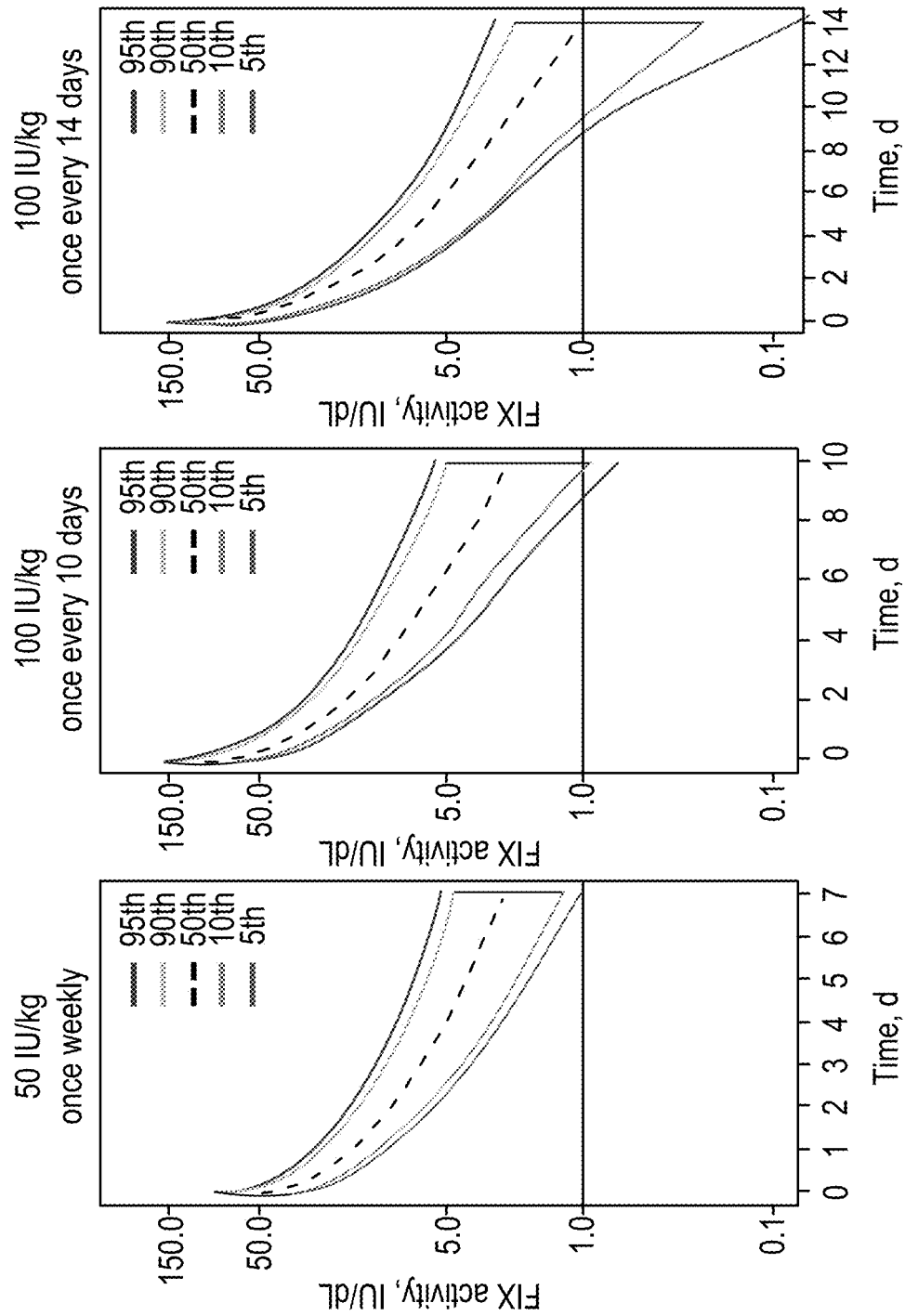

FIGS. 13A-13C show a population simulation of steady-state FIX activity time profile (5th-95th percentile). FIG. 13A shows the profile for 50 IU/kg dosage at a dosing interval of once weekly. FIG. 13B shows the profile for 100 IU/kg dosage at a dosing interval of once every 10 days. FIG. 13C shows the profile for 100 IU/kg dosage at a dosing interval of once every 14 days.

Figure 14:
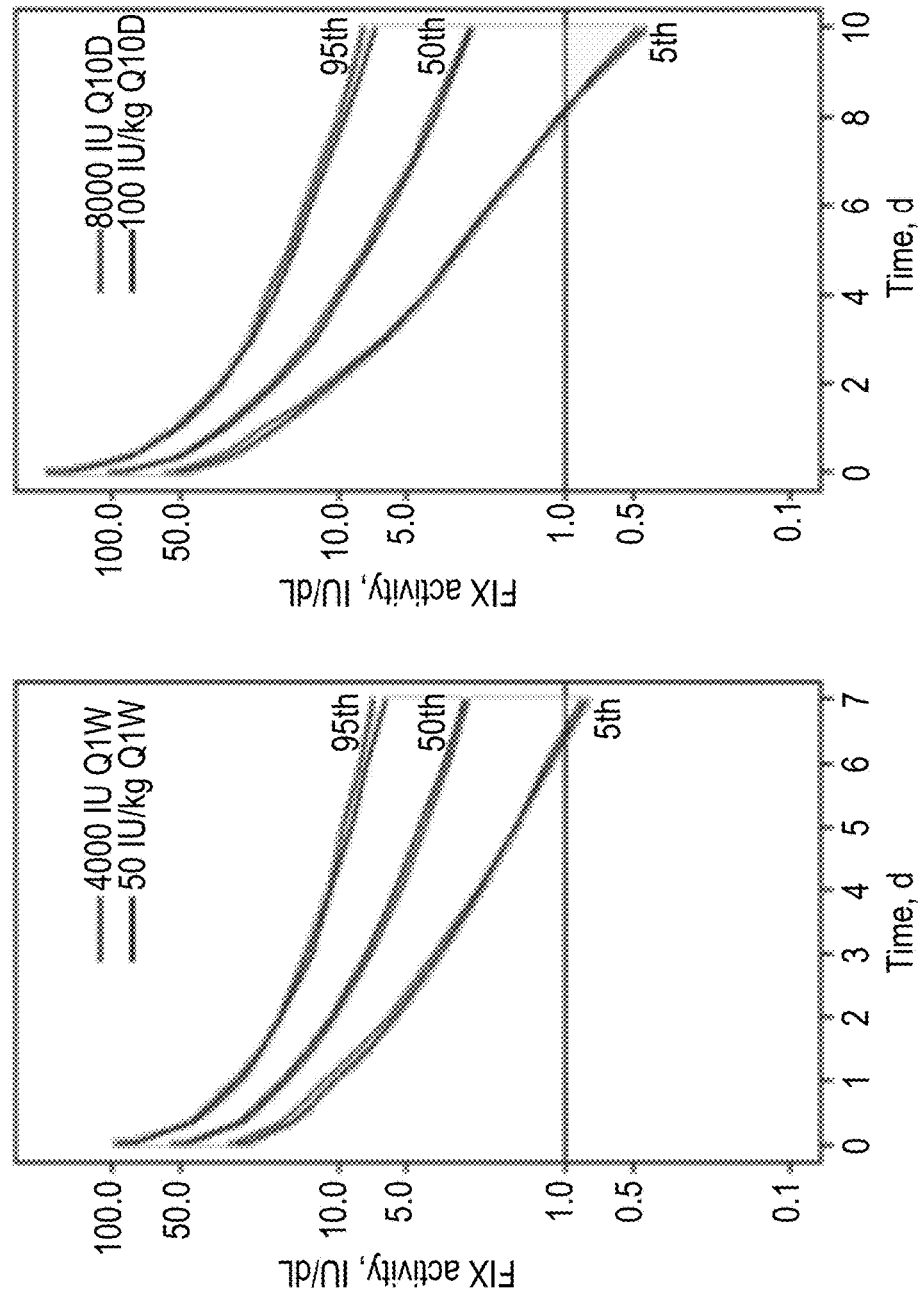

FIG. 14 shows a simulation of steady-state FIX activity vs. time profile comparing 50 IU/kg vs 4000 IU once weekly and 100 IU/kg vs 8000 IU every 10 days in 5th to 95th percentile of the population.

FIG. 15 shows a proposed output for individual PK assessment.

Figure 16:
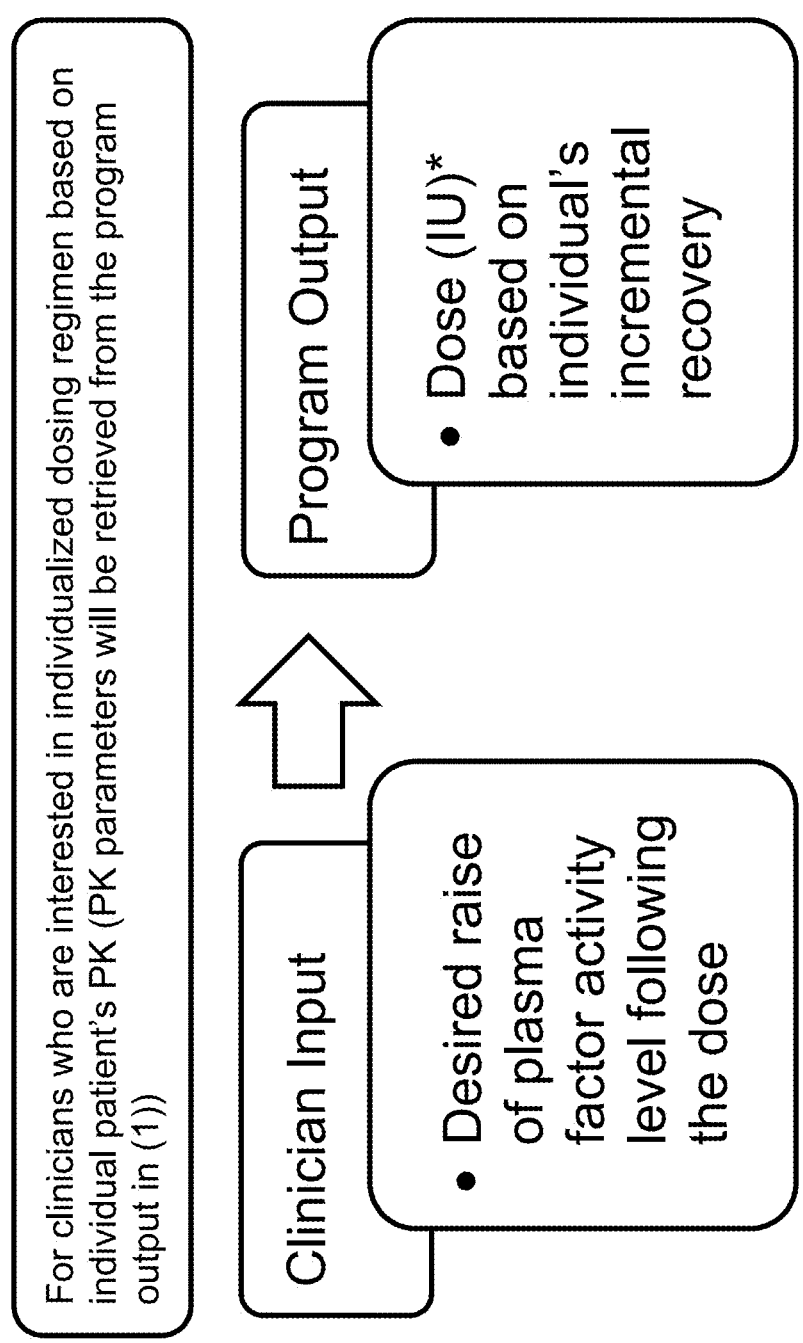

FIG. 16 shows a proposed output for individualized dosing regimen selection for episodic treatment.

Figure 17:
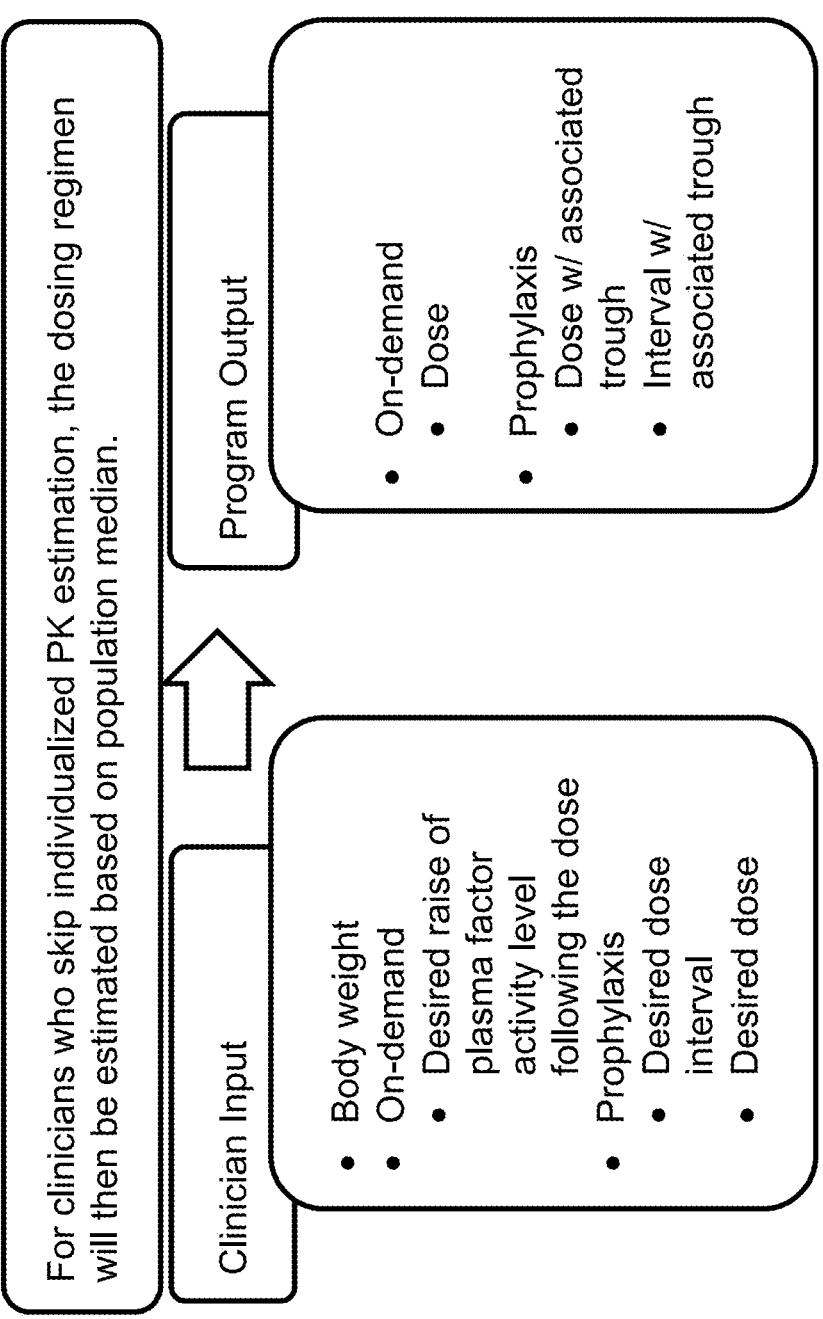

FIG. 17 shows a proposed output for dosing regimen selections without individualized PK assessment.

FIG. 18 shows another proposed output for dosing regimen selections without individualized PK assessment.

Figure 19:
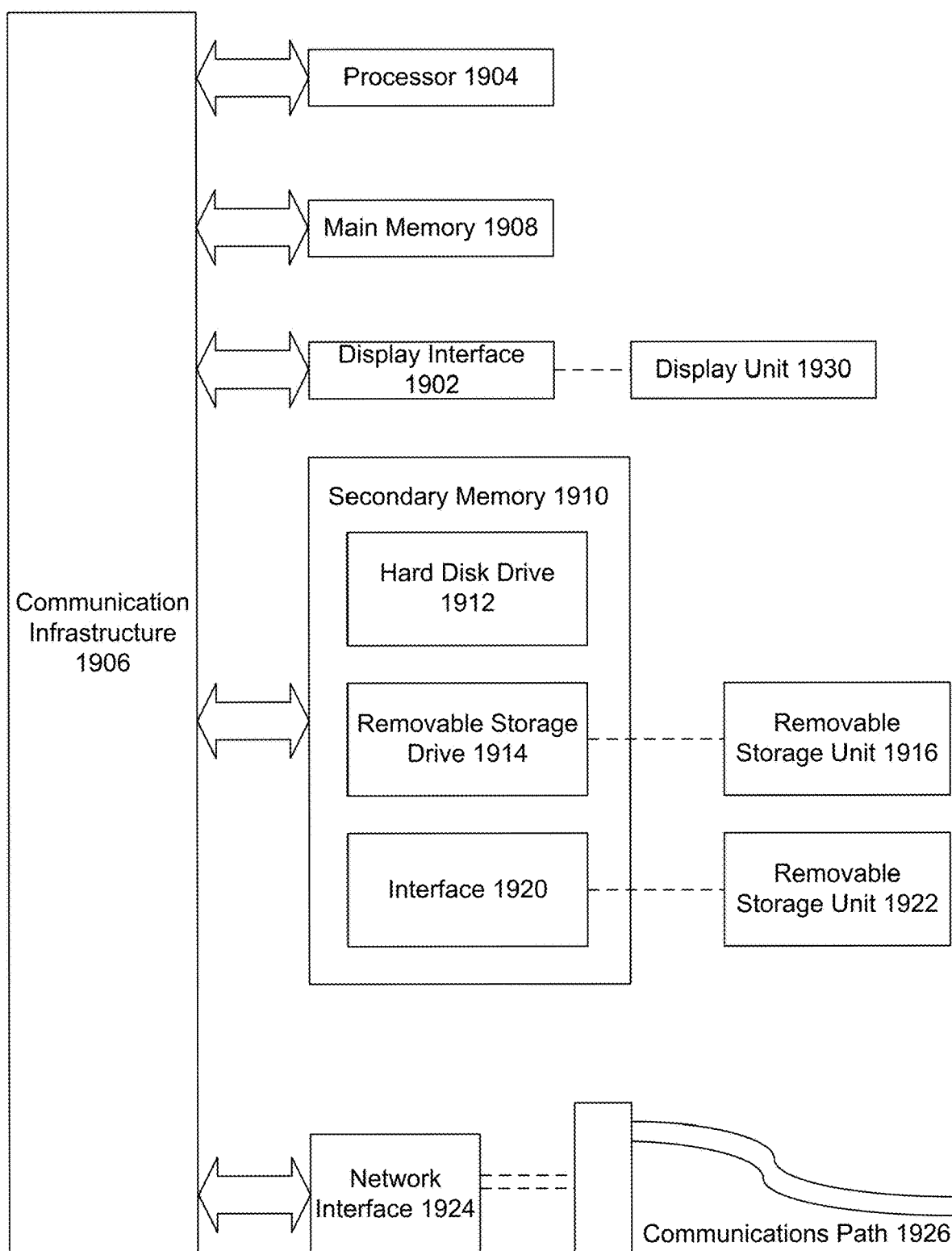

FIG. 19 shows an example computer system that can be used in embodiments.

Figure 20:
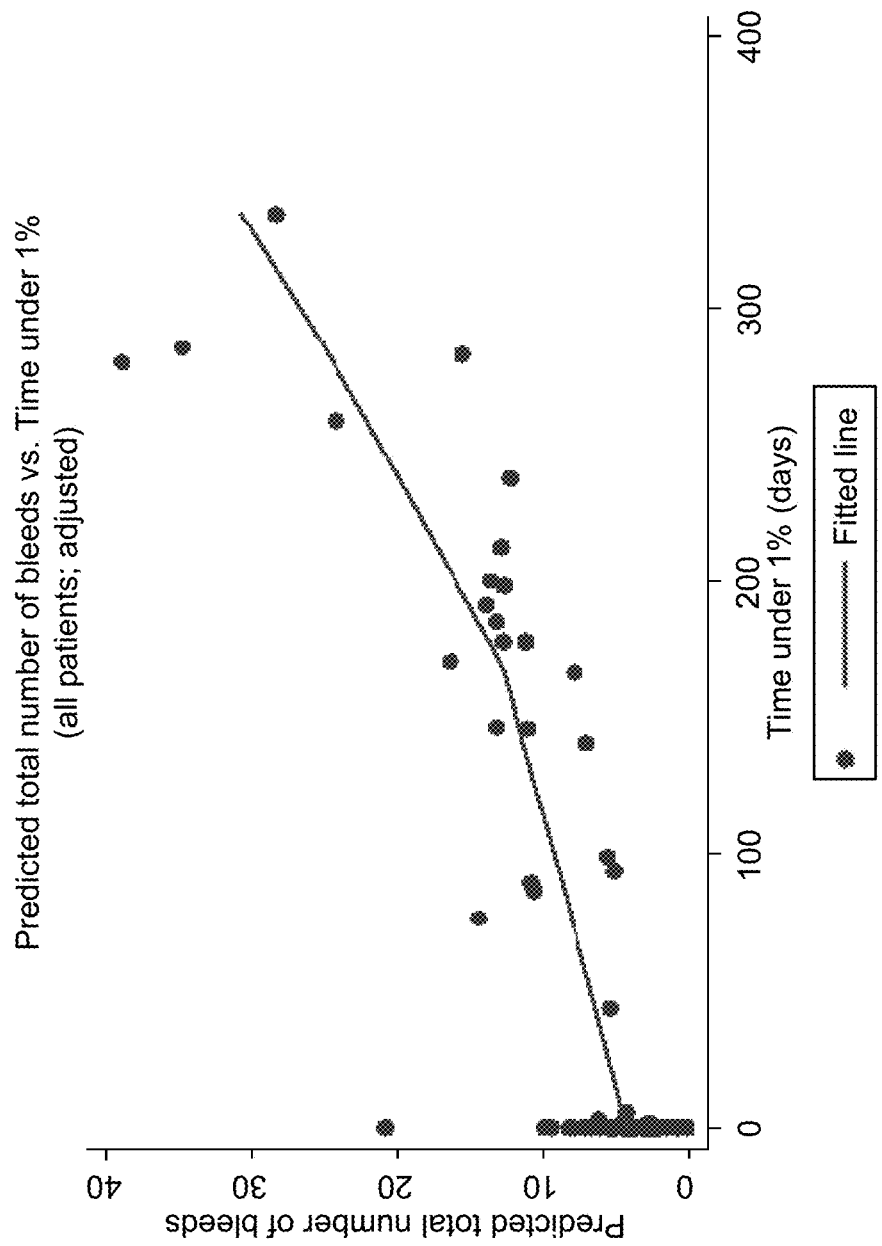

FIG. 20 shows a graph plotting the predicted total number of bleeds vs. time under 1% FIX activity level.

Figure 21:
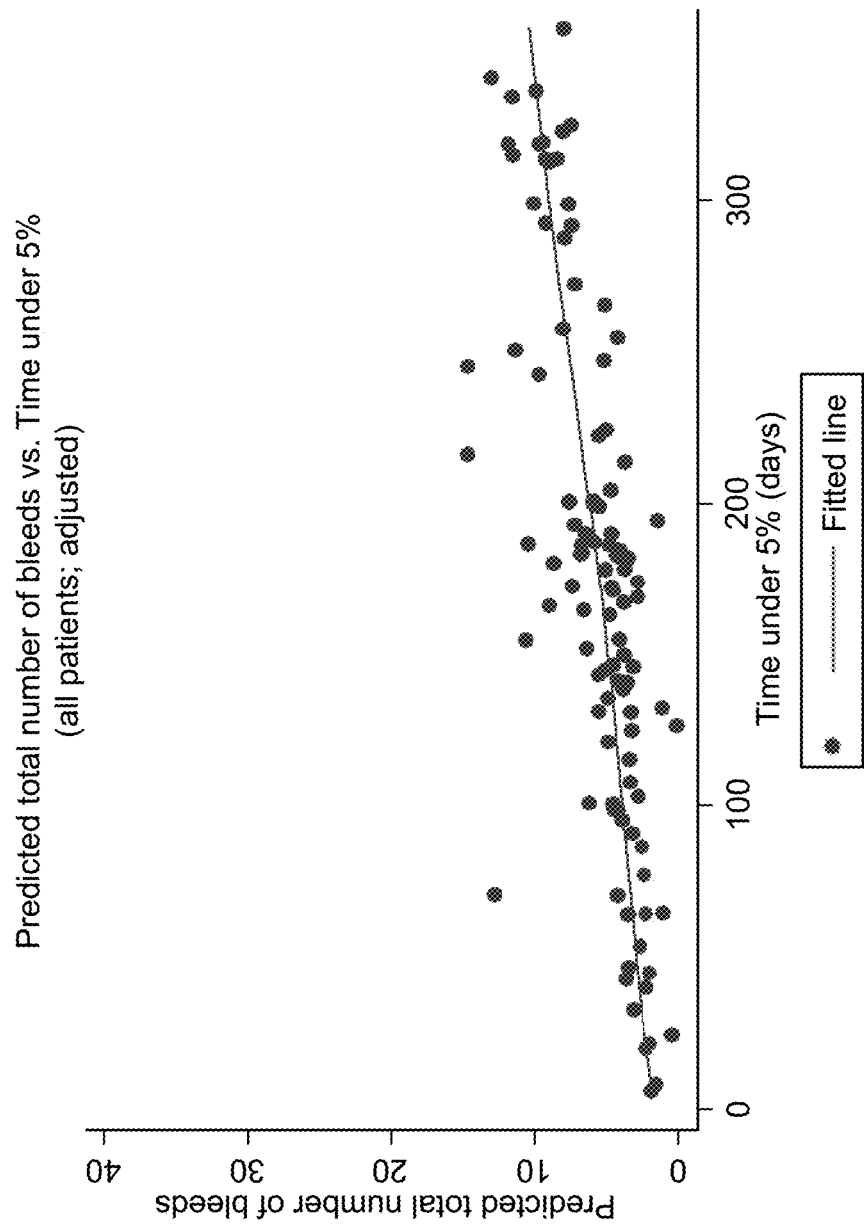

FIG. 21 shows a graph plotting the predicted total number of bleeds vs. time under 5% FIX activity level.

Figure 22:
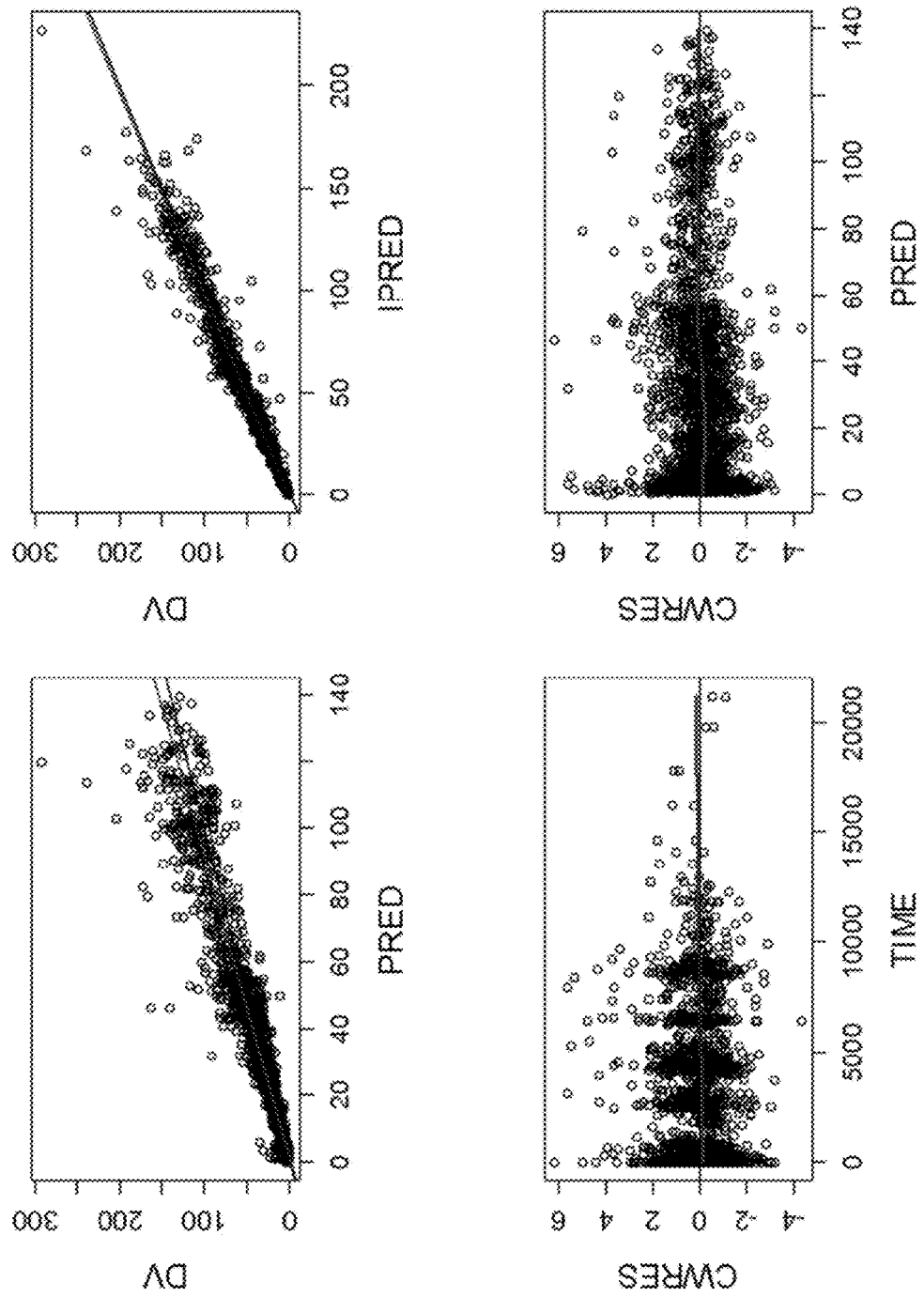

FIG. 22 shows goodness-of-fit plots for the full dataset model. The solid line is the unit line; the dashed line represents the linear regression line in the upper panel and the LOESS smoother in the lower panel; DV is observed FIX activity (adjusted for baseline activity and residual decay) and unit is IU/dL (%); PRED is the prediction by population PK parameter estimates and unit is IU/dL; IPRED is the prediction by individual PK parameter estimates and unit is IU/dL; CWRES is conditional weighted residual; TIME unit is hour. DV dependent variable, FIX factor IX, PK pharmacokinetic.

DETAILED DESCRIPTION OF THE INVENTION

The present invention provides a method of treating FIX deficiency, e.g., Hemophilia B, with FIX using a longer dosing interval, a longer dosing frequency, and/or improved pharmacokinetic parameters than is possible with currently known Factor IX products. The present invention also provides improved, long-acting FIX polypeptides, FIX chimeric polynucleotides, and methods of production.

I. Definitions

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "polypeptide," "peptide" and "protein" are used interchangeably and refer to a polymeric compound comprised of covalently linked amino acid residues.

The term "polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses. Polynucleotides include those in Table 18, which encode the polypeptides of Table 19 (see Table 18). Polynucleotides also include fragments of the polynucleotides of Table 18, e.g., those that encode fragments of the polypeptides of Table 19, such as the Factor IX, Fc, signal sequence, propeptide, 6His and other fragments of the polypeptides of Table 19.

The term "administering," as used herein, means to or prescribe or give a pharmaceutically acceptable long-acting FIX polypeptide of the invention to a subject via a pharmaceutically acceptable route. Examples of routes of administration include, but are not limited to, intravenous, e.g., intravenous injection and intravenous infusion, e.g., via central venous access. Additional routes of administration include subcutaneous, intramuscular, oral, nasal, and pulmonary administration, preferably subcutaneous. A long-acting FIX polypeptides (a FIX chimeric or hybrid proteins) can be administered as part of a pharmaceutical composition comprising at least one excipient. Advantages of the present invention include: improved regimen compliance; reduced break through bleeds; increased protection of joints from bleeds; prevention of joint damage; reduced morbidity; reduced mortality; prolonged protection from bleeding; decreased thrombotic events; and improved quality of life.

The term "chimeric polypeptide," as used herein, means a polypeptide that includes within it at least two polypeptides (or portions thereof such as subsequences or peptides) from different sources. Chimeric polypeptides can include two, three, four, five, six, seven, or more polypeptides or portions thereof from different sources, such as different genes, different cDNAs, or different animal or other species. Chimeric polypeptides can include one or more linkers joining the different polypeptides or portions thereof. Thus, the polypeptides or portions thereof can be joined directly or they can be joined indirectly, via linkers, or both, within a single chimeric polypeptide. Chimeric polypeptides can include additional peptides such as signal sequences and sequences such as 6His and FLAG that aid in protein purification or detection. In addition, chimeric polypeptides can have amino acid or peptide additions to the N- and/or C-termini. Exemplary chimeric polypeptides of the invention are Factor IX-FcRn BP chimeric polypeptides, e.g., Factor IX-Fc chimeric polypeptides such as the FIXFc in SEQ ID NO:2 (Table 19) with or without its signal sequence and propeptide.

The terms "long-acting" and "long-lasting" are used interchangeably herein. In one embodiment, the term "long-acting" or "long-lasting" indicates that a FIX activity as a result of administration of the "long-acting" FIX polypeptide is longer than the FIX activity of a wild-type FIX (e.g., BENEFIX® or plasma-derived FIX ("pdFIX")). The "longer" FIX activity can be measured by any known methods in the art, e.g., aPTT assay, chromogenic assay, ROTEM, TGA, and etc. In one embodiment, the "longer" FIX activity can be shown by the $T_{1/2beta}$ (activity). In another embodiment, the "longer" FIX activity can be shown the level of FIX antigen present in plasma, e.g., by the $T_{1/2beta}$ (antigen). In other embodiments, the long-acting or long-lasting FIX polypeptide works longer in a coagulation cascade, e.g., is active for a longer period, compared to a wild-type FIX polypeptide (i.e., a polypeptide consisting of amino acids 1 to 415 of SEQ ID NO: 2, i.e., BENEFIX® or pdFIX).

Factor IX coagulant activity is expressed as International Unit(s) (IU). One IU of Factor IX activity corresponds approximately to the quantity of Factor IX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®).

The term "lyophilisate" (also can be used interchangeably with "lyophilizate") as used herein in connection with the formulation according to the invention denotes a formulation which is manufactured by freeze-drying methods known in the art per se. The solvent (e.g. water) is removed by freezing following sublimation under vacuum and desorption of residual water at elevated temperature. In the pharmaceutical field, the lyophilisate usually has a residual moisture of about 0.1 to 5% (w/w) and is present as a powder or a physical stable cake. The lyophilisate is characterized by a fast dissolution after addition of a reconstitution medium.

The term "reconstituted formulation" as used herein denotes a formulation which is lyophilized and re-dissolved by addition of a diluent. The diluent can contain, without limitation, water for injection (WFI), bacteriostatic water for injection (BWFI), sodium chloride solutions (e.g. 0.9% (w/v) NaCl), glucose solutions (e.g. 5% glucose), surfactant containing solutions (e.g. 0.01% polysorbate 20 or polysorbate 80), a pH-buffered solution (e.g. phosphate-buffered solutions) and combinations thereof.

"Dosing interval," as used herein, means the amount of time that elapses between multiple doses being administered to a subject. Dosing interval can thus be indicated as ranges. The dosing interval in the methods of the invention using a chimeric FIX-FcRn BP, e.g., a chimeric FIX-Fc, can be at least about one and one-half to eight times longer than the dosing interval required for an equivalent amount (in IU/kg) of said Factor IX without the FcRn BP, e.g., Fc portion (i.e., a polypeptide consisting of said FIX). The dosing interval when administering, e.g., a Factor IX-Fc chimeric polypeptide (or a hybrid) of the invention can be at least about one and one-half times longer than the dosing interval required for an equivalent amount of said Factor IX without the FcRn BP, e.g., Fc, portion (i.e., a polypeptide consisting of said Factor IX). The dosing interval can be at least about one and one-half to eight times longer than the dosing interval required for an equivalent amount of said Factor IX without, e.g., the Fc portion (or a polypeptide consisting of said Factor IX).

The term "dosing frequency" as used herein refers to the frequency of administering doses of a long-acting FIX polypeptide in a given time. Dosing frequency can be indicated as the number of doses per a given time, e.g., once a week or once in two weeks.

The term "bleeding episode" as used herein is given a standardized definition: A bleeding episode starts from the first sign of a bleed, and ends 72 hours after the last treatment for the bleeding, within which any symptoms of bleeding at the same location, or injections less than or equal to 72 hours apart, is considered the same bleeding episode. See Blanchette V. (2006) *Haemophilia* 12:124-7. As used herein, any injection to treat the bleeding episode, taken more than 72 hours after the preceding one, is considered the first injection to treat a new bleeding episode at the same location. Likewise, any bleeding at a different location is considered a separate bleeding episode regardless of time from the last injection.

The term "prophylaxis of one or more bleeding episode" or "prophylactic treatment" as used herein means administering a Factor IX polypeptide in multiple doses to a subject over a course of time to increase the level of Factor IX activity in a subject's plasma. In one embodiment, "prophylaxis of one or more bleeding episode" indicates use of a long-acting FIX polypeptide to prevent or inhibit occurrence of one or more spontaneous or uncontrollable bleeding or bleeding episodes or to reduce the frequency of one or more spontaneous or uncontrollable bleeding or bleeding episodes. In another embodiment, the increased FIX activity level is sufficient to decrease the incidence of spontaneous bleeding or to prevent bleeding in the event of an unforeseen injury. Prophylactic treatment decreases or prevents bleeding episodes, for example, those described under on-demand treatment. Prophylactic treatment can be individualized, as discussed under "dosing interval", e.g., to compensate for inter-subject variability.

The term "about once a week" as used herein means approximate number, and "about once a week" can include every seven days±two days, i.e., every five days to every nine days. The dosing frequency of "once a week" thus can be every five days, every six days, every seven days, every eight days, or every nine days.

The term "individualized interval prophylaxis" as used herein means use of a long-acting FIX polypeptide for an individualized dosing interval or frequency to prevent or inhibit occurrence of one or more spontaneous and/or uncontrollable bleeding or bleeding episodes or to reduce the frequency of one or more spontaneous and/or uncontrollable bleeding or bleeding episodes. In one embodiment, the "individualized interval" includes every 10 days±3 days, i.e. every seven days to every 13 days. The dosing frequency of the "individualized interval prophylaxis" thus can be every seven days, every eight days, every nine days, every ten days, every 11 days, every 12 days, or every 13 days.

The term "on-demand treatment," as used herein, means treatment that is intended to take place over a short course of time and is in response to an existing condition, such as a bleeding episode, or a perceived short term need such as planned surgery. The "on-demand treatment" is used interchangeably with "episodic" treatment. Conditions that can require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these are also included. The subject can be in need of surgical prophylaxis, peri-operative management, or treatment for surgery. Such surgeries include minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, intrathoracic surgery. Surgeries other than these are also included.

Additional conditions that can require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for peri-operative management for surgery or dental extraction, major surgery, extensive oral surgery, urologic surgery, hernia surgery, orthopedic surgery such as replacement of knee, hip, or other major joint.

The term "treatment" or "treating" as used herein means amelioration or reduction of one or more symptoms of bleeding diseases or disorders including, but not limited to, hemophilia B. In one embodiment, "treatment of" or "treating" a bleeding disease or disorder includes prevention of one or more symptoms of a bleeding disease or disorder. In a bleeding disease or disorder caused by a FIX deficiency (e.g., a low baseline FIX activity), the term "treatment" or "treating" means a FIX replacement therapy. By administering a long-acting FIX polypeptide to a subject, the subject can achieve and/or maintain a plasma trough level of a FIX activity at about 1 IU/dl or above 1 IU/dl. In other embodiments, "treatment" or "treating" means reduction of the frequency of one or more symptoms of bleeding diseases or disorders, e.g., spontaneous or uncontrollable bleeding episodes. "Treatment," however, need not be a cure.

The term "perioperative management" as used herein means use of a long-acting FIX polypeptide before, concurrently with, or after an operative procedure, e.g., a surgical operation. The use for "perioperative management" of one or more bleeding episode includes surgical prophylaxis before (i.e., preoperative), during (i.e., intraoperative), or after (i.e., postoperative) a surgery to prevent one or more bleeding or bleeding episode or reducing or inhibiting spontaneous and/or uncontrollable bleeding episodes before, during, and after a surgery.

Pharmacokinetic (PK) parameters include the terms above and the following terms, which have their ordinary meaning in the art, unless otherwise indicated. Some of the terms are explained in more detail in the Examples. PK parameters can be based on FIX antigen level (often denoted parenthetically herein as "antigen") or FIX activity level (often denoted parenthetically herein as "activity"). In the literature, PK parameters are often based on FIX activity level due to the presence in the plasma of some subjects of endogenous, inactive FIX, which interferes with the ability to measure administered (i.e., exogenous) FIX using antibody against FIX. However, when FIX is administered as part of a fusion or hybrid protein containing a heterologous polypeptide such as an FcRn BP, administered (i.e., exogenous) FIX antigen can be accurately measured using antibody to the heterologous polypeptide. In addition, certain PK parameters can be based on model predicted data (often denoted parenthetically herein as "model predicted") or on observed data (often denoted parenthetically herein as "observed"), and preferably are based on observed data.

"Baseline," as used herein, is the lowest measured plasma Factor IX level in a subject prior to administering a dose. The Factor IX plasma levels can be measured at two time points prior to dosing: at a screening visit and immediately prior to dosing. Alternatively, (a) the baseline in subjects whose pretreatment FIX activity is <1%, who have no detectable FIX antigen, and have nonsense genotypes can be defined as 0%, (b) the baseline for subjects with pretreatment FIX activity <1% and who have detectable FIX antigen can be set at 0.5%, (c) the baseline for subjects whose pretreatment FIX activity is between 1-2% is Cmin (the lowest activity throughout the PK study), and (d) the baseline for subjects whose pretreatment FIX activity is ≥2% can be set at 2%. Activity above the baseline pre-dosing can be considered residue drug from prior treatment, and can be decayed to baseline and subtracted from the PK data following rFIXFc dosing.

"$T_{1/2\beta}$," or "$T_{1/2\ beta}$" or "Beta HL," as used herein, is half-life associated with elimination phase, $t_{1/2\beta}=(\ln 2)$/elimination rate constant associated with the terminal phase. The $T_{1/2\ beta}$ can be measured by FIX activity or by FIX antigen level in plasma. The $T_{1/2\ beta}$ based on activity is shown as $T_{1/2\ beta}$ (activity), and the $T_{1/2\ beta}$ based on the FIX antigen level can be shown as $T_{1/2\ beta}$ (antigen). Both $T_{1/2\ beta}$ (activity) and $T_{1/2\ beta}$ (antigen) can be shown as ranges or a geometric mean.

"Trough," as used herein, is the lowest plasma Factor IX activity level reached after administering a dose of chimeric polypeptide of the invention or another Factor IX molecule and before the next dose is administered, if any. Trough is used interchangeably herein with "threshold." Baseline Factor IX levels are subtracted from measured Factor IX levels to calculate the trough level.

The term "annualized bleeding rate" ("ABR) as used herein refers to the number of bleeding episodes (including spontaneous and traumatic bleeds) experienced by a subject during a defined time period, extrapolated to 1 year. For example two bleeds in six months would indicate an ABR of four. The median ABR provides a single number to describe all subjects, indicating that half of the subjects had individual ABRs less than or equal to the median and half had ABRs greater than or equal to the median. For example, an ABR can be calculated according to the following formula:

Annualized bleeding rate=Number of bleeding episodes during the efficacy period/Total number of days during the efficacy period×365.25

"Subject," as used herein means a human. Subject as used herein includes an individual who is known to have at least one incidence of uncontrolled bleeding episodes, who has been diagnosed with a disease or disorder associated with uncontrolled bleeding episodes, e.g., a bleeding disease or disorder, e.g., hemophilia B, who are susceptible to uncontrolled bleeding episodes, e.g., hemophilia, or any combinations thereof. Subjects can also include an individual who is in danger of one or more uncontrollable bleeding episodes prior to a certain activity, e.g., a surgery, a sport activity, or any strenuous activities. The subject can have a baseline FIX activity less than 1%, less than 0.5%, less than 2%, less than 2.5%, less than 3%, or less than 4%. Subjects also include pediatric humans. Pediatric human subjects are birth to 20 years, preferably birth to 18 years, birth to 16 years, birth to 15 years, birth to 12 years, birth to 11 years, birth to 6 years, birth to 5 years, birth to 2 years, and 2 to 11 years of age.

"Therapeutic dose," "dose," "effective dose," or "dosing amount" as used herein, means a dose that achieves a plasma trough level of a FIX activity at least about 1 IU/dl or above 1 IU/dl in the subject administered with the long-acting FIX polypeptide. For the purpose of this invention, in one embodiment, the "dose" refers to the amount of the doses that a plasma trough level of a FIX activity is maintained at least about 1 IU/dl or above 1 IU/dl, at least about 2 IU/dl or above 2 IU/dl, at least about 3 IU/dl or above 3 IU/dl, at least about 4 IU/dl or above 4 IU/dl, or at least about 5 IU/dl or above 5 IU/dl throughout the administration of the long-acting FIX polypeptide. In another embodiment, the "dose" reduces or decreases frequency of bleeding or bleeding disorder. In other embodiments, the "dose" stops ongoing, uncontrollable bleeding or bleeding episodes. In still other embodiments, the "dose" prevents spontaneous bleeding or bleeding episodes in a subject susceptible to such spontaneous bleeding or bleeding episodes. The "dose" or "therapeutic dose" need not cure hemophilia.

"Variant," as used herein, refers to a polynucleotide or polypeptide differing from the original polynucleotide or polypeptide, but retaining essential properties thereof, e.g., Factor IX coagulant activity or Fc (FcRn binding) activity. Generally, variants are overall closely similar, and, in many regions, identical to the original polynucleotide or polypeptide. Variants include polypeptide and polynucleotide fragments, deletions, insertions, and modified versions of original polypeptides.

II. Method of Administering

The present invention provides methods of administering a long-acting Factor IX (FIX) polypeptide to a human subject in need thereof, comprising administering to the subject a dose of a long-acting FIX polypeptide at a dosing interval. Administration of the long-acting FIX polypeptide is a replacement therapy by adding a recombinant FIX to a subject with FIX deficiency. Administration of the long-acting FIX polypeptide can reduce or prevent a number of bleeding or bleeding episodes in the subject.

The subject for the methods of the invention includes those in need of control or prevention of bleeding or bleeding episodes. The subject can be bleeding at the time of administration or be expected to be bleeding, or can be susceptible to bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such subjects also include those in need of peri-operative management, such as management of bleeding associated with surgery or dental extraction. In one embodiment, the subject is in need of prophylaxis of one or more bleeding episodes. In another embodiment, the subject is in need of individualized interval prophylaxis. In other embodiments, the subject is in need of on-demand treatment of one or more bleeding episodes. In still other embodiments, the subject is in need of perioperative management of one or more bleeding episodes.

The present invention also identifies the appropriate dosing amount and the dosing interval that can treat or prevent one or more bleeding episodes. Administration of the appropriate dosing amount for the dosing interval can achieve a plasma trough level of a FIX activity at least about 1 IU/dl or above 1 IU/dl during the interval in a subject administered with a long-acting FIX polypeptide. In one embodiment, the invention includes a dosing amount (or ranges of the dosing amount) and a dosing interval (or ranges of the dosing interval) that can maintain a plasma trough level of a FIX activity at least about 1 IU/dl (1%) or above 1 IU/dl (1%), at least about 2 IU/dl (2%) or above 2 IU/dl (2%), at least about 3 IU/dl (3%) or above 3 IU/dl (3%), at least about 4 IU/dl (4%) or above 4 IU/dl (4%), or at least about 5 IU/dl (5%) or above 5 IU/dl (5%) throughout the interval. In another embodiment, a dosing amount (or ranges of the dosing amount) and a dosing interval (or ranges of the dosing interval) that reduces or decreases frequency of bleeding or bleeding disorder. In other embodiments, the dosing amount (or ranges of the dosing amount) and the dosing interval (or ranges of the dosing interval) of a long-acting FIX polypeptide stops on-going, uncontrollable bleeding or bleeding episodes in a subject administered with the dosing amount during the dosing interval. In still other embodiments, the dosing amount (or ranges of the dosing amount) and the dosing interval (or ranges of the dosing interval) of a long-acting FIX polypeptide prevents spontaneous bleeding or bleeding episodes in a subject susceptible to such spontaneous bleeding or bleeding episodes. Various dosing amounts and dosing intervals are described in International Appl. No. PCT/US2011/043569 filed Jul. 11, 2011 and published as WO 2012/006624 on Jan. 12, 2012, which is incorporated herein by reference in its entirety.

The doses that can be used in the methods of the invention are about 10 IU/kg to about 200 IU/kg, about 10 IU/kg to about 180 IU/kg, or about 25 IU/kg to about 200 IU/kg. In one embodiment, the dose of a long-acting FIX polypeptide is about 10 IU/kg to about 50 IU/kg, about 10 IU/kg to about 100 IU/kg, about 25 IU/kg to about 75 IU/kg, about 25 IU/kg to about 100 IU/kg, about 25 IU/kg to about 125 IU/kg, about 25 IU/kg to about 150 IU/kg, about 25 IU/kg to about 50 IU/kg, about 50 IU/kg to about 100 IU/kg, about 50 IU/kg to about 150 IU/kg, about 100 IU/kg to about 150 IU/kg, about 150 IU/kg to about 200 IU/kg, or any combinations thereof.

In another embodiment, a dose of a long-acting FIX polypeptide for at least about every five days or longer are as follows: about 25 to about 110, about 30 to about 110, about 40 to about 110, about 50 to about 110, about 60 to about 110, about 70 to about 110, about 80 to about 110, about 90 to about 110, and about 100 to about 110; about 30 to about 100, about 30 to about 90, about 30 to about 80, about 30 to about 70, about 30 to about 60, about 30 to about 50, about 30 to about 40 IU/kg; about 40 to about 110, about 50 to about 100, about 60 to about 90, and about 70 to about 80 IU/kg; about 40 to about 50, about 50 to about 60, about 60 to about 70, about 70 to about 80, about 80 to about 90, about 90 to about 100, and about 100 to about 110 IU/kg; about 25, about 30, about 35, about 40, about 45, about 50, about 55, about 60, about 65, about 70, about 75, about 80, about 85, about 90, about 95, about 100, about 105, or about 110 IU/kg.

In certain embodiments, a dose of a long-acting FIX polypeptide is an amount sufficient for weekly prophylaxis of a bleeding episode. For example, the doses for the weekly dosing interval include about 10 to about 50, about 20 to about 60, about 20 to about 70, about 20 to about 80, about 20 to about 90, about 30 to about 40, about 30 to about 50, about 30 to about 60, about 30 to about 70, about 30 to about 80, about 30 to about 90, about 40 to about 50, about 40 to about 60, about 50 to about 70, about 40 to about 80, about 40 to about 90, about 50 to about 60, about 50 to about 70, about 50 to about 80, about 50 to about 90, about 60 to about 70, about 60 to about 80, about 60 to about 90, about 70 to about 80, about 70 to about 90 IU/kg. Doses can be lower than 20 IU/kg if effective for a given subject, e.g., about 10, about 11, about 12, about 13, about 14, about 15, about 16, about 17, about 18, or about 19 IU/kg.

The dosing interval can, alternatively, be an individualized interval that is determined for each subject based on pharmacokinetic data or other information about that subject. The individualized dose/dosing interval combination can be the same as those for fixed interval regimens in the preceding paragraphs, or can differ. The regimen can initially be at a fixed dosing interval, and then it can change to an individualized dosing interval.

In some embodiments, a dose of a long-acting FIX polypeptide is an amount sufficient for individualized interval prophylaxis of a bleeding episode. In one example, the individualized interval is every nine days, every 10 days, every 11 days, every 12 days, every 13 days, every 14 days, every 15 days, every 16 days, every 17 days, every 18 days, every 19 days or two times monthly. Examples of the doses for the individualized interval include, but are not limited to: about 50 IU/kg to about 180 IU/kg, about 60 IU/kg to about 180 IU/kg, about 70 IU/kg to about 180 IU/kg, about 80 IU/kg to about 180 IU/kg, about 90 IU/kg to about 180 IU/kg, about 100 IU/kg to about 180 IU/kg, about 110 IU/kg to about 180 IU/kg, about 120 IU/kg to about 180 IU/kg, about 130 IU/kg to about 180 IU/kg, about 140 IU/kg to about 180 IU/kg, about 60 IU/kg to about 170 IU/kg, about 60 IU/kg to about 160 IU/kg, about 60 IU/kg to about 150

IU/kg, about 60 IU/kg to about 140 IU/kg, about 70 IU/kg to about 140 IU/kg, about 70 IU/kg to about 130 IU/kg, about 80 IU/kg to about 130 IU/kg, about 80 IU/kg to about 140 IU/kg, about 90 IU/kg to about 140 IU/kg, about 90 IU/kg to about 130 IU/kg, about 90 IU/kg to about 120 IU/kg, about 90 IU/kg to about 110 IU/kg, about 90 IU/kg to about 100 IU/kg, about 100 IU/kg to about 140 IU/kg, about 100 IU/kg to about 130 IU/kg, about 100 IU/kg to about 120 IU/kg, or about 100 IU/kg to about 110 IU/kg.

In still other embodiments, the individualized dosing interval is at least about once in two weeks, at least about 15 days, at least about 16 days, at least about 17 days, at least about 18 days, at least about 19 days, at least about 20 days, at least about 21 days, at least about once in three weeks, at least about 22 days, at least about 23 days, at least about 24 days, at least about 25 days, at least about 26 days, at least about 27 days, at least about 28 days, at least about 29 days, at least about 30 days, or at least about once a month. For example, the doses for the individualized dosing interval are about 120 IU/kg to about 200 IU/kg, about 130 IU/kg to about 200 IU/kg, about 140 IU/kg to about 200 IU/kg about 150 IU/kg to about 200 IU/kg, about 160 IU/kg to about 200 IU/kg, about 170 IU/kg to about 200 IU/kg, about 180 IU/kg to about 200 IU/kg, about 120 IU/kg to about 180 IU/kg, about 130 IU/kg to about 180 IU/kg, about 140 IU/kg to about 180 IU/kg, about 150 IU/kg to about 180 IU/kg, about 160 IU/kg to about 180 IU/kg, about 120 IU/kg to about 170 IU/kg, about 130 IU/kg to about 170 IU/kg, about 140 IU/kg to about 170 IU/kg, about 150 IU/kg to about 170 IU/kg, about 160 IU/kg to about 170 IU/kg, about 120 IU/kg to about 160 IU/kg, about 130 IU/kg to about 160 IU/kg, about 140 IU/kg to about 160 IU/kg, about 150 IU/kg to about 160 IU/kg, about 120 IU/kg to about 150 IU/kg, about 130 IU/kg to about 150 IU/kg, about 140 IU/kg to about 150 IU/kg, about 120 IU/kg to about 140 IU/kg, or about 130 IU/kg to about 140 IU/kg. In other examples, a dose for an individualized dosing interval is about 60 IU/kg, about 70 IU/kg, about 80 IU/kg, about 90 IU/kg, about 95 IU/kg, about 100 IU/kg, about 105 IU/kg, about 110 IU/kg, about 115 IU/kg, about 120 IU/kg, about 125 IU/kg, about 130 IU/kg, about 135 IU/kg, about 140 IU/kg, about 145 IU/kg, about 150 IU/kg, about 155 IU/kg, about 160 IU/kg, about 165 IU/kg, about 170 IU/kg, about 175 IU/kg, or about 180 IU/kg.

In some embodiments, a dose of a long-acting FIX polypeptide is sufficient for on-demand treatment of one or more bleeding episodes. The doses for the on-demand treatment can vary depending on the various factors, e.g., subject's baseline FIX activity, subject's body weight, subject's likelihood of experiencing bleeding episode, and etc. In one example, the doses for the on-demand treatment can be about 10 to about 50, about 15 to about 100, about 20 to about 100, about 20 to about 50, about 50 to about 100, about 10, about 20, about 40, about 50, and about 100 IU/kg. In another example, the doses for the on-demand treatment can be about 20 to about 50, about 20 to about 100, about 20 to about 180, 25 to about 110, about 30 to about 110, about 40 to about 110, about 50 to about 110, about 60 to about 110, about 70 to about 110, about 80 to about 110, about 90 to about 110, about 100 to about 110, about 30 to about 100, about 30 to about 90, about 30 to about 80, about 30 to about 70, about 30 to about 60, about 30 to about 50, about 30 to about 40 IU/kg, about 40 to about 110, about 50 to about 100, about 60 to about 90, about 70 to about 80 IU/kg, about 40 to about 50, about 50 to about 60, about 60 to about 70, about 70 to about 80, about 80 to about 90, about 90 to about 100, about 100 to about 110 IU/kg, about 20, about 25, about 30, about 35, about 40, about 45, about 50, about 55, about 60, about 65, about 70, about 75, about 80, about 85, about 90, about 95, about 100, about 105, and about 110 IU/kg. In other examples, the doses for the on-demand treatment can be about 90 to about 180, about 100 to about 180, about 110 to about 180, about 120 to about 180, about 130 to about 180, about 140 to about 180, about 150 to about 180, about 160 to about 180, and about 170 to about 180 IU/kg. In still other examples, the doses for the on-demand treatment are about 90 to about 170, about 90 to about 160, about 90 to about 150, about 90 to about 140, about 90 to about 130, about 90 to about 120, about 90 to about 110, and about 90 to about 100 IU/kg. In examples, the doses for the on-demand treatment are about 100 to about 170, about 110 to about 160, about 120 to about 150, and about 130 to about 140 IU/kg. In yet other examples, the dose for the on-demand treatment are about 90 to about 100, about 100 to about 110, about 110 to about 120, about 120 to about 130, about 130 to about 140, about 140 to about 150, about 150 to about 160, and about 160 to about 170 IU/kg. The dose for the on-demand treatment can be about 115, about 120, about 125, about 130, about 135, about 140, about 145, about 150, about 155, about 160, about 165, about 170, about 175, and about 180 IU/kg.

In certain embodiments, a dosing amount and a dosing interval combination for a subject is 20 IU/kg once weekly, 40 IU/kg once weekly, 50 IU/kg once weekly, 100 IU/kg every 10 days, and 100 IU/kg every two weeks (or twice monthly). Additional combinations of dose and dose interval include: a dose at least about 50 IU/kg and a dosing interval at least about 7 days, a dose at least about 100 IU/kg and a dosing interval at least about 9 days, a dose at least about 100 IU/kg and a dosing interval at least about 12 days, a dose at least about 100 IU/kg and a dosing interval at least about 13 days, a dose at least about 100 IU/kg and a dosing interval at least about 14 days, a dose at least about 100 IU/kg and a dosing interval at least about 15 days, a dose at least about 150 IU/kg and a dosing interval at least about 14 days, 20-50 or 20-100 IU/kg and said dosing interval is one time weekly, a dose of 20-50 IU/kg and a dosing interval of 7 days, a dose of 50-100 IU/kg and a dosing interval of 10-14 days, or a dose of 100-150 IU/kg and a dosing interval of 14-16 days. Non-limiting examples of the combinations of dosing interval and dose also include 10-50 IU/kg for 7 days, 15-100 IU/kg for 10-13 days, 50-150 IU/kg for 14-15 days, 10-30 IU/kg for 7 days, 15-50 IU/kg for 10 days, 20-70 IU/kg for 11 days, 25-85 IU/kg for 12 days, 30 to 100 IU/kg for 13 days, 40 to 125 IU/kg for 14 days, and 50-150 IU/kg for 15 days.

In one embodiment, a dosing interval is at least about once a week, at least about once in two weeks, at least about twice a month, at least about once in three weeks, at least about once in four weeks, or at least about once a month. In another embodiment, a dosing interval of a long-acting FIX polypeptide is about once in five days to about once in two months, about once in five days to about once in month, or about once a week to about once a month. In other embodiments, the dosing interval is at least about every five days, about every six days, at least about every seven days, at least about every eight days, at least about every nine days, at least about every ten days, at least about every 11 days, at least about every 12 days, at least about every 13 days, at least about every 14 days, at least about every 15 days, at least about every 16 days, at least about every 17 days, at least about every 18 days, at least about every 19 days, at least about every 20 days, or at least about every 21 days. In still other embodiments, a dosing interval is 9-18 days, e.g., about 9-17, about 9-16, about 9-15, about 9-14, about 9-13, about 9-12, about 9-11, about 9-10 days, about 10-18, about 11-18, about 12-18, about 13-18, about 14-18, about 15-18, about 16-18, about 17-18 days, about 10-11, about 11-12, about 12-13, about 13-14, about 14-15, about 15-16, and about 16-17 days, about 9, about 10, about 11, about 12, about 13, about 14, about 15, about 16, about 17, or about 18 days. In yet other embodiments, the dosing interval is about 10-14 days. The dosing interval can be longer than 18 days, e.g., about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days.

In one embodiment, a dosing frequency for a long-acting FIX polypeptide is about every two weeks or twice monthly. In another embodiment, the dosing frequency is every 7 days for 25-50 IU/kg, every 10-13 days for 50-100 IU/kg, or every 14 days for 100-150 IU/kg. The interval (or frequency) and dose are determined such that the combination of interval (or frequency) and dose will result in a trough level of at least about 1-5 or at least about 1-3, or at least about 1, at least about 2, at least about 3 IU/dl FIX activity in the subject. Examples of the dose and dosing interval can also be 7 days for 20-50 IU/kg, 10-14 days for 50-100 IU/kg, 14-16 days for 100-150 IU/kg, 7 days for 10-50 IU/kg, 10-13 days for 15-100 IU/kg, or 14-15 days for 50-150 IU/kg. Additional examples of the dose and dosing interval include, but are not limited to, 7 days for 10-30 IU/kg, 10 days 15-50 IU/kg, 11 days 20-70 IU/kg, 12 days 25-85 IU/kg, 13 days 30 to 100 IU/kg, 14 days 40 to 125 IU/kg, and 15 days for 50-150 IU/kg.

In some embodiments, the dosing interval is 20 IU/kg once weekly, 40 IU/kg every 10 days, 50 IU/kg once weekly, or 100 IU/kg every two weeks (twice monthly).

In some embodiments of the invention, an annualized bleeding rate (ABR) of a bleeding episode is controlled by the present methods. For example, the dosing amount and dosing interval can be administered to reduce or decrease an annualized bleeding rate to a certain level. In one embodiment, administration of a long-acting FIX polypeptide at a dose and a dosing interval for prophylaxis of a bleeding episode results in an annual bleeding rate of less than 2, less than 2.5, less than 3, less than 3.5, less than 4, less than 4.5, less than 5, less than 5.5, less than 6, less than 6.5, less than 7, less than 7.5, less than 8, less than 8.5, less than 9, less than 9.5, or less than 10. For example, ABR of weekly prophylaxis of a bleeding episode can be 2.95. In another embodiment, administration of a long-acting FIX polypeptide at a dose and a dosing interval for individualized interval prophylaxis of a bleeding episode results in an ABR of less than 1, less than 1.5, less than 2, less than 2.5, less than 3, less than 3.5, less than 4, less than 4.5, less than 5, less than 5.5, less than 6, less than 6.5, less than 7, less than 7.5, less than 8, less than 8.5, or less than 9. For example, ABR for individualized interval prophylaxis can be 1.38. In other embodiments, administration of a long-acting FIX polypeptide at a dose and a dosing interval for on-demand treatment (i.e., episodic treatment) of a bleeding episode results in an ABR of less than 10, less than 11, less than 12, less than 13, less than 14, less than 15, less than 16, less than 17, less than 18, less than 19, less than 20, less than 21, less than 22, less than 23, less than 24, less than 25, or less than 26. For example, ABR for on-demand treatment can be 17.69.

The long-acting FIX polypeptide of the invention can provide a half-life, e.g., $T_{1/2beta}$ (activity) or $T_{1/2beta}$ (antigen), that is longer than wild-type FIX (i.e., a polypeptide consisting of amino acids 1 to 415 of SEQ ID NO: 2; BENEFIX®; or pdFIX). In one embodiment, a $T_{1/2beta}$ (activity) of a long-acting FIX polypeptide is at least about 40 hours, at least about 45 hours, at least about 50 hours, at least about 55 hours, at least about 60 hours, at least about 65 hours, at least about 70 hours, at least about 75 hours, at least about 80 hours, at least about 85 hours, at least about 90 hours, at least about 95 hours, at least about 100 hours, at least about 105 hours, at least about 110 hours, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, or at least about 193. In another embodiment, a $T_{1/2beta}$ (activity) of a long-acting FIX polypeptide is about 40 to about 193 hours, about 35 hours to about 190 hours, about 45 hours to about 193 hours, about 50 hours to about 198 hours, about 55 hours to about 188 hours, about 60 hours to about 200 hours, about 30 hours to about 205 hours, about 43 hours to about 210 hours. In a specific embodiment, a $T_{1/2beta}$ (activity) is about 40 hours to about 193 hours.

In some embodiments, the $T_{1/2\ beta}$ (activity) of a long-acting FIX polypeptide is expressed as a mean. For example, a mean of the $T_{1/2\ beta}$ (activity) of a long-acting FIX polypeptide is at least about 76 hours, at least about 77 hours, at least about 78 hours, at least about 79 hours, at least about 80 hours, at least about 81 hours, at least about 82 hours, at least about 83 hours, at least about 84 hours, at least about 85 hours, at least about 86 hours, at least about 87 hours, at least about 88 hours, at least about 89 hours, at least about 90 hours, at least about 91 hours, or at least about 92 hours. In a specific embodiment, a mean of the $T_{1/2\ beta}$ (activity) of a long-acting FIX polypeptide is 82 hours.

In other embodiments, the $T_{1/2\ beta}$ (activity) of a long-acting FIX polypeptide is shown as a comparison to a $T_{1/2\ beta}$ (activity) of wild-type mature FIX (i.e., BENEFIX®). In one example, the mean of the $T_{1/2\ beta}$ (activity) is at least about 2.0 fold higher than wild-type mature FIX (a polypeptide consisting of amino acids 1 to 415 of SEQ ID NO:2, i.e., BENEFIX® or pdFIX). In another example, the mean of the $T_{1/2\ beta}$ (activity) is at least about 2.0 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold, at least about 3.0 fold, at least about 3.1 fold, or at least about 3.2 fold higher than wild-type mature FIX (a polypeptide consisting of amino acids 1 to 415 of SEQ ID NO:2, i.e., BENEFIX®; pdFIX).

In still other embodiments, the invention provides administering a long-acting FIX polypeptide to a subject who can exhibit a longer $T_{1/2\ beta}$ (activity). In one embodiment, the methods of the invention includes administering a long-acting FIX polypeptide to a subject who exhibits at least about 80 hours, at least about 81 hours, at least about 82 hours, at least about 83 hours, at least about 84 hours, at least about 85 hours, at least about 86 hours, at least about 87 hours, at least about 88 hours of the $T_{1/2\ beta}$ (activity). In another embodiment, the methods include administering a long-acting FIX polypeptide to a subject who has a baseline FIX activity less than 2%, less than 1.5%, less than 1%, or less than 0.5%, thereby resulting in a $T_{1/2\ beta}$ (activity) higher than about 80 hours, about 81 hours, about 82 hours, about 83 hours, about 84 hours, about 85 hours, about 86 hours, about 87 hours, or about 88 hours.

In certain embodiments, a $T_{1/2beta}$ (antigen) of a long-acting FIX polypeptide is at least about 63 hours, at least about 70 hours, at least about 80 hours, at least about 90 hours, at least about 100 hours, at least about 110 hours, at least about 120 hours, at least about 130 hours, at least about 140 hours, at least about 150 hours, at least about 160 hours, at least about 170 hours, at least about 180 hours, at least about 190 hours, at least about 200 hours, at least about 210, at least about 220, at least about 230, at least about 240, at least about 250, at least about 260, at least about 270, at least about 280, at least about 290, at least about 300, at least about 310, at least about 320, at least about 330, at least about 340, at least about 350, at least about 360, or at least about 370. In another embodiment, a $T_{1/2beta}$ (antigen) of a long-acting FIX polypeptide is about 63 to about 372 hours, about 50 hours to about 380 hours, about 40 hours to about 390 hours, about 70 hours to about 360 hours, about 80 hours to about 400 hours, about 90 hours to about 410 hours, about 50 hours to about 400 hours, about 40 hours to about 380 hours. In a specific embodiment, a $T_{1/2beta}$ (antigen) is about 63 hours to about 372 hours.

In some embodiments, the $T_{1/2\ beta}$ (antigen) of a long-acting FIX polypeptide is expressed as a mean. For example, a mean of the $T_{1/2\ beta}$ (antigen) of a long-acting FIX polypeptide is at least about 110 hours, at least about 111 hours, at least about 112 hours, at least about 113 hours, at least about 114 hours, at least about 115 hours, at least about 116 hours, at least about 117 hours, at least about 118 hours, at least about 119 hours, at least about 120 hours, at least about 121 hours, at least about 122 hours, at least about 123 hours, at least about 124 hours, at least about 125 hours, at least about 126 hours, at least about 127 hours, at least about 128 hours, at least about 129 hours, at least about 130 hours, or at least about 131 hours. In a specific embodiment, a mean of the $T_{1/2\ beta}$ (antigen) of a long-acting FIX polypeptide is 118 hours or 126 hours.

In other embodiments, the $T_{1/2\ beta}$ (antigen) of a long-acting FIX polypeptide is shown as a comparison to a $T_{1/2\ beta}$ (antigen) of wild-type mature FIX (a polypeptide consisting of amino acids 1 to 415 of SEQ ID NO: 2, i.e., BENEFIX® or pdFIX). In one example, the mean of the $T_{1/2\ beta}$ (antigen) is at least about 2.0 fold higher than wild-type mature FIX (a polypeptide consisting of amino acids 1 to 415 of SEQ ID NO:2, i.e., BENEFIX® or pdFIX). In another example, the mean of the $T_{1/2\ beta}$ (antigen) is at least about 2.0 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold than wild-type mature FIX (a polypeptide consisting of amino acids 1 to 415 of SEQ ID NO:2, i.e., BENEFIX®; pdFIX).

In still other embodiments, the invention provides administering a long-acting FIX polypeptide to a subject who can exhibit a longer $T_{1/2\ beta}$ (antigen). In one embodiment, the methods of the invention includes administering a long-acting FIX polypeptide to a subject who exhibits at least about 115 hours, at least about 116 hours, at least about 117 hours, at least about 118 hours, at least about 119 hours, at least about 120 hours, at least about 121 hours, at least about 122 hours, at least about 123 hours, at least about 124 hours, at least about 125 hours, at least about 126 hours, or at least about 127 hours of the $T_{1/2\ beta}$ (antigen). In another embodiment, the methods include administering a long-acting FIX polypeptide to a subject who has a baseline FIX activity less than 2%, less than 1.5%, less than 1%, or less than 0.5%, thereby resulting in a $T_{1/2\ beta}$ (activity) higher than about 115 hours, about 116 hours, about 117 hours, about 118 hours, about 119 hours, about 120 hours, about 121 hours, about 122 hours, about 123 hours, about 124 hours, about 125 hours, about 126 hours, about 127 hours, about 128 hours, or about 129 hours.

In certain embodiments, the $T_{1/2beta}$ (activity) is measured by one stage clotting assay.

In other embodiments, the long-acting FIX polypeptide has a Mean Residence Time (MRT) of at least about 50 hours, at least about 60 hours, at least about 70 hours, at least about 80 hours, at least about 90 hours, at least about 100 hours, at least about 110 hours, at least about 120 hours, at least about 130 hours, at least about 140 hours, at least about 150 hours, at least about 160 hours, at least about 170 hours, at least about 180 hours, or at least about 190 hours. In some embodiments, the MRT is about 50 to about 200 hours, about 60 hours to about 210 hours, about 60 hours to about 183 hours, about 70 hours to about 150 hours, about 70 hours to about 140 hours, about 70 hours to about 130 hours, about 80 hours to about 120 hours, about 80 hours to about 110 hours, or about 88 hours to about 110 hours. In a particular embodiment, the MRT is at least about 2.0 fold (e.g., 2.1 fold, 2.2 fold, 2.3 fold, 2.4 fold, 2.5 fold, 2.6 fold, 2.7 fold, 2.7 fold, 2.8 fold, 2.9 fold, or 3 fold) higher than a polypeptide consisting of amino acids 1 to 415 of SEQ ID NO: 2 or BENEFIX®.

In certain embodiments of the invention, the method of the invention further comprises measuring a baseline FIX activity of a subject prior to the initial administration of a long-acting FIX polypeptide. Measuring of a baseline FIX activity can employ any known clotting assays in the art, e.g., one step aPTT assay, two step chromogenic assay, ROTEM, TGA, or etc.

In some embodiments, the method of the invention further comprises measuring a $T_{1/2beta}$ (activity) or $T_{1/2beta}$ (antigen) of the long-acting FIX polypeptide in the subject after administration of a long-acting FIX polypeptide.

In other embodiments, after administration of a given dose or doses of a long-acting FIX polypeptide, the plasma trough level of the long-acting FIX polypeptide is maintained at about 1 IU/dl (1%) or above 1 IU/dl (1%) in the subject. In yet other embodiments, the plasma through level of the long-acting FIX polypeptide is maintained between about 1 IU/dl (1%) and about 5 IU/dl (5%) in the subject. In yet other embodiments, a plasma trough level is maintained between about 1% and about 5%, between about 1% and about 6%, between about 1% and about 7%, between about 1% and about 8%, between about 1% and about 9%, between about 1% and about 10%, between about 1% and about 12%, between about 1% and about 14%, between about 1% and about 15%, between about 1% and about 17%, between about 1% and about 19%, between about 1% and about 20%, between about 1% and about 22%, between about 1% and about 24%, between about 1% and about 25%, between about 1% and about 30%, between about 1% and about 35%.

In some embodiments, the trough is 1-5 or 1-3 IU/dl after about 6, about 7, about 8, about 9, about 10, about 11, about 12, about 13 or about 14 days after administration of a long-acting FIX polypeptide. In some embodiments, the plasma level of the FIX polypeptide reaches an average trough of at least about 1 IU/dl after at least about 6 days or reaches a trough of at least about 1, 2, 3, 4, or 5 IU/dl after at least about 6 days in a subject. In some embodiments, the plasma level of said chimeric polypeptide reaches an average trough of about 1-5 or 1-3 IU/dl. Such trough or average trough can be reached after about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days.

III. Long-Acting FIX Polypeptide

A long-acting or long-lasting FIX polypeptide useful for the invention is a chimeric polypeptide comprising a FIX polypeptide and an FcRn binding partner. In certain embodiments, the rFIXFc is a fusion protein comprising a single molecule of human recombinant coagulation FIX (rFIX) covalently linked to the dimeric Fc domain of immunoglobulin G1 (IgG1) with no intervening sequence. The FIX polypeptide of the invention comprises a functional Factor IX polypeptide in its normal role in coagulation, unless otherwise specified. Thus, the FIX polypeptide includes variant polypeptides that are functional and the polynucleotides that encode such functional variant polypeptides. In one embodiment, the FIX polypeptides are the human, bovine, porcine, canine, feline, and murine FIX polypeptides. The full length polypeptide and polynucleotide sequences of FIX are known, as are many functional variants, e.g., fragments, mutants and modified versions. FIX polypeptides include full-length FIX, full-length FIX minus Met at the N-terminus, full-length FIX minus the signal sequence, mature FIX (minus the signal sequence and propeptide), and mature FIX with an additional Met at the N-terminus. FIX can be made by recombinant means ("recombinant Factor IX" or "rFIX"), i.e., it is not naturally occurring or derived from plasma.

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses FIX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2, which is herein incorporated by reference in its entirety, discloses FIX mutants that exhibit increased clotting activity at page 5, line 14 to page 6, line 5. International publication number WO 09/051717 A2, which is herein incorporated by reference in its entirety, discloses FIX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant FIX molecules that have an increased number of glycosylation sites, which result in an increased half-life, at page 4, line 26 to page 12, line 6. International publication number WO 09/140015 A2, which is herein incorporated by reference in its entirety, discloses functional FIX mutants that an increased number of Cys residues, which can be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In addition, hundreds of non-functional mutations in FIX have been identified in hemophilia subjects, many of which are disclosed in Table 5, at pages 11-14 of International publication number WO 09/137254 A2, which is herein incorporated by reference in its entirety. Such non-functional mutations are not included in the invention, but provide additional guidance for which mutations are more or less likely to result in a functional FIX polypeptide.

In one embodiment, the Factor IX (or Factor IX portion of a chimeric polypeptide) can be at least 70%, at least 80%, at least 85%, at least 90%, at least 95%, at least 96%, at least 97%, at least 98%, at least 99%, or 100% identical to a FIX amino acid sequence shown in Table 19A without a signal sequence and propeptide sequence (amino acids 1 to 415 of SEQ ID NO:2), or alternatively, with a propeptide sequence, or with a propeptide and signal sequence (full length FIX).

Factor IX coagulant activity is expresses as International Unit(s) (IU). One IU of FIX activity corresponds approximately to the quantity of FIX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®). See, e.g., Example 3.

FcRn binding partner ("FcRn BP") comprises functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term FcRn BP includes any variants of IgG Fc that are functional. For example, the region of the Fc portion of IgG that binds to the FcRn receptor has been described based on X-ray crystallography (Burmeister et al. 1994, Nature 372:379, incorporated herein by reference in its entirety). The major contact area of the Fc with the FcRn is near the junction of the CH2 and CH3 domains. Fc-FcRn contacts are all within a single Ig heavy chain. FcRn BPs include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al. 1994, J. Exp. Med. 180: 2377), incorporated herein by reference in its entirety.) An FcRn BP can comprise the CH2 and CH3 domains of an immunoglobulin with or without the hinge region of the immunoglobulin. Exemplary FcRn BP variants are provided in WO 2004/101740 and WO 2006/074199, incorporated herein by reference in its entirety.

FcRn BP (or FcRn BP portion of a chimeric polypeptide) can contain one or more mutations, and combinations of mutations.

FcRn BP (or FcRn BP portion of a chimeric polypeptide) can contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of U.S. 2009/0264627 A1, which is incorporated herein by reference in its entirety; and the mutants disclosed at page 2, paragraphs [0014] to [0021] of U.S. 20090163699 A1, which is incorporated herein by reference in its entirety.

FcRn BP (or FcRn BP portion of a chimeric polypeptide) can also include the following mutations: The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. In addition to alanine other amino acids can be substituted for the wild type amino acids at the positions specified above. Mutations can be introduced singly into Fc giving rise to more than one hundred FcRn binding partners distinct from native Fc. Additionally, combinations of two, three, or more of these individual mutations can be introduced together, giving rise to hundreds more FcRn binding partners. Certain of these mutations can confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie 1995, Therapeutic Immunology 2:77, which is incorporated herein by reference in its entirety; and Armour et al. 1999, Eur. J. Immunol. 29:2613, which is incorporated herein by reference in its entirety). As a further example of new functionality arising from mutations described above, affinity for FcRn can be increased beyond that of wild type in some instances. This increased affinity can reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591, which is incorporated herein by reference in its entirety).

The FcRn BP (or FcRn BP portion of a chimeric polypeptide) can be at least 70%, at least 80%, at least 85%, at least 90%, at least 95%, at least 96%, at least 97%, at least 98%, at least 99%, or 100% identical to the Fc amino acid sequence shown in Table 19A or B without a signal sequence (amino acids 1 to 227 of SEQ ID NO:2), or alternatively, with a signal sequence.

A chimeric polypeptide comprising a FIX polypeptide and an FcRn binding partner can comprise an amino acid sequence at least 70%, at least 80%, at least 85%, at least 90%, at least 95%, at least 96%, at least 97%, at least 98%, at least 99%, or 100% identical to the Factor IX and FcRn BP, e.g., the Fc amino acid sequence shown in Table 19A without a signal sequence and propeptide sequence (amino acids 1 to 642 of SEQ ID NO:2), or alternatively, with a propeptide sequence, or alternatively with a signal sequence and a propeptide sequence.

A long-acting or long-lasting FIX polypeptide can be a hybrid FIX polypeptide. Hybrid FIX polypeptide means a combination of a FIX chimeric polypeptide with a second polypeptide. The chimeric polypeptide and the second polypeptide in a hybrid can be associated with each other via non-covalent protein-protein interactions, such as charge-charge or hydrophobic interactions. The chimeric polypeptide and the second polypeptide in a hybrid can be associated with each other via covalent bond(s) such as disulfide bonds. The chimeric peptide and the second peptide can be associated with each other via more than one type of bond, such as non-covalent and disulfide bonds. Hybrids are described in WO 2004/101740, WO 2005/001025, U.S. Pat. No. 7,404,956, U.S. Pat. No. 7,348,004, and WO 2006/074199, each of which is incorporated herein by reference in its entirety. The second polypeptide can be a second copy of the same chimeric polypeptide or it can be a non-identical chimeric polypeptide. In other embodiments, the second polypeptide is a polypeptide comprising an FcRn BP, e.g., Fc. In some embodiments, the chimeric polypeptide is a Factor IX-FcRn BP, e.g., Factor IX-Fc chimeric polypeptide, and the second polypeptide consists essentially of Fc. See, e.g., Table 19 (SEQ ID NOs:2 and 4). See, e.g., U.S. Pat. No. 7,404,956, which is incorporated herein by reference in its entirety.

The second polypeptide in a hybrid can comprise or consist essentially of a sequence at least 70%, at least 80%, at least 85%, at least 90%, at least 95%, at least 96%, at least 97%, at least 98%, at least 99%, or 100% identical to the amino acid sequence shown in Table 19B without a signal sequence (amino acids 1 to 227 of SEQ ID NO:4), or alternatively, with a signal sequence.

In some embodiments, a long-acting FIX polypeptide is a FIX monomer dimer hybrid. Monomer-dimer hybrid can comprise two polypeptide chains, one chain comprising a FIX polypeptide and a first Fc region, and another chain comprising, consisting essentially of, or consisting of a second Fc region. In certain aspects, a FIX monomer dimer hybrid consists essentially of or consists of two polypeptide chains, a first chain consisting essentially of or consisting of a FIX polypeptide and a second chain consisting essentially of or consisting of a second Fc region.

A long-acting FIX polypeptide can be encoded by a nucleotide sequence which is at least 85%, 90%, 95%, 96%, 97%, 98% or 99% identical to, for example, the nucleotide coding sequence in SEQ ID NO:1 or 3 (the Factor IX portion, the Fc portion, individually or together) or the complementary strand thereto, the nucleotide coding sequence of known mutant and recombinant Factor IX or Fc such as those disclosed in the publications and patents cited herein or the complementary strand thereto, a nucleotide sequence encoding the polypeptide of SEQ ID NO:2 or 4 (the Factor IX portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

By a nucleic acid having a nucleotide sequence at least, for example, 95% "identical" to a reference nucleotide sequence, it is intended that the nucleotide sequence of the nucleic acid is identical to the reference sequence except that the nucleotide sequence can include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. The query sequence can be, for example, the entire sequence shown in SEQ ID NO:1 or 3, the ORF (open reading frame), or any fragment specified as described herein.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al. (Comp. App. Biosci. (1990) 6:237-245), which is herein incorporated by reference in its entirety. In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NO:2 (the Factor IX portion, the Fc portion, individually or together) or 4, or a known Factor IX or Fc polypeptide sequence, can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al., Comp. App. Biosci. 6:237-245 (1990), incorporated herein by reference in its entirety. In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

The polynucleotide variants can contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. The authors of Ron et al., J. Biol. Chem. 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988), incorporated herein by reference in its entirety.)

Moreover, ample evidence demonstrates that variants often retain a biological activity similar to that of the naturally occurring protein. For example, Gayle and coworkers (J. Biol. Chem. 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild type.

As stated above, polypeptide variants include modified polypeptides. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

IV. Pharmaceutical Composition

A long-acting FIX polypeptide can be formulated as a pharmaceutical composition. The pharmaceutical composition can be formulated for administration to humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Various methods of formulating the invention is well known in the art.

A long-acting FIX polypeptide can be formulated as a pharmaceutical composition or formulation. In certain formulations provided herein, a long-acting FIX polypeptide is formulated as a sterile, preservative-free, non-pyrogenic, lyophilized, white to off-white powder to cake, for intravenous (IV) administration. The formulation can be provided in a single-use vial. Certain exemplary formulations of a long-acting FIX polypeptide are also referred to as eftrenonacog alfa.

In certain embodiments, a long-acting FIX polypeptide (e.g., rFIXFc) formulation is provided in a single-use vial manufactured to contain, following reconstitution with an appropriate amount of diluent, about 50 IU/ml, about 100 IU/ml, about 200 IU/ml, about 400 IU/ml, or about 600 IU/ml of the long-acting FIX polypeptide. In certain embodiments in which diluent is added to a final volume of about 5 ml, a single-use vial can nominally contain about 250, about 500, about 1000, about 2000, or about 3000 International Units (IU) of the long-acting FIX polypeptide (e.g., rFIXFc).

In certain embodiments, rFIXFc polypeptide comprises an amino acid sequence at least 90%, 95%, or 100% identical to amino acids 1 to 642 of SEQ ID NO:2.

In certain embodiments the formulation includes, in addition to the active long-acting FIX polypeptide (e.g., rFIXFc): sucrose (which can act as a stabilizer or bulking agent), mannitol (which can act as a stabilizer or bulking agent), L-histidine (which can act as a buffer), and polysorbate 20 or polysorbate 80 (which can act as a stabilizer). The formulation is provided with a diluent comprising a sterile sodium chloride solution. In certain embodiments, the diluent is provided in a pre-filled syringe.

Accordingly, provided herein is a pharmaceutical composition comprising a specified amount of a long-acting FIX polypeptide (e.g., rFIXFc) (in IU), along with the excipients sucrose, mannitol, L-histidine, NaCl, and polysorbate 20 or polysorbate 80. The compositions provided herein comprise various concentrations of the various excipients, and the concentrations can be expressed in various ways. For example, the concentration of a given excipient can be expressed as a molar concentration (e.g., M or mM) as a weight/volume percent, e.g., grams per 100 ml diluent), or as milligrams per milliliter (mg/ml). Formulations provided herein can contain specified amounts of the various excipients at a level of precision ranging from approximate, e.g., concentrations expressed only to one significant figure (e.g., about 0.1% (w/v)), or with more precision, e.g., out to 2, 3, 4, 5, or 6 significant figures (e.g., about 3.88 mg/ml, with precision out to three significant figures). The necessary level of precision can vary depending on, e.g., the requirements of a given regulatory agency, or the manufacturing process. In certain embodiments the pharmaceutical composition comprises a reconstituted formulation, which can be provided as a lyophilisate, optionally accompanied by a diluent.

In certain embodiments, the pharmaceutical composition comprises about 25 IU/ml to about 1200 IU/ml rFIXFc, e.g., 50 IU/ml, 100 IU/ml, 200 IU/ml, 400 IU/ml, or 600 IU/ml of a long-acting FIX polypeptide (e.g., rFIXFc). In certain embodiments, the pharmaceutical composition comprises 50 IU/ml, 100 IU/ml, 200 IU/ml, or 400 IU/ml of a long-acting FIX polypeptide (e.g., rFIXFc) in a formulation comprising about 3.88 mg/ml or about 25 mM L-histidine, about 23.8 mg/ml or about 2.4% (w/v) mannitol, about 11.9 mg/ml or about 1.2% (w/v) sucrose, about 0.10 mg/ml or about 0.010% (w/v) polysorbate 20 or polysorbate 80, and about 3.25 mg/ml or about 55.6 mM NaCl.

In certain embodiments, the pharmaceutical composition comprises 600 IU/ml of a long-acting FIX polypeptide (e.g., rFIXFc) in a formulation comprising about 5.43 mg/ml or about 35 mM L-histidine, about 33.3 mg/ml or about 3.3% (w/v) mannitol, about 16.7 mg/ml or about 1.7% (w/v) sucrose, about 0.14 mg/ml or about 0.014% (w/v) polysorbate 20 or polysorbate 80, and about 3.25 mg/ml or about 55.6 mM NaCl.

In certain embodiments, the pharmaceutical composition comprises a pharmaceutically acceptable amount of sucrose. In certain embodiments, the pharmaceutical composition comprises about 1% (w/v) to about 2% (w/v) sucrose, e.g., about 1.2% (w/v) sucrose or about 1.7% (w/v) sucrose. In certain related embodiments the pharmaceutical composition comprises about 10 mg/ml to about 20 mg/ml sucrose, e.g., about 11.9 mg/ml sucrose or about 16.7 mg/ml sucrose.

In certain embodiments, the pharmaceutical composition comprises a pharmaceutically acceptable amount of mannitol. In certain embodiments, the pharmaceutical composition comprises about 2% (w/v) to about 4% (w/v) mannitol, e.g., about 2.4% (w/v) mannitol or about 3.3% (w/v) mannitol. In certain related embodiments the pharmaceutical composition comprises about 20 mg/ml to about 40 mg/ml mannitol, e.g., about 23.8 mg/ml mannitol or about 33.3 mg/ml mannitol.

In certain embodiments, the pharmaceutical composition comprises pharmaceutically acceptable amounts of both sucrose and mannitol. In certain embodiments, the pharmaceutical composition comprises about 1.0% to about 2.0% sucrose and about 2.0% (w/v) to about 4.0% (w/v) mannitol, e.g., about 1.2% (w/v) sucrose and about 2.4% (w/v) mannitol or about 1.7% (w/v) sucrose and about 3.3% (w/v) mannitol. In certain related embodiments the pharmaceutical composition comprises about 10 mg/ml to about 20 mg/ml sucrose and about 20 mg/ml to about 40 mg/ml mannitol, e.g., about 11.9 mg/ml sucrose and about 23.8 mg/ml mannitol or about 16.7 mg/ml sucrose and about 33.3 mg/ml mannitol. In certain embodiments, sucrose and mannitol are provided as part of a lyophilisate, which, upon reconstitution with an appropriate amount of diluent provides sucrose and mannitol at the desired concentration.

In certain embodiments, the pharmaceutical composition comprises between about 50 mM and about 60 mM NaCl, e.g., about 55.6 mM NaCl. In certain related embodiments, the pharmaceutical composition comprises between about 3 mg/ml and about 4 mg/ml NaCl, e.g., about 3.25 mg/ml NaCl. In certain embodiments, NaCl is provided at the desired concentration in a diluent solution in which a lyophilisate comprising a long-acting FIX polypeptide (e.g., rFIXFc) is reconstituted.

In certain embodiments, the pharmaceutical composition comprises a pharmaceutically acceptable amount of L-histidine. In certain embodiments, the pharmaceutical composition comprises between about 20 mM and about 40 mM L-histidine, e.g., about 25 mM L-histidine or about 35 mM L-histidine. In certain related embodiments the pharmaceutical composition comprises between about 3 mg/ml and about 6 mg/ml L-histidine, e.g., about 3.88 mg/ml L-histidine or about 5.43 mg/ml L-histidine. In certain embodiments, L-histidine is provided as part of a lyophilisate, which, upon reconstitution with an appropriate amount of diluent provides L-histidine at the desired concentration.

In certain embodiments, the pharmaceutical composition comprises a pharmaceutically acceptable amount of polysorbate 20 or polysorbate 80. In certain related embodiments the pharmaceutical composition comprises between about 0.008% (w/v) and about 0.020% (w/v) polysorbate 20 or polysorbate 80, e.g., about 0.010% (w/v) polysorbate 20 or polysorbate 80 or about 0.014% (w/v) polysorbate 20 or polysorbate 80. In certain related embodiments the pharmaceutical composition comprises between about 0.08 mg/ml and about 0.2 mg/ml polysorbate 20 or polysorbate 80, e.g., about 0.10% mg/ml polysorbate 20 or polysorbate 80 or about 0.14 mg/ml polysorbate 20 or polysorbate 80. In certain embodiments, polysorbate 20 or polysorbate 80 is provided as part of a lyophilisate, which, upon reconstitution with an appropriate amount of diluent provides polysorbate 20 or polysorbate 80 at the desired concentration.

In certain embodiments, the pharmaceutical composition comprises: between about 25 IU/ml and about 700 IU/ml of a long-acting FIX polypeptide (e.g., rFIXFc); between about 1% (w/v) and about 2% (w/v) of sucrose; between about 2% (w/v) and about 4% (w/v) of mannitol; between about 50 mM and about 60 mM NaCl; between about 20 mM and about 40 mM L-histidine; and between about 0.008% (w/v) and about 0.015% of polysorbate 20 or polysorbate 80. In certain embodiments the pharmaceutical composition is provided as a lyophilisate and a diluent. In certain embodiments the amount of lyophilizate provides about 5 ml of a pharmaceutical composition with the desired ingredients at the desired concentrations.

In certain embodiments, the pharmaceutical composition comprises: between about 25 IU/ml and about 700 IU/ml of a long-acting FIX polypeptide (e.g., rFIXFc); between about 10 mg/ml and about 20 mg/ml of sucrose; between about 20 mg/ml and about 40 mg/ml of mannitol; between about 3 mg/ml and about 4 mg/ml NaCl; between about 3 mg/ml and about 6 mg/ml L-histidine; and between about 0.08 mg/ml and about 0.15 mg/ml of polysorbate 20 or polysorbate 80. In certain embodiments the pharmaceutical composition is provided as a lyophilisate and a diluent. In certain embodiments the amount of lyophilizate provides about 5 ml of a pharmaceutical composition with the desired ingredients at the desired concentrations.

Exemplary compositions are provided in Table 1 and in Table 2 in the Examples.

For example, the disclosure provides a pharmaceutical composition comprising: about 50 IU/ml of a long-acting FIX polypeptide (e.g., rFIXFc); about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 100 IU/ml of a long-acting FIX polypeptide (e.g., rFIXFc); about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 200 IU/ml of a long-acting FIX polypeptide (e.g., rFIXFc); about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 400 IU/ml of a long-acting FIX polypeptide (e.g., rFIXFc); about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 600 IU/ml of a long-acting FIX polypeptide (e.g., rFIXFc); about 1.7% (w/v) of sucrose; about 3.3% (w/v) of mannitol; about 55.6 mM NaCl; about 35 mM L-histidine; and about 0.014% (w/v) of polysorbate 20 or polysorbate 80.

The disclosure further provides a pharmaceutical composition comprising: about 50 IU/ml of a long-acting FIX polypeptide (e.g., rFIXFc); about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 100 IU/ml of a long-acting FIX polypeptide (e.g., rFIXFc); about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 200 IU/ml of a long-acting FIX polypeptide (e.g., rFIXFc); about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 400 IU/ml of a long-acting FIX polypeptide (e.g., rFIXFc); about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 600 IU/ml of a long-acting FIX polypeptide (e.g., rFIXFc); about 16.7 mg/ml of sucrose; about 33.3 mg/ml of mannitol; about 3.25 mg/ml NaCl; about 5.43 mg/ml L-histidine; and about 0.14 mg/ml of polysorbate 20 or polysorbate 80.

This disclosure also provides the components of a pharmaceutical kit. Such a kit includes one or more containers and optional attachments. A kit as provided herein facilitates administration of an effective amount of the long-acting FIX polypeptide (e.g., rFIXFc) to a subject in need thereof. In certain embodiments, the kit facilitates administration of the long-acting FIX polypeptide (e.g., rFIXFc) via intravenous infusion. In certain embodiments, the kit facilitates self-administration of the long-acting FIX polypeptide (e.g., rFIXFc) via intravenous infusion.

In certain embodiments, the disclosure provides a pharmaceutical kit comprising: a first container comprising a lyophilized powder or cake, where the powder or cake comprises: (i) a long-acting FIX polypeptide (e.g., rFIXFc), (ii) sucrose; (iii) mannitol; (iv) L-histidine; and (v) polysorbate 20 or polysorbate 80; and a second container comprising a 0.325% (w/v) NaCl diluent solution to be combined with the lyophilized powder of the first container. In certain embodiments, sufficient diluent is provided to produce about 5 ml of a long-acting FIX polypeptide (e.g., rFIXFc) formulation with desired properties as disclosed herein. In certain embodiments, the second container is a pre-filled syringe associated with a plunger, to allow addition of the diluent to the first container, reconstitution of the contents of the first container, and transfer back into the syringe. In certain embodiments, the kit further provides an adaptor for attaching the syringe to the first container. In certain embodiments the kit further provides a needle and infusion tubing, to be attached to the syringe containing the reconstituted long-acting FIX polypeptide (e.g., rFIXFc) formulation to allow IV infusion of the formulation.

In certain embodiments a long-acting FIX polypeptide (e.g., rFIXFc) is provided in a total amount from about 200 IU to about 4000 IU, e.g., about 250 IU, about 500 IU, about 1000 IU, about 2000 IU, or about 3000 IU.

In one embodiment, a pharmaceutical kit is provided which comprises a first container comprising a lyophilized powder, where the powder comprises (i) about 250 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 50 IU/ml of a long-acting FIX polypeptide (e.g., rFIXFc); (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 500 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 100 IU/ml of a long-acting FIX polypeptide (e.g., rFIXFc); (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 1000 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 200 IU/ml of a long-acting FIX polypeptide (e.g., rFIXFc); (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 2000 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 400 IU/ml of a long-acting FIX polypeptide (e.g., rFIXFc); (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 3000 IU of a long-acting FIX polypeptide (e.g., rFIXFc), (ii) about 83.3 mg of sucrose; (iii) about 167 mg of mannitol; (iv) about 27.2 mg of L-histidine; and (v) about 0.7 mg of polysorbate 20 or polysorbate 80; and a second container comprising 0.325% (w/v) NaCl at a volume sufficient to produce, when combined with the lyophilized powder of the first container, a solution comprising: (i) about 600 IU/ml of a long-acting FIX polypeptide (e.g., rFIXFc); (ii) about 1.7% (w/v) of sucrose; (iii) about 3.3% (w/v) of mannitol; (iv) about 55.6 mM NaCl; (v) about 35 mM L-histidine; and (vi) about 0.014% (w/v) of polysorbate 20 or polysorbate 80.

In a further embodiment, a pharmaceutical kit is provided which comprises a first container comprising a lyophilized powder, where the powder comprises: (i) about 250 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 50 IU/ml of a long-acting FIX polypeptide (e.g., rFIXFc); (ii) about 11.9 mg/ml of sucrose; (iii) about 23.8 mg/ml of mannitol; (iv) about 3.25 mg/ml NaCl; (v) about 3.88 mt·ml L-histidine, and (vi) about 0.10 mg/ml of polysorbate 20 or polysorbate 80.

In a further embodiment, a pharmaceutical kit is provided which comprises a first container comprising a lyophilized powder, where the powder comprises: (i) about 500 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 100 IU/ml of a long-acting FIX polypeptide (e.g., rFIXFc); (ii) about 11.9 mg/ml of sucrose; (iii) about 23.8 mg/ml of mannitol; (iv) about 3.25 mg/ml NaCl; (v) about 3.88 mg/ml L-histidine; and (vi) about 0.10 mg/ml of polysorbate 20 or polysorbate 80.

In a further embodiment, a pharmaceutical kit is provided which comprises a first container comprising a lyophilized powder, where the powder comprises: (i) about 1000 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 200 IU/ml of a long-acting FIX polypeptide (e.g., rFIXFc); (ii) about 11.9 mg/ml of sucrose; (iii) about 23.8 mg/ml of mannitol; (iv) about 3.25 mg/ml NaCl; (v) about 3.88 mg/ml L-histidine; and (vi) about 0.10 mg/ml of polysorbate 20 or polysorbate 80.

In a further embodiment, a pharmaceutical kit is provided which comprises a first container comprising a lyophilized powder, where the powder comprises: (i) about 2000 IU of a long-acting FIX polypeptide (e.g., rFIXFc), (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 400 IU/ml of a long-acting FIX polypeptide (e.g., rFIXFc); (ii) about 11.9 mg/ml of sucrose; (iii) about 23.8 mg/ml of mannitol; (iv) about 3.25 mg/ml NaCl; (v) about 3.88 mg/ml L-histidine; and (vi) about 0.10 mg/ml of polysorbate 20 or polysorbate 80.

In a further embodiment, a pharmaceutical kit is provided which comprises a first container comprising a lyophilized powder, where the powder comprises: (i) about 3000 IU of a long-acting FIX polypeptide (e.g., rFIXFc), (ii) about 83.3 mg of sucrose; (iii) about 167 mg of mannitol; (iv) about 27.2 mg of L-histidine; and (v) about 0.7 mg of polysorbate 20 or polysorbate 80; and a second container comprising 0.325% (w/v) NaCl at a volume sufficient to produce, when combined with the lyophilized powder of the first container, a solution comprising: (i) about 600 IU/ml of a long-acting FIX polypeptide (e.g., rFIXFc); (ii) about 16.7 mg/ml of sucrose; (iii) about 33.3 mg/ml of mannitol; (iv) about 3.25 mg/ml NaCl; (v) about 5.43 mg/ml L-histidine; and (vi) about 0.14 mg/ml of polysorbate 20 or polysorbate 80.

In certain embodiments the first container of a pharmaceutical kit provided herein is a glass vial comprising a rubber stopper. In certain embodiments, the second container a pharmaceutical kit provided herein is a syringe body, associated with a plunger. In certain embodiments, the syringe is a pre-filled syringe containing the diluent. In certain embodiments, a pharmaceutical kit provided herein further comprises an adaptor to connect the glass vial to the syringe body. In certain embodiments a pharmaceutical kit provided herein further comprises infusion tubing associated with a needle to be connected to the syringe, suitable for intravenous infusion.

In certain embodiments, a desired dose of a long-acting FIX polypeptide (e.g., rFIXFc) can be achieved through the use of one pharmaceutical kit as provided herein. In certain embodiments, more than one pharmaceutical kit can be used to achieve a desired dose. Provided herein is a method of combining, or pooling the formulations contained in two or more pharmaceutical kits as provided herein in order to achieve a desired dose.

In some embodiments, the pharmaceutical composition further comprises a short-acting FIX polypeptide. A short-acting FIX polypeptide can comprise or consist of wild-type FIX. Non-limiting examples of the short-acting FIX polypeptide includes BENEFIX, MONONINE, or ALPHANINE.

The pharmaceutical composition of the invention can be formulated as a liquid formulation, lyophilized powder, or suspension. A container comprising the pharmaceutical compositions can be a vial, a cartridge, or a syringe. In a particular embodiment, a syringe comprising the pharmaceutical composition is a dual chamber syringe.

In certain embodiments, the pharmaceutical composition of the invention or the reconstitution solution for the lyophilized powder comprises a preservative in an amount sufficient to provide antimicrobial activity. Pharmaceutically acceptable preservatives that are useful for pharmaceutical composition are well known in the art. For example, examples of the pharmaceutically acceptable preservatives include, but are not limited to, phenol, m-cresol, benzyl alcohol, chlorobutanol, methyl paraben, propylparaben, phenoxyethanol, any other pharmaceutically acceptable preservative, and any combinations thereof. In a particular embodiment, the preservative is benzyl alcohol. In some embodiments, the pharmaceutical composition comprises benzyl alcohol at a concentration between 0.5% and 0.9%.

Having now described the present invention in detail, the same will be more clearly understood by reference to the following examples, which are included herewith for purposes of illustration only and are not intended to be limiting of the invention. All patents and publications referred to herein are expressly incorporated by reference.

V. Method of Making

A long-acting FIX polypeptide can be manufactured in a host cell comprising a vector encoding the long-acting FIX polypeptide. In one embodiment, the host cell is transformed with one or more vectors comprising a first nucleotide sequence encoding a FIX polypeptide and a first FcRn polypeptide, a second nucleotide sequence encoding a second FcRn polypeptide, and optionally a third nucleotide sequence encoding a protein convertase, e.g., PC5. As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

Examples of vectors include, but are not limited to viral vectors or plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

The expression vector or vectors are then transfected or co-transfected into a suitable target cell, which will express the polypeptides. Transfection techniques known in the art include, but are not limited to, calcium phosphate precipitation (Wigler et al. (1978) Cell 14:725), electroporation (Neumann et al. (1982) EMBO J 1:841), and liposome-based reagents. A variety of host-expression vector systems can be utilized to express the proteins described herein including both prokaryotic and eukaryotic cells. These include, but are not limited to, microorganisms such as bacteria (e.g., E. coli) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., Mol. Biotechnol. 34(2): 165-78 (2006).

The method can further comprise purification steps. Various known purifications steps are well known in the art.

VI. Method, System, and Storage Medium for Estimating Patient Individualized Dosing Information, Patient Individualized PK Information, and Patient Median PK Information The invention also includes a method of estimating a rFIXFc dosing information individualized for a patient, the method comprising: (a) receiving, by a computer-based system containing the rFIXFc population pharmacokinetic (popPK) model of Example 6, e.g., Table 21, and, optionally, a Bayesian estimation program, at least one of patient information and desired treatment outcome information, (b) calculating, by the computer-based system, individualized rFIXFc dosing information using the popPK model, the optional Bayesian estimation program, and the received information, and (c) outputting, by the computer-based system, the individualized dosing information.

In some embodiments, the method also comprises selecting a dosing regimen based on the output individualized dosing information of (c) and administering rFIXFc to the patient according to the selected dosing regimen.

In some embodiments, the desired treatment outcome information is desired rise in plasma FIX activity level following dosing and the output information is dose for acute treatment.

In some embodiments, the desired treatment outcome information is desired dosing interval and the output information is dose for prophylaxis.

In some embodiments, the desired treatment outcome information is desired dose and the output information is interval for prophylaxis.

The invention also includes a method of estimating a rFIXFc dosing regimen based on median popPK, the method comprising: (a) receiving, by a computer-based system containing the rFIXFc popPK model of Example 6, e.g., Table 21, and, optionally, a Bayesian estimation program, at least one of patient information and desired treatment outcome information, (b) calculating, by the computer-based system, median rFIXFc PK information using the popPK model, the optional Bayesian estimation program, and the received information, and (c) outputting, by the computer-based system, the median PK information.

In some embodiments, the method also comprises selecting a dosing regimen based on the output median PK information of (c), and administering rFIXFc to a patient according to the selected dosing regimen.

The invention also includes a method of estimating individual patient rFIXFc PK, the method comprising: (a) receiving, by a computer-based system containing the rFIXFc population pharmacokinetic (popPK) model of Example 6, e.g., Table 21, and, optionally, a Bayesian estimation program, individual rFIXFc PK information, (b) estimating, by the computer-based system, individualized patient rFIXFc PK information using the popPK model, the optional Bayesian estimation program, and the received information, and (c) outputting, by the computer-based system, the individualized patient PK information.

In some embodiments, the method also comprises selecting a dosing regimen based on the output individualized patient PK information of (c), and administering rFIXFc to the patient according to the selected regimen.

In some embodiments (a) further comprises receiving, by the computer-based system, patient information.

In some embodiments the patient information is age, e.g., 12 and older, or body weight. Additional patient information includes diagnostic (baseline) FIX level, PK determinations, time of PK sampling, dosing history if PK samples were taken from multiple doses, actual dose, FIX activity level, etc.

In some embodiments, desired treatment outcome information is, e.g., desired PK or desired regimen outcome, e.g., desired rise in plasma FIX activity level following dose, desired dosing interval, and desired dose.

In some embodiments, output information is, e.g., PK curve, PK parameter such as incremental recovery (Cmax/dose), mean residence time, terminal t1/2, clearance, Vss, AUC/dose, doses and associated troughs, and intervals and associated troughs.

For example, for assessing individualized patient PK, the system can recommend that the user input 2-3 optimized PK sampling time points. In this case, system output can include PK curve and one or more selected PK parameters, e.g., incremental recovery (Cmax/Dose), mean residence time, terminal t1/2, clearance, Vss, AUC, and time to 1 or X %, etc. E.g., FIG. 15.

As additional examples, to select an individualized dosing regimen using the output individual PK parameters discussed in the preceding paragraph, (i) the dose selected for acute treatment can be based on user input of the desired rise in plasma FIX activity level following the dose, (ii) the dose selected for prophylaxis can be based on user input of the desired dosing interval, or (iii) the selected interval for prophylaxis can be based on user input for the desired dose. In the first case, the system can output the dose (IU) based in the patient's incremental recovery. E.g., FIG. 16. In the second case, system output can be a table of doses and associated troughs, e.g., x IU/kg, 1% trough, y IU/kg, 2% trough, etc. E.g., FIG. 17, top. In the third case, system output can be a table of intervals and associated troughs, e.g., x days, 1% trough, y IU/kg, 2% trough, etc., E.g., FIG. 17, bottom.

The user may wish to use the system without inputting any individualized PK data. In this case, the dosing output would be based on the population median rather than being individualized for the particular patient, e.g., FIG. 18. In this way, the user inputs, e.g., body weight and age, and (i) the desired rise in plasma FIX activity level following the dose, (ii) the desired dose interval for prophylaxis, or (iii) the desired dose for prophylaxis. In the first case, the system can output the dose. In the second case, the system can output the dose and associated trough, e.g., Table 16. In the third case, the system can output the interval and associated trough, e.g., Table 16.

In some embodiments, the system is compliant with patient privacy laws. In some embodiments, the system is encrypted, e.g., with SSL. In some embodiments, input patient information is made anonymous.

In some embodiments, the system includes a user help function.

The method can be carried out by, e.g., a physician, a nurse, or another healthcare practitioner.

Additional embodiments include a computer readable storage medium having instructions stored thereon that, when executed by a processor, cause the processor to perform any of the above methods.

Additional embodiments include a system comprising a processor and a memory, the memory having instructions stored thereon that, when executed by the processor, cause the processor to perform any of the above methods.

The user of the system or computer readable storage medium, can be, e.g., a physician, a nurse, or another healthcare practitioner.

For additional embodiments of these aspects of the invention, see Examples 5, 6, and 8 and the Figures discussed therein.

VII. Example Computing Environment

Various modeling techniques, dosage calculations, and estimations described herein can be implemented by software, firmware, hardware, or a combination thereof. FIG. 19 illustrates an example computer system 1900 in which the embodiments, or portions thereof, can be implemented as computer-readable code. For example, the modeling of Examples 5 and 6, and/or the patient treatment simulation of Example 8 can be implemented in system 1900.

Computer system 1900 includes one or more processors, such as processor 1904. Processor 1904 is connected to a communication infrastructure 1906 (for example, a bus or network).

Computer system 1900 also includes a main memory 1908, preferably random access memory (RAM), and may also include a secondary memory 1910. In accordance with implementations, user interface data may be stored, for example and without limitation, in main memory 1908. Main memory 1908 may include, for example, cache, and/or static and/or dynamic RAM. Secondary memory 1910 may include, for example, a hard disk drive and/or a removable storage drive. Removable storage drive 1914 may include a floppy disk drive, a magnetic tape drive, an optical disk drive, a flash memory, or the like. The removable storage drive 1914 reads from and/or writes to removable storage unit 1916 in a well-known manner. Removable storage unit 1916 may include a floppy disk, magnetic tape, optical disk, etc. which is read by and written to by removable storage drive 1914. As will be appreciated by persons skilled in the relevant art(s), removable storage unit 1916 includes a computer readable storage medium having stored therein computer software and/or data.

Computer system 1900 may also include a display interface 1902. Display interface 1902 may be adapted to communicate with display unit 1930. Display unit 1930 may include a computer monitor or similar means for displaying graphics, text, and other data received from main memory 1908 via communication infrastructure 1906. In alternative implementations, secondary memory 1910 may include other similar means for allowing computer programs or other instructions to be loaded into computer system 1900. Such means may include, for example, a removable storage unit 1922 and an interface 1920. Examples of such means may include a program cartridge and cartridge interface (such as that found in video game devices), a removable memory chip (such as an EPROM, or PROM) and associated socket, and other removable storage units 1922 and interfaces 1920 which allow software and data to be transferred from the removable storage unit 1922 to computer system 1900.

Computer system 1900 may also include a communications interface 1924. Communications interface 1924 allows software and data to be transferred between computer system 1900 and external devices. Communications interface 1924 may include a modem, a network interface (such as an Ethernet card), a communications port, a PCMCIA slot and card, or the like. Software and data transferred via communications interface 1924 are in the form of signals which may be electronic, electromagnetic, optical, or other signals capable of being received by communications interface 1924. These signals are provided to communications interface 1924 via a communications path 1926. Communications path 1926 carries signals and may be implemented using wire or cable, fiber optics, a phone line, a cellular phone link, an RF link or other communications channels.

In this document, the term "computer readable storage medium" is used to generally refer to non-transitory storage media such as removable storage unit 1916, removable storage unit 1922, and a hard disk installed in hard disk drive 1912. Computer readable storage medium can also refer to one or more memories, such as main memory 1908 and secondary memory 1910, which can be memory semiconductors (e.g. DRAMs, etc.). These computer program products are means for providing software to computer system 1900.

Computer programs (also called computer control logic) are stored in main memory 1908 and/or secondary memory 1910. Computer programs may also be received via communications interface 1924 and stored on main memory 1908 and/or secondary memory 1910. Such computer programs, when executed, enable computer system 1900 to implement embodiments as discussed herein. In particular, the computer programs, when executed, enable processor 1904 to implement processes of the present disclosure, such as certain methods discussed above. Accordingly, such computer programs represent controllers of the computer system 1900. Where embodiments use software, the software may be stored in a computer program product and loaded into computer system 1900 using removable storage drive 1914, interface 1920, or hard drive 1912.

Embodiments may be directed to computer program products comprising software stored on any computer readable medium. Such software, when executed in one or more data processing device, causes a data processing device(s) to operate as described herein. Embodiments may employ any computer useable or readable medium. Examples of computer readable storage media include, but are not limited to, non-transitory primary storage devices (e.g., any type of random access memory), and non-transitory secondary storage devices (e.g., hard drives, floppy disks, CD ROMS, ZIP disks, tapes, magnetic storage devices, and optical storage devices, MEMS, nano-technological storage device, etc.). Other computer readable media include communication mediums (e.g., wired and wireless communications networks, local area networks, wide area networks, intranets, etc.).

EXAMPLES

Example 1. Product Description rFIXFc is a long-acting, fully recombinant fusion protein consisting of human coagulation Factor IX (FIX) covalently linked to the Fc domain of human immunoglobulin G1 (IgG1). The Factor IX portion of rFIXFc has a primary amino acid sequence that is identical to the Thr$^{148}$ allelic form of plasma derived Factor IX and has structural and functional characteristics similar to endogenous Factor IX. The Fc domain of rFIXFc contains the hinge, CH2 and CH3 regions of IgG1. rFIXFc contains 869 amino acids with a molecular weight of approximately 98 kilodaltons.

rFIXFc is produced by recombinant DNA technology in a human embryonic kidney (HEK) cell line, which has been extensively characterized. The cell line expresses rFIXFc into a defined cell culture medium that does not contain any proteins derived from animal or human sources. rFIXFc is purified by a series of chromatography steps that does not require use of a monoclonal antibody. The process includes multiple viral clearance steps including 15 nm virus-retaining nano-filtration. No human or animal additives are used in the cell culture, purification, and formulation processes.

rFIXFc is in the pharmacotherapeutic group: antihemorrhagics, B02BD04. It is provided as a sterile, preservative-free, non-pyrogenic, lyophilized, white to off-white powder to cake, for intravenous (IV) administration in a single-use vial, accompanied by a liquid diluent in a pre-filled syringe. In addition to rFIXFc, the pharmaceutical composition comprises in the lyophilizate Sucrose, L-Histidine, Mannitol, and Polysorbate 20, and comprising in a sterile solvent Sodium Chloride Solution (0.325%). Each single-use vial contains nominally 250, 500, 1000, 2000, or 3000 International Units (IU) of rFIXFc. When reconstituted with provided diluent, the product contains the following excipients: sucrose, sodium chloride, L-histidine, mannitol, and polysorbate 20, at the concentrations shown in Table 1 or Table 2 below. The pharmaceutical composition is formulated for intravenous administration only after reconstitution.

Each pack contains a powder vial (type 1 glass) with a stopper (butyl) and a flip-off seal (aluminum), 5 ml solvent in a pre-filled syringe (type 1 glass) with a plunger stopper (butyl), a tip-cap (butyl), and a sterile vial adapter reconstitution device.

TABLE 1 rFIXFc Formulations

| rFIXFc IU/ml* | % (w/v) Sucrose | % (w/v) Mannitol | NaCl (mM) | L-histidine (mM) | % (w/v) Polysorbate-20 |
|---|---|---|---|---|---|
| 50 IU/ml | 1.2 | 2.4 | 55.6 | 25 | 0.010 |
| 100 IU/ml | 1.2 | 2.4 | 55.6 | 25 | 0.010 |
| 200 IU/ml | 1.2 | 2.4 | 55.6 | 25 | 0.010 |
| 400 IU/ml | 1.2 | 2.4 | 55.6 | 25 | 0.010 |
| 600 IU/ml | 1.7 | 3.3 | 55.6 | 35 | 0.014 |

TABLE 2 rFIXFc Formulations

| Component | Concentration | | | | |
|---|---|---|---|---|---|
| | 250 IU/vial | 500 IU/vial | 1000 IU/vial | 2000 IU/vial | 3000 IU/vial |
| rFIXFc* | 50 IU/mL | 100 IU/mL | 200 IU/mL | 400 IU/mL | 600 IU/mL |
| L-Histidine | 3.88 mg/mL | 3.88 mg/mL | 3.88 mg/mL | 3.88 mg/mL | 5.43 mg/mL |
| Mannitol | 23.8 mg/mL | 23.8 mg/mL | 23.8 mg/mL | 23.8 mg/mL | 33.3 mg/mL |
| Sucrose | 11.9 mg/mL | 11.9 mg/mL | 11.9 mg/mL | 11.9 mg/mL | 16.7 mg/mL |
| Polysorbate 20 | 0.10 mg/mL | 0.10 mg/mL | 0.10 mg/mL | 0.10 mg/mL | 0.14 mg/mL |
| NaCl | 3.25 mg/mL | 3.25 mg/mL | 3.25 mg/mL | 3.25 mg/mL | 3.25 mg/mL |
| Water for Injection | | | 5 mL | | |

*The potency (IU) is determined using One Stage Activated Partial Thromboplastin Time (aPTT) as per Ph. Eur 2.7.11 and USP <32> against an in-house standard that is referenced to the WHO concentrate standard. The specific activity of rFIXFc is ≥55 IU/mg protein.

Example 2: Method of Formulation

The rFIXFc drug product is a sterile lyophilized powder for injection intended for intravenous administration. It is supplied in aseptically filled single use vials which contain nominally 250, 500, 1000, 2000, and 3000 IU per vial. The vials are 10 mL USP/Ph. Eur. Type 1 glass vials sealed with a 20 mm Teflon-coated butyl rubber lyophilization stopper and aluminum flip-off crimp seal. Prior to lyophilization, the nominal fill volume target for 250 through 2000 IU vials is 5 mL and 7 mL for the 3000 IU vial. The composition of the formulation excipients prior to lyophilization is the same for all dosage strengths. The powder for injection is reconstituted with 5 mL of diluent comprising 0.325% (w/v) sodium chloride supplied in a sterile prefilled syringe.

The compositions of the drug product solutions prior to lyophilization are presented in Table 3 and composition of the lyophilized powders are presented in Table 4. The compositions of the drug products following reconstitution are presented in Table 1 or in Table 2. (Example 1).

Administration can be carried out by attaching the syringe to a standard IV-infusion tubing/needle set, and delivering the rFIXFc intravenously by standard methods known to those of ordinary skill in the art.

Example 3: Dosage and Method of Administration/Method of Calculating Initial Estimated Dose rFIXFc is long-acting anti-hemophilic factor (recombinant) indicated in adults and children (≥12 years) with hemophilia B (congenital Factor IX deficiency) for, e.g., control and prevention of bleeding episodes, routine prophylaxis to prevent or reduce the frequency of bleeding episodes, and perioperative management (surgical prophylaxis).

Dosing of rFIXFc, formulated as described in Example 1, can be estimated as described in this example, but can also be determined by standard tests such as FIX activity assays described elsewhere herein.

1 IU of rFIXFc per kg body weight is expected to increase the circulating level of Factor IX by 1% [IU/dL]. rFIXFc has been shown to have a prolonged circulating half-life.

No dose adjustment for recovery is generally required. Since subjects can vary in their pharmacokinetic (e.g., half-life, in vivo recovery) and clinical responses to rFIXFc, the expected in vivo peak increase in Factor IX level expressed as IU/dL (or % of normal) or the required dose can be estimated using the following formulas:

TABLE 3 rFIXFc Powder for Injection Composition Per mL Prior to Lyophilization

| Component | Function | Quantity[i] 250 IU Vial | 500 IU Vial | 1000 IU Vial | 2000 IU Vial | 3000 IU vial |
|---|---|---|---|---|---|---|
| rFIXFc | Active ingredient | 50 IU | 100 IU | 200 IU | 400 IU | 429 IU |
| L-Histidine[ii] | Buffer | 3.88 mg | 3.88 mg | 3.88 mg | 3.88 mg | 3.88 mg |
| D-Mannitol | Bulking agent | 23.8 mg | 23.8 mg | 23.8 mg | 23.8 mg | 23.8 mg |
| Sucrose | Stabilizer | 11.9 mg | 11.9 mg | 11.9 mg | 11.9 mg | 11.9 mg |
| Polysorbate 20 | Stabilizer | 0.10 mg | 0.10 mg | 0.10 mg | 0.10 mg | 0.10 mg |
| Water for Injection | Solvent | | | QS to 1 mL | | |

[i]Amounts are nominal
[ii]Small amounts of Hydrochloric Acid and/or Sodium Hydroxide are added during compounding to adjust the pH to 7.1.

TABLE 4

Nominal rFIXFc Powder for Injection Composition Per Vial

| Component | Function | Quantity[i] 250 IU Vial | 500 IU Vial | 1000 IU Vial | 2000 IU Vial | 3000 IU Vial |
|---|---|---|---|---|---|---|
| rFIXFc | Active ingredient | 250 IU | 500 IU | 1000 IU | 2000 IU | 3000 IU |
| L-Histidine[ii] | Buffer | 19.4 mg | 19.4 mg | 19.4 mg | 19.4 mg | 27.2 mg |
| Mannitol | Stabilizer/bulking agent | 119 mg | 119 mg | 119 mg | 119 mg | 167 mg |
| Sucrose | Stabilizer/bulking agent | 59.5 mg | 59.5 mg | 59.5 mg | 59.5 mg | 83.3 mg |
| Polysorbate 20 | Stabilizer | 0.5 mg | 0.5 mg | 0.5 mg | 0.5 mg | 0.7 mg |

IU/dL (or % of normal)=[Total Dose (IU)/body weight (kg)]×recovery (IU/dL per IU/kg)

OR

Dose (IU)=body weight (kg)×Desired Factor IX Rise (IU/dL or % of normal)×reciprocal of recovery (IU/kg per IU/dL)

The following table (Table 5) can be used to guide dosing in bleeding episodes:

TABLE 5

Guide to rFIXFc Dosing for Treatment of Bleeding

| Severity of Bleed | Factor IX Level Required (IU/dL or % of normal) | Dose (IU/kg)/Frequency of Doses (hrs) |
|---|---|---|
| Minor and Moderate For example: joint, superficial muscle/no neurovascular compromise (except iliopsoas), superficial soft tissue, mucous membranes | 30-60 | 30-60 IU/kg Repeat every 48 hours if there is further evidence of bleeding |
| Major For example: iliopsoas and deep muscle with neurovascular injury, or substantial blood loss, retroperitoneum, CNS | 80-120 | For repeat dosing, follow guidelines for major surgery [see Table 6] |

Adapted from: Roberts and Eberst, WFH 2008, and WFH 2012

Subsequent dosage and duration of treatment depends on the individual clinical response, the severity of the Factor IX deficiency, and the location and extent of bleeding (see pharmacokinetics in Example 5 below).

The following table (Table 6) can be used to guide dosing for and perioperative management (surgical prophylaxis):

TABLE 6

Guide to rFIXFc Dosing for Perioperative Management (Surgical Prophylaxis)*

| Type of Surgery | Initial Factor IX Level Required (IU/dL or % of normal) | Dose (IU/kg)/Frequency of Doses (hrs) |
|---|---|---|
| Minor Minor operations including uncomplicated dental extraction | 50 to 80 | 50-80 IU/kg A single infusion may be sufficient. Repeat as needed after 24-48 hours. |
| Major | 60 to 120 (initial level) Days 1-3: maintain level 40-60% Days 4-6: maintain level 30-50% Days 7-14: maintain level 20-40% | 100 IU/kg (initial dose) A repeat dose at 80 IU/kg should be considered after 6-10 hours and then every 24 hours for the first 3 days. Based on the long half-life of rFIXFc, the dose may be reduced and frequency of dosing in the post-surgical setting may be extended after day 3 to every 48 hours. |

Adapted from: Roberts and Eberst, WFH 2008, and WFH 2012
*See Pharmacokinetics (Example 5 below)

For routine prophylaxis, The recommended starting regimens are either: 50 IU/kg once weekly, or 100 IU/kg once every 10-14 days. Either regimen can be adjusted based on subject response (see Pharmacokinetics, Example 5 below).

rFIXFc is contraindicated in subjects who have manifested severe hypersensitivity reactions, including anaphylaxis, to the product or its components.

The clinical response to rFIXFc may vary. If bleeding is not controlled with the recommended dose, the plasma level of Factor IX can be determined, and a sufficient dose of rFIXFc can be administered to achieve a satisfactory clinical response. If the subject's plasma Factor IX level fails to increase as expected or if bleeding is not controlled after rFIXFc administration, the subject's plasma can be tested for the presence of an inhibitor, e.g., neutralizing antibodies. Subjects using rFIXFc can be monitored for the development of Factor IX inhibitors by appropriate clinical observations and laboratory tests known to those of ordinary skill in the art.

Subject's plasma can be monitored for Factor IX activity levels by performing, e.g., the one-stage clotting assay to confirm adequate Factor IX levels have been achieved and maintained, when clinically indicated. Subject's plasma can further be monitored for the development of Factor IX inhibitors.

Example 4. Safety, Efficacy, and Improved Pharmacokinetics Demonstrated in a Phase 3 Clinical Trail of Extended Half-Life Recombinant Fc Fusion Factor IX ("B-LONG" Study)

B-LONG Study Design

Design of the study is global, open-label, nonrandomized, multicenter (50 investigational sites in 17 countries), Phase 3 study.

Figure 1:
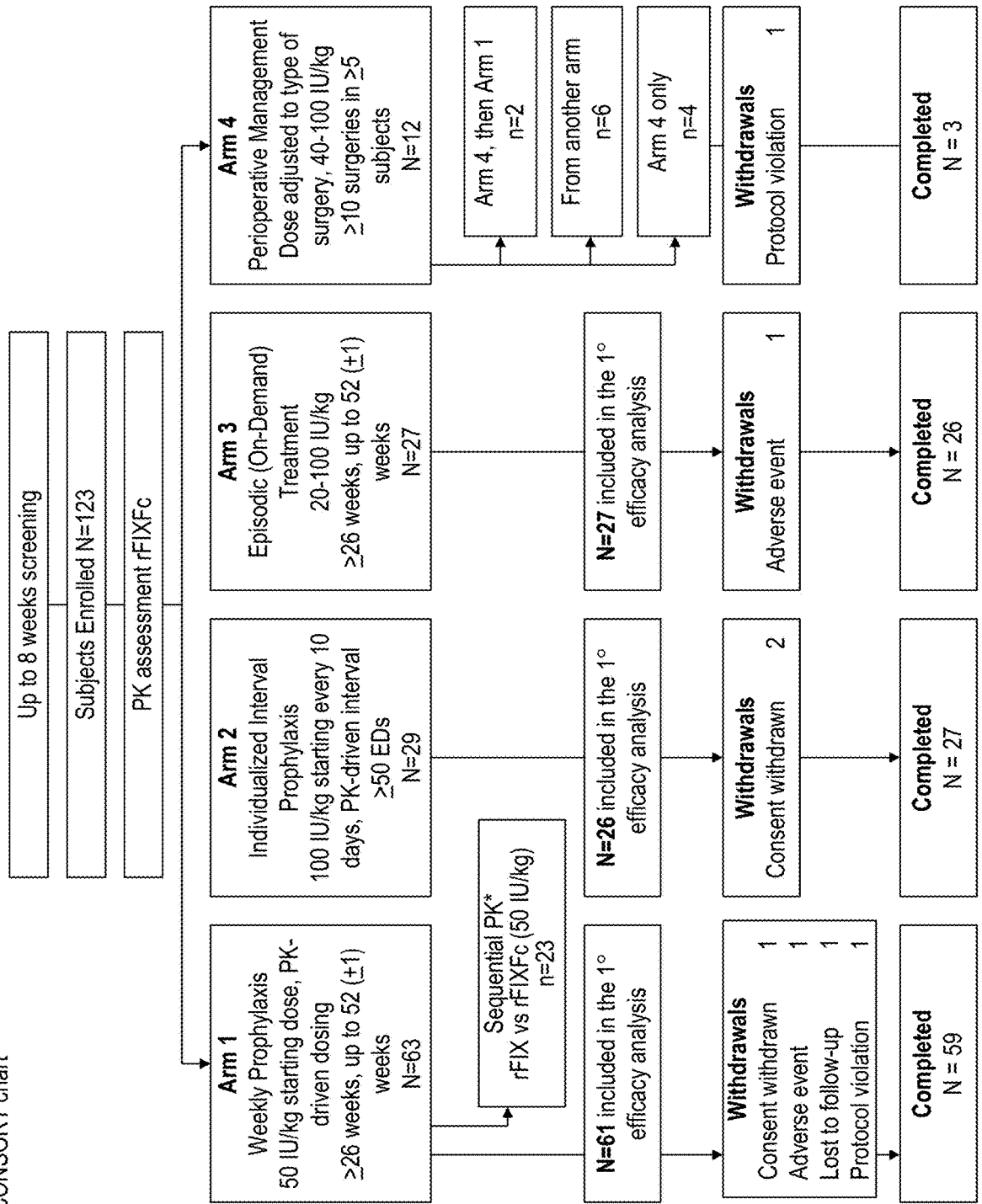

Objectives is to evaluate the efficacy, tolerability, pharmacokinetics (PK), and safety of intravenously-injected recombinant factor IX Fc fusion protein (rFIXFc) in the control and prevention of bleeding episodes, routine prophylaxis, and/or perioperative management in individuals (previously treated subjects (PTP)) with severe hemophilia B. FIG. 1 shows a diagram of the study design. The study disclosed in present example was the largest registrational trial of any therapeutic for hemophilia B, with the most extensive PK analysis conducted to date. The study duration was about 72 weeks.

Key inclusion criteria includes (1) male, (2) older than 12 years of age (weighing at least 40 kg), (3) having diagnosis of severe hemophilia B defined as ≤2% (≤2 IU/dL FIX:C) endogenous factor IX activity, (5) having history of ≥100 prior documented exposure days (EDs) with any currently marketed FIX product, bleeding events and/or treatment with FIX during the 12 weeks prior to enrollment, or at least 8 bleeds in the 52 weeks prior to enrollment if they had been treated episodically, (6) subjects with a history of inhibitors or anaphylaxis associated with FIX or intravenous immunoglobulin, other coagulation disorders, uncontrolled HIV infection, renal dysfunction, or active severe hepatic disease were excluded from the study, and (7) subjects unable or unwilling to adhere to the prophylaxis regimen or diary requirements or those who had received immunosuppressant drugs ≤12 months prior to the study were also excluded.

Three treatment arms are Arm 1 (fixed weekly interval prophylaxis) Arm 2 (individualized interval prophylaxis) Arm 3 (episodic [on-demand regimen] treatment) Arm 4 (perioperative management).

Figure 2:
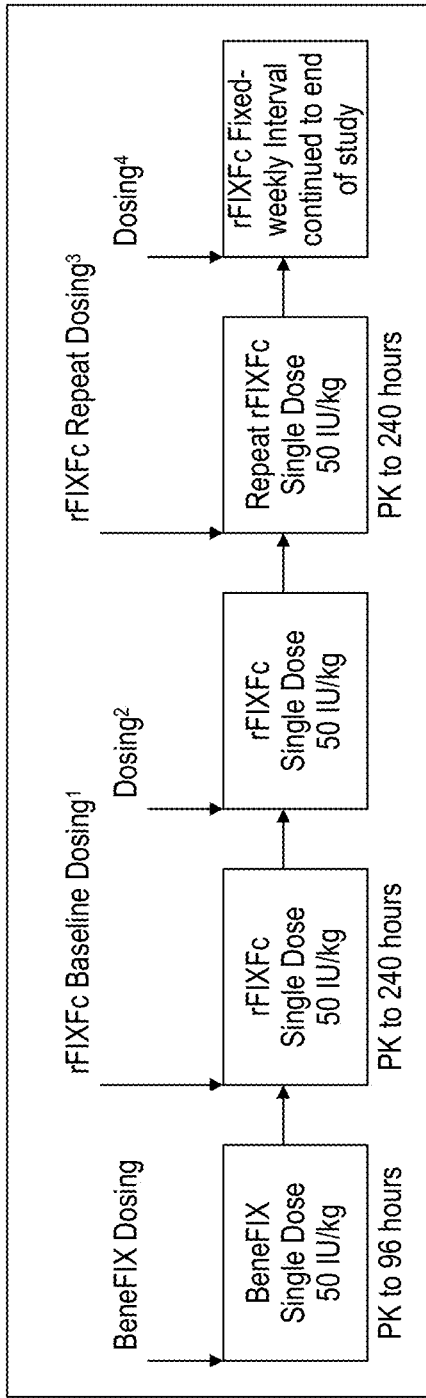
FIG. 2 shows a summary of Arm 1 sequential dosing and PK sampling.

Under Arm 1, subjects were treated weekly with an initial dose of 50 IU/kg, which was subsequently adjusted based on PK profile to maintain trough factor levels sufficient to prevent bleeding in order to maintain 1-3 IU/dL above baseline at trough and/or if subjects experienced ≥2 spontaneous bleeds over 3 consecutive months. A diagram showing the sequential PK subgroup dosing and PK sampling of Arm 1 is shown in FIG. 2. Specifically, adjustments to rFIXFc dose were made based on monitoring of trough at weeks 4, 16, 26, and 39. If the pharmacokinetic values indicated the patient's trough level was 3 IU/dl above baseline or higher at the end of the week, the dose was reduced to target a trough of 1 to 3 IU/dl above baseline. If the pharmacokinetic values indicated the patient's trough level would be less than 1 IU/dl above baseline at the end of the week, the dose was increased to target a trough of 1 to 3 IU/dl above baseline. If the target range could not be achieved, a plasma sample was run to rule out the presence of inhibitors. A repeat trough level was done approximately 1 month after making any dosage adjustments and was repeated monthly until no additional adjustments were necessary. Only the dose of rFIXFc was adjusted in this treatment arm.

Under Arm 2, subjects were treated with 100 IU/kg, at an initial interval of 10 days, which was subsequently adjusted to maintain trough factor levels sufficient to prevent bleeding (interval adjusted per subject's PK profile to maintain 1-3 IU/dL activity above baseline at trough and/or if subject experienced ≥2 spontaneous bleeds over 3 consecutive months). Monitoring took place at weeks 4, 16, 26, and 39 to ensure that this FIX trough level was maintained. Only the interval of rFIXFc was adjusted in this treatment arm.

For any patients in arm 1 or arm 2 who experienced unacceptable bleeding, with two or more spontaneous bleeds over 3 consecutive months, the dose (arm 1) or interval (arm 2) were adjusted to target a FIX trough level of 3 to 5 IU/dl above baseline. If unacceptable bleeding did not occur on rFIXFc at a target trough of 3 to 5 IU/dl above baseline, at the investigator's discretion, and after agreement with the sponsor, rFIXFc could be re-adjusted for a target trough of 1 to 3 IU/dl.

Under Arm 3, subjects received rFIXFc episodic treatment as needed for bleeding (e.g., 20 IU/kg to 100 IU/kg depending on bleeding severity). Minor bleeding episodes were treated with 20-30 IU/kg, moderate to major bleeding episodes with 25-50 IU/kg, and major to life-threatening bleeding episodes with 50-100 IU/kg to target trough FIX levels of 20-30%, 25-50%, and 50-100%, respectively, based on the patient's pharmacokinetic profile.

Under Arm 4, 40-100 IU/kg rFIXFc was administered prior to and following major surgery with dose adjusted to type of surgery; subjects were allowed to enroll directly into the surgery arm, and then move into one of the treatment arms (Arm 1, Arm 2, or Arm 3) post-surgery; or to move into the surgery arm from another arm during the perioperative period if they required a surgery during the study.

Those in Arms 1 and 3 received rFIXFc for up to 52±1 weeks of treatment and Arm 2 for up to 50 exposure days (EDs). Subjects on a previous prophylaxis regimen were only entered into Arm 1 or 2, while those previously using episodic treatment could be enrolled into any of the treatment arms.

A sequential PK subgroup in Arm 1 received 50 IU/kg rFIX at baseline, followed by a ≥5-day washout prior to first administration of rFIXFc. After 120 hours post-injection of rFIX with PK assessment, subjects received a 50 IU/kg of rFIXFc and blood samples were collected over 240 hours for PK profiling. The sequential PK subgroup repeated rFIXFc PK profiling at Week 26. All remaining subjects in the study also underwent non-sequential PK evaluations with rFIXFc for 168-336 hours (7-14 days: Arm 1=10; Arm 2=14; Arm 3=7).

For PK Assessment, all subjects in all arms had an initial PK assessment after their first dose of rFIXFc. A subset of subjects from Arm 1 were assigned to a protocol-specified sequential PK subgroup to compare the PK of rFIXFc with recombinant factor IX (rFIX, BeneFIX®) as follows: following a 120-hour washout period, patients in the sequential pharmacokinetic subgroup in arm 1 received an injection of 50 IU/kg recombinant FIX (rFIX, BeneFIX®) and underwent pharmacokinetic sampling up to 96 hours as follows: pre-injection, 10 (±2) min, 1 h (±15 min), 3 h (±15 min), 6 h (±15 min), 24 (±2) h, 48 (±2) h, 72 (±3) h, and 96 (±3) h from the start of the injection. Each patient had to complete a minimally evaluable pharmacokinetic sampling through 72-hour timepoint to be included in the pharmacokinetics analysis set.

After completion of rFIX pharmacokinetic sampling and ≥5-day from the last rFIX dose, patients received a dose of 50 IU/kg of rFIX Fc fusion protein (rFIXFc) with pharmacokinetic assessment over 240 hours. The rFIXFc sampling was done as follows: pre-injection, 10 (±2) min, 1 h (±15 min), 3 h (±15 min), 6 h (±15 min), 24 (±2) h, 48 (±2) h, 96 (±3) h, 144 (±3) h, 168 (±3) h, 192 (±3) h, and 240 (±3) h from the start of the injection. Each patient had to complete a minimally evaluable pharmacokinetic sampling through 168-hour timepoint to be included in the pharmacokinetics analysis set. A repeat pharmacokinetic assessment of rFIXFc with the same sampling schedule was also performed at week 26.

In arms 1 and 2, the efficacy period started with the date and time of first prophylactic dose following a completed pharmacokinetic sampling period and ended with the last dose administered (for prophylaxis or a bleeding episode) as recorded in the electronic Case Report Form (eCRF) or electronic diary (eDiary). The efficacy period was interrupted for the repeat pharmacokinetic period in arm 1 (sequential pharmacokinetic subgroup) and for all surgical/rehabilitation periods (for both major and minor surgeries) in arms 1 and 2. The efficacy period continued up to the last dose (for prophylaxis or treatment of a bleeding episode) before the repeat pharmacokinetic dose or up to the last dose (for prophylaxis or treatment of a bleeding episode) before the start of a surgical/rehabilitation period, and then resumed at the next prophylactic dose following the end of the pharmacokinetic or surgical/rehabilitation period.

In arm 3, the efficacy period started 1 minute following the last pharmacokinetic sampling timepoint and ended with either the date of last contact or the date of the last entry into the eDiary, whichever was later. The efficacy period was interrupted 1 minute before the start of a surgical/rehabilitation period and restarted at 00:01 the day following the end of the surgical/rehabilitation period.

Plasma FIX activity was measured by the one-stage (activated partial thromboplastin time [aPTT]) clotting assay, which was validated for rFIXFc, BeneFIX®, and human FIX in human plasma samples. FIX activity in citrated plasma samples was measured on an MDA 180 coagulation instrument using commercially available aPTT reagents, e.g., Trinity Biotech (Automated APTT [silica-based activator and phospholipid mixture]), Precision BioLogic (CRYOCHECK™ Factor IX-depleted plasma), and normal reference plasma (Precision BioLogic) as a calibrator (LLOQ 1 IU/dl), which has a potency assigned against the World Health Organization 3rd or 4th plasma International Standard. For all three FIX proteins, the accuracy was within 95% to 104%, and the intra- and inter-assay precision was typically within 10%.

Neutralizing antibodies were detected as follows: The Nijmegen-modified Bethesda assay to detect neutralizing antibodies was performed at screening, baseline, and each visit during study treatment to monitor for the development of an inhibitor. Following the first dose with rFIXFc, inhibitor testing in arms 1 and 2 was conducted at trough at each scheduled clinic visit, with trough defined as a point after the longest interval between scheduled doses. Inhibitor testing in arm 3 was performed following a washout of at least 72 hours (3 days). For new patients entering arm 4, inhibitor testing was performed at screening and after a total of at least 4 EDs were achieved with rFIXFc, within 4 weeks prior to scheduled surgery. Formation of an inhibitor was defined as a neutralizing antibody value ≥0.6 Bethesda units (BU)/ml, confirmed in a second, separately drawn sample within 2-4 weeks. The confidence interval on the inhibitor incidence rate was evaluated using the Clopper-Pearson exact method for a binomial proportion.

Key efficacy outcome measures include (1) annualized bleeding rate (ABR) in Arms 1, 2, and 3 (comparing each of 2 prophylaxis cohorts with the episodic (on-demand) treatment cohort) (i.e., (a) weekly prophylaxis arm (Arm 1) compared with the episodic treatment arm (Arm 3) and (b) individualized interval prophylaxis arm (Arm 2) compared with the episodic treatment arm (Arm 3); (2) response to treatment of bleeding episodes using four-point bleeding response scale (i.e., (a) consumption per subject; (b) weekly dose for Arm 1; (c) dosing interval for Arm 2; and (d) number of injections and dose per injection required to stop a bleeding episode; and (3) treating physicians' assessments of subjects' response to surgery with rFIXFc using a 4-point scale; number of injections and dose required to maintain hemostasis during the surgical period; estimated blood loss during surgery; and number of transfusions required for surgery. For the annualized bleeding rate measurements.

Pharmacokinetic (PK) outcome measures include the followings: (1) PK profiles were assessed by a user-defined 2-compartmental model based on the decay of plasma FIX activity over time as measured by the one-stage (activated partial thromboplastin time) clotting assay in a central laboratory and verified for use in the PK analysis and (2) PK of rFIXFc and recombinant factor IX (rFIX, BENEFIX®) and time to 1% above baseline.

For FIX activity pharmacokinetic analysis, the baseline (endogenous FIX activity) was pre-defined as the lowest observed FIX activity at either screening, pre-dose, post-dose, or from the patient's historical clinical records. For patients whose lowest observed FIX activity was below 1%, the baseline FIX activity was set as zero; for patients whose lowest observed FIX activity was between 1 and 2 IU/dl, the baseline FIX activity was set at the actual observed FIX value. The residual drug was decayed following first order decay with the decay rates determined on an individual basis. The FIX activity over time profiles, corrected by baseline and residual drug, were analyzed using a user-defined and verified two-compartmental model. The user-defined code automated the calculation of additional secondary pharmacokinetic parameters (e.g., Time 1% and 3%), which are not included in the secondary parameter list of the WinNonlin library mode (PHOENIX® WinNonlin 6.2.1.51; Pharsight), thus eliminating the need for manual handling of data outside of the primary analysis and minimizing the risk of introducing human error.

Key safety outcome measures include the followings: (a) clinically significant changes from baseline in laboratory values; (b) incidence of inhibitor development; and (c) incidence of adverse events (AEs) occurring outside of the perioperative management arm (Arms 1, 2, and 3 but not 4).

Statistical Analysis—: Median annualized bleeding rates (ABR) were reported and estimated ABR was calculated using a negative binomial model, which accounted for over-dispersion, to compare ABR between Arms 1 and 2 (prophylaxis regimens) and Arm 3 (episodic treatment). Descriptive statistics were used to provide median and interquartile range (IQR) values for each of arms 1-3. The sequential PK analysis population included Arm 1 subjects with blood samples collected through a minimum of 72 hours from the start of the injection for 50 IU/kg rFIX and a minimum of 168 hours for 50 IU/kg rFIXFc. An analysis of variance model (ANOVA) with variables for study treatment (rFIX or rFIXFc) and subject was used and 95% confidence intervals were provided for geometric means for each treatment. The study was sufficiently powered to detect statistical significance for the occurrence of inhibitors, based FDA guidance that the occurrence of inhibitors in a clinical study can be adequately modeled using the binomial distribution that results in a 2-sided, 95% CI for the true inhibitor incidence of (0.05% to 10.65%) using the exact, Clopper-Pearson method. All statistical tests were performed at the two-sided, 5% significance level. The study was terminated following an interim analysis when prespecified number of major surgical procedures had been completed.

B-LONG Results

Subjects

A total of 123 subjects were enrolled in the study. 115 (93.5%) of subjects completed the study (3 withdrew consent; 1 lost to follow-up; 2 withdrawn due to protocol violation; and 2 discontinued due to adverse events). Subjects underwent a washout period of 96 hours prior to initial study dosing, at which time PK assessments were performed. Enrolled subjects were entered into one of four treatment arms as described in detail above (See also FIG. 1).

Arm 1 (weekly prophylaxis), n=63 (59 completed)
Arm 2 (individualized interval prophylaxis), n=29 (27 completed)
Arm 3 (episodic treatment), n=27 (26 completed)
Arm 4 (perioperative management), n=12 (3 completed), 14 surgeries (8 of the 12 subjects also participated in other treatment arms (Arms 1, 2, and 3))

Baseline characteristics of study subjects (see Table 7) showed a diverse population with substantial co-morbidities of human immunodeficiency virus and hepatitis C virus infection, reflective of the general hemophilia B population. The genotype profile was consistent with that expected in the study population (55% having a missense mutation).

TABLE 7

Subject baseline characteristics

| | Arm 1 N = 63 | Arm 2 (N = 29) | Arm 3 (N = 27) | Arm 4 (N = 12) | Total (N = 123) |
|---|---|---|---|---|---|
| Age, median (min-max) | 28 (12-71) | 33 (12-62) | 36 (14-64) | 34 (17-61) | 30 (12-71) |
| Weight (kg), median (min-max) | 70.2 (45.2-186.7) | 76.0 (50.0-128.0) | 65.0 (45.0-91.7) | 65.0 (47.9-100.5) | 73.3 (45.0-186.7) |

TABLE 7-continued

Subject baseline characteristics

| | Arm 1 N = 63 | Arm 2 (N = 29) | Arm 3 (N = 27) | Arm 4 (N = 12) | Total (N = 123) |
|---|---|---|---|---|---|
| BMI (kg/m²), median (min-max) | 24.29 (16.3-49.6) | 25.69 (18.6-36.6) | 24.16 (15.2-29.4) | 22.86 (18.3-32.8) | 24.78 (15.2-49.6) |
| Race, n (%) | | | | | |
| White | 41 (65.1) | 18 (62.1) | 11 (40.7) | 6 (50.0) | 73 (59.3) |
| Black | 7 (11.1) | 2 (6.9) | 1 (3.7) | 2 (16.7) | 10 (8.1) |
| Asian | 7 (11.1) | 7 (24.1) | 14 (51.9) | 2 (16.7) | 29 (23.6) |
| American Indian or Alaska Native | 0 (0.0) | 0 (0.0) | 1 (3.7) | 0 (0.0) | 1 (0.8) |
| Other | 8 (12.7) | 2 (6.9) | 0 (0.0) | 2 (16.7) | 10 (8.1) |
| Geographic location, n (%) | | | | DNS | 35 (29.4)* |
| Europe | 21 (33.3) | 12 (41.4) | 2 (7.4) | DNS | 36 (30.3) |
| North America | 18 (28.6) | 7 (24.1) | 11 (40.7) | DNS | 48 (40.3)* |
| Other† | 24 (38.1) | 10 (34.5) | 14 (51.9) | DNS | |
| Baseline FIX level, n (%) | | | | DNS | 98 (82.4)* |
| <1 IU/dl | 50 (79.4) | 22 (75.9) | 26 (96.3) | DNS | 21 (17.6)* |
| 1-2 IU/dl | 13 (20.6) | 7 (24.1) | 1 (3.7) | DNS | |
| Genotype, n (%) | | | | | |
| Missense mutation | 34 (54.0) | 19 (65.5) | 14 (51.9) | 6 (50.0) | 68 (55.3) |
| Nonsense mutation | 11 (17.5) | 6 (20.7) | 6 (22.2) | 1 (8.3) | 23 (18.7) |
| Frameshift | 6 (9.5) | 1 (3.4) | 1 (3.7) | 2 (16.7) | 9 (7.3) |
| Unknown | 2 (3.2) | 0 (0.0) | 6 (22.2) | 1 (8.3) | 9 (7.3) |
| Splice mutation | 6 (9.5) | 2 (6.9) | 0 (0.0) | 0 (0.0) | 8 (6.5) |
| Large deletions | 3 (4.8) | 0 (0.0) | 0 (0.0) | 2 (16.7) | 4 (3.3) |
| Partial gene deletion | 1 (1.6) | 1 (3.4) | 0 (0.0) | 0 (0.0) | 2 (1.6) |
| Pre-study FIX regimen, n (%) | | | | DNS | 48 (40.7)* |
| Prophylaxis | 33 (53.2) | 15 (51.7) | 0 | DNS | 70 (59.3)* |
| episodic | 29 (46.8) | 14 (48.3) | 27 (100.0) | DNS | |
| Est. bleeds prior 12 mo, median no. (min, max) | 10.5 | 10.0 | 18.0 | DNS | 2.0 (0, 21)* |
| Prior prophylaxis | 2.5 (0, 21) | 2.0 (0, 7) | 0 | DNS | 22.0 (5, 100)* |
| Prior episodic | 23.0 (6, 70) | 25.0 (10, 100) | 18.0 (5, 50) | DNS | 58 (48.7)* |
| ≥1 Target joint, n (%) | 36 (57.1) | 8 (27.6) | 14 (51.9) | DNS | 35 (29.4)* |
| Est. bleeds prior 12 mo, median no. (min, max) | 10.5 | 10.0 | 18.0 | DNS | 36 (30.3)* |
| Family history of inhibitor, n (%) | 0 ( ) | 0 ( ) | 2 (7.4) | 0 ( ) | 2 (1.6) |
| HIV positive, n (%) | 5 (7.9) | 1 (3.4) | 2 (7.4) | 2 (16.7) | 9 (7.3) |
| HCV positive, n (%) | 38 (60.3) | 15 (51.7) | 14 (51.9) | 7 (58.3) | 70 (56.9) |

*totals for Arms 1-3 only
BMI, body mass index; HIV, human immunodeficiency virus; HCV, hepatitis C virus; DNS, data not shown.

Of the 48 subjects on a previous prophylaxis regimen, >80% were infusing ≥2 times weekly. Subjects in the prophylaxis cohorts (Arms 1 and 2) were well balanced for prior regimen and bleeding history. There were fewer subjects with target joints in Arm 2 and more subjects with a baseline FIX activity <1 IU/dL in Arm 3. The median (minimum, maximum) durations of treatment in arms 1, 2, and 3 were 51.6 (<1, 97), 58.3 (<1, 126), and 40.9 (28, 54) weeks, respectively, and the median (minimum, maximum) days of exposure were 55.0 (1, 105), 38.0 (1, 71), and 16.0 (4, 35), respectively. A total of 5243 of rFIXFc injections were administered during this study, corresponding to 5144 EDs (117.1 patient-years of exposure). Treatment adherence, in subjects who were ≥80% compliant with their prescribed dose (Arm 1) or dosing interval (Arm 2), was 96.6% overall in the prophylaxis arms (Arm 1=95.1%, Arm 2=100%).

For patients in arm 4, major surgery was defined as any surgical procedure (elective or emergent) that usually, but not always, involves general anesthesia and/or respiratory assistance in which a major body cavity is penetrated and exposed, or a substantial impairment of physical or physiological functions is produced (e.g., laparotomy, thoracotomy, craniotomy, joint replacement, or limb amputation).

Study Visit Schedule:

For arms 1-3, study visits occurred at screening (8 weeks), baseline, week 4, week 16, week 26, week 39, and week 52. Additionally, patients in arms 1-3 had a 30-day follow-up phone call, unless they enrolled in the ongoing extension study (NCT01425723). Patients in arm 4 had study visits at screening, baseline, the day of surgery, 1 week after surgery, and 1 week post-recovery.

Sequential Pharmacokinetic Subgroup

Length of sampling times for rFIX and rFIXFc were based upon previously reported half-lives, allowing sufficient time for decay (normally three to five times the previously observed half-life) for accurate description of pharmacokinetics. Following a 120-hour washout period, patients in the sequential pharmacokinetic subgroup in arm 1 received an injection of 50 IU/kg recombinant FIX (rFIX) and underwent pharmacokinetic sampling up to 96 hours as follows: pre-injection, 10 (±2) min, 1 h (±15 min), 3 h (±15 min), 6 h (±15 min), 24 (±2) h, 48 (±2) h, 72 (±3) h, and 96 (±3) h from the start of the injection. Each patient had to complete a minimally evaluable pharmacokinetic sampling through 72-hour timepoint to be included in the pharmacokinetics analysis set.

After completion of rFIX pharmacokinetic sampling and ≥5-day from the last rFIX dose, patients received a dose of 50 IU/kg of rFIX Fc fusion protein (rFIXFc) with pharmacokinetic assessment over 240 hours. The rFIXFc sampling was done as follows: pre-injection, 10 (±2) min, 1 h (±15 min), 3 h (±15 min), 6 h (±15 min), 24 (±2) h, 48 (±2) h, 96 (±3) h, 144 (±3) h, 168 (±3) h, 192 (±3) h, and 240 (±3) h from the start of the injection. Each patient had to complete a minimally evaluable pharmacokinetic sampling through 168-hour timepoint to be included in the pharmacokinetics analysis set. A repeat pharmacokinetic assessment of rFIXFc with the same sampling schedule was also performed at week 26.

Efficacy

In total, 119 subjects were included in the efficacy analysis. Median annualized bleeding rate (ABR) with the $25^{th}$ and $75^{th}$ percentiles (interquartile range (IQR)), which were driven primarily by spontaneous bleeds, were determined for Arms 1, 2, and 3 as shown in FIGS. 3A, 3B, and Table 8 and summarized below:

Weekly prophylaxis arm (Arm 1): 2.95 (1.01-4.35)
Individualized interval prophylaxis arm (Arm 2): 1.38 (0-3.43)
Episodic treatment arm (Arm 3): 17.69 (10.77-23.24)

(a) Prophylaxis Dose and Interval Titration, and Episodic Treatment of Bleeding Episodes Samples to measure FIX levels were drawn for all patients during the course of the study to estimate each patient's pharmacokinetics parameters to guide the appropriate dose or dosing interval adjustments toward a target trough of 1-3 IU/dl of FIX levels above baseline.

In arm 1 (fixed weekly interval): All patients in this arms initially received rFIXFc 50 IU/kg injection once weekly. Adjustments to rFIXFc dose were made based on monitoring of trough at weeks 4, 16, 26, and 39. If the pharmacokinetic values indicated the patient's trough level was 3 IU/dl above baseline or higher at the end of the week, the dose was reduced to target a trough of 1 to 3 IU/dl above baseline. If the pharmacokinetic values indicated the patient's trough level would be less than 1 IU/dl above baseline at the end of the week, the dose was increased to target a trough of 1 to 3 IU/dl above baseline. If the target range could not be achieved, a plasma sample was run to rule out the presence of inhibitors. A repeat trough level was done approximately 1 month after making any dosage adjustments and was repeated monthly until no additional adjustments were necessary. Only the dose of rFIXFc was adjusted in this treatment arm.

In arm 2 (individualized dosing interval), a dose of 100 IU per kilogram of rFIXFc was administered IV at an interval based on the patient's baseline pharmacokinetic assessment to achieve a target trough of 1 to 3 IU/dl above baseline. Monitoring took place at weeks 4, 16, 26, and 39 to ensure that this FIX trough level was maintained. Only the interval of rFIXFc was adjusted in this treatment arm.

For any patients in arm 1 or arm 2 who experienced unacceptable bleeding, with two or more spontaneous bleeds over 3 consecutive months, the dose (arm 1) or interval (arm 2) were adjusted to target a FIX trough level of 3 to 5 IU/dl above baseline. If unacceptable bleeding did not occur on rFIXFc at a target trough of 3 to 5 IU/dl above baseline, at the investigator's discretion, and after agreement with the sponsor, rFIXFc could be re-adjusted for a target trough of 1 to 3 IU/dl.

In arm 3 (episodic treatment), minor bleeding episodes were treated with 20-30 IU/kg, moderate to major bleeding episodes with 25-50 IU/kg, and major to life-threatening bleeding episodes with 50-100 IU/kg to target trough FIX levels of 20-30%, 25-50%, and 50-100%, respectively, based on the patient's pharmacokinetic profile.

(b) Efficacy Period

In arms 1 and 2, the efficacy period started with the date and time of first prophylactic dose following a completed pharmacokinetic sampling period and ended with the last dose administered (for prophylaxis or a bleeding episode) as recorded in the electronic Case Report Form (eCRF) or electronic diary (eDiary). The efficacy period was interrupted for the repeat pharmacokinetic period in arm 1 (sequential pharmacokinetic subgroup) and for all surgical/rehabilitation periods (for both major and minor surgeries) in arms 1 and 2. The efficacy period continued up to the last dose (for prophylaxis or treatment of a bleeding episode) before the repeat pharmacokinetic dose or up to the last dose (for prophylaxis or treatment of a bleeding episode) before the start of a surgical/rehabilitation period, and then resumed at the next prophylactic dose following the end of the pharmacokinetic or surgical/rehabilitation period.

In arm 3, the efficacy period started 1 minute following the last pharmacokinetic sampling timepoint and ended with either the date of last contact or the date of the last entry into the eDiary, whichever was later. The efficacy period was interrupted 1 minute before the start of a surgical/rehabilitation period and restarted at 00:01 the day following the end of the surgical/rehabilitation period.

Treatment Compliance

Compliance with treatment dosing was monitored and documented by site staff. For between-visit administration, patients self-administered rFIXFc and recorded treatment in the hand-held eDiary, which was reviewed during periodic calls to the patient and at each visit by study site staff and the clinical monitor.

Analysis of patients' compliance was based on data from the eCRF and eDiary. Analyses of compliance included patients' compliance with the prescribed prophylactic regimens. For weekly prophylaxis, analyses included percentage of nominal doses taken per patient within the 80% to 125% range. Similarly, for individualized interval prophylaxis, analysis included the percentage of doses taken per patient within ±36 hours of the prescribed interval. Patients were considered compliant if the calculated compliance rate was at least 80%.

Analytical Method

Plasma FIX activity was measured by the one-stage (activated partial thromboplastin time [aPTT]) clotting assay, which was validated for rFIXFc, BeneFIX, and human FIX in human plasma samples. FIX activity in citrated plasma samples was measured on an MDA 180 coagulation instrument using commercially available aPTT reagents, e.g., Trinity Biotech (Automated APTT [silica-based activator and phospholipid mixture]), Precision Bio-Logic (Cryocheck™ Factor IX-depleted plasma), and normal reference plasma (Precision BioLogic) as a calibrator (LLOQ 1 IU/dl), which has a potency assigned against the World Health Organization 3rd or 4th plasma International Standard. For all three FIX proteins, the accuracy was within 95% to 104%, and the intra- and inter-assay precision was typically within 10%.

TABLE 8

Summary of Median (IQR*) Annualized Bleed Rate (ABR) by Treatment Arm

| Bleeding Episode Etiology | Prophylaxis Fixed Weekly Interval (N = 61) | Prophylaxis Individualized Interval (N = 26) | Episodic (On Demand) (N = 27) | Total |
|---|---|---|---|---|
| Number of weeks on rFIXFc treatment, median (min, max) | 51.6 (<1, 97) | 58.3 (<1, 126) | 40.9 (28, 54) | 51.4 (<1, 126) |
| ABR, negative binomial regression model (95% CI) | 3.12 (2.46, 3.95) | 2.40 (1.67, 3.47) | 18.67 (14.01, 24.89) | |
| % Reduction vs. arm 3 (P value)* | 83% (<0.001) | 87% (<0.001) | | |
| ABR by type, location of bleeds, and baseline trough level, median (IQR): | | | | |
| Overall | 2.95 (1.01, 4.35) | 1.38 (0.00, 3.43) | 17.69 (10.77, 23.24) | |
| Spontaneous | 1.04 (0.00, 2.19) | 0.88 (0.00, 2.30) | 11.78 (2.62, 19.78) | |
| Traumatic | 0.99 (0.00, 2.13) | 0.00 (0.00, 0.78) | 2.21 (0.00, 6.81) | |
| Joint | 1.1 (0, 4.0) | 0.4 (0, 7.8) | 13.6 (6.1, 21.6) | |
| Spontaneous | 1.0 (0.0, 2.8) | 0.0 (0, 6.2) | 5.1 (0.0, 17.3) | |
| Traumatic | 0.0 (0.0, 1.1) | 0.0 (0.0, 7.5) | 1.3 (0.0, 3.5) | |
| Muscle | 0.0 (0.0, 1.0) | 0.0 (0.0, 0.0) | 4.0 (1.0, 6.8) | |
| Spontaneous | 0.0 (0.0, 0.0) | 0.0 (0.0, 0.0) | 1.0 (0.0, 3.5) | |
| Traumatic | 0.0 (0.0, 0.0) | 0.0 (0.0, 0.0) | 1.1 (0.0, 2.7) | |
| Baseline trough level | | | | |
| <1 IU/dl | 2.6 (1.0, 4.1) | 1.1 (0.0, 2.9) | 18.5 (13.2, 23.2) | |
| 1-2 IU/dl | 4.5 (0.0, 6.4) | 3.4 (0.0, 5.7) | 7.7 (7.7, 7.7) | |

*Reduction in ABR compared with arm 3, calculated using negative binomial model.

The ABR was significantly reduced for both prophylaxis arms, by 83% and 87% compared with episodic treatment based on estimates from a negative binominal regression model (3.12, 2.40, and 18.67 for arms 1, 2, and 3, respectively; P<0.001 Table 8). The lower ABR in the prophylaxis arms was consistent across all demographic and disease-based subgroups in prespecified subgroup analyses (FIG. 3 and Table 2). Furthermore, limiting the analysis to patients on a prior episodic regimen, the reductions in ABRs of 83% and 89% for arms 1 and 2, respectively, were consistent with the primary analysis. The proportion of patients without any bleeding episodes on prophylaxis during the study was 23.0% for arm 1 and 42.3% for arm 2. Additionally, analyses of bleeding episodes by type and location showed a low ABR in both prophylactic arms (Table 8). The median (IQR) weekly does of rFIXFc for subjects in Arm 1 in the last 3 months of the study was 40.5 IU/kg. The dosing interval for approximately half of the study population in the individualized interval prophylaxis arm (Arm 2) was ≥14 days during the last 6 months on study. A summary of the median dosing for Arm 1 and Arm 2 is shown in Tables 9A and 9B.

TABLE 9A

Arm 1 and Arm 2 Dosing Summary

| | n | Arm 1 | n | Arm 2 |
|---|---|---|---|---|
| Median dose, IU/kg/wk (IQR) | | | | |
| Overall | 61 | 45.2 (38.1-53.7) | | |
| Last 3 months | 58 | 40.5 (30.3-53.8) | | |
| Median dosing interval (IQR) | | | | |
| Overall | | | 26 | 12.5 (10.4-13.4) |
| Last 3 months[a] | | | 26 | 14.0 (11.3-14.0) |

[a]Based on subjects in study ≥6 months
IQR = 25th and 75th percentiles.
IQR, interquartile range.

TABLE 9B

Arm 1 and Arm 2 Dosing Summary

| | Arm 1 | Arm 2 | Arm 3 | Total |
|---|---|---|---|---|
| Number of injections per episode required for resolution of bleeding, % of episodes | | | | |
| 1 | 85.0 | 85.1 | 93.5 | 90.4 |
| 2 | 9.0 | 11.9 | 5.2 | 6.9 |
| 3 | 6.0 | 3.0 | 1.2 | 2.7 |
| ≥4 | 0.0 | 0.0 | 0.0 | 0.0 |
| Dose of rFIXFc required for resolution of bleeding episodes, median IU/kg (min, max) | 47.1 (16.6, 99.1) | 44.8 (14.3, 110.1) | 46.0 (7.9, 111.1) | |
| Weekly prophylactic dose in arm 1[†], median IU/kg (min, max) | | | | |
| Overall | 45.2 (25.0, 74.3) | | | |
| Last 6 mo on study[‡] | 40.7 (21.3, 82.7) | | | |

TABLE 9B-continued

Arm 1 and Arm 2 Dosing Summary

|  | Arm 1 | Arm 2 | Arm 3 | Total |
|---|---|---|---|---|
| Last 3 mo on study§ | 40.5 (16.7, 87.6) | | | |
| Prophylactic dosing interval in arm 2†, median days (min, max) | | | | |
| Overall | | 12.5 (7.8, 15.9) | | |
| Last 6 mo on study‡ | | 13.8 (7.8, 19.1) | | |
| Last 3 mo on study§ | | 14.0 (7.7, 20.8) | | |
| Subject's assessment of response to rFIXFc injections, n (% of injections)* | | | | |
| Excellent or Good | 146 (76.4) | 57 (77.0) | 363 (85.4) | 566 (82.0) |
| Moderate | 40 (20.9) | 15 (20.3) | 55 (12.9) | 110 (15.9) |
| No Response | 5 (2.6) | 2 (2.7) | 7 (1.6) | 14 (2.0) |
| Physicians' global assessment of rFIXFc response score, n (% of visits)** | | | | |
| Excellent or Effective | 264 (98.8) | 122 (99.2) | 94 (97.9) | 580 (98.8) |
| Partially Effective | 3 (1.1) | 1 (0.8) | 2 (2.1) | 6 (1.2) |
| Ineffective | 0 | 0 | 0 | 0 |

†Pharmacokinetic driven dosing (arm 1) or interval (arm 2) changes were permitted to achieve trough levels 1% to 3% above baseline. If patients had two breakthrough spontaneous bleeding episodes in a rolling 3-month period, doses (arm 1) or intervals (arm 2) could be adjusted to provide more protection.
‡In patients on study for ≥9 months
§In patients on study for ≥6 months
ABR denotes annualized bleeding rate,
CI confidence interval,
IQR interquartile range ($25^{th}$ and $75^{th}$ percentiles),
rFIXFc recombinant factor IX Fc fusion protein,
SD standard deviation.
*Excellent: Abrupt pain relief and/or improvement in signs of bleeding within approximately 8 hours after the initial injection; Good: Definite pain relief and/or improvement in signs of bleeding within approximately 8 hours after an injection, but possibly requiring more than one injection after 24 to 48 hours for complete resolution; Moderate: Probable or slight beneficial effect within 8 hours after the initial injection and requiring more than one injection; No response: No improvement, or condition worsened, within approximately 8 hours after the initial injection.
**Excellent: Bleeding episodes responded to less than or equal to the usual number of injections or less than or equal to the usual dose of rFIXFc, or the rate of breakthrough bleeding during prophylaxis was less than or equal to that usually observed. Effective: Most bleeding episodes responded to the same number of injections and dose, but some required more injections or higher doses, or there was a minor increase in the rate of breakthrough bleeding. Partially Effective: Bleeding episodes most often required more injections and/or higher doses than expected, or adequate breakthrough bleeding prevention during prophylaxis required more frequent injections and/or higher doses. Ineffective: routine failure to control hemostasis or hemostatic control required additional agents.

Control of bleeding: A total of 636 bleeding episodes (Arm 1=167, Arm 2=67, Arm 3=402) in 89 subjects were treated, over 90% (90.4%) of bleeding episodes were controlled by a single injection of rFIXFc and 97.3% were controlled by ≤2 injections. The median number of injections needed to resolve bleeding episodes was 1.0 regardless of type, compliance status, or location of bleeding episode, excluding two internal bleeding episodes in Arm 2 that required 2 injections for resolution. The median dose per injection was 46.1 IU/kg and the median total dose for the bleeding episodes was 47.0 IU/kg. For the 61 (9.6%) of bleeding episodes that required >1 injection for resolution, the median interval between the first and second injection was 45 hours. Overall, subject assessment of response to treatment with rFIXFc was excellent or good for 76.4%, 77.0%, and 85.4% of injections in Arms 1, 2, and 3, respectively. Physician' global assessment of subject response to their rFIXFc regimen was rated as excellent or effective for 98.8%, 99.2%, and 97.9% in Arms 1, 2, and 3, respectively. Bleeding episodes are summarized in Table 10.

TABLE 10

Summary of Efficacy in Control of Bleeding

| New Bleeding episodes | (N = 636) |
|---|---|
| # of Injections to treat bleeding episodes | |
| 1 injection | 575 (90.4%) |
| 2 injections | 44 (6.9%) |
| 3 injections | 17 (2.7%) |
| Median dose per injection (IU/kg) to treat a bleeding episode (IQR) | 46.07 (32.86, 57.03) |
| Median total dose (IU/kg) to treat a bleeding episode (IQR) | 46.99 (33.33, 62.50) |
| Response to first injection | (N = 613) |
| Excellent or good | 513 (83.7%) |
| Moderate | 90 (14.7%) |
| No response | 10 (1.6%) |

This efficacy was similar when examined across arms, on a per subject basis, and for subjects who treated an episode more than 8 hours after the onset of symptoms.

The dosing interval for subjects in Arm 2 increased from the initial 10 days to 53.8% of subjects achieving a median dose interval of ≥14 days during the last 3 months on the study.

Perioperative management: Endpoints for Arm 4 included investigators'/surgeons' assessments of subjects' response to surgery with rFIXFc; number of injections and dose required to maintain hemostasis during the surgical period; estimated blood loss during and after surgery; and number of transfusions required for surgery. Overall, 14 major surgeries were performed in 12 subjects, including knee arthroscopy (n=4) and ankle arthroscopy (n=1), knee replacements (n=4), and others (n=5). Hemostasis was rated as excellent (13/14) or good (1/14) by the investigator/surgeon. The median estimated bleed loss was 65.5 mL (range: 0.0-300.0 mL) during surgery and 0.0 mL (range: 0.0-500 mL) post-operatively. No blood transfusions were required during surgery, but two subjects received transfusions in the post-operative period. A single injection of rFIXFc was required in 85.7% of surgeries to maintain hemostasis during surgery, at a median dose of 90.9 IU/kg per injection. On the pre-operative day, 1-2 injections were administered and 2-3 injections during the 3-day post-operative period. On the day of surgery, post-operative days 1-3, and post-operative days 4-14, the median rFIXFc consumption (summarized over all injections during referenced time period) was 146.1 IU/kg, 168.2 IU/kg, and 277.1 IU/kg, respectively. Overall, ≥1 adverse event (AE) was reported for 10 (83.3%) of the 12 subjects and 3 subjects reported 6 serious AEs, all of which were resolved and judged as unrelated to rFIX treatment. Treating physicians rated the hemostatic efficacy of rFIXFc as excellent or good in 100% of surgeries.

One injection was sufficient to resolve 90.4% of bleeding episodes in Arm 1, with a median dose per injection of 46 IU/kg. Overall, 82.0% of rFIXFc injections were rated by subjects as producing an excellent or good response. The physicians' global assessment of subject response to rFIXFc was rated as excellent or effective for 98.8% of the subject visits.

The weekly rFIXFc dose for subjects in Arm 1 decreased from the initial 50 IU/kg to a median of 45 IU/kg when averaged over the course of the study. The initial dosing interval of 10 days for subjects in Arm 2 increased over the course of the study to 12.5 days, with 12 subjects (46%) achieving a dose interval of ≥14 days for the last 6 months, and 14 subjects (53.8%) for the last 3 months on the study.

Hemostasis in Arm 4 was rated as excellent or good by investigators or surgeons for 100% of 14 major surgeries performed in 12 subjects. Types of major surgeries included treatment of a dental abscess and pilonidal cyst to knee arthroplasty or knee replacement (n=6) and amputation of a finger (n=2). A single injection of rFIXFc was sufficient to maintain hemostasis during 85.7% of major surgeries and the median average dose per injection for the 14 surgeries was 91 IU/kg.

Hemostatic response to dosing during surgery and post-operatively is summarized in Table 11.

TABLE 11

Summary of Hemostatic Response During Surgery and Post-Operatively

| | Number of Procedures | Response | | | |
|---|---|---|---|---|---|
| | (Number of Subjects) | Excellent | Good | Fair | Poor/None |
| Major Surgery | | | | | |
| Total Knee Replacement | 5 (5) | 4 | 1 | | |
| Arthroscopic Procedure | 1 (1) | 1 | | | |
| Arthroscopic Ankle Fusion | 1 (1) | 1 | | | |

TABLE 11-continued

Summary of Hemostatic Response During Surgery and Post-Operatively

| | Number of Procedures | Response | | | |
|---|---|---|---|---|---|
| | (Number of Subjects) | Excellent | Good | Fair | Poor/None |
| Closure of Rectal Fistula | 1 (1) | 1 | | | |
| External Fixation of Knee | 1 (1) | 1 | | | |
| Tendon Transfer | 1 (1) | 1 | | | |
| I & D[1] of Dental Abscess with Extractions | 1 (1) | 1 | | | |
| I & D[1] Pilonidal Cyst | 1 (1) | 1 | | | |
| Debridement, Partial Amputation | 1 (1) | 1 | | | |
| Amputation of Finger | 1 (1) | 1 | | | |
| Minor surgery[2] | 15 (13) | 10 | 1 | 1 | |

[1]Incision and Drainage
[2]Assessment of response not provided for 3 minor surgeries

PK

For FIX activity pharmacokinetic analysis, the baseline (endogenous FIX activity) was pre-defined as the lowest observed FIX activity at either screening, pre-dose, post-dose, or from the patient's historical clinical records. For patients whose lowest observed FIX activity was below 1%, the baseline FIX activity was set as zero; for patients whose lowest observed FIX activity was between 1 and 2 IU/dl, the baseline FIX activity was set at the actual observed FIX value. The residual drug was decayed following first order decay with the decay rates determined on an individual basis. The FIX activity over time profiles, corrected by baseline and residual drug, were analyzed using a user-defined and verified two-compartmental model. The user-defined code automated the calculation of additional secondary pharmacokinetic parameters (e.g., Time 1% and 3%), which are not included in the secondary parameter list of the WinNonlin library mode (PHOENIX® WinNonlin 6.2.1.51; Pharsight), thus eliminating the need for manual handling of data outside of the primary analysis and minimizing the risk of introducing human error.

The geometric mean terminal half-life of rFIXFc was approximately 82 hours, which is 2.4-fold (i.e., 2.43 fold) longer than that of BENEFIX® (approximately 34 hours) in the 96-=hour sample (p<0.001). With the 48-hour sampling, a 4.83-fold increase in half-life was observed. rFIXFc had a 2.39-fold longer mean residence time (MRT) compared with rFIX, resulting in 2.21-fold and 2.04-fold extensions of time to 1 IU/dL and 3 IU/dL above baseline, respectively (P<0.001). Comparative data for rFIXFc at baseline and Week 26 was available for 21 subjects and showed no statistical difference for any PK parameters. Table 12 shows comparative PK data for rFIXFc versus rFIX from 22 subjects in the Arm 1 sequential PK subgroup, using compartmental models for the one-stage clotting assay.

As shown in Table 12, incremental recovery was comparable between rFIX and rFIXFc (P=0.713). There was a 2.43-fold increase in the terminal FIX half-life following rFIXFc compared with rFIX when a 96-hour sampling schedule was used (82.1 vs 33.8, respectively; P<0.001); see Table 12 and FIG. 4). Using the traditional 48-hour sampling schedule, which has been used to show the generally accepted half-life of rFIX (~18 hours), rFIXFc showed a 4.84-fold increased half-life compared to rFIX. Compared with rFIX, rFIXFc had a 2.39-fold longer mean residence time (MRT: 41.2 vs 98.6 hours; P<0.001), resulting in 2.21-fold extension of time to 1 IU/dL above baseline (5.1 vs 11.2 days; P<0.001). rFIXFc time to 1 IU/dL (1%) FIX and time to 3 IU/dL (3%) IU/dL were 11.2 and 5.8 days, respectively (see Table 12 and FIG. 4). Intra-individual rFIXFc PK parameters were comparable between baseline and Week 26, indicating that the PK profile of rFIXFc was stable following repeated dosing over 26 weeks.

TABLE 12A

Sequential PK parameters in Arm 1 subgroup (N = 22) of rFIXFc compared with rFIX.

| PK Parameter* | Geometric mean for rFDCFc PK (95% CI) | Geometric mean for rFIX PK (95% CI) | Geometric mean ratio (95% CI), P-value |
|---|---|---|---|
| Terminal $t_{1/2}$ (h) | 82.1 (71.4, 94.5) | 33.8 (29.1, 39.2) | 2.43 (2.02, 2.92) P < 0.001 |
| Terminal $t_{1/2}$ (h) 48-hour PK | NA | 17.0 (15.9, 18.3) | — |
| $C_{max}$ (IU/dL) | 40.8 (33.6, 49.6) | 43.1 (36.7, 50.6) | 0.95 (0.81, 1.11) P = 0.491 |
| CL (mL/h/kg) | 3.19 (2.84, 3.59) | 6.34 (5.64, 7.13) | 0.50 (0.46, 0.55) P < 0.001 |
| $V_{ss}$ (mL/kg) | 314.8 (277.8, 356.8) | 261.1 (222.9, 305.9) | 1.21 (1.06, 1.38) P = 0.008 |
| AUC/dose (IU*h/dL per IU/kg) | 31.3 (27.9, 35.2) | 15.8 (14.0, 17.7) | 1.99 (1.82, 2.17) P < 0.001 |
| MRT (h) | 98.6 (88.2, 110.3) | 41.2 (36.0, 47.2) | 2.39 (2.12, 2.71) P < 0.001 |
| Incremental recovery (IU/dL per IU/kg) | 0.9 (0.8, 1.1) | 0.9 (0.8, 1.1) | 0.97 (0.84, 1.12) P = 0.713 |
| Time to 1 IU/dL above baseline** (days) | 11.2 (10.2, 12.4) | 5.1 (4.6, 5.7) | 2.21 (2.04, 2.39) P < 0.001 |
| Time to 3 IU/dL above baseline** (days) | 5.8 (5.1, 6.6) | 2.8 (2.6, 3.1) | 2.04 (1.87, 2.21) P < 0.001 |

*User-defined 2-compartmental model one-stage clotting assay
**Following 50-IU/kg dose
$t_{1/2}$, half-life;
$C_{max}$, maximal concentration;
CL, clearance;
Vss, volume of distribution at steady state;
MRT, mean residence time;
CI, confidence interval;
AUC, area under the concentration curve All subjects had an initial PK evaluation to characterize the PK of rFIXFc in a representative population of subjects with Hemophilia B.

More extensive PK sampling was conducted in a subset of subjects in the weekly prophylaxis arm (Arm 1) at baseline after a single dose of BENEFIX® 50 IU/kg followed by a single dose of rFIXFc 50 IU/kg. Blood samples were taken for BENEFIX® over a period of 96 hours. Blood samples were then taken for rFIXFc over a period of 240 hours. PK assessment of rFIXFc was repeated at 26 weeks.

The 100-IU/kg dose was selected based on PK results from the Phase 1/2 study, which showed this dose elevated FIX levels to approximately 100% of normal (Shapiro et al 2011). In the Phase 1/2 study, with rFIXFc 100 IU/kg (n=5), the time to FIX levels 1% above baseline was approximately 11 days, and ranged from 9 to 14 days. Based on these data, Arm 2 was designed to test whether a fixed dose of 100 IU/kg could provide protection from bleeding beyond one week.

rFIXFc resulted in low median ABRs of 2.95 in the weekly prophylaxis arm, 1.38 in the individualized interval prophylaxis arm. In contrast, the episodic treatment arm had an ABR of 17.69.

In the individualized interval prophylaxis arm, the median dosing interval was 14 days during the last 6 months on study.

The terminal half-life (activity) measured by one stage clotting assay was approximately 82 hours (82.1 hours) for rFIXFc and approximately 34 hours (33.8 hours) for BENEFIX®.

Overall, greater than 90% of bleeding episodes were controlled by a single injection. Hemostatic efficacy of rFIXFc for perioperative management was rated by treating physicians as excellent or good in 100% of surgeries (14 major surgeries performed on 12 subjects).

The median ABRs for the rFIXFc weekly prophylaxis and individualized interval arms were 2.95 and 1.38, respectively.

Greater than 90% of bleeding episodes were resolved with one injection of rFIXFc.

The terminal half-life of BENEFIX® of approximately 34 hours determined in B-LONG is longer than that reported in the BENEFIX® package insert (~18 hours) as well as a number of studies (13.7 to 19.3 hours) (Ewenstein 2002; Kisker et al. 2003; Negrier et al. 2011) that followed EMA guidelines on FIX PK assessment using a 48-hour sampling duration. However, in published PK studies in which BENEFIX® was sampled up to 72 hours post dosing, a longer terminal half-life was also reported to be 21.3 to 33.4 hours (Ragni et al. 2002, Lambert et al. 2007, Chang et al. 2007, and Martinowitz et al. 2012).

To determine whether the discrepancy in terminal half-life of BENEFIX® resulted from the longer PK sampling schedule of 96 hours adopted in this study, BENEFIX® PK data were also analyzed using data only up to 48 hours post dose. This analysis yielded a significantly shortened terminal half-life of BENEFIX® (~17 hours) that is consistent with previous reports using 48-hour sampling duration. A summary of the comparative data for BENEFIX® is presented in Table 12B.

TABLE 12B

Estimation of Terminal Half-life for rFIX (BENEFIX ®) as Determined from 96-Hour vs 48-Hour Sampling Duration.

|  | Arithmetic Estimates (hours) | | Geometric Estimates (hours) | |
| --- | --- | --- | --- | --- |
|  | Mean | SD | Mean | 95% CI |
| BeneFIX package insert[2] | 18.1 | 5.1 | — | — |
| Study BeneFIX estimate (48 hours)[a] | 17.2 | 2.7 | 17.0 | (15.9, 18.3) |
| Study BeneFIX estimate (96 hours)[a] | 35.7 | 13.6 | 33.8 | (29.1, 39.2) |

[a]Two-compartmental analysis.
CI denotes confidence interval,
SD standard deviation.

In the B-LONG study, a head-to head comparison was made between rFIXFc and BENEFIX®, whereas in the Phase 1/2 study, the half-life of rFIXFc was compared to the historical data reported in the BENEFIX® Product Insert (2009). The measure of PK improvement of rFIXFc over BENEFIX® from the B-LONG study was more reliable and accurate.

Safety rFIXFc was well tolerated and had significantly improved PK relative to the current standard of care, rFIX. One serious AE (obstructive uropathy) was assessed as possibly related to treatment; the event resolved and the subject continued on study. Good control of bleeds and low ABRs seen with weekly to bi-weekly (every 2 weeks) dosing suggest that this therapy may substantially improve management of acute bleeds and markedly lengthen prophylactic regimens in hemophilia B, thereby potentially improving subject adherence and outcomes.

For detection of inhibitors (neutralizing antibodies), the Nijmegen-modified Bethesda assay to detect neutralizing antibodies was performed at screening, baseline, and each visit during study treatment to monitor for the development of an inhibitor. Following the first dose with rFIXFc, inhibitor testing in arms 1 and 2 was conducted at trough at each scheduled clinic visit, with trough defined as a point after the longest interval between scheduled doses. Inhibitor testing in arm 3 was performed following a washout of at least 72 hours (3 days). For new patients entering arm 4, inhibitor testing was performed at screening and after a total of at least 4 EDs were achieved with rFIXFc, within 4 weeks prior to scheduled surgery. Formation of an inhibitor was defined as a neutralizing antibody value ≥0.6 Bethesda units (BU)/ml, confirmed in a second, separately drawn sample within 2-4 weeks. The confidence interval on the inhibitor incidence rate was evaluated using the Clopper-Pearson exact method for a binomial proportion. The acceptable inhibitor risk in clinical trials of previously treated FIX patients allows 1 of 50 patients to experience an inhibitor while on the study, with each patient requiring at least two valid tests for inhibitors over 50 to 75 EDs.

For detection of non-neutralizing antibodies (rFIXFc binding antibodies), monitoring for non-neutralizing antibodies (NNAs) that bind to rFIXFc was performed at the same time points as testing for inhibitors. A bridging assay format was employed to detect all possible classes of antibodies, with electrochemiluminescent readout on an MSD instrument. Samples were positive if the signal was above a statistically derived cut point and confirmed by inhibition with excess rFIXFc product. Positive samples were further characterized for binding to rFIX or Fc. Testing of inhibitor-positive control samples showed that this assay was approximately 100-fold more sensitive than the Nijmegen-modified Bethesda assay.

The study was designed to include ≥50 subjects with ≥50 EDs to detect the risk of inhibitors. The US Food and Drug Administration guidance for adequate demonstration of acceptable inhibitor risk in clinical trials of previously treated FIX subjects allows 1 out of 50 subjects to experience an inhibitor, with each subject requiring ≥50 EDs to the study treatment. Under the assumption that the occurrence of inhibitors in a clinical study can be adequately modeled using the binomial distribution, ≥50 EDs would allow for a 2-sided, 95% confidence interval for the true inhibitor incidence of (0.05%-10.65%) using the exact Clopper-Pearson method if 1 case of inhibitor formation was observed. There were no reported deaths, allergic reactions, thrombotic events, or inhibitor development in any study subjects, including 55 subjects with ≥50 EDs and 94 patients with ≥25 EDs. No inhibitors (neutralizing antibodies) were detected in any subject in the study. Low positive results for non-neutralizing antibodies (NNA) were found in 3 subjects at baseline, which did not impact the PK of rFIXFc and all 3 reverted to NNA negative status during the study. One subject had borderline negative results during the study, and a borderline positive result at the end of the study. rFIXFc clearance was not impacted and the NNA were not associated with any increased bleeding frequency and/or higher consumption of rFIXFc. The incidence of AEs was similar across all treatment arms, with 45 subjects (71.4%) in Arm 1, 23 subjects (79.3%) in Arm 2, and 20 subjects (74.1%) in Arm 3 reporting ≥1 AE. The majority of the AEs were judged by the Investigator as unrelated or unlikely related to treatment. AEs judged as possibly related or related to treatment were reported in 10 (8.4%) of the 119 subjects in Arms 1, 2, and 3 combined. No discernable trends were detected for coagulation activation markers (F1+2, D-dimer, thrombin-antithrombin complex) in the sequential PK subgroup, nor for total IgG and subclass levels in any of the Arms.

Long-lasting rFIXFc was efficacious in maintaining perioperative hemostasis in subjects with hemophilia B. The high rating of perioperative hemostasis by surgeons and investigators for all major surgeries conducted suggests that blood loss was comparable to that expected for a subject without hemophilia.

The results disclosed herein show that rFIXFc provided effective control of acute bleeding episodes and demonstrated efficacious prophylaxis, for both weekly and individualized interval prophylaxis of longer interval duration (e.g., every 1-2 weeks) and/or higher trough levels. Notably, approximately 50% of subjects in the individualized prophylaxis cohort (Arm 2) showed dosing intervals of ≥2 weeks. Compared with rFIX, rFIXFc showed a substantially improved PK profile, which allowed longer dosing intervals for prophylactic regimens that can be less burdensome to subjects. The PK profile of rFIXFc was stable over time. These results show that rFIXFc is a first in its class long-lasting recombinant factor IX therapy, which may offer a treatment shift toward less frequent injections and still provide prolonged protection from bleeding, thereby promoting increased adherence to prophylaxis and improved outcomes in hemophilia B subjects.

To ensure consistency of laboratory analyses, one central laboratory was used for each type of assay. Analyses of clinical safety samples and central sample management were performed at LabCorp (Cranford, N.J., USA). FIX activity and inhibitor assays were conducted at LabCorp (Englewood, Colo., USA). Genotyping of samples was done at Hemostasis Lab, Puget Sound Blood Center (Seattle, Wash., USA). ICON Development Solutions (Whitesboro, N.Y., USA) analyzed FIX antigen and non-neutralizing antibody (NNA) samples, and Chimera Biotech GmbH (Dortmund, Germany) analyzed rFIXFc concentration samples.

The study could conclude early when all of the following predefined criteria were met:
1) 13 patients in the Sequential Pharmacokinetics subgroup in arm 1 completed pharmacokinetic sampling to adequately estimate the terminal half-life for BeneFIX at baseline and for rFIXFc at baseline and week 26.
2) 53 patients from any treatment arm completed at least 50 EDs with rFIXFc.
3) 20 patients from arm 2 and 16 patients from arm 3 completed at least 26 (±1) weeks on study.
4) 73 patients from any treatment arm completed at least 50 EDs with rFIXFc and underwent inhibitor testing; or 53 patients completed at least 50 EDs and underwent inhibitor testing with no more than 1 patient with a positive inhibitor as confirmed by retesting; or 34 patients completed at least 50 EDs and underwent inhibitor testing, with no patients with a positive inhibitor as confirmed by retesting.
5) Approximately 10 major surgeries were conducted in at least 5 patients and postoperative follow-up was completed.

When all of these criteria had been met, all ongoing patients were asked to return to the clinic for end-of-study assessments.

Impact on Quality of Life

Quality of Life was measured using the HAEM-A-QoL, a quality of life instrument specific to hemophilia. HAEM-A-QoL was performed in adults (aged 18 and older) in the prophylactic treatment arms. Change from baseline at Week 26 in the combined prophylaxis arms by pre-study regimen are summarized in Table 13.

Control of bleeding: Over 90% (90.4%) of bleeding episodes were controlled by a single injection of rFIXFc.

Perioperative management: Treating physicians rated the hemostatic efficacy of rFIXFc as excellent or good in 100% of surgeries.

Adverse drug reactions (ADRs) were reported in 10 of 119 (8.4%) subjects treated with routine prophylaxis or episodic (on-demand) therapy. Adverse drug reactions are considered adverse events assessed by the investigator as related or possibly related to treatment with rFIXFc. Adverse drug reactions are summarized in Tables 14A and 14B.

The incidence of adverse events was similar across all treatment arms, with at least one adverse event reported in 45 patients (71.4%) in arm 1, 23 patients (79.3%) in arm 2, and 20 patients (74.1%) in arm 3. The majority were judged by investigators as unrelated or unlikely related to treatment. Adverse events judged as related or possibly related to treatment were reported in 10 (8.4%) of the 119 patients in arms 1, 2, and 3 combined. One serious adverse event judged as possibly related to treatment by the investigator was a case of an obstructive clot in the urinary collecting system that resolved with hydration and the patient continued the study treatment. There were no reports of hypersensitivity, anaphylaxis, or thrombotic events, and there were no deaths in the study. There were no clinically meaningful changes in coagulation activation markers (F1+2, D-dimer, thrombin-antithrombin complex) or for total IgG and subclass levels.

No subject was withdrawn from study due to an adverse drug reaction. In the study, no inhibitors were detected and no events of anaphylaxis were reported.

rFIXFc was well-tolerated, with no evidence of neoantigenicity, and adverse events were consistent with those expected in a hemophilia population. Notably, the high rate of compliance in this study (96.6%) and corresponding high study completion rate (93.5%) further support the tolerabil-

TABLE 13

Median Change from Baseline for the Haem-A-QoL Questionnaire (Fixed Weekly Interval and Individualized Interval Arms Pooled)

| | Pre-Study Regimen | | | | |
|---|---|---|---|---|---|
| | Prophylaxis | | | Episodic (On-demand) | |
| | N | Change from baseline | N | Change from baseline | |
| Total score | 27 | −6.82 (−22.8, 6.1) | 26 | −6.25 | (−25.5, 12.8) |
| Domains, during the past month | | | | | |
| 1. Physical health | 27 | −10.00 (−45.0, 20.0) | 31 | −15.00 | (−60.0, 15.0) |
| 2. Feeling | 27 | 0.00 (−43.8, 50.0) | 31 | 0.00 | (−43.8, 62.5) |
| 3. View of yourself | 27 | −5.00 (−25.0, 15.0) | 30 | −5.00 | (−35.0, 25.0) |
| 4. Sports and leisure | 22 | −7.50 (−70.0, 25.0) | 21 | −20.00 | (−40.0, 35.0) |
| 5. Work and school | 22 | 0.00 (−31.3, 52.1) | 25 | −6.25 | (−31.3, 18.8) |
| 6. Dealing with hemophilia | 27 | 0.00 (−100.0, 100.0) | 31 | −8.33 | (−66.7, 75.0) |
| 7. Treatment | 27 | −6.25 (−18.8, 18.8) | 31 | 0.00 | (−53.1, 37.5) |
| Domains, recently | | | | | |
| 8. Future | 26 | −5.00 (−25.0, 10.0) | 30 | 0.00 | (−30.0, 20.0) |
| 9. Family planning | 15 | 0.00 (−29.2, 12.5) | 13 | 0.00 | (−43.8, 25.0) |
| 10. Partnership and sexuality | 26 | 0.00 (−50.0, 66.7) | 30 | 0.00 | (−25.0, 25.0) |

NOTE:
Summary statistics are median (minimum, maximum).

The median dosing interval in the individualized interval prophylaxis arm was 14 days during the last 6 months on study.

ity of rFIXFc. The risk of inhibitors has been reported to be up to 3% in the naïve hemophilia B population. See Tandra A, and Shapiro AD (2010) in Lee C A, Berntorp E, Hoots W K, eds. Textbook of hemophilia, 2nd ed. Hoboken, N.J.: Wiley-Blackwell; and DiMichele D. (2007) Br J Haematol 138:305-15. Patients generally develop inhibitors within the first 50 EDs to exogenous FIX replacement therapy (see Dimichele D. (2002) Haemophilia 8:280-287), which supported the end of study criteria. B-LONG included a total of 5144 EDs (117.1 patient-years of exposure), with 55 patients having ≥50 EDs, and no inhibitors were detected in any patients. In this study, low-titer NNAs were observed in a small proportion of patients (3%) at screening and baseline, and became negative in three of four cases during rFIXFc treatment. The low-titer NNAs observed in this study had no discernible effect on rFIXFc pharmacokinetics or bleeding rates.

TABLE 14A

Adverse Drug Reactions reported for rFIXFc

| MedDRA System Organ Class | MedDRA Preferred Term | N = 119* Number of Subjects n (%) |
|---|---|---|
| Nervous system disorders | Headache | 2 (1.7) |
| | Dizziness | 1 (0.8) |
| | Dysgeusia | 1 (0.8) |
| Gastrointestinal disorders | Paresthesia oral | 2 (1.7) |
| | Breath odor | 1 (0.8) |
| General disorders and administration site conditions | Fatigue | 1 (0.8) |
| | Infusion site pain | 1 (0.8) |
| Cardiac disorders | Palpitations | 1 (0.8) |
| Renal and urinary disorders | Obstructive uropathy | 1 (0.8) |
| Vascular disorders | Hypotension | 1 (0.8) |

*119 previously treated subjects (PTPs) on routine prophylaxis or episodic (on-demand) therapy
The incidence of the adverse reactions below is expressed according to the following categories:
Very common (≥1/10)
Common (≥1/100 to <1/10)
Uncommon (≥1/1,000 to <1/100)
Rare (≥1/10,000 to <1/1,000)
Very rare ( <1/10,000)

TABLE 14B

Further Summary of Adverse Events.

| AE | Arm 1: Weekly Prophylaxis (Fixed Interval) (N = 63) | Arm 2: Individualized Interval Prophylaxis (Fixed Dose) (N = 29) | Arm 3: Episodic Treatment (N = 27) |
|---|---|---|---|
| Total AEs, n | 158 | 76 | 52 |
| Patients with ≥1 AE | 45 (71.4) | 23 (79.3) | 20 (74.1) |
| Most common AEs (≥5%), n (%) | | | |
| Nasopharyngitis | 13 (20.6) | 4 (13.8) | 1 (3.7) |
| Influenza | 5 (7.9) | 0 | 4 (14.8) |
| Arthralgia | 6 (9.5) | 2 (6.9) | 0 |
| Upper respiratory tract infection | 4 (6.3) | 2 (6.9) | 1 (3.7) |
| Headache | 2 (3.2) | 2 (6.9) | 2 (7.4) |
| Hypertension | 3 (4.8) | 2 (6.9) | 1 (3.7) |
| Dizziness | 3 (4.8) | 2 (6.9) | 0 |
| Sinusitis | 3 (4.8) | 2 (6.9) | 0 |
| Musculoskeletal pain | 2 (3.2) | 2 (6.9) | 0 |
| AEs judged as related or possibly related to treatment, n (%) | 5 (7.9) | 4 (13.8) | 1 (3.7) |
| Breath odor | 1 (1.6) | | |
| Paresthesia oral | 1 (1.6) | 1 (3.4) | |
| Fatigue | 1 (1.6) | | |
| Headache | 1 (1.6) | | |
| Hypotension | 1 (1.6) | | |

TABLE 14B-continued

Further Summary of Adverse Events.

| AE | Arm 1: Weekly Prophylaxis (Fixed Interval) (N = 63) | Arm 2: Individualized Interval Prophylaxis (Fixed Dose) (N = 29) | Arm 3: Episodic Treatment (N = 27) |
|---|---|---|---|
| Palpitations | | 1 (3.4) | |
| Dizziness | | 1 (3.4) | |
| Dysgeusia | | 1 (3.4) | |
| Obstructive uropathy* | | 1 (3.4) | |
| Injection site pain | | | 1 (3.7) |

*This event was the only serious adverse event (AE) related or possibly related to recombinant factor IX Fc fusion protein (rFIXFc) treatment. This patient had a history of painful hematuria. Approximately 4 months after his first dose of rFIXFc, he developed urinary obstruction/pain and passed clots with relief. Three days later, symptoms recurred and resolved with hydration. The patient continued on rFIXFc during this time and continued on study.

Example 5. The Clinical Implications of Population Pharmacokinetics of rFIXFc in Routine Prophylaxis, Control of Bleeding and Perioperative Management for Hemophilia B Subjects BACKGROUND: Clinical dosing of factor IX (FIX) in treatment of hemophilia B is well established based on empirical practice and clinical outcomes. Since pharmacokinetics (PK) of FIX activity is the surrogate efficacy marker, we utilized population PK (popPK) modeling and simulation to evaluate dosing regimens of long-acting recombinant FIX Fc fusion protein (rFIXFc). The PK of rFIXFc, from 135 single-dose and 21 repeat-dose profiles in subjects ≥12 years old (body weight (BW): 45-186.7 kg), was best described by a 3-compartmental model, which showed modest inter-individual variability (IIV) of 17.7% for clearance (CL) and 21.7% for volume of central compartment (V1). The proportional residue error of 10.6% approximates the variability of the one-stage clotting assay for FIX activity. The only covariate that showed a weak association with rFIXFc PK is BW, which accounted for ~3% of IIV for CL and V1, suggesting that BW-independent flat dosing of rFIXFc may be feasible for treating adult hemophilia B subjects.

AIMS: To simulate the BW-based and flat dosing regimens for routine prophylaxis, control of bleeding and perioperative management in the hemophilia B population.

METHOD: The validated 3-compartmental popPK model, including inter-occasion variability and BW as the covariate on CL and V1, was used for dosing simulations. For BW-based dosing regimen, PK profiles were simulated for 1000 subjects with BW distribution representative of the phase 3 study. BW distribution was simulated using a power function $Z=BW-0.5$. The generated BW (1000 values) distribution has a median of 74.9 kg and a range of 38.9 to 172.6 kg, which is similar to our studies (median, 73.3 kg; min and max, 45 and 186.7 kg). For fixed dosing regimen, three populations (n=1000 each) were stratified based on low (≤10th percentile), typical (10th-90th percentile) and high (≥90th percentile) BW. Variability of exposure parameters, percentage of population maintaining target Cmax and trough, and deviations of median exposure parameters in extreme BW groups were compared with BW-based and flat dosing regimens. To simulate steady-state in prophylaxis regimen, six doses were applied for all dosing regimens (once weekly, every 10 days, or every 14 days), with each dosing interval assigned as one occasion. To simulate the PK profile following an episodic treatment, a single dose was applied.

RESULT: Consistent with the observations from the phase 3 study, popPK simulation of 50 IU/kg once weekly or 100 IU/kg every 10-14 days predicted peak FIX activity within the physiologic range (Cmax<150%) and trough ≥1% in majority of the population. All simulated regimens predicted that the majority of the population will maintain trough activity at or above 1% (Table 15).

TABLE 15

Predicted percentage of population with steady-state trough at or above 1% for various prophylaxis dosing regimens

| Regimen | Total weekly dose | % of population with trough ≥1% |
| --- | --- | --- |
| 50 IU/kg weekly | 50 | 95.4 |
| 100 IU/kg weekly | 100 | 99.6 |
| 100 IU/kg every 10 days | 70 | 89.2 |
| 100 IU/kg every 14 days | 50 | 52.8 |

A plot showing a population simulation of steady-state FIX activity vs. time is shown in FIGS. 13A-13C. Table 16 shows the predicted steady state FIX activity over the course of 14 days for two dosing regimens: 50 IU/kg weekly and 100 IU/kg every 14 days.

TABLE 16

Predicted steady state FIX activity

| Dose, IU/kg | EOI median [5th, 95th] | Day 1 median [5th, 95th] | Day 3 median [5th, 95th] | Day 5 median [5th, 95th] | Day 7 median [5th, 95th] | Day 10 median [5th, 95th] | Day 14 median [5th, 95th] |
| --- | --- | --- | --- | --- | --- | --- | --- |
| 50 IU/kg weekly | 52.6 [32.1, 89.3] | 16.9 [11.2, 26.1] | 7.17 [3.85, 12.3] | 4.16 [1.93, 7.83] | 2.67 [1.02, 5.49] | NA | NA |
| 100 IU/kg every 14 days | 102 [60.0, 166] | 30.0 [19.6, 46.7] | 12.0 [6.62, 19.9] | 6.78 [3.24, 12.2] | 4.28 [1.82, 8.06] | 2.29 [0.688, 5.33] | 1.07 [0.0758, 3.23] |

TABLE 17

Predicted FIX activity profile after a single dose of rFIXFc in the 5th to 95th percentile of the population

| | rFIXFc dose, median [5th, 95th] | |
| --- | --- | --- |
| | 50 IU/kg | 100 IU/kg |
| End of infusion | 50.8 [30.4, 84.5] | 102 [60.8, 169] |
| 12 hours | 21.1 [13.5, 33.6] | 42.3 [26.8, 67.3] |
| 24 hours (day 1) | 14.8 [9.78, 22.7] | 29.5 [19.6, 45.5] |
| 36 hours | 10.9 [6.79, 17.1] | 21.8 [13.7, 34.1] |
| 48 hours (day 2) | 8.51 [5.14, 13.2] | 17.0 [10.5, 26.6] |
| 72 hours (day 3) | 5.57 [3.05, 9.27] | 11.1 [6.22, 18.5] |
| Day 5 | 3.07 [1.44, 5.62] | 6.14 [3.05, 11.0] |
| Day 7 | 1.93 [0.795, 3.71] | 3.88 [1.82, 7.28] |
| Day 10 | 1.1 [0.277, 2.33] | 2.19 [0.775, 4.56] |
| Day 14 | 0.559 [0, 1.38] | 1.08 [0.125, 2.58] |

Analysis of 12 major surgeries and 2 minor surgeries found that the FIX activities measured during the perioperative period were largely consistent with the prediction by popPK based on subjects' pre-surgery baseline PK, indicating no substantial factor consumption in these surgeries. A representative plot of observed and predicted perioperative FIX activity is shown in FIG. 12. Simulated and observed FIX activities were compared within the first 21 days after the first rFIXFc surgical dose (n=14; 12 major surgeries, 2 minor surgeries). There was good correlation between the Furthermore, BW-based and flat dosing resulted in comparable PK profiles with comparable exposure parameters, e.g., 50 IU/kg and 4000 IU once weekly predicted a median (5th, 95th percentile) Cmax of 52.6 (32.1, 89.3) IU/dL and 56.1 (36.2, 90.9) IU/dL, respectively. Both dosing regimens predicted that >95% of the population maintains Cmax<150% and trough ≥1% (FIG. 14). However, BW-based and flat dosing showed differential effects on the exposure parameters in extreme (≤10th or ≥90th percentile) BW populations. This suggests that BW-independent flat dosing may be feasible for patients 12 years and older.

The popPK model was used to simulate dosing regimens for episodic treatment. The model predicts that for the control of bleeding episodes, a single dose of 50 or 100 IU/kg of rFIXFc is sufficient to maintain the plasma FIX peak activity levels at 40 to 80 IU/dL (Table 17) as recommended by the World Federation of Hemophilia (WFH) guidelines.

observed FIX activity data and that predicted by the PK model (relative prediction error [95% CI], 0.332% [−2.08%, 1.42%]).

CONCLUSION: PopPK provides a robust and effective means to evaluate potential dosing regimens. The predictions by popPK simulation for rFIXFc corroborate the results from the phase 3 study. The simulations of BW-based and flat dosing of rFIXFc achieved similar PK profiles. Considering the wide therapeutic range for factor replacement therapy, flat dosing of rFIXFc and rFIX products may be a potentially viable approach in adult hemophilia B subjects that warrants further clinical investigation. Furthermore, using a population PK model, it is feasible to develop a general dosing guidance to achieve target FIX levels recommended for perioperative management in patients with haemophilia B.

Example 6. Population Pharmacokinetic Analysis of a Long-Acting Recombinant Factor IX-Fc Fusion Protein (rFIXFc) in Subjects with Severe Hemophilia B BACKGROUND: Population pharmacokinetic (PK) models are developed to understand the sources of variability in dose requirements (covariates) and to help individualize dosing regimens if necessary. Dosing histories and subject-specific data are used to gain an understanding of drug disposition in order to discern specific demographic and/or clinical factors that may be predictors of PK parameters. By characterizing the population PK (popPK) of long-acting FIX-Fc (rFIXFc) in subjects with severe hemophilia B (≤2 IU/dL plasma FIX activity), a model of estimated population PK parameters of rFIXFc can be established. This model may assist physicians who wish to tailor dosing for individual subjects with sparse PK samples.

METHODS: Male subjects with severe hemophilia B were included from a phase 1/2a study (n=12) and the phase 3 study (B-LONG, n=123) described above. The subjects ranged in age from 12 to 76 years and in body weight from 45 to 186 kg. The modeling dataset included 135 baseline PK profiles at Week 1, as well as 21 repeat PK profiles at Week 26, with a total of 1400 measured FIX activity records. The final population PK model was validated using 1027 trough/peak FIX activity records from 119 subjects.

In the popPK analysis, plasma FIX activity was measured by the one-stage (activated partial thromboplastin time) clotting assay. Corrected FIX activity was calculated using the formula:

Corrected FIX activity=Measured FIX activity−Baseline−Residual decay.

Baseline FIX activity was defined as the lowest level of activity (LLACT) recorded at screening, predose, postdose, or from historical clinical records. When the baseline is equal to 0, the LLACT is less than 1% (lower limit of quantification). When the baseline FIX activity is equal to LLACT, LLACT is greater than or equal to 1% and less than or equal to 2%.

Prestudy residual decay was performed using terminal half-life obtained from a noncompartmental analysis of the individual data by the following formula:

Residual decay=(predose−baseline)$\times e^{-decay\ rate \times time}$.

For the popPK model development, NONMEM VII version 1.0 (ICON Development Solutions, Ellicott City, Md.) was used. The modeling and qualification steps are presented below in Table 20.

TABLE 20

Modeling and Qualification Steps

| Steps | Model selection |
|---|---|
| Base model and Inter-individual variability (IIV) evaluation | Base Model, IIV on CL/V1/Q2/V2/Q3 |
| Inter-occasion variability (IOV) evaluation | Base Model with IOV on CL and V1 |
| Covariate Modelling | Final model, body weight as covariate on CL and V1 |
| Internal qualification (bootstrap and VPC) | |
| External qualification using trough/peak records | |

CL, clearance;
V, volume of distribution;
Q, inter-compartmental clearance;
VPC, visual predictive check A first order conditional estimation with interaction method (FOCEI) was used to estimate the popPK parameters. Residual errors were modeled as combined proportional and additive errors. Stepwise forward addition (p<0.005) and backward elimination (p<0.001) covariate modeling was performed. Potential covariates assessed in this analysis included: body weight (BW), Age, Race, Blood type, Human Immunodeficiency Virus status, Hepatitis C Virus status, haematocrit, $IgG_1$ and albumin concentration, and FIX genotype.

Model qualifications included bootstrap, visual predictive check (VPC) and validation with trough/peak records. The mean relative prediction error (an indicator of accuracy) was calculated as:

$$\frac{1}{N}\sum_{i=1}^{i=N}\frac{[DV-IPRED]}{DV}$$

RESULTS: The rFIXFc disposition was best described by a three-compartment base model (FIG. 5). The model was further improved by including intra-subject random changes at different occasions (i.e., inter-occasion variability, IOV) for CL and V1 (FIG. 6). IOV was smaller than inter-individual variability (IIV), indicating that individual PK was more accurate than the mean popPK for individual PK prediction.

Body weight was found to be a significant covariate for rFIXFc disposition (FIG. 7), although the impact of BW was limited. For example, the BW exponent on CL and V1 was 0.436 and 0.396, respectively, and inclusion of BW reduced inter-individual variability (IIV) for both CL and V1 only by 3.4% and 2.5%, respectively. None of the other covariates assessed, including age, race, blood type or genotype, were significant covariates in this model.

The final popPK model is summarized below in Table 21.

TABLE 21

Summary of the final rFIXFc population pharmacokinetic model.

| Parameter | Population Estimate | 95% non-parametric CI from bootstrap[a] | IIV[b] (%) | IOV (%) |
|---|---|---|---|---|
| $CL = Typical\ CL \times \left(\frac{BW}{73}\right)^{0.436}$ | | | | |
| Typical CL for a 73 kg subject (dL/h) | 2.39 | 2.29, 2.49 | 17.7 | 15.1 |
| BW exponent on CL | 0.436 | 0.272, 0.584 | | |
| $V1 = Typical\ V1 \times \left(\frac{BW}{73}\right)^{0.396}$ | | | | |
| Typical V1 for a 73 kg subject (dL) | 71.4 | 58.5, 76.0 | 21.7 | 17.4 |
| BW exponent on V1 | 0.396 | 0.169, 0.580 | | |
| Q2 (dL/h) | 1.67 | 1.35, 1.89 | 35.8 | — |
| V2 (dL) | 87.0 | 79.0, 95.5 | 46.2 | — |
| Q3 (dL/h) | 39.3 | 16.6, 141 | — | — |
| V3 (dL) | 39.9 | 36.6, 52.4 | 37.7 | — |
| Residual Error: Proportional 10.6% Additive 0.24 IU/dL | | | | |

CI confidence interval;
IIV, inter-individual variability;
IOV, inter occasion variability;
CL, clearance;
BW, body weight;
V, volume of distribution;
Q, inter-compartmental clearance For a typical 73 kg subject, the predicted popPK values for clearance, volume of central compartment, and volume of distribution at steady state are 2.39 dL/h, 71.4 dL, and 198 dL, respectively. Goodness-of-fit plots show that the predicted popPK data generated by the model closely mimic the observed FIX activity data (FIGS. 8A-8D).

The results of the popPK model were validated using the observed FIX activity data. The median and 80% interval for observed and predicted FIX activity time profiles nearly overlapped, indicating that the final model was able to reproduce both the central tendency and variability of the observed FIX activity data on the time scale (FIGS. 9A-9D). The strong correlation between observed and predicted FIX activities in the trough/peak dataset suggested that the final popPK model is predictive (FIG. 10).

Finally, the overall relative prediction error was −3.23% with a 95% confidence interval of −5.27% to −1.23%. Post hoc estimates from this popPK analysis were very similar to the results from the conventional PK analysis shown below in Table 22.

TABLE 22

Post hoc empirical Bayesian estimates of key PK parameters.

| Parameter | Phase 3 Mean (SD) | Phase 1/2a Mean (SD) |
|---|---|---|
| Clearance (CL), mL/h/kg | 3.42 (0.89) | 2.82 (0.58) |
| Volume of central compartment (V1), mL | 102 (29.6) | 96.2 (24.7) |
| Incremental in vivo recovery, IU/dL per IU/kg | 1.02 (0.45) | 1.04 (0.19) |
| Volume of distribution at steady-state (Vss), mL/kg | 297 (90.5) | 234 (70.8) |
| Terminal Half-life, h | 86.7 (27.9) | 70.9 (13.9) |
| Mean residence time (MRT), h | 89.4 (25.9) | 82.5 (15.5) |

SD, standard deviation

CONCLUSIONS: The three-compartment popPK model predicted disposition of rFIXFc with modest inter-individual variability (IIV). Individual PK parameters derived from the three-compartment popPK model were similar to those derived from the two-compartment conventional PK analysis, indicating a limited 3rd compartment contribution. For a typical 73 kg subject, the popPK model predicted a clearance of 2.39 dL/h; volume of central compartment of 71.4 dL; and volume of distribution at steady state of 198 dL. The only significant covariate assessed in the popPK model was BW, although its impact on rFIXFc PK variability was limited.

The final popPK model can be used to simulate dosing regimens and intervals for routine prophylaxis, control and prevention of bleeding episodes, and peri-operative management. This model may assist physicians who wish to tailor dosing for individual subjects with sparse PK samples.

Example 7. Pediatric Study

Study Design

A phase 3, open-label, multicenter, paediatric study to evaluate the safety, PK, and efficacy of rFIXFc for the control and prevention of bleeding in previously treated children (<12 years of age) with severe hemophilia B (endogenous FIX activity ≤2 IU/dL [2%]) is described.

The enrolment is approximately 26 children with hemophilia B. Eligibility criteria for this pediatric previously treated subject (PTP) study requires the children to have had ≥50 documented prior exposure days (EDs) to FIX products, weigh ≥13 kg at the time of consent, and have no current or history of inhibitors to FIX products. The treatment regimen is for prophylaxis (see study design shown in FIG. 11). PK analysis of FIX and rFIXFc will be performed in participants prior to initiation of prophylactic treatment with rFIXFc.

Primary and secondary outcome measures will include frequency of inhibitor development (for the primary outcome measures) and number of annualized bleeding episodes and/or response to treatment with rFIXFc for bleeding episodes (for the secondary outcome measures).

The safety and efficacy of rFIXFc in previously untreated subjects (PUPs), defined by the European Medicines Agency as subjects with no prior exposure to any factor products will also be assessed. The results of the paediatric PTP and PUP studies will provide further insight into the clinical safety and hemostatic parameters of rFIXFc for treating hemophilia in children.

Interim Analysis

Prophylaxis with factor IX (FIX) is the optimal treatment for patients with hemophilia B; however, due to the short half-life of currently available FIX products, frequent injections may be required to prevent bleeding episodes. To prolong half-life and reduce injection frequency, a long-lasting recombinant FIX Fc fusion protein (rFIXFc) consisting of one rFIX molecule covalently linked to the Fc domain of immunoglobulin G1 (IgG1) was developed. In a phase 3 study in adults and adolescents, rFIXFc had a 2.43-fold increase in half-life and 50% reduction in clearance (CL) compared with FIX (BeneFIX®) (J Thromb Haemost. 2013; 11[2]:241). The Kids B-LONG study (NCT01440946) was designed to evaluate the pharmacokinetics (PK), safety, and efficacy of rFIXFc prophylaxis in previously treated pediatric subjects with hemophilia B. The objective of this planned interim analysis was to determine the PK parameters of rFIXFc in subjects enrolled in Kids B-LONG and compare these parameters to their pre-study FIX PK parameters.

Methods: This multicenter, open-label, phase 3 study is currently enrolling previously treated subjects aged <12 years with severe hemophilia B (≤2 IU/dL endogenous FIX), at least 50 exposure days (EDs) to FIX products, and no inhibitors to FIX. Subjects were stratified into two age cohorts (<6 and 6 to <12 years of age). A weekly prophylactic regimen of 50-60 IU/kg of rFIXFc was administered to all subjects, with subsequent dose and interval adjustments based upon PK data and bleeding frequency. Subjects will continue treatment until they achieve 50 EDs. The primary endpoint is the incidence of inhibitor formation. A sequential PK analysis was performed to compare the PK parameters of rFIXFc with that of pre-study FIX products. PK sampling of pre-study FIX occurs at baseline prior to first dose of FIX (50 IU/kg) and at 5 additional time points through 48 hours. PK sampling of rFIXFc occurs prior to first dose of 50 IU/kg rFIXFc and at 7 additional time points through 168 hours following the first dose; a washout period of 96 hours is required before the first dose of both pre-study FIX and rFIXFc. Plasma FIX activity is measured using the one-stage clotting assay calibrated against a commercially available FIX plasma standard and the FIX activity-over-time profiles are analyzed by non-compartmental analysis (NCA) using the PK data analysis software PHOENIX™ WinNonlin 6.2.1.51. A data cut-off date of 23 Apr. 2013 was used to report PK data in this interim analysis.

Results: At the time of this interim analysis, 24 subjects were enrolled and had received at least one dose of pre-study FIX and/or rFIXFc. Of 18 subjects with evaluable PK profiles, 15 had complete PK profiles for both pre-study FIX (BENEFIX®, HAEMOSOLVEX®, or ALPHANINE®) and rFIXFc. A comparison of PK parameters for rFIXFc versus FIX for both age cohorts is presented in Table 23. rFIXFc had a more than 3-fold prolongation in half-life and a more than 60% reduction in CL compared to the FIX products.

TABLE 23

PK of FIX products and rFIXFc in pediatric subjects (geometric mean [95% CI])

| | | Half-life (hr) | CL (mL/dL/kg) | IR (IU/dL per IU/kg) | Vss (mL/kg) |
|---|---|---|---|---|---|
| <6 yrs | FIX (pre-study) n = 5 | 19.4 (16.6-22.7) | 10.6 (7.6-14.9) | 0.5 (0.4-0.7) | 286.0 (207.0-395.0) |
| | rFIXFc (on-study) n = 6 | 71.8 (50.1-103.0) | 4.1 (3.5-4.8) | 0.6 (0.5-0.8) | 347.0 (251.0-480.0) |
| | rFIXFc/FIX Ratio n = 4 | 3.7 (2.6-5.3) | 0.4 (0.3-0.5) | 1.1 (1.0-1.3) | 1.2 (1.2-1.3) |
| 6 to <12 yrs | FIX (pre-study) n = 13 | 17.9 (15.9-20.2) | 8.6 (7.0-10.6) | 0.6 (0.5-0.9) | 214.0 (154.0-298.0) |
| | rFIXFc (on-study) n = 13 | 71.4 (62.7-81.2) | 3.3 (2.9-3.9) | 0.8 (0.6-0.9) | 281.0 (224.0-352.0) |
| | rFIXFc/FIX Ratio n = 11 | 4.0 (3.4-4.7) | 0.4 (0.3-0.5) | 1.2 (0.9-1.4) | 1.3 (1.0-1.7) |

Conclusion: In comparison to currently available FIX products, rFIXFc had a prolonged half-life and reduced CL in pediatric subjects, which was similar to previous observations in adults and adolescents. The final analysis of the Kids B-LONG study will provide further PK information and evaluate the safety and efficacy of rFIXFc in children.

Example 8. Use of the Population Pharmacokinetic Model of rFIXFc to Simulate or Estimate Individualized and Median Patient Treatment Information As is discussed in Examples 5 and 6, a model of estimated population PK parameters of rFIXFc has been established that can assist physicians and other healthcare practitioners who wish to tailor dosing for individual subjects with, e.g., sparse PK samples. Alternatively, the model can be used to determine dosing based on PK data for the whole population (median PK).

Thus, individualized patient treatment, e.g., pharmacokinetics (PK) and dosing regimens, can be selected using Bayesian estimation (or similar machine learning algorithm) based on the population pharmacokinetic (popPK) model described in Example 6, above (e.g., Table 21). In this way, one can determine alternative prophylactic dosing regimens and optimized dosing regimens for peri-operative management that have not previously been studied in the B-LONG trials. Alternatively, the selected dosing regimen is based on population PK (median PK) rather than making an individualized selection.

In some embodiments, the rFIXFc popPK model of Example 6 (e.g., Table 21) is used without the Bayesian or similar machine learning algorithm.

In some embodiments of this aspect of the invention, the method is carried out on a computer-based system, e.g., a server, a desk top computer, a lap top computer, a tablet, a hand held device, or a smart phone. In some embodiments, the computer-based system is a computer application. The computer-based system includes a storage medium for the rFIXFc popPK model discussed in Example 6, e.g., the parameters of Table 21. In some embodiments, the storage medium can also contain a Bayesian estimating program, e.g., NONMEM or Phoenix NLME. E.g., Example 6; Kiang et al., *Clin. Pharmacokinet* 51:515-525 (2012).

In some embodiments, the system comprises two or more computer-based systems. In some embodiments, the user can input information into a first computer-based system that communicates with a second computer-based system, and the second computer-based system carries out calculations and communicates output information to the first computer-based system. This output information can include recommendations about individualized or non-individualized dosing regimens.

In some embodiments, the user inputs information into the system and the system calculates and outputs one or more PK or dosing regimens. In some embodiments, the system uses the received information to calculate and output individualized or median PK information. In some embodiments, the system calculates individualized dosing or interval information.

Information that can be input by a user and received by the system includes patient information and desired treatment outcome information. Based on the type and value of the received information, the computer-based system calculates output information based on the rFIXFc popPK model and optional machine learning algorithm on the storage medium.

Patient information includes, e.g., age, body weight, diagnostic (baseline) FIX level, PK determinations, time of PK sampling, dosing history if PK samples were taken from multiple doses, actual dose, FIX activity level, etc.

Desired treatment outcome information includes desired PK or desired regimen outcome, e.g., desired rise in plasma FIX activity level following dose, desired dosing interval, and desired dose.

Based on the information that was input and received by the system, the system can output various information, e.g., PK curve, PK parameter such as incremental recovery (Cmax/dose), mean residence time, terminal t1/2, clearance, Vss, AUC/dose, doses and associated troughs, and intervals and associated troughs.

For example, for assessing individualized patient PK, the system can recommend that the user input 2-3 optimized PK sampling time points. In this case, system output can include PK curve and one or more selected PK parameters, e.g., incremental recovery (Cmax/Dose), mean residence time, terminal t1/2, clearance, Vss, AUC, and time to 1 or X %, etc. E.g., FIG. 15.

As additional examples, to select an individualized dosing regimen using the output individual PK parameters discussed in the preceding paragraph, (i) the dose selected for acute treatment can be based on user input of the desired rise in plasma FIX activity level following the dose, (ii) the dose selected for prophylaxis can be based on user input of the desired dosing interval, or (iii) the selected interval for prophylaxis can be based on user input for the desired dose. In the first case, the system can output the dose (IU) based in the patient's incremental recovery. E.g., FIG. 16. In the second case, system output can be a table of doses and associated troughs, e.g., x IU/kg, 1% trough, y IU/kg, 2% trough, etc. e.g., FIG. 17, top. In the third case, system output can be a table of intervals and associated troughs, e.g., x days, 1% trough, y IU/kg, 2% trough, etc., E.g., FIG. 17, bottom.

The user may wish to use the system without inputting any individualized PK data. In this case, the dosing output would be based on the population median rather than being individualized for the particular patient. E.g., FIG. 18. In this way, the user inputs, e.g., body weight and age, and (i) the desired rise in plasma FIX activity level following the dose, (ii) the desired dose interval for prophylaxis, or (iii) the desired dose for prophylaxis. In the first case, the system can output the dose. In the second case, the system can output the dose and associated trough, e.g., Table 16. In the third case, the system can output the interval and associated trough, e.g., Table 16.

Age can be input to determine if the system is suitable for the patient because the current version of the popPK model was built for patients 12 years and older.

In some embodiments, the system is compliant with patient privacy laws. In some embodiments, the system is encrypted, e.g., with SSL. In some embodiments, input patient information is made anonymous.

In some embodiments, the system includes a user help function.

The user can be, e.g., a physician, a nurse, or another healthcare practitioner.

In some embodiments, the method further includes selecting a dosing regimen based on the system's output information and administering rFIXFc to the patient according to the selected regimen.

Example 9. Association of Bleeding Tendency with Time Under Target FIX Activity Levels in Severe Hemophilia B Patients Treated with rFIXFc The goal of prophylactic treatment with coagulation factor replacement in hemophilia patients has been to convert severe hemophilia, defined as <1% endogenous factor activity levels, to moderate (1% to 5%) and mild (5 to 40%) disease. Increased time spent under 1% FVIII activity may be associated with an increase in total bleeding episodes and hemarthroses in patients with severe hemophilia A. No studies to date have documented this association for FIX activity in patients with severe hemophilia B. We report here the analysis of bleeding tendency in relation to FIX activity from the recently completed phase 3, B-LONG study. The B-LONG study evaluated the pharmacokinetics (PK), safety, and efficacy of a recombinant FIX Fc fusion protein (rFIXFc) in severe hemophilia B patients. Briefly, the B-LONG study had 4 treatment arms: weekly prophylaxis, tailored prophylaxis, episodic treatment, and perioperative management. The corresponding median annualized bleeding rates for the first 3 treatment arms were 2.95, 1.38, and 17.69, respectively.

Methods: A 3-compartmental population PK model of rFIXFc was developed based on activity-time profiles in 12 subjects from a Phase 1/2a study and 123 subjects (>12 years) from B-LONG, collected over ≤52 weeks of treatment. Individual post-hoc PK parameters were then derived to construct continuous FIX activity-time profiles for each dose administered over the course of the study for subjects in B-LONG. The cumulative time under target 1%, 3%, and 5% FIX level for each individual on study was calculated and normalized to obtain annualized time under the respective target FIX level. Negative binomial regression models were used to evaluate associations between the number of bleeding events (overall, spontaneous, traumatic, and joint) and annualized time (days) under 1%, 3%, and 5% of FIX activity for all subjects in B-LONG. Models were adjusted for age, body mass index, baseline HIV and HCV status, FIX genotype, number of bleeding episodes in the 12 months prior to study entry, and each subject's time on study.

Results: The multivariable negative binomial regression analysis estimated that overall bleeding events increased with increased time spent under 1% of FIX activity (p<0.001). The association, however, is largely driven by subjects on episodic treatment. The median annualized time under 1% for subjects on episodic treatment was 171 days, in contrast to the median of 0 days for subjects on either weekly prophylaxis or tailored prophylaxis, respectively, as the tailored PK-driven dosing regimens were designed to maintain a target trough above 1%. The association is consistent with the distribution of bleeding events, most of which occurred at predicted FIX activity levels under 1% in subjects on episodic treatment. Since the distribution of predicted FIX trough levels in subjects on prophylaxis were largely in the range of 1% to 5%, the analysis was repeated for cumulative time under 3% and 5%. Both analyses found statistically significant increases in predicted bleeding events as time spent below the respective FIX activity levels increased (FIGS. 20 and 21). The significant association was also observed for spontaneous, traumatic, or joint bleeds analyzed separately for all 3 target FIX activity levels. When comparing across thresholds (1% vs. 3% vs. 5%), the predicted bleeding rate was significantly reduced and the predicted probability of being bleed-free improved as the trough increased. Additionally, the odds of having joint bleeds increased significantly with increasing time spent under the respective target trough (1%, 3%, or 5%).

Conclusions: This is the first study to demonstrate a correlation between increased time spent under a target therapeutic FIX activity level (1%, 3% or 5%) and increased bleeding tendency, as well as a reduced probability of being bleed-free, in adolescent and adult subjects treated with rFIXFc. Based on population PK simulations for FIX activity, these findings confirm the importance of a minimum therapeutic threshold of 1% and provide additional support for establishing prophylactic dosing regimens for patients with severe hemophilia B.

Example 10. Population Pharmacokinetic Modeling of Long-Acting Recombinant Factor IX Fc Fusion Protein in Patients with Hemophilia B Abstract: To elucidate the pharmacokinetic characteristics of recombinant factor IX Fc fusion protein (rFIXFc) in patients with hemophilia B and identify covariates that affect rFIXFc disposition, population PK analysis using NONMEM® (ICON Development Solutions, Ellicott City, Md.) was performed with clinical data from two completed trials in previously treated patients with severe to moderate hemophilia B. Twelve patients from a phase 1/2a study and 123 patients from a registrational phase 3 study were included in this population PK analysis. A three-compartmental model was found to best describe the PK of rFIXFc. For a typical 73-kg patient, population predicted clearance (CL), volume of central compartment (V1), and volume of distribution at steady state (Vss) were 2.39 dL/h, 71.4 dL and 198 dL, respectively. Because of repeat PK profiles at week 26 for patients in a subgroup, inclusion of inter-occasion variability (IOV) on CL and V1 were evaluated and significantly improved the model. The magnitude of IOV on CL and V1 were both low to moderate (<20%) and less than the corresponding inter-individual variability. Body weight (BW) was found to be the only significant covariate for rFIXFc disposition. However, the impact of BW was limited, as the BW power exponent on CL and V1 were 0.436 and 0.396, respectively. This is the first population PK analysis that systematically characterized the PK of long-acting rFIXFc in patients with hemophilia B. The population PK model for rFIXFc can potentially be utilized to evaluate and optimize dosing regimens for the treatment of patients with hemophilia B.

Hemophilia B is a rare bleeding disorder caused by a deficiency of coagulation factor IX (FIX). The disease is caused by a mutation on the X chromosome and affects approximately 1 in 30,000 males [1, 2]. Hemophilia B results in abnormal clot formation, causing prolonged and abnormal bleeding, including bleeding into joints, soft tissue, muscle and body cavities. Bleeding episodes may be associated with trauma or occur in the absence of trauma (spontaneous bleeding). If not treated appropriately, bleeding can be life-threatening or result in significant morbidity [2, 3]. Current mainstay of the treatment is the FIX replacement therapy.

rFIXFc (recombinant factor IX Fc fusion protein) is a recombinant protein consisting of a single molecule of FIX covalently fused to the Fc domain of human immunoglobulin G1 (IgG1) with no intervening sequence. The Fc domain is responsible for the long circulating half-life of IgG1 through interaction with the neonatal Fc receptor (FcRn) that is expressed in many different cell types [4, 5]. rFIXFc was therefore designed as a long-acting version of recombinant FIX, e.g., BeneFIX® (Pfizer Inc, New York, N.Y.) [6, 7]. rFIXFc has the potential to fulfill an unmet medical need by providing a long-acting therapy for control and prevention of bleeding episodes, routine prophylaxis and perioperative management in patients with hemophilia B. Two clinical trials with rFIXFc have been completed in previously treated patients with severe to moderate hemophilia B (with ≤2 IU/dL [%] endogenous FIX): one single dose phase 1/2a study in 14 patients (12 of them who received doses ≥12.5 IU/kg had PK assessment) [6], and one registrational phase 3 study in 123 patients. rFIXFc was shown to be well tolerated and efficacious in the treatment of bleeding, routine prophylaxis and perioperative management.

The purpose of this analysis is to characterize the population pharmacokinetics (PK) of rFIXFc in patients with hemophilia B and to identify demographic and clinical factors that are potential determinants of rFIXFc PK variability. The population PK model of rFIXFc can be used to evaluate and guide dosing regimens of rFIXFc in the treatment of patients with hemophilia B.

Methods.

Clinical Studies: FIX activity data were obtained from two completed clinical trials in previously treated patients with severe to moderate hemophilia B. Twelve evaluable patients from the phase 1/2a study and 123 patients from the phase 3 study (B-LONG) who had measurable FIX activities were included in this population PK analysis. The clinical studies are summarized in FIGS. 1 and 2. The trials were registered at worldwideweb.clinicaltrials.gov as NCT00716716 (phase 1/2a) and NCT01027364 (phase 3). All subjects were patients with severe to moderate hemophilia B previously treated with FIX products, from 12.1 to 76.8 years of age. All patients, or patient guardians, gave informed written consent. The studies were conducted in accordance with the International Conference on Harmonisation guidelines for Good Clinical Practice.

Pharmacokinetic Sampling and Bioanalytical Methods: In the phase 1/2a study, 12 patients underwent rFIXFc PK sampling up to 14 days. In the phase 3 study, PK samples were collected for rFIXFc in all patients according to the schedule in Table 24. PK profiles of rFIXFc were assessed at week 1 (baseline) for all patients and at week 26 for the Arm 1 sequential PK subgroup. For patients on prophylaxis in Arms 1 and 2, additional trough and peak samples were collected at clinical visits throughout the study.

TABLE 24 rFIXFc PK Sampling Schemes

| Study Arm/Subgroup | Sampling Timepoints |
|---|---|
| Phase 1/2a 12.5 to 100 IU/kg rFIXFc | Predose; end of infusion (10 min), 15 min after the end of infusion, 1, 3, 6, 24, 48, 72, 96, 120, 168, 240 h (288 h and 336 h if FIX activity was above baseline at day 13) |
| Phase 3 Arm 1/sequential PK[a] | Predose; 10 min, 1, 3, 6, 24, 48, 96, 144, 168, 192 and 240 h[c] |
| Phase 3 Arm 1/non-sequential PK[a] | Predose; 10 min, 3, 24, 48, 96, 168 and 240 h |
| Phase 3 Arm 2[b] | Predose; 10 min, 3, 24, 48, 96, 168, 240, 288 and 336 h |
| Phase 3 Arms 3 and 4[a] | Predose; 10 min, 3, 24, 48, 96 and 168 h |

[a]PK dose was 50 IU/kg
[b]PK dose was 100 IU/kg
[c]Same sampling schedule was used for repeat PK at week 26

The population PK modeling was performed using plasma FIX activity data as measured by the one-stage activated partial thromboplastin time (aPTT) clotting assay using commercially available aPTT reagents (Trinity Biotech) and normal reference plasma (Precision BioLogic). Lower limit of quantitation (LLOQ) was 1 IU/dL (%). The accuracy of the assay was within 95-104%, and the intra- and inter-assay precision was approximately 10%.

Data Handling: A total of 11 data post-infusion were below the limit of quantification (BLQ, below LLOQ of 1%). Since those post-infusion BLQ values represent <0.5% of the observations, they were excluded from the analysis as the first step of data handling [9-11].

The one-stage clotting assay does not distinguish FIX activities resulting from endogenous baseline, residual activity from incomplete washout of the pre-study FIX product or the input study drug rFIXFc. Therefore, the baseline and residual activity corrections were applied to the observed FIX activity data (Eq. 1 and 2). The corrected FIX activities were recorded as the dependent variable (DV) in the population PK dataset. Similar baseline and residual activity corrections were reported previously for the PK analyses of other FIX products [12-15].

$$\text{Residual decay correction} = (\text{Predose} - \text{baseline}) \times e^{-decay\ rate \times time} \quad (1)$$

$$\text{Corrected FIX activity} = \text{Measured FIX activity} - \text{baseline} - \text{residual decay correction} \quad (2)$$

The endogenous baseline FIX activity level is dictated by the defective FIX genotype and thus stable in each individual subject, yet could be overestimated in patients receiving FIX replacement therapy who underwent incomplete washout. Therefore the baseline FIX activity was defined as the lowest FIX activity observed throughout the study, including all the screening, pre-dose and post-dose records. For patients whose lowest observed FIX activity was <1% (LLOQ), the baseline FIX activity was set at 0; for patients whose lowest observed FIX activity was between 1-2%, the baseline FIX activity was set at the lowest observed FIX activity. The study enrollment is limited to subjects with baseline FIX activity ≤2%.

Residual activity was defined as pre-dose minus baseline FIX activity. For subjects in the Arm 1 sequential PK subgroup who underwent PK assessment with the comparator FIX product (BeneFIX) prior to the rFIXFc PK assessment, the residual activity was decayed using the individual subject's BeneFIX terminal first-order decay rate estimated by the non-compartmental analysis in Phoenix™ WinNonlin 6.2 (Pharsight, Sunnyvale, Calif.). For all other subjects who did not have a BeneFIX PK assessment, the residual activity was decayed from the rFIXFc PK profiles using the average BeneFIX terminal first-order decay rate from the Arm 1 sequential PK subgroup.

In summary, for each individual subject, the baseline activity was first subtracted from observed FIX activities and then residual activity, if any, was decayed from baseline-corrected FIX activities to obtain the corrected FIX activities.

Modeling Strategy and Datasets: Demographic and clinical factors collected and examined in the analysis included age, body weight (BW), race, height, human immunodeficiency virus (HIV) and hepatitis C virus (HCV) status, IgG1 and albumin concentration, hematocrit (HCT) level, FIX genotype and blood type. A summary of categorical factors and baselines for continuous factors is listed in Table 25.

TABLE 25

Summary of categorical demographic and clinical factors and baseline values for continuous demographic and clinical factors

Categorical Demographic and Clinical Factors

| Factor | Category | Number | Percent |
|---|---|---|---|
| Race | American Indian or Alaska Native | 1 | 0.74 |
| | Asian | 30 | 22.2 |
| | Black or African American | 12 | 8.9 |
| | White | 82 | 60.7 |
| | Other | 10 | 7.4 |
| HIV | Yes | 5 | 3.7 |
| | No | 130 | 96.3 |
| HCV | Yes | 52 | 38.5 |
| | No | 83 | 61.5 |
| Blood type | A | 72 | 53.3 |
| | B | 21 | 15.6 |
| | AB | 7 | 5.2 |
| | O | 35 | 25.9 |
| FIX genotype | Missense | 75 | 55.5 |
| | Nonsense | 24 | 17.8 |
| | Frameshift | 18 | 13.3 |
| | Splice mutation | 4 | 3.0 |
| | Others | 14 | 10.4 |

Continuous Demographic and Clinical Factors (Baseline)

| Parameter (units) | N | Median | Mean | SD | Minimum | Maximum |
|---|---|---|---|---|---|---|
| Age (year) | 135 | 31.3 | 34.6 | 15.2 | 12.1 | 76.8 |
| Weight (kg) | 135 | 73.3 | 75.9 | 20.1 | 45 | 186.7 |
| IgG1 (mg/mL) | 123 | 7.19 | 7.68 | 2.62 | 3.34 | 18.3 |
| Albumin (g/L) | 134 | 46 | 46 | 3.43 | 30 | 56 |
| HCT (volume/volume) | 135 | 0.44 | 0.44 | 0.05 | 0.21 | 0.55 |

N Number of subjects,
SD Standard deviation,
HCT hematocrit,
IgG1 immunoglobulin,
FIX factor IX,
HCV hepatitis C virus,
HIV human immunodeficiency virus The PK dataset was split into the modeling dataset, which was used to build the population PK model and validation dataset, which was used to qualify the final model. The modeling dataset for rFIXFc included 1400 FIX activity records from 135 baseline PK profiles in both phase 1/2a and 3 studies, as well as 21 repeat PK profiles that were collected at week 26 from the Arm 1 sequential PK subgroup in the phase 3 study. The validation dataset included 1027 trough/peak FIX activity records from the phase 3 study, excluding the records during and after surgeries. A summary of the modeling and validation datasets is listed in Table 26.

TABLE 26

Summary of modeling and validation datasets

| Dataset | No. of patients | No. of FIX activity records | Median age (range) | Median body weight (range) |
|---|---|---|---|---|
| Modeling dataset | 12 (Phase ½a) 123 (Phase 3) | 1,400 | 31.3 (12.1-76.8) | 73.3 (45.0-186.7) |
| Validation dataset | 100 (Phase 3) | 1,027 | 30.7 (12.1-71.6) | 72.5 (45.2-186.7) |

FIX factor IX

The modeling strategy was a two-step approach. The first step was to build the population PK model using the modeling dataset and the second step was to validate the model with goodness-of-fit plots, bootstrapping, visual prediction check (VPC) and the trough/peak validation dataset [16]. As a comparison, the rFIXFc model using the full dataset, which combined the modeling and validation dataset, was also developed.

Population PK Modeling: NONMEM® 7 version 1.0 (ICON Development Solutions, Ellicott City, Md.) with an Intel Fortran compiler (version 12) was used for the population PK model development. Statistical program R (version 2.15.0, R Foundation for Statistical Computing, Vienna, Austria) was used to compile NONMEM datasets and generate graphics. Perl Speaks NONMEM (PsN, version 3.5.3) [17] was used to conduct bootstrapping. PsN and Xpose 4 [18] were used to perform VPC.

A first order conditional estimation with interaction method (FOCEI) was used to estimate population PK parameters. Inter individual variability (IIV) was modeled using exponential function. The inclusion of IIV terms on PK parameters was tested sequentially, with the most significant objective function value (OFV) reduction (P<0.005) entering the model first. Inter-occasion variability (IOV) [19] was also evaluated. For the modeling dataset, two occasions were defined including baseline PK at week 1 and repeat PK profiling at week 26. For the full dataset, six occasions were defined according to the data density. Residual errors were modeled as combined proportional and additive errors.

Plots of IIV versus covariates were used to screen for potential demographic and clinical factors that affect rFIXFc PK. For continuous covariates, scatter plots of ETA (IIV code used in NONMEM) versus covariates were overlaid with a non-parametric locally weighted smoother LOESS line to determine functional relationships; for categorical covariates, box and whisker plots were used to identify potential differences between groups (data not shown). A clear trend of positive or negative slopes and noteworthy correlation coefficients (data not shown) would suggest a possible influence by the continuous covariates; pronounced differences among the groups would suggest a possible influence by the categorical covariates. After identifying potential covariates, a full stepwise forward addition (P<0.005) and backward elimination (P<0.001) procedure was conducted for covariate modeling.

Besides statistical considerations, model selection was also aided by goodness-of-fit plots, including DV versus population prediction (PRED), DV versus individual prediction (IPRED), conditional weighted residual (CWRES) versus TIME and PRED plots [20, 21]. Other diagnostics also helped to select the proper model, including parameter precision, ETA, and CWRES distribution and shrinkage [22, 23].

Model Qualification: Bootstrapping was conducted with 1,000 datasets generated by random sampling through replacement [24]. Non-parametric median and 95% ($2.5^{th}$ and $97.5^{th}$ percentiles) confidence intervals (CIs) of PK parameters were obtained and compared with final model estimates.

To check the predictive performance of the model, VPC was performed to obtain 1,000 simulated PK profiles [24]. Median, $10^{th}$ and $90^{th}$ percentile of simulated and observed FIX activities, stratified by dose (50 and 100 IU/kg), were plotted.

The trough/peak validation dataset was used to check the predictability of the model [16, 24, 25]. Specifically, the model was used to derive Bayesian feedback predictions of FIX activities at trough/peak time points by setting MAXEVAL=0 in NONMEM control stream. The mean relative prediction error (an indicator of accuracy) was calculated using Eq. 3.

$$\frac{1}{N}\sum_{i=1}^{i=N}\frac{DV-IPRED}{DV} \quad (3)$$

Results

Structural Model and Evaluation of IIV: Based on previous conventional PK analyses of rFIXFc [6], a two-compartment model appropriately described individual PK, hence a two-compartment model was evaluated first followed by a three-compartment model. IIV (ETA, η values) was assumed for clearance (CL) and volume of compartment 1 (V1). A covariance between CL and V1 was also included. The three-compartment model resulted in a reduction of OFV by over 400 units (for additional four parameters) compared with the two-compartment model, thus was selected as the base model. Primary PK parameters included CL, V1, volume of compartment 2 (V2) and 3 (V3), inter-compartmental clearance between compartments 1 and 2 (Q2), as well as between 1 and 3 (Q3). The inclusion of IIV for the rest of the PK parameters (V2, V3, Q2 and Q3) led to further improvement in the model fitting. However, IIV on Q3 was associated with a high standard error (87%), indicating that the data cannot support a precise estimation of IIV on Q3, which was thus not included in the model. No additional covariance between IIV of PK parameters could be estimated with precision, thus the only covariance between IIV retained in the model was the covariance between IIV on CL and V1.

Evaluation of IOV: Since the Arm 1 sequential PK subgroup had repeat PK profiles at week 26 in addition to baseline PK profiles at week 1, IOV was evaluated with baseline PK as occasion 1 and repeat PK as occasion 2. The inclusion of IOV on CL significantly improved the model with a reduction of OFV by 171.6 units. The inclusion of IOV on both CL and V1 achieved an additional OFV drop of 41.6 units, whereas IOV on V2 or Q2 did not improve the model fit (P>0.05). The IOV on V3 improved the model fit at P<0.005 but with a large percentage of relative standard error (78.4%); Therefore, IOV was only included for CL and V1.

Pairwise comparisons of CL and V1 estimates for baseline and repeat PK, derived from the base model with IOV, were plotted in FIG. 6. The changes of either CL or V1 between the two occasions were random and small with only one exception, and the mean CL or V1 for the two occasions were similar.

Overall, the inclusion of IOV reduced the corresponding IIV on CL and V1 from 24.0% and 29.6% to 21.1% and 24.2%, respectively. The inclusion of IOV also reduced proportional and additive residual errors from 12.1% and 0.30 IU/dL, to 10.5% and 0.24 IU/dL, respectively. The base model with IOV provided a reasonable fit to the data, and explained the random as well as small PK changes between occasions studied in the trial, therefore was chosen for further covariate modeling.

Covariate Modeling: Based on ETA versus covariate plots, BW, albumin and race on CL, and "study" on V2 were speculated to be potential covariates. Covariate modeling included BW on all PK parameters, albumin on CL, and "study" on V2 and CL. BW was assessed for all PK parameters because it is an important physiology factor. "Study" was assessed on CL because of the importance of CL.

A full stepwise forward addition and backward elimination procedure was performed. Following the forward covariate inclusion, the full covariate model was identified with BW on CL and V1, and "study" on V2. However, "study" on V2 was removed following the backward elimination procedure (P>0.001).

Further, potential residual variability difference between the phase 1/2a and 3 studies was tested by including two sets of proportional and additive errors for two studies in the residual error model. No significant reduction in OFV was observed (13.7 units, df=2). Therefore, although the phase 1/2a and phase 3 studies have different dosing and sampling schemes, the population PK modeling did not suggest a PK difference between the two studies.

Final Model: The final model of rFIXFc had IIV on CL/V1/Q2/V2/V3 but not Q3, IOV on CL and V1 and BW as a covariate on CL and V1. The model described the data well (FIGS. 8A-8D). There were no outstanding trends observed in the CWRES plots and most CWRES randomly distributed between −2 and 2, indicating overall small discrepancies between measured FIX activities and population predictions (FIGS. 8C and 8D). Population PK parameter estimates, IIV and IOV, as well as residual errors were estimated with precision, evidenced by narrow 95% CIs for each PK parameter (Table 27). The IIV for CL and V1 were 17.7 and 21.7%, respectively, which are low to moderate, and IOV for CL and V1 were low at 15.1 and 17.4%, respectively.

The magnitude of ETA shrinkage on the IIVs was moderate (<30% for all PK parameters with IIV terms), while the magnitude of ETA shrinkage on the IOV was occasion-specific, moderate at first occasion (around 30% on CL and V1) and higher at occasion 2 (around 70%) because there were fewer PK profiles for the second occasion (21 for occasion 2 repeat PK vs. 135 for occasion 1 baseline PK). The distributions of ETAs and CWRES showed approximate normal distribution centered around zero without apparent skewness (data not shown). This was consistent with the ETABAR P values, all of which were non-significant (P>0.05).

Model Qualification: Non-parametric bootstrapping was applied to the final model to assess the model stability. Bootstrapping generated medians and CIs for the PK parameters, IIV and IOV estimates (Table 27). The median values from the bootstrapping were very similar to the model estimates for all the PK parameters.

TABLE 27

Summary of rFIXFc population PK final model

| Parameter | Model estimate | Bootstrap median (95% CI[a]) |
|---|---|---|
| CL = Typical CL × (BW/73)$^{0.436}$ | | |
| Typical CL for a 73-kg patient (dL/h) | 2.39 | 2.39 (2.29, 2.49) |
| BW exponent on CL | 0.436 | 0.437 (0.272, 0.584) |
| V1 = Typical V1 × (BW/73)$^{0.396}$ | | |
| Typical V1 for a 73-kg patient (dL) | 71.4 | 71.2 (58.5, 76.0) |
| BW exponent on V1 | 0.396 | 0.390 (0.169, 0.580) |
| Q2 (dL/h) | 1.67 | 1.66 (1.35, 1.89) |
| V2 (dL) | 87.0 | 87.0 (79.0, 95.5) |
| Q3 dL/h | 39.3 | 39.0 (16.6, 141) |
| V3 (dL) | 39.9 | 41.2 (36.6, 52.4) |
| IIV[b] on CL, % | 17.7 | 17.5 (11.8, 22.4) |
| IOV[c] on CL, % | 15.1 | 15.0 (10.7, 19.1) |
| IIV on V1, % | 21.7 | 22.4 (15.5, 32.1) |
| IOV on V1, % | 17.4 | 16.5 (8.7, 22.8) |
| IIV on Q2, % | 35.8 | 35.0 (22.6, 45.8) |
| IIV on V2, % | 46.2 | 45.9 (38.0, 55.3) |
| IIV on V3, % | 41.2 | 37.9 (30.2, 54.3) |
| Correlation between IIV on CL and V1, % | 75.6 | 74.8 |
| Proportional residual error, % | 10.6 | 10.4 (8.64, 12.0) |
| Additive residual error, IU/dL | 0.24 | 0.24 (0.17, 0.31) |

[a]95% CI: Non-parametric 95% CI from bootstrap results with 1,000 datasets
[b]IIV calculated as (variance)1/2 × 100%
[c]IOV calculated as (variance)1/2 × 100%
BW body weight,
CI confidence interval,
CL clearance,
IIV inter-individual variability,
IOV inter-occasion variability,
PK pharmacokinetic,
Q2 inter-compartmental clearance of compartment 2,
Q3 inter-compartmental clearance of compartment 3,
rFIXFc recombinant factor IX Fc,
V1 volume of compartment 1,
V2 volume of compartment 2,
V3 volume of compartment 3

The graphic results of the VPC of the final model stratified by the dose are presented in FIGS. 9A-9D. The median and 80% interval (10th to 90th percentile) time-activity observed and predicted profiles nearly overlapped, indicating that the final model was able to reproduce both the central tendency and variability of the observed FIX activity time profiles.

The predictive capability of the final model was further evaluated using a validation dataset, which contains the trough/peak FIX activity records that were not included in the modeling dataset. The final model was used to derive the individual predictions for the trough and peak observations. Individual predictions showed good correlation (R2=0.9857, P<0.001) with the observations (FIG. 10). The mean relative prediction error was low at −3.23%, indicating that the final model was qualified to predict rFIXFc PK in the hemophilia B patient population.

Figure 9B:
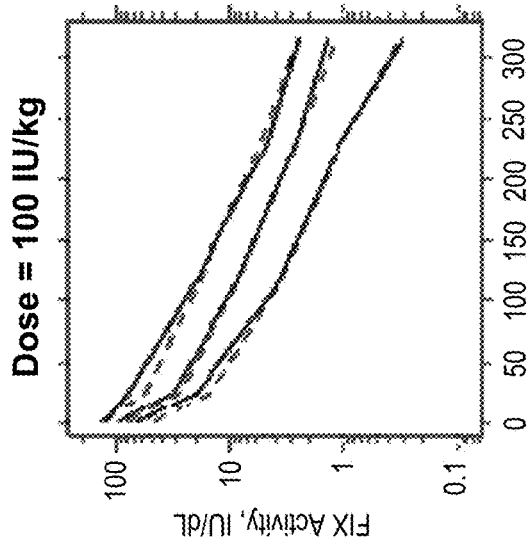
Figure 9D:
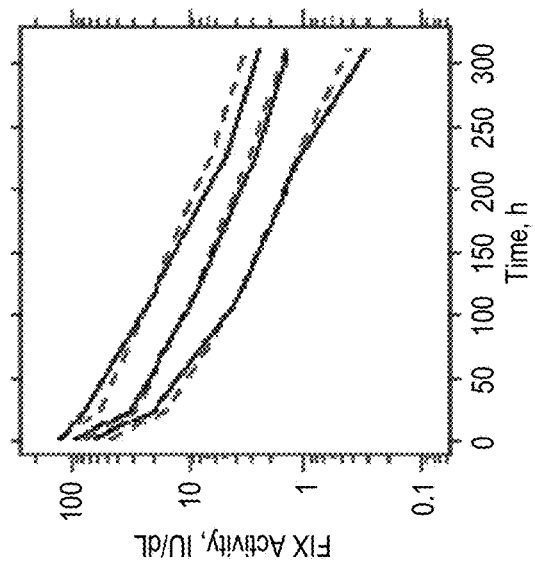
Figure 9A:
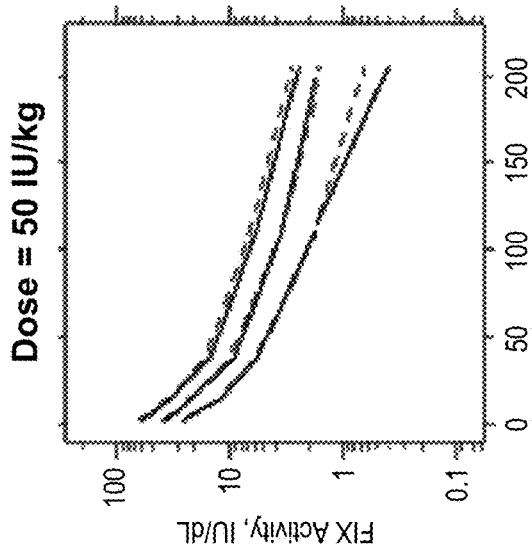
Figure 9C:
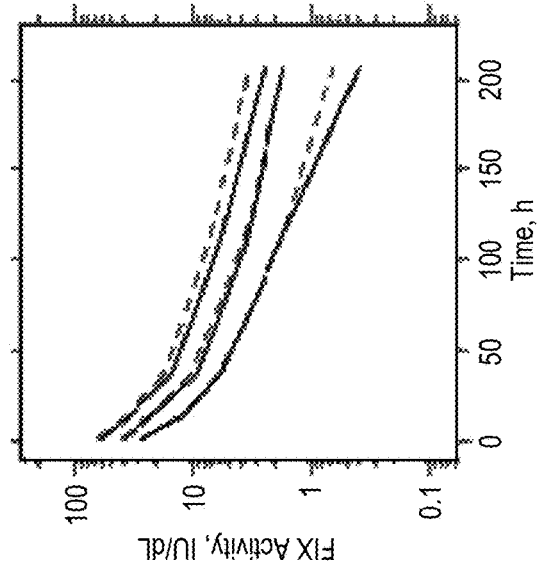

Full Dataset Model: Further, a population PK model of rFIXFc was also built based on the full dataset, including both PK profile and trough/peak data. The population parameter estimates of the resulting model, as well as IIV and IOV (Table 28), were comparable with those of the final model derived from the modeling dataset (Table 27). The goodness-of-fit plots indicated that the model also described the data adequately (FIG. 22). A slightly more over-prediction of FIX activity in the lower range (<10 IU/dL) was observed for the VPC of the full dataset model. (FIGS. 9C and 9D).

TABLE 28

Summary of rFIXFc population PK model derived from the full dataset

| Parameter | Population estimate (95% CI)[a] |
|---|---|
| CL = Typical CL × (BW/73)$^{0.432}$ | |
| Typical CL for a 73-kg patient (dL/h) | 2.21 (2.10, 2.32) |
| BW exponent on CL | 0.432 (0.251, 0.613) |
| V1 = Typical V1 × (BW/73)$^{0.517}$ | |
| Typical V1 for a 73-kg patient (dL) | 70.6 (66.3, 74.9) |
| BW exponent on V1 | 0.517 (0.282, 0.752) |
| Q2 (dL/h) | 1.63 (1.39, 1.87) |
| V2 (dL) | 99.1 (84.6, 114) |
| Q3 (dL/h) | 45.6 (35.6, 55.6) |
| V3 (dL) | 40.7 (38.3, 43.1) |
| IIV[b] on CL, % | 19.7 (16.6, 22.8) |
| IOV[c] on CL, % | 17.8 (17.0, 18.7) |

TABLE 28-continued

Summary of rFIXFc population PK model derived from the full dataset

| Parameter | Population estimate (95% CI)[a] |
|---|---|
| IIV on V1, % | 21.7 (17.9, 25.6) |
| IOV on V1, % | 13.8 (12.3, 15.3) |
| IIV on Q2, % | 48.1 (38.5, 57.6) |
| IIV on V2, % | 51.0 (40.6, 61.3) |
| Correlation between IIV on CL and V1, % | 60.7 |
| Proportional residual error, % | 14.8 (9.56, 20.1) |
| Additive residual error, IU/dL | 0.279 (0.112, 0.445) |

[a]95% CI: The lower and upper limits for 95% CI were calculated asymptotically using the standard errors estimated by the covariance stem in NONMEM
[b]IIV calculated as (variance)$^{1/2}$ × 100%
[c]IOV calculated as (variance)$^{1/2}$ × 100%
BW body weight,
CI confidence interval,
CL clearance,
IIV inter-individual variability,
IOV inter-occasion variability,
PK pharmacokinetic,
rFIXFc recombinant factor IX Fc,
RSE relative standard error,
Q2 inter-compartmental clearance of compartment 2,
Q3 inter-compartmental clearance of compartment 3,
V1 volume of compartment 1,
V2 volume of compartment 2,
V3 volume of compartment 3.

This is the first systematic population PK modeling of rFIXFc in patients with hemophilia B. A three-compartment model described the PK of rFIXFc well. For a typical 73-kg patient, V1 for rFIXFc at 71.4 dL is larger than the plasma volume, which is around 30 dL for a typical adult, indicating that rFIXFc is not limited in the plasma for the initial distribution phase after intravenous administration, similar to that of FIX which is known to bind to collagen IV in the subendothelium.[26] The IIV for CL and V1 were low to moderate at 17.7% and 21.7%, respectively, which are consistent with those reported for plasma-derived FIX (23% for CL and 19% for V1) [12]. Residual errors were small with a proportional error of 10.6% and additive error of 0.24 IU/dL. The proportional residual error is similar to the inter-assay variability of the one stage aPTT clotting assay. The small IIV and residual errors indicate that the model described the data adequately and rFIXFc PK do not vary substantially among patients. The estimated IOVs for CL and V1 were 15.1% and 17.4%, respectively, similar to those reported for plasma-derived FIX (15% for CL and 12% for V1) [12]. The small and randomly distributed IOV on CL and V1 indicate that rFIXFc PK is relatively stable at different occasions.

The approach of using the model to estimate baseline and differentiate baseline from residual activity for the pre-dose of each individual was investigated. However, the population modeling cannot reliably separate baseline from residual activity because not every FIX activity profile returned to baseline at the last sampling time point, i.e., the baseline (endogenous) and exogenous signals were confounded. We also investigated setting baseline activity at 0, 0.5 or individualized baseline. The individualized baseline resulted in a relatively conservative PK estimates and more accurate prediction of the trough levels in individual subjects. Therefore, individualized baseline was chosen to handle the activity data in the population PK modeling, which was also utilized in the conventional PK analysis[8].

BW on CL and V1 was the only covariate that showed a statistically significant impact on rFIXFc PK. It was suggested that the exponent of a physiological or PK parameter shall not revolve around a fixed number [27]. Hence, the exponents of BW on CL and V1 were estimated during the modeling instead of fixed at presumed values, e.g., 0.75 for CL and 1 for V1. The estimated BW exponents for CL and V1 in the final model were markedly lower at 0.436 and 0.396, respectively. Furthermore, inclusion of BW as a covariate decreased IIV for CL by only 3.4% and for V1 by only 2.5%, suggesting that a considerable portion of the variability was not explained by BW.

The limited impact of BW was not unique to rFIXFc PK, which was also observed for BeneFIX in the phase 3 study (data not shown). The weak correlation between BW and PK in our studies differs from a previous report, which showed that BW, with an exponent of 0.7 on CL, accounted for a significant portion of the variability in BeneFIX PK in a two-compartment population PK model [28]. The discrepancy probably can be explained by the different populations studied, i.e., the adult patients (>19 years) in our study versus pooled data from 111 children (≤15 years), including 53 infants (<2 years) and 80 adults (>15 years). This previous report represents a wider range for age and BW than in our study [29]. A recently published paper reported that BeneFIX PK in 56 patients aged 4-56 years and weighing 18-133 kg, described also by a three-compartment model, had allometric exponent of CL terms of 0.66 and volume terms of 0.64 [29]. The slightly reduced allometric exponent of CL compared with the previous report [28] might also be explained by the difference of age and BW range studied.

Data splitting is a useful internal model validation approach in population PK modeling [24]. Because in the clinic intensive PK profile data are used to predict subsequent trough/peak sparse data, the data was split into modeling dataset including the intensive PK profile data from all the subjects at week 1 and week 26 and validation dataset including the sparse peak and trough data throughout the phase 3 study. To verify that our modeling strategy was robust, i.e., building the model with the baseline/repeat PK profiles without additional trough/peak FIX activity records, we also built the model using the full dataset consisting of all the FIX activity records from both the modeling and validation datasets. The two models were highly comparable with <10% difference in the PK parameters, IIV and IOV estimates (Tables 27 and 28). The comparability between the two models was also demonstrated by the similar VPC plots for the two models (FIGS. 9A-9D). FIX activities in the lower range (<10 IU/dL) were slightly more over-predicted by the full dataset model. This difference might be attributed to the imprecise recordings of the peak/trough collection time in the full dataset, which was recorded by patients retrospectively into their electronic diary following the clinic visit. The final model derived from the modeling dataset is slightly more accurate in predicting trough levels, which is essential for maintenance of the therapeutic efficacy. Therefore, the final model derived from the modeling dataset is robust and predictive to be used for simulation of the dosing regimens for rFIXFc.

Finally, the population PK predictions were largely consistent with the results derived from the conventional two-stage PK analysis, which used a two-compartment model, despite a minority (~14%) of the PK profiles could also be described by a three compartmental model. The ambiguity in the model selection in the conventional PK analysis was at least partially due to the different sampling schemes in different study arms. Such ambiguity was avoided using population PK modeling. The post-hoc estimates from this population PK analysis were very similar to the results from the conventional PK analysis (Table 29; [8]). For example, the geometric mean t1/2 estimated in population PK and conventional PK are 81.1 h and 82.1 h, respectively. The highly comparable PK parameters derived from a two-compartment conventional PK analysis and a three-compartment population PK analysis suggests that the contribution of the third compartment to rFIXFc PK was probably limited, but nevertheless provided better profile definition for the more complex population modeling. The advantage of developing a population PK model for rFIXFc is that the model can be utilized for dosing regimen simulation taking into account IIV and IOV, because FIX activity is considered as a surrogate for efficacy [12]; Further, the population PK model combined with individual sparse PK data can be used to derive an individualized dosing regimen through Bayesian estimation, which can alleviate the requirement for extensive sampling. Since hemophilia is a life-long disease impacting children as well as adults, the benefit of PK-tailored dosing regimens based on data from limited blood sampling is of great interest to the hemophilia community.

TABLE 29

Comparison of PK parameters derived from population PK post hoc analysis and conventional PK analysis for phase III study

| Parameter (units) | Population PK post hoc (n = 123) Geometric mean (95% CI) | Conventional PK analysis (n = 22)[a] Geometric mean (95% CI) |
| --- | --- | --- |
| CL (mL/h/kg) | 3.3 (3.2, 3.5) | 3.2 (2.8, 3.6) |
| $V_{ss}$ (mL/kg) | 280.8 (266.4, 296) | 314.8 (277.8, 356.8) |
| Terminal half-life (h) | 81.1 (76.5, 86.1) | 82.1 (71.4, 94.5) |
| MRT (h) | 84.1 (79.8, 88.6) | 98.6 (88.2, 110.3) |

[a]PK parameters derived from 22 patients with intensive sampling schedule in Arm 1 sequential PK subgroup [8]
CI confidence interval,
CL clearance,
PK pharmacokinetic,
MRT mean residual time,
$V_{ss}$ volume of distribution at steady state Conclusion: This is the first population PK analysis that systematically characterized the PK of the long-acting rFIXFc in patients with hemophilia B. The disposition of rFIXFc was well described by a three-compartment model with low to moderate IIV and IOV. Body weight was found to be the only statistically significant but weak covariate on CL and V1 with limited impact. The qualified population PK model for rFIXFc is accurate and predictive, providing a valuable tool to evaluate and optimize dosing regimens of rFIXFc for the treatment of patients with hemophilia B.

REFERENCES

1. Mannucci P M, et al., N Engl J Med. 2001; 344(23):1773-9.
2. Giangrande P., et al., Expert Opin Pharmacother. 2005; 6(9):1517-24.
3. Srivastava A., et al., Haemophilia. 2013; 19(1):e1-47.
4. Roopenian D C., et al., Nat Rev Immunol. 2007; 7(9):715-25.
5. Kuo T T., et al., MAbs. 2011; 3(5):422-30.
6. Shapiro A D et al., Blood. 2012; 119(3):666-72.
7. Peters R T, et al., Blood. 2010; 115(10):2057-64.
8. Powell J O M et al., J Thromb Haemost. 2013; 11(Supplemental 2):OC 70.1.
9. Beal S L., et al., J Pharmacokinet Pharmacodyn. 2001; 28(5):481-504.
10. Byon W., et al., CPT Pharmacometrics Syst Pharmaco. 2013; 2:e51.
11. Bergstrand M., et al., AAPS J. 2009; 11(2):371-80.
12. Bjorkman S., et al., Eur J Clin Pharmacol. 2012; 68(6):969-77.
13. Bjorkman S., et al., Eur J Clin Pharmacol. 1994; 46(4):325-32.
14. Bjorkman S., et al., Haemophilia. 2001; 7(2):133-9.
15. Carlsson M., et al., Haemophilia. 1998; 4(2):83-8.
16. Guidance for industry on Population Pharmacokinetics; availability. Food and Drug Administration, HHS. Notice. Fed Regist. 1999; 64(27):6663-4.
17. Lindbom L., et al., Comput Methods Programs Biomed. 2004; 75(2):85-94.
18. Jonsson E N., et al., Comput Methods Programs Biomed. 1999; 58(1):51-64.
19. Karlsson M O., et al., J Pharmacokinet Biopharm. 1993; 21(6):735-50.
20. Wade J R., et al., AAPS J. 2005; 7(2):45.
21. Ette E I., et al., Pharm Res. 1995; 12(12):1845-55.
22. Savic R M, et al., AAPS J. 2009; 11(3):558-69.
23. Xu X S., et al., AAPS J. 2012; 14(4):927-36.
24. Sherwin C M., et al., Clin Pharmacokinet. 2012; 51(9):573-90.
25. Brendel K., et al., Clin Pharmacokinet. 2007; 46(3):221-34.
26. Gui T., et al., Blood. 2002; 100(1):153-8.
27. Mahmood I., et al., J Pharm Sci. 2010; 99(7):2927-33.
28. Udata C., et al., Blood. 2008; 112(11):443-4.
29. Bjorkman S., et al., Haemophilia. 2013; 19(5):753-7.

Embodiments

E1. A pharmaceutical composition comprising:
(a) a long-acting Factor IX polypeptide;
(b) a carbohydrate mixture comprising sucrose and mannitol;
(c) sodium chloride (NaCl);
(d) L-histidine; and
(e) polysorbate 20 or polysorbate 80.
E2. The pharmaceutical composition of embodiment E1, comprising about 1% (w/v) to about 2% (w/v) sucrose.
E3. The pharmaceutical composition of embodiment E2, comprising about 1.2% (w/v) sucrose.
E4. The pharmaceutical composition of embodiment E2, comprising about 1.7% (w/v) sucrose.
E5. The pharmaceutical composition of embodiment E1, comprising about 10 mg/ml to about 20 mg/ml sucrose.
E6. The pharmaceutical composition of embodiment E5, comprising about 11.9 mg/ml sucrose.
E7. The pharmaceutical composition of embodiment E5, comprising about 16.7 mg/ml sucrose.
E8. The pharmaceutical composition of any one of embodiments E1 to E7, comprising about 2% (w/v) to about 4% (w/v) mannitol.
E9. The pharmaceutical composition of embodiment E8, comprising about 2.4% (w/v) mannitol.
E10. The pharmaceutical composition of embodiment E8, comprising about 3.3% (w/v) mannitol.
E11. The pharmaceutical composition of any one of embodiments E1 to E7, comprising about 20 mg/ml to about 40 mg/ml mannitol.
E12. The pharmaceutical composition of embodiment E11, comprising about 23.8 mg/ml mannitol.
E13. The pharmaceutical composition of embodiment E11, comprising about 33.3 mg/ml mannitol.

E14. The pharmaceutical composition of embodiment E1, comprising about 1.0% to about 2.0% sucrose and about 2.0% (w/v) to about 4.0% (w/v) mannitol.

E15. The pharmaceutical composition of embodiment E14, comprising about 1.2% (w/v) sucrose and about 2.4% (w/v) mannitol.

E16. The pharmaceutical composition of embodiment E14, comprising about 1.7% (w/v) sucrose and about 3.3% (w/v) mannitol.

E17. The pharmaceutical composition of embodiment E1, comprising about 10 mg/ml to about 20 mg/ml sucrose and about 20 mg/ml to about 40 mg/ml mannitol.

E18. The pharmaceutical composition of embodiment E17, comprising about 11.9 mg/ml sucrose and about 23.8 mg/ml mannitol.

E19. The pharmaceutical composition of embodiment E17, comprising about 16.7 mg/ml sucrose and about 33.3 mg/ml mannitol.

E20. The pharmaceutical composition of any one of embodiments E1 to E19, comprising between about 50 mM and about 60 mM NaCl.

E21. The pharmaceutical composition of embodiment E20, comprising about 55.6 mM NaCl.

E22. The pharmaceutical composition of any one of embodiments E1 to E19, comprising between about 3 mg/ml and about 4 mg/ml NaCl.

E23. The pharmaceutical composition of embodiment E22, comprising about 3.25 mg/ml NaCl.

E24. The pharmaceutical composition of any one of embodiments E1 to E23, comprising between about 20 mM and about 40 mM L-histidine.

E25. The pharmaceutical composition of embodiment E24, comprising about 25 mM L-histidine.

E26. The pharmaceutical composition of embodiment E24, comprising about 35 mM L-histidine.

E27. The pharmaceutical composition of any one of embodiments E1 to E23, comprising between about 3 mg/ml and about 6 mg/ml L-histidine.

E28. The pharmaceutical composition of embodiment E27, comprising about 3.88 mg/ml L-histidine.

E29. The pharmaceutical composition of embodiment E27, comprising about 5.43 mg/ml L-histidine.

E30. The pharmaceutical composition of any one of embodiments E1 to E29, comprising between about 0.008% (w/v) and about 0.020% (w/v) polysorbate 20 or polysorbate 80.

E31. The pharmaceutical composition of embodiment E30, comprising about 0.010% (w/v) polysorbate 20 or polysorbate 80.

E32. The pharmaceutical composition of embodiment E30, comprising about 0.014% (w/v) polysorbate 20 or polysorbate 80.

E33. The pharmaceutical composition of any one of embodiments E1 to E29, comprising between about 0.08 mg/ml and about 0.2 mg/ml polysorbate 20 or polysorbate 80.

E34. The pharmaceutical composition of embodiment E33, comprising about 0.10% mg/ml polysorbate 20 or polysorbate 80.

E35. The pharmaceutical composition of embodiment E33, comprising about 0.14 mg/ml polysorbate 20 or polysorbate 80.

E36. The pharmaceutical composition of any one of embodiments E1 to E35, wherein the long-acting FIX polypeptide comprises human FIX fused to an FcRn binding partner.

E37. The pharmaceutical composition of embodiment E36, wherein the long-acting FIX polypeptide comprises a first subunit comprising an amino acid sequence at least 90%, at least 95%, or 100% identical to amino acids 1 to 642 of SEQ ID NO:2, and a second subunit comprising an amino acid sequence at least 90% to 95% identical to amino acids 1 to 227 of SEQ ID NO:4.

E38. The pharmaceutical composition of any one of embodiments E1 to E37, which comprises the long-acting FIX polypeptide at a concentration of between about 25 IU/ml and about 1200 IU/ml.

E39. The pharmaceutical composition of embodiment E38, comprising 50 IU/ml, 100 IU/ml, 200 IU/ml, 400 IU/ml, or 600 IU/ml of the long-acting FIX polypeptide.

E40. The pharmaceutical composition of embodiment E39, comprising 50 IU/ml, 100 IU/ml, 200 IU/ml, or 400 IU/ml of the long-acting FIX polypeptide.

E41. The pharmaceutical composition of embodiment E39, comprising 600 IU/ml of the long-acting FIX polypeptide.

E42. The pharmaceutical composition of embodiment E1, comprising:
  (a) between about 25 IU/ml and about 700 IU/ml of the long-acting FIX polypeptide;
  (b) between about 1% (w/v) and about 2% (w/v) of sucrose;
  (c) between about 2% (w/v) and about 4% (w/v) of mannitol;
  (d) between about 50 mM and about 60 mM NaCl;
  (e) between about 20 mM and about 40 mM L-histidine; and
  (f) between about 0.008% (w/v) and about 0.015% of polysorbate 20 or polysorbate 80.

E43. The pharmaceutical composition of embodiment E42, comprising:
  (a) about 50 IU/ml of the long-acting FIX polypeptide;
  (b) about 1.2% (w/v) of sucrose;
  (c) about 2.4% (w/v) of mannitol;
  (d) about 55.6 mM NaCl;
  (e) about 25 mM L-histidine; and
  (f) about 0.010% (w/v) of polysorbate 20 or polysorbate 80.

E44. The pharmaceutical composition of embodiment E42, comprising:
  (a) about 100 IU/ml of the long-acting FIX polypeptide;
  (b) about 1.2% (w/v) of sucrose;
  (c) about 2.4% (w/v) of mannitol;
  (d) about 55.6 mM NaCl;
  (e) about 25 mM L-histidine; and
  (f) about 0.010% (w/v) of polysorbate 20 or polysorbate 80.

E45. The pharmaceutical composition of embodiment E42, comprising:
  (a) about 200 IU/ml of the long-acting FIX polypeptide;
  (b) about 1.2% (w/v) of sucrose;
  (c) about 2.4% (w/v) of mannitol;
  (d) about 55.6 mM NaCl;
  (e) about 25 mM L-histidine; and
  (f) about 0.010% (w/v) of polysorbate 20 or polysorbate 80.

E46. The pharmaceutical composition of embodiment E42, comprising:
  (a) about 400 IU/ml of the long-acting FIX polypeptide;
  (b) about 1.2% (w/v) of sucrose;
  (c) about 2.4% (w/v) of mannitol;
  (d) about 55.6 mM NaCl;
  (e) about 25 mM L-histidine; and (f) about 0.010% (w/v) of polysorbate 20 or polysorbate 80.

E47. The pharmaceutical composition of embodiment E42, comprising:
(a) about 600 IU/ml of the long-acting FIX polypeptide;
(b) about 1.7% (w/v) of sucrose;
(c) about 3.3% (w/v) of mannitol;
(d) about 55.6 mM NaCl;
(e) about 35 mM L-histidine; and
(f) about 0.014% (w/v) of polysorbate 20 or polysorbate 80.

E48. The pharmaceutical composition of embodiment E1, comprising:
(a) between about 25 IU/ml and about 700 IU/ml of the long-acting FIX polypeptide;
(b) between about 10 mg/ml and about 20 mg/ml of sucrose;
(c) between about 20 mg/ml and about 40 mg/ml of mannitol;
(d) between about 3 mg/ml and about 4 mg/ml NaCl;
(e) between about 3 mg/ml and about 6 mg/ml L-histidine; and
(f) between about 0.08 mg/ml and about 0.15 mg/ml of polysorbate 20 or polysorbate 80.

E49. The pharmaceutical composition of embodiment E48, comprising:
(a) about 50 IU/ml of the long-acting FIX polypeptide;
(b) about 11.9 mg/ml of sucrose;
(c) about 23.8 mg/ml of mannitol;
(d) about 3.25 mg/ml NaCl;
(e) about 3.88 mg/ml L-histidine; and
(f) about 0.10 mg/ml of polysorbate 20 or polysorbate 80.

E50. The pharmaceutical composition of embodiment E48, comprising:
(a) about 100 IU/ml of the long-acting FIX polypeptide;
(b) about 11.9 mg/ml of sucrose;
(c) about 23.8 mg/ml of mannitol;
(d) about 3.25 mg/ml NaCl;
(e) about 3.88 mg/ml L-histidine; and
(f) about 0.10 mg/ml of polysorbate 20 or polysorbate 80.

E51. The pharmaceutical composition of embodiment E48, comprising:
(a) about 200 IU/ml of the long-acting FIX polypeptide;
(b) about 11.9 mg/ml of sucrose;
(c) about 23.8 mg/ml of mannitol;
(d) about 3.25 mg/ml NaCl;
(e) about 3.88 mg/ml L-histidine; and
(f) about 0.10 mg/ml of polysorbate 20 or polysorbate 80.

E52. The pharmaceutical composition of embodiment E48, comprising:
(a) about 400 IU/ml of the long-acting FIX polypeptide;
(b) about 11.9 mg/ml of sucrose;
(c) about 23.8 mg/ml of mannitol;
(d) about 3.25 mg/ml NaCl;
(e) about 3.88 mg/ml L-histidine; and
(f) about 0.10 mg/ml of polysorbate 20 or polysorbate 80.

E53. The pharmaceutical composition of embodiment E48, comprising:
(a) about 600 IU/ml of the long-acting FIX polypeptide;
(b) about 16.7 mg/ml of sucrose;
(c) about 33.3 mg/ml of mannitol;
(d) about 3.25 mg/ml NaCl;
(e) about 5.43 mg/ml L-histidine; and
(f) about 0.14 mg/ml of polysorbate 20 or polysorbate 80.

E54. A pharmaceutical kit comprising:
(a) a first container comprising a lyophilized powder, where the powder comprises
(i) a long-acting FIX polypeptide,
(ii) sucrose;
(iii) mannitol;
(iv) L-histidine; and
(v) polysorbate 20 or polysorbate 80; and
(b) a second container comprising 0.325% (w/v) NaCl to be combined with the lyophilized powder of the first container.

E55. The pharmaceutical kit of embodiment E54, comprising:
(a) a first container comprising a lyophilized powder, where the powder comprises
(i) about 250 IU of the long-acting FIX polypeptide,
(ii) about 59.5 mg of sucrose;
(iii) about 119 mg of mannitol;
(iv) about 19.4 mg of L-histidine; and
(v) about 0.50 mg of polysorbate 20 or polysorbate 80; and
(b) a second container comprising 0.325% (w/v) NaCl at a volume sufficient to produce, when combined with the lyophilized powder of the first container, a solution comprising:
(i) about 50 IU/ml of the long-acting FIX polypeptide;
(ii) about 1.2% (w/v) of sucrose;
(iii) about 2.4% (w/v) of mannitol;
(iv) about 55.6 mM NaCl;
(v) about 25 mM L-histidine; and
(vi) about 0.01% (w/v) of polysorbate 20 or polysorbate 80.

E56. The pharmaceutical kit of embodiment E54, comprising:
(a) a first container comprising a lyophilized powder, where the powder comprises
(i) about 500 IU of the long-acting FIX polypeptide,
(ii) about 59.5 mg of sucrose;
(iii) about 119 mg of mannitol;
(iv) about 19.4 mg of L-histidine; and
(v) about 0.50 mg of polysorbate 20 or polysorbate 80; and
(b) a second container comprising 0.325% (w/v) NaCl at a volume sufficient to produce, when combined with the lyophilized powder of the first container, a solution comprising:
(i) about 100 IU/ml of the long-acting FIX polypeptide;
(ii) about 1.2% (w/v) of sucrose;
(iii) about 2.4% (w/v) of mannitol;
(iv) about 55.6 mM NaCl;
(v) about 25 mM L-histidine; and
(vi) about 0.01% (w/v) of polysorbate 20 or polysorbate 80.

E57. The pharmaceutical kit of embodiment E54, comprising:
(a) a first container comprising a lyophilized powder, where the powder comprises
(i) about 1000 IU of the long-acting FIX polypeptide,
(ii) about 59.5 mg of sucrose;
(iii) about 119 mg of mannitol;
(iv) about 19.4 mg of L-histidine; and
(v) about 0.50 mg of polysorbate 20 or polysorbate 80; and (b) a second container comprising 0.325% (w/v) NaCl at a volume sufficient to produce, when combined with the lyophilized powder of the first container, a solution comprising:
- (i) about 200 IU/ml of the long-acting FIX polypeptide;
- (ii) about 1.2% (w/v) of sucrose;
- (iii) about 2.4% (w/v) of mannitol;
- (iv) about 55.6 mM NaCl;
- (v) about 25 mM L-histidine; and
- (vi) about 0.01% (w/v) of polysorbate 20 or polysorbate 80.

E58. The pharmaceutical kit of embodiment E54, comprising:
(a) a first container comprising a lyophilized powder, where the powder comprises
- (i) about 2000 IU of the long-acting FIX polypeptide,
- (ii) about 59.5 mg of sucrose;
- (iii) about 119 mg of mannitol;
- (iv) about 19.4 mg of L-histidine; and
- (v) about 0.50 mg of polysorbate 20 or polysorbate 80; and (b) a second container comprising 0.325% (w/v) NaCl at a volume sufficient to produce, when combined with the lyophilized powder of the first container, a solution comprising:
- (i) about 400 IU/ml of the long-acting FIX polypeptide;
- (ii) about 1.2% (w/v) of sucrose;
- (iii) about 2.4% (w/v) of mannitol;
- (iv) about 55.6 mM NaCl;
- (v) about 25 mM L-histidine; and
- (vi) about 0.01% (w/v) of polysorbate 20 or polysorbate 80.

E59. The pharmaceutical kit of embodiment E54, comprising:
(a) a first container comprising a lyophilized powder, where the powder comprises
- (i) about 3000 IU of the long-acting FIX polypeptide,
- (ii) about 83.3 mg of sucrose;
- (iii) about 167 mg of mannitol;
- (iv) about 27.2 mg of L-histidine; and
- (v) about 0.7 mg of polysorbate 20 or polysorbate 80; and (b) a second container comprising 0.325% (w/v) NaCl at a volume sufficient to produce, when combined with the lyophilized powder of the first container, a solution comprising:
- (i) about 600 IU/ml of the long-acting FIX polypeptide;
- (ii) about 1.7% (w/v) of sucrose;
- (iii) about 3.3% (w/v) of mannitol;
- (iv) about 55.6 mM NaCl;
- (v) about 35 mM L-histidine; and
- (vi) about 0.014% (w/v) of polysorbate 20 or polysorbate 80.

E60. The pharmaceutical kit of embodiment E54, comprising:
(a) a first container comprising a lyophilized powder, where the powder comprises
- (i) about 250 IU of the long-acting FIX polypeptide,
- (ii) about 59.5 mg of sucrose;
- (iii) about 119 mg of mannitol;
- (iv) about 19.4 mg of L-histidine; and
- (v) about 0.50 mg of polysorbate 20 or polysorbate 80; and (b) a second container comprising 0.325% (w/v) NaCl at a volume sufficient to produce, when combined with the lyophilized powder of the first container, a solution comprising:
- (i) about 50 IU/ml of the long-acting FIX polypeptide;
- (ii) about 11.9 mg/ml of sucrose;
- (iii) about 23.8 mg/ml of mannitol;
- (iv) about 3.25 mg/ml NaCl;
- (v) about 3.88 mg/ml L-histidine; and
- (vi) about 0.10 mg/ml of polysorbate 20 or polysorbate 80.

E61. The pharmaceutical kit of embodiment E54, comprising:
(a) a first container comprising a lyophilized powder, where the powder comprises
- (i) about 500 IU of the long-acting FIX polypeptide,
- (ii) about 59.5 mg of sucrose;
- (iii) about 119 mg of mannitol;
- (iv) about 19.4 mg of L-histidine; and
- (v) about 0.50 mg of polysorbate 20 or polysorbate 80; and (b) a second container comprising 0.325% (w/v) NaCl at a volume sufficient to produce, when combined with the lyophilized powder of the first container, a solution comprising:
- (i) about 100 IU/ml of the long-acting FIX polypeptide;
- (ii) about 11.9 mg/ml of sucrose;
- (iii) about 23.8 mg/ml of mannitol;
- (iv) about 3.25 mg/ml NaCl;
- (v) about 3.88 mg/ml L-histidine; and
- (vi) about 0.10 mg/ml of polysorbate 20 or polysorbate 80.

E62. The pharmaceutical kit of embodiment E54, comprising:
(a) a first container comprising a lyophilized powder, where the powder comprises
- (i) about 1000 IU of the long-acting FIX polypeptide,
- (ii) about 59.5 mg of sucrose;
- (iii) about 119 mg of mannitol;
- (iv) about 19.4 mg of L-histidine; and
- (v) about 0.50 mg of polysorbate 20 or polysorbate 80; and (b) a second container comprising 0.325% (w/v) NaCl at a volume sufficient to produce, when combined with the lyophilized powder of the first container, a solution comprising:
- (i) about 200 IU/ml of the long-acting FIX polypeptide;
- (ii) about 11.9 mg/ml of sucrose;
- (iii) about 23.8 mg/ml of mannitol;
- (iv) about 3.25 mg/ml NaCl;
- (v) about 3.88 mg/ml L-histidine; and
- (vi) about 0.10 mg/ml of polysorbate 20 or polysorbate 80.

E63. The pharmaceutical kit of embodiment E54, comprising:
(a) a first container comprising a lyophilized powder, where the powder comprises
- (i) about 2000 IU of the long-acting FIX polypeptide,
- (ii) about 59.5 mg of sucrose;
- (iii) about 119 mg of mannitol;
- (iv) about 19.4 mg of L-histidine; and
- (v) about 0.50 mg of polysorbate 20 or polysorbate 80; and (b) a second container comprising 0.325% (w/v) NaCl at a volume sufficient to produce, when combined with the lyophilized powder of the first container, a solution comprising:
- (i) about 400 IU/ml of the long-acting FIX polypeptide;
- (ii) about 11.9 mg/ml of sucrose;
- (iii) about 23.8 mg/ml of mannitol;
- (iv) about 3.25 mg/ml NaCl;
- (v) about 3.88 mg/ml L-histidine; and (vi) about 0.10 mg/ml of polysorbate 20 or polysorbate 80.

E64. The pharmaceutical kit of embodiment E54, comprising:
(a) a first container comprising a lyophilized powder, where the powder comprises
(i) about 3000 IU of the long-acting FIX polypeptide,
(ii) about 83.3 mg of sucrose;
(iii) about 167 mg of mannitol;
(iv) about 27.2 mg of L-histidine; and
(v) about 0.7 mg of polysorbate 20 or polysorbate 80; and
(b) a second container comprising 0.325% (w/v) NaCl at a volume sufficient to produce, when combined with the lyophilized powder of the first container, a solution comprising:
(i) about 600 IU/ml of the long-acting FIX polypeptide;
(ii) about 16.7 mg/ml of sucrose;
(iii) about 33.3 mg/ml of mannitol;
(iv) about 3.25 mg/ml NaCl;
(v) about 5.43 mg/ml L-histidine; and
(vi) about 0.14 mg/ml of polysorbate 20 or polysorbate 80.

E65. The kit of any one of embodiments E54 to E64, wherein the first container is a glass vial comprising a rubber stopper.

E66. The kit of any one of embodiments E54 to E65, wherein the second container is a syringe body, and wherein the syringe body is associated with a plunger.

E67. The kit of embodiment E66 further comprising an adaptor to connect the glass vial to the syringe body.

E68. The kit of embodiment E66 or embodiment E67, further comprising infusion tubing associated with a needle to be connected to the syringe, suitable for intravenous infusion.

E69. A method of administering a long-acting FIX polypeptide to a hemophilia B subject in need of prophylaxis, comprising intravenously administering to the subject the pharmaceutical composition of any one of embodiments E1 to E53 at an initial dose of about 50 IU/kg, administered once per week, wherein the administration prevents or reduces the frequency of bleeding episodes in the subject.

E70. A method of administering a long-acting FIX polypeptide to a hemophilia B subject in need of prophylaxis, comprising intravenously administering to the subject the pharmaceutical composition of any one of embodiments E1 to E53 at an initial dose of about 100 IU/kg, administered once every 10 to 14 days, wherein the administration prevents or reduces the frequency of bleeding episodes in the subject.

E71. The method of embodiment E69 or embodiment E70, wherein the prophylactic dose amount or dose frequency is subsequently adjusted based on the subject's response.

E72. A method of administering a long-acting FIX polypeptide to a hemophilia B subject in need of treatment of a minor to moderate bleeding episode, comprising intravenously administering to the subject the pharmaceutical composition of any one of embodiments 1 to 53 at an initial dose of about 30 IU/kg to about 60 IU/kg, wherein the administration controls, alleviates, or reverses the bleeding episode.

E73. The method of embodiment E72, further comprising administering one or more additional doses every 48 hours if the subject exhibits further evidence of bleeding.

E74. A method of administering a long-acting FIX polypeptide to a hemophilia B subject in need of treatment of a major bleeding episode, comprising intravenously administering to the subject the pharmaceutical composition of any one of embodiments E1 to E53 at an initial dose of about 100 IU/kg, wherein the administration controls, alleviates, or reverses the bleeding episode.

E75. The method of embodiment E74, further comprising administering an additional dose of the pharmaceutical composition at about 80 IU/kg after about 6 to 10 hours if the bleeding episode continues.

E76. The method of embodiment E75, further comprising administering one or more additional doses of the pharmaceutical composition at 80 IU/kg every 24 hours for three days if the bleeding episode continues.

E77. The method of embodiment E76, further comprising administering one or more additional doses of the pharmaceutical composition at 80 IU/kg every 48 hours until the bleeding episode is controlled.

E78. A method of administering a long-acting FIX polypeptide to a hemophilia B subject in need of surgical prophylaxis, comprising intravenously administering to a hemophilia B subject undergoing minor surgery the pharmaceutical composition of any one of embodiments E1 to E53 at a dose of about 50 IU/kg to 80 IU/kg, wherein the administration controls bleeding in the subject during and after surgery.

E79. The method of embodiment E78, further comprising administering an additional dose of the pharmaceutical composition at about 50 IU/kg to 80 IU/kg at about 24 to about 48 hours after surgery if needed to control post-operative bleeding.

E80. A method of administering a long-acting FIX polypeptide to a hemophilia B subject in need of surgical prophylaxis, comprising intravenously administering to a hemophilia B subject undergoing major surgery the pharmaceutical composition of any one of embodiments E1 to E53 at a dose of about 100 IU/kg, wherein the administration controls bleeding in the subject during and after surgery.

E81. The method of embodiment E80, further comprising administering an additional dose of the pharmaceutical composition at about 80 IU/kg after about 6 to 10 hours if needed to control post-operative bleeding.

E82. The method of embodiment E81, further comprising administering one or more additional doses of the pharmaceutical composition at 80 IU/kg every 24 hours for three days if needed to control post-operative bleeding.

E83. The method of embodiment E82, further comprising administering one or more additional doses of the pharmaceutical composition at 80 IU/kg every 48 hours if needed to control post-operative bleeding.

E84. The method of any one of embodiments E69 to E82, wherein the desired dose of the long-acting FIX polypeptide is obtainable from a single pharmaceutical kit of any one of embodiments 54 to 68.

E85. The method of any one of embodiments E69 to E82, wherein the desired dose of the long-acting FIX polypeptide is obtainable from two or more pharmaceutical kits of any one of embodiments 54 to 68, and wherein the contents of the two or more pharmaceutical kits are pooled prior to administration.

E86. The pharmaceutical composition of any one of embodiments E1 to E53, wherein the long-acting FIX polypeptide has a mean $T_{1/2beta}$ (activity) of about 70 hours to about 95 hours following a single IV infusion of 50 IU/kg of the long-acting FIX polypeptide.

E87. The pharmaceutical composition of any one of embodiments E1 to E53, wherein the mean $T_{1/2beta}$ (activity) is about 82 hours.

E88. The pharmaceutical composition of embodiment E86 or embodiment E87, wherein the mean $T_{1/2beta}$ (activity) is at least about 2-fold to about 3-fold higher than a polypeptide consisting of full-length mature Factor IX (BENEFIX®), following a single IV infusion of 50 IU/kg BENEFIX®.

E89. The pharmaceutical composition of embodiment E88, wherein the mean $T_{1/2beta}$ (activity) is about 2.4-fold higher than a polypeptide consisting of full-length mature Factor IX (BENEFIX®).

E90. The pharmaceutical composition of any one of embodiments E1 to E53 or E86 to E89, wherein the long-acting FIX polypeptide has a mean $C_{max}$ of about 30 IU/dL to about 50 IU/dL following a single IV infusion of 50 IU/kg of the long-acting FIX polypeptide.

E91. The pharmaceutical composition of embodiment E90, wherein the mean $C_{max}$ is about 40.8 IU/dL.

E92. The pharmaceutical composition of any one of embodiments E1 to E53 or E86 to E91, wherein the long-acting FIX polypeptide has a mean area under the curve per dose (AUC/Dose) of about 27 IU*h/dL per IU/kg to about 35 IU*h/dL per IU/kg following a single IV infusion of 50 IU/kg of the long-acting FIX polypeptide.

E93. The pharmaceutical composition of embodiment E92, wherein the mean AUC/Dose is about 31.32 IU*h/dL per IU/kg.

E94. The pharmaceutical composition of embodiment E92 or embodiment E93, wherein the mean AUC/Dose is at least about 1.8-fold to about 2.1-fold higher than a polypeptide consisting of full-length mature Factor IX (BENEFIX®), following a single IV infusion of the polypeptide consisting of full-length mature Factor IX (BENEFIX®) at 50 IU/kg.

E95. The pharmaceutical composition of embodiment E94, wherein the mean AUC/Dose is about 1.99-fold higher than a polypeptide consisting of full-length mature Factor IX (BENEFIX®).

E96. A method of reducing a hemophilia B subject's annualized bleeding rate, comprising administering fixed or individualized doses of the pharmaceutical composition of any one of embodiments 1 to 53 and 86 to 95 prophylactically at regular or individualized dosing intervals.

E98. The method of embodiment E96, wherein the pharmaceutical composition is administered to the subject by a fixed dose at a fixed dosing interval.

E98. The method of embodiment E97, wherein the fixed dose of the pharmaceutical composition is about 50 IU/kg, and the fixed dosing interval is about one week.

E99. The method of embodiment E97, wherein the fixed dose of the pharmaceutical composition is about 100 IU/kg, and the fixed dosing interval is between about 10 days and about 14 days.

E100. The method of embodiment E96, wherein the pharmaceutical composition is administered to the subject at an individualized dose at a fixed dosing interval.

E101. The method of embodiment E100, wherein the fixed dosing interval is about one week.

E102. The method of embodiment E100 or embodiment E101, wherein the individualized dose is adjusted to achieve a plasma trough level of FIX activity of between about 1 IU/dl and about 3 IU/dl.

E103. The method of any one of embodiments 101 to 102, wherein the individualized dose is between about 30 IU/kg and about 60 IU/kg, administered about once weekly.

E104. The method of embodiment E103, wherein the individualized dose is between about 32 IU/kg and about 54 IU/kg, administered about once weekly.

E105. The method of embodiment E104, wherein the average individualized dose is about 41 IU/kg, administered about once weekly.

E106. The method of any one of embodiments E100 to E105, wherein the subject's annualized bleeding rate is reduced by about 70% to about 90% over the average annualized bleeding rate of hemophilia B subjects being treated by episodic or on-demand dosing.

E107. The method of embodiment E106, wherein the subject's annualized bleeding rate is reduced by about 76% to about 89%.

E108. The method of embodiment E107, wherein the subject's annualized bleeding rate is reduced by about 83%.

E109. The method of embodiment E96, wherein the pharmaceutical composition is administered to the subject at a fixed dose at an individualized dosing interval.

E110. The method of embodiment E109, wherein the fixed dose is about 100 IU/kg.

E111. The method of embodiment E109 or embodiment E110, wherein the individualized dosing interval is adjusted to achieve a plasma trough level of FIX activity of between about 1 IU/dl and about 3 IU/dl.

E112. The method of any one of embodiments E109 to E111, wherein the individualized dosing interval is between about 10 days to about 14 days.

E113. The method of embodiment E112, wherein the individualized dosing interval is about 13 days.

E114. The method of any one of embodiments E109 to E113, wherein the subject's annualized bleeding rate is reduced by about 80% to about 95% over the average annualized bleeding rate of hemophilia B subjects being treated by episodic or on-demand dosing.

E115. The method of embodiment E114, wherein the subject's annualized bleeding rate is reduced by about 80% to about 92%.

E116. The method of embodiment E115, wherein the subject's annualized bleeding rate is reduced by about 87%.

E117. The pharmaceutical composition of any one of embodiments E1 to E53 and E86 to E95, further comprising a short-acting FIX polypeptide.

E118. The pharmaceutical composition of embodiment E117, wherein the short-acting FIX polypeptide comprises or consists of wild-type FIX.

E119. The pharmaceutical composition of any one of embodiments E1 to E53, E86 to E95, and E117 and E118, which is a liquid formulation.

E120. The pharmaceutical composition of any one of embodiments E1 to E53, E86 to E95, and E117 and E118, which is a lyophilized powder.

E121. The pharmaceutical composition of any one of embodiments E1 to E53, E86 to E95, and E117 and E118, which is a suspension.

E122. A vial comprising the pharmaceutical composition of any one of embodiments E119 to E121.

E123. A cartridge comprising the pharmaceutical composition of embodiment E119.

E124. A syringe comprising the pharmaceutical composition of embodiment E119 or E120.

E125. The syringe of embodiment E124, which is a dual chamber syringe.

E126. The kit of any one of embodiments E54 to E68, wherein the second container comprises a preservative in an amount sufficient to provide antimicrobial activity.

E127. The pharmaceutical composition of embodiment E119, wherein the liquid formulation further comprises a preservative in an amount sufficient to provide antimicrobial activity.

E128. The kit of embodiment E126 or the pharmaceutical composition of claim 127, wherein the preservative is selected from the group consisting of phenol, m-cresol, benzyl alcohol, chlorobutanol, methyl paraben, propylparaben, phenoxyethanol, any other pharmaceutically acceptable preservative, and any combinations thereof.

E129. The kit of any one of embodiments E126 or E128 or the pharmaceutical composition of embodiment E127 or E128, wherein the preservative is benzyl alcohol.

E130. The kit or the pharmaceutical composition of embodiment E129, wherein the benzyl alcohol is at a concentration between 0.5% and 0.9%.

E131. A method of estimating a rFIXFc dosing information individualized for a patient, the method comprising:
  (a) receiving, by a computer-based system containing the rFIXFc population pharmacokinetic (popPK) model of Example 6 and a Bayesian estimation program, at least one of patient information and desired treatment outcome information, (b) calculating, by the computer-based system, individualized rFIXFc dosing information using the popPK model, the Bayesian estimation program, and the received information, and (c) outputting, by the computer-based system, the individualized dosing information.

E132. The method of embodiment E131, further comprising selecting a dosing regimen based on the output individualized dosing information of (c) and administering rFIXFc to the patient according to the selected dosing regimen.

E133. A computer readable storage medium having instructions stored thereon that, when executed by a processor, cause the processor to perform the method of embodiment E131.

E134. A system comprising a processor and a memory, the memory having instructions stored thereon that, when executed by the processor, cause the processor to perform the method of embodiment E131.

E135. A method of estimating a rFIXFc dosing regimen based on median popPK, the method comprising:
(a) receiving, by a computer-based system containing the rFIXFc popPK model of Example 6 and a Bayesian estimation program, at least one of patient information and desired treatment outcome information,
(b) calculating, by the computer-based system, median rFIXFc PK information using the popPK model, the Bayesian estimation program, and the received information, and
(c) outputting, by the computer-based system, the median PK information.

E136. The method of embodiment E135, further comprising selecting a dosing regimen based on the output median PK information of (c), and administering rFIXFc to a patient according to the selected dosing regimen.

E137. A computer readable storage medium having instructions stored thereon that, when executed by a processor, cause the processor to perform the method of embodiment E135.

E138. A system comprising a processor and a memory, the memory having instructions stored thereon that, when executed by the processor, cause the processor to perform the method of embodiment E135.

E139. A method of estimating individual patient rFIXFc PK, the method comprising:
(a) receiving, by a computer-based system containing the rFIXFc population pharmacokinetic (popPK) model of Example 6 and a Bayesian estimation program, individual rFIXFc PK information;
(b) estimating, by the computer-based system, individualized patient rFIXFc PK information using the popPK model, the Bayesian estimation program, and the received information, and
(c) outputting, by the computer-based system, the individualized patient PK information.

E140. The method of embodiment E139, further comprising selecting a dosing regimen based on the output individualized patient PK information of (c), and administering rFIXFc to the patient according to the selected regimen.

E141. A computer readable storage medium having instructions stored thereon that, when executed by a processor, cause the processor to perform the method of embodiment E139.

E142. A system comprising a processor and a memory, the memory having instructions stored thereon that, when executed by the processor, cause the processor to perform the method of embodiment E139.

E143. The method of embodiment 131, wherein the desired treatment outcome information is desired rise in plasma FIX activity level following dosing and the output information is dose for acute treatment.

E144. The method of embodiment 131, wherein the desired treatment outcome information is desired dosing interval and the output information is dose for prophylaxis.

E145. The method embodiment 131, wherein the desired treatment outcome information is desired dose and the output information is interval for prophylaxis.

E146. The method of embodiment 139, wherein (a) further comprises receiving, by the computer-based system, additional patient information.

E147. The method of any of embodiments 131, 135, or 146, wherein the patient information is age or body weight.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

TABLE 18

Polynucleotide Sequences: FIX-Fc

A. FIX-Fc Chain DNA Sequence (SEQ ID NO: 1, which encodes SEQ ID NO: 2)

pSYN-FIX-030 Nucleotide sequence (nt 1 to 7583):
FIX exon 1 (signal peptide, 1st amino acid propeptide): nt 690-777
FIX mini intron: nt 778-1076
FIX propeptide sequence: nt 1077-1126
Mature FIX sequence: nt 1127-2371
Fc: nt 2372-3052
gcgcgcgttgacattgattattgactagttattaatagtaatcaattac
ggggtcattagttcatagcccatatatggagttccgcgttacataactt
acggtaaatggcccgcctggctgaccgcccaacgaccccccgcccattga
cgtcaataatgacgtatgttcccatagtaacgccaatagggactttcca
ttgacgtcaatgggtggagtatttacggtaaactgcccacttggcagta
catcaagtgtatcatatgccaagtacgccccctattgacgtcaatgacg
gtaaatggcccgcctggcattatgcccagtacatgaccttatgggactt
tcctacttggcagtacatctacgtattagtcatcgctattaccatggtg
atgcggttttggcagtacatcaatgggcgtggatagcggtttgactcac
ggggatttccaagtctccacccccattgacgtcaatgggagtttgttttg
gcaccaaaatcaacgggactttccaaaatgtcgtaacaactccgcccca
ttgacgcaaatgggcggtaggcgtgtacggtgggaggtctatataagca
gagctctctggctaactagagaacccactgcttactggcttatcgaaat
taatacgactcactatagggagacccaagcttcgcgacgtacggccgcc
accatgcagcgcgtgaacatgatcatggcagaatcaccaggcctcatca
ccatctgccttttaggatatctactcagtgctgaatgtacaggtttgtt
tcctttttttaaaatacattgagtatgcttgccttttagatatagaaata
tctgatgctgtcttcttcactaaattttgattacatgatttgacagcaa
tattgaagagtctaacagccagcacgcaggttggtaagtactgtgggaa
catcacagattttggctccatgccctaaagagaaattggctttcagatt
atttggattaaaaacaaagacttctctaagagatgtaaaattttcatga
tgttttcttttttgctaaaactaaagaattattcttttacatttcagtt
tttcttgatcatgaaaacgccaacaaaattctgaatcggccaaagaggt
ataattcaggtaaattggaagagtttgttcaagggaatctagagagaga
atgtatggaagaaaagtgtagttttgaagaagcacgagaagttttgaa
aacactgaaagaacaactgaattttggaagcagtatgttgatggagatc
agtgtgagtccaatccatgtttaaatggcggcagttgcaaggatgacat
taattcctatgaatgttggtgtccctttggatttgaaggaaagaactgt
gaattagatgtaacatgtaacattaagaatggcagatgcgagcagtttt
gtaaaaatagtgctgataacaaggtggtttgctcctgtactgagggata
tcgacttgcagaaaaccagaagtcctgtgaaccagcagtgccatttcca
tgtgaagagtttctgtttcacaaacttctaagctcacccgtgctgaga
ctgttttcctgatgtggactatgtaaattctactgaagctgaaaccat
tttggataacatcactcaaagcacccaatcatttaatgacttcactcgg
gttgttggtggagaagatgccaaaccaggtcaattccctttggcaggttg
ttttgaatggtaaagttgatgcattctgtggaggctctatcgttaatga

TABLE 18-continued

Polynucleotide Sequences: FIX-Fc aaaatggattgtaactgctgcccactgtgttgaaactggtgttaaaatt
acagttgtcgcaggtgaacataatattgaggagacagaacatacagagc
aaaagcgaaatgtgattcgaattattcctcaccacaactacaatgcagc
tattaataagtacaaccatgacattgccttctggaactggacgaaccc
ttagtgctaaacagctacgttacacctatttgcattgctgacaaggaat
acacgaacatcttcctcaaatttggatctggctatgtaagtggctgggg
aagagtcttccacaaagggagatcagcttttagttcttcagtaccttaga
gttccacttgttgaccgagccacatgtcttcgatctacaaagttcacca
tctataacaacatgttctgtgctggctccatgaaggaggtagagattc
atgtcaaggagatagtgggggaccccatgttactgaagtggaagggacc
agtttcttaactggaattattagctggggtgaagagtgtgcaatgaaag
gcaaatatggaatatataccaaggtgtcccggtatgtcaactggattaa
ggaaaaaacaaagctcactgacaaaactcacacatgcccaccgtgccca
gctccggaactcctgggcggaccgtcagtcttcctcttcccccaaaac
ccaaggacaccctcatgatctcccggaccctgaggtcacatgcgtggt
ggtggacgtgagccacgaagaccctgaggtcaagttcaactggtacgtg
gacggcgtggaggtgcataatgccaagacaaagccgcgggaggagcagt
acaacagcacgtaccgtgtggtcagcgtcctcaccgtcctgcaccagga
ctggctgaatggcaaggagtacaagtgcaaggtctccaacaaagccctc
ccagcccccatcgagaaaaccatctccaaagccaaagggcagccccgag
aaccacaggtgtacaccctgcccccatcccgggatgagctgaccaagaa
ccaggtcagcctgacctgcctggtcaaaggcttctatcccagcgacatc
gccgtggagtgggagagcaatgggcagccggagaacaactacaagacca
cgcctcccgtgttggactccgacggctccttcttcctctacagcaagct
caccgtggacaagagcaggtggcagcaggggaacgtcttctcatgctcc
gtgatgcatgaggctctgcacaaccactacacgcagaagagcctctccc
tgtctccgggtaaatgagaattcagacatgataagatacattgatgagt
ttggacaaaccacaactagaatgcagtgaaaaaaatgctttatttgtga
aatttgtgatgctattgctttattgtaaccattataagctgcaataaa
caagttgggtgggcgaagaactccagcatgagatccccgcgctggagg
atcatccagccggcgtcccggaaaacgattccgaagcccaaccttcat
agaaggcgcggtgaatcgaaatctcgtagcacgtgtcagtcctgctc
ctcggcccacgaagtgcacgcagttgccgccgggtcgcgcagggcgaac
tcccgcccccacggctgctcgccgatctcggtcatgccggcccggagg
cgtcccggaagttcgtggacacgacctccgaccactcggcgtacagctc
gtccaggccgcgcacccacacccaggccagggtgttgtccggccaccac
tggtcctggaccgcgctgatgaacagggtcacgtcgtcccggaccacac
cggcgaagtcgtcctccacgaagtcccgggagaacccgagccggtcggt
ccagaactcgaccgctccggcgacgtcgcgcgcggtgagcaccggaacg
gcactggtcaacttggccatggttttagttcctcacctggtctgtattata
ctatgccgatatactatgccgatgattaattgtcaacacgtgctgatca
gatccgaaaatggatatacaagctcccgggagcttttttgcaaaagccta
ggcctccaaaaaagcctcctcactacttctggaatagctcagaggcaga
ggcggcctcggcctctgcataaataaaaaaaattagtcagccatggggc
ggagaatgggcggaactgggcggagttaggggcggatgggcggagtta
ggggcgggactatggttgctgactaattgagatgcatgctttgcatact
tctgcctgctggggagcctggggactttccacacctggttgctgactaa
ttgagatgcatgctttgcatactctgcctgctggggagcctggggactt
ttccacaccctcgtcgagctagcttcgtgagcctccggtgccctgtcagt
gggcagagcgcacatcgcccacagtccccgagaagttggggggaggggt
cggcaattgaaccggtgcctagagaaggtggcgcggggtaaactgggaa
agtgatgtcgtgtactggctccgcctttttcccgagggtgggggagaac
cgtatataagtgcagtagtcgccgtgaacgttctttttcgcaacgggtt
tgccgccagaacacaggtaagtgccgtgtcgtgtttcccgcgggcctggc
ctctttacgggttatgcccttgcgtgccttgaattacttccacctggc
tccagtacgtgattcttgatcccgagctggagccaggggcgggccttgc
gctttaggagccccttcgcctcgtgcttgagttgaggcctggcgtgga
gctgggccgccgcgtgcgaatctggtggcaccttcgcgcctgtctcgc
tgctttcgataagtctctagccatttaaaattttttgatgacctgctgcg
acgcttttttctggcaagatagtcttgtaaatgcgggccaggatctgc
acactggtatttcggttttggggccgcgggcggcgacggggcccgtgg
gtccagcgcacatgttcggcgaggcgggtcgcgagcgcggccaccg
agaatcggacggggtagtctcaagctggccggcctgctctggtgcctg
gcctcgcgccgccgtgtatcgccccgcctgggcggcaaggctggccg
gtcggcaccagttgcgtgagcggaaagatggccgcttcccggccctgct
ccaggggctcaaatgaggacgcggcgctcgggagacgggcgggtg
agtcacccacacaaaggaaaggggcctttccgtcctcagccgtcgcttc
atgtgactccacggagtaccggggccgtccaggcacctcgattagttc
tggagctttttggagtacgtcgtctttaggttgggggagggttttatg
cgatggagtttccccacactgagtgggtggagactgaagttaggccagc
ttggcacttgatgtaattctccttggaatttgcccttttttgagtttgga
tcttggttcattctcaagcctcagacagttggtcaaagtttttttcttc
catttcaggtgtcgtgaacactggtcgcgccgcgccgccaccatgga
gacagacacactcctgctatgggtactgctgctctgggttccaggttcc
actggtgacaaaactcacacatgcccaccgtgcccagcacctgaactcc
tgggaggaccgtcagtcttcctcttcccccaaaacccaaggacaccct
catgatctcccggacccctgaggtcacatgcgtggtggtggacgtgagc
cacgaagaccctgaggtcaagttcaactggtacgtggacggcgtggagg tgcataatgccaagacaaagccgcgggaggagcagtacaacagcacgta
ccgtgtggtcagcgtcctcaccgtcctgcaccaggactggctgaatggc
aaggagtacaagtgcaaggtctccaacaaagcccctcccagcccccatcg
agaaaaccatctccaaagccaaagggcagccccgagaaccacaggtgta
caccctgcccccatcccgcgatgagctgaccaagaaccaggtcagcctg
acctgcctggtcaaaggcttctatcccagcgacatcgccgtggagtggg
agagcaatgggcagccggagaacaactacaagaccacgcctcccgtgtt
ggactccgacggctccttcttcctctacagcaagctcaccgtggacaag
agcaggtggcagcaggggaacgtcttctcatgctccgtgatgcatgagg
ctctgcacaaccactacacgcagaagagcctctccctgtctccgggtaa
atgactcgagagatctggccggctgggccccgtttcgaaggtaagcctat
ccctaaccctctcctcggtctcgattctacgcgtaccggtcatcatcac
catcaccattgagtttaaaaccgctgatcagcctcgactgtgccttcta
gttgccagccatctgttgtttgcccctcccccgtgccttccttgaccct
ggaaggtgccactcccactgtcctttcctaataaaatgaggaaattgca
tcgcattgtctgagtaggtgtcattctattctggggggtggggtggggc
aggacagcaaggggaggattgggaagacaatagcaggcatgctgggga
tgcggtgggctctatggcttctgaggcggaaagaaccagtggcggtaat
acggttatccacagaatcagggatgaaccaggaaagaacatgtgagca
aaaggccagcaaaaggccaggaaccgtaaaaaggccgcgttgctggcgt
ttttccataggctccgcccccctgacgagcatcacaaaaatcgacgctc
aagtcagaggtggcgaaacccgacaggactataaagataccaggcgttt
ccccctagaagctccctcgtgcgctctcctgttccgaccctgccgctta
ccggatacctgtccgcctttctccttcgggaagcgtggcgcttttctca
tagctcacgctgtaggtatctcagttcggtgtaggtcgttcgctccaag
ctgggctgtgtgcacgaaccccccgttcagcccgaccgctgcgcctat
ccggtaactatcgtcttgagtccaacccggtaagacacgacttatcgcc
actggcagcagccactggtaacaggattagcagagcgaggtatgtaggc
ggtgctacagagttcttgaagtggtggcctaactacggctacactagaa
gaacagtatttggtatctgcgctctgctgaagccagttaccttcggaaa
aagagttggtagctcttgatccggcaaacaaaccaccgctggtagcggt
ggtttttttgtttgcaagcagcagattacgcgcagaaaaaaaggatctc
aagaagatcctttgatcttttctacggggtctgacgctcagtggaacga
aaactcacgttaagggattttggtcatgacattaacctataaaaatagg
cgtatcacgaggccctttcgtctcgcgcgtttcggtgatgacggtgaaa
acctctgacacatgcagctcccggagacggtcacagcttgtctgtaagc
ggatgccgggagcagacaagcccgtcagggcgcgtcagggtgttggc
gggtgtcggggctggcttaactatgcggcatcagagcagattgtactga
gagtgcaccatatatgcggtgtgaaataccgcacagatgcgtaaggaga
aaataccgcatcaggcgccattcgccattcaggctgcgcaactgttggg
aagggcgatcggtgcgggcctcttcgctattacgcca B. Fc DNA sequence (mouse Igκ signal peptide underlined) (SEQ ID NO: 3, which encodes SEQ ID NO: 4) This is the Fc cassette from pSYN-FIX-030. In addition, there is a separate Fc expression cassette that was transfected into the cell line in plasmid pSYN-Fc-015 that encodes the same amino acid sequence, but contains a few noncoding changes. The second copy of Fc encoding sequence enables a better monomer: dimer ratio.

<u>atggagacagacacactcctgctatgggtactgctgctctgggttccag
gttccactggt</u>gacaaaactcacacatgcccaccgtgcccagcacctga
actcctgggaggaccgtcagtcttcctcttcccccaaaacccaaggac
accctcatgatctcccggacccctgaggtcacatgcgtggtggtggacg
tgagccacgaagaccctgaggtcaagttcaactggtacgtggacggcgt
ggaggtgcataatgccaagacaaagccgcgggaggagcagtacaacagc
acgtaccgtgtggtcagcgtcctcaccgtcctgcaccaggactggctga
atggcaaggagtacaagtgcaaggtctccaacaaagcccctcccagccc
catcgagaaaaccatctccaaagccaaagggcagccccgagaaccacag
gtgtacaccctgcccccatcccgcgatgagctgaccaagaaccaggtca
gcctgacctgcctggtcaaaggcttctatcccagcgacatcgccgtgga
gtgggagagcaatgggcagccggagaacaactacaagaccacgcctccc
gtgttggactccgacggctccttcttcctctacagcaagctcaccgtgg
acaagagcaggtggcagcaggggaacgtcttctcatgctccgtgatgca
tgaggctctgcacaaccactacacgcagaagagcctctccctgtctccg
ggtaaa

TABLE 19

| Polypeptide Sequences |
|---|
| FIX-Fc Monomer Hybrid: created by coexpressing<br>FIX-Fc and Fc chains.<br>A. FIX-Fc chain (SEQ ID NO: 2):<br>(28 amino acid signal sequence underlined, 18 amino acid<br> propeptide double underlined, Fc portion in italics.)<br>The C-terminal lysine is not present in either subunit;<br>this processing is often observed in recombinant<br>proteins produced in mammalian cell culture, as well as<br>with plasma derived proteins.<br>FIXFC-SC SUBUNIT:<br>FIX Signal Peptide: -46 <u>MQRVNMIMAE SPGLITICLL GYLLSAEC</u><br>FIX Propeptide: -18 <u><u>TVFLDHENAN KILNRPKR</u></u><br>   1   YNSGKLEEFV QGNLERECME EKCSFEEARE VFENTERTTE FWKQYVDGDQ<br>  51   CESNPCLNGG SCKDDINSYE CWCPFGFEGK NCELDVTCNI KNGRCEQFCK<br> 101   NSADNKVVCS CTEGYRLAEN QKSCEPAVPF PCGRVSVSQT SKLTRAETVF<br> 151   PDVDYVNSTE AETILDNITQ STQSFNDFTR VVGGEDAKPG QFPWQVVLNG<br> 201   KVDAFCGGSI VNEKWIVTAA HCVETGVKIT VVAGEHNIEE TEHTEQKRNV<br> 251   IRIIPHHNYN AAINKYNHDI ALLELDEPLV LNSYVTPICI ADKEYTNIFL<br> 301   KFGSGYVSGW GRVFHKGRSA LVLQYLRVPL VDRATCLRST KFTIYNNMFC<br> 351   AGFHEGGRDS CQGDSGGPHV TEVEGTSFLT GIISWGEECA MKGKYGIYTK<br> 401   VSRYVNWIKE KTKLT*DKTHT CPPCPARELL GGPSVFLFPP KPKDTLMISR*<br> 451   *TREVTCVVVD VSHEDPEVKF NWYVDGVEVH NAKTKRREEQ YNSTYRVVSV*<br> 501   *LTVLHQDWLN GKEYKCKVSN KALPAPIEKT ISKAKGQPRE PQVYTLPPSR*<br> 551   *DELTKNQVSL TCLVKGFYPS DIAVEWESNG QREYNYKTTP PVLDSDGSFF*<br> 601   *LYSKLTVDKS RWQQGNVFSC SVMHEALHMH YTQKSLSLSP GK*<br><br>B. Fc chain (SEQ ID NO: 4)<br>20 amino acid heterologous mouse Igκ light chain signal peptide (underlined):<br>-20 <u>METDTLLLWV LLLWVPGSTG</u><br>Mature Fc sequence (corresponding to human IgG1 amino acids 221 to 447, EU numbering)<br>   1   DKTHTCPPCP APELLGGPSV FLFPPKPKDT LMISRTPEVT CVVVDVSHED<br>  51   PEVKFNWYVD GVEVHNAKTK PREEQYNSTY RVVSVLTVLH QDWLNGKEYK<br> 101   CKVSNKALPA PIEKTISKAK GQPREPQVYT LPPSRDELTK NQVSLTCLVK<br> 151   GFYPSDIAVE WESNGQPENN YKTTPPVLDS DGSFFLYSKL TVDKSRWQQG<br> 201   NVFSCSVMHE ALHNHYTQKS LSLSPGK |

What is claimed is:

1. A method of reducing or decreasing an annualized bleeding rate in a human subject with hemophilia B, comprising administering to the subject multiple doses of a pharmaceutical composition comprising:
   (a) a chimeric Factor IX(FIX) polypeptide comprising human FIX and a first Fc region;
   (b) sucrose;
   (c) mannitol; and
   (d) polysorbate 20 or polysorbate 80,
wherein each of the multiple doses comprises 10 IU/kg to 200 IU/kg of the chimeric FIX polypeptide wherein each of the multiple doses is administered at a dosing interval of about 7 days to about 14 days, wherein the annualized bleeding rate of the bleeding episodes is reduced to less than 5; and wherein the bleeding episodes are spontaneous bleeding episodes.

2. The method of claim 1, wherein each of the multiple doses of the chimeric FIX polypeptide is 50 IU/kg to 100 IU/kg.

3. The method of claim 1, wherein each of the multiple doses is about 50 IU/kg or about 100 IU/kg and the dosing interval is about 10 days to about 14 days.

4. The method of claim 1, wherein each of the multiple doses is for individualized interval prophylaxis of one or more spontaneous bleeding episodes.

5. The method of claim 4, wherein the annualized bleeding rate of the one or more spontaneous bleeding episodes is reduced to less than 4.

6. The method of claim 1, wherein the dosing interval is every 7 days to 14 days.

7. The method of claim 1, wherein each of the multiple doses is about 25 IU/kg to about 50 IU/kg and the dosing interval is about 7 days.

8. The method of claim 1, wherein the chimeric FIX polypeptide further comprises a second Fc region.

9. The method of claim 1, wherein the annualized bleeding rate of the spontaneous bleeding episodes is reduced to less than 1.

10. The method of claim 1, wherein each of the multiple doses is 25 IU/kg to 50 IU/kg.

11. The method of claim 1, wherein the chimeric FIX polypeptide comprises a first subunit comprising an amino acid sequence at least 99% identical to SEQ ID NO: 2, and a second subunit comprising an amino acid sequence at least 99% identical to SEQ ID NO: 4.

12. The method of claim 1, wherein the chimeric FIX polypeptide comprises a first subunit comprising amino acids 1 to 641 of SEQ ID NO: 2, and a second subunit comprising amino acids 1 to 226 of SEQ ID NO: 4.

13. The method of claim 12, wherein each of the multiple doses is about 50 IU/kg and the dosing interval is about 7 days.

14. The method of claim 12, wherein each of the multiple doses is about 100 IU/kg and the dosing interval is about 10 days.

15. The method of claim 3, wherein the annualized bleeding rate of the spontaneous bleeding episodes is reduced to less than 4.

16. The method of claim 3, wherein the annualized bleeding rate of the spontaneous bleeding episodes is reduced to less than 3.

17. The method of claim 3, wherein the annualized bleeding rate of the spontaneous bleeding episodes is reduced to less than 2.

18. The method of claim 7, wherein the annualized bleeding rate of the spontaneous bleeding episodes is reduced to less than 4.

19. The method of claim 7, wherein the annualized bleeding rate of the spontaneous bleeding episodes is reduced to less than 3.

20. The method of claim 7, wherein the annualized bleeding rate of the spontaneous bleeding episodes is reduced to less than 2.

* * * * *